(12) United States Patent
Ma et al.

(10) Patent No.: US 12,289,988 B2
(45) Date of Patent: Apr. 29, 2025

(54) NITROGEN-CONTAINING COMPOUNDS, ELECTRONIC ELEMENTS AND ELECTRONIC DEVICES

(71) Applicant: Shaanxi Lighte Optoelectronics Material Co., Ltd., Xi'an (CN)

(72) Inventors: Tiantian Ma, Xi'an (CN); Qiqi Nie, Xi'an (CN); Jiamei Cao, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 748 days.

(21) Appl. No.: 17/620,353

(22) PCT Filed: Oct. 16, 2020

(86) PCT No.: PCT/CN2020/121656
§ 371 (c)(1),
(2) Date: Dec. 17, 2021

(87) PCT Pub. No.: WO2021/082958
PCT Pub. Date: May 6, 2021

(65) Prior Publication Data
US 2022/0416164 A1    Dec. 29, 2022

(30) Foreign Application Priority Data

Oct. 31, 2019 (CN) .......................... 201911054976.6
Sep. 25, 2020 (CN) .......................... 202011025290.7

(51) Int. Cl.
| | |
|---|---|
| C07C 211/61 | (2006.01) |
| C07D 209/88 | (2006.01) |
| C07D 307/91 | (2006.01) |
| C07D 333/76 | (2006.01) |
| C07D 405/12 | (2006.01) |
| H10K 85/60 | (2023.01) |
| H10K 50/15 | (2023.01) |

(52) U.S. Cl.
CPC .......... *H10K 85/633* (2023.02); *C07C 211/61* (2013.01); *C07D 209/88* (2013.01); *C07D 307/91* (2013.01); *C07D 333/76* (2013.01); *C07D 405/12* (2013.01); *H10K 85/636* (2023.02); *C07C 2603/18* (2017.05); *C07C 2603/94* (2017.05); *H10K 50/156* (2023.02); *H10K 85/623* (2023.02); *H10K 85/626* (2023.02); *H10K 85/6572* (2023.02); *H10K 85/6574* (2023.02); *H10K 85/6576* (2023.02)

(58) Field of Classification Search
None
See application file for complete search history.

(56) References Cited

U.S. PATENT DOCUMENTS

| | | | |
|---|---|---|---|
| 2021/0130313 A1* | 5/2021 | Ma ........................ | H10K 85/636 |
| 2021/0253512 A1* | 8/2021 | Ha ........................ | H10K 85/633 |

FOREIGN PATENT DOCUMENTS

| | | |
|---|---|---|
| CN | 107459466 A | 12/2017 |
| WO | 2001060811 A1 | 8/2001 |
| WO | 2020032574 A1 | 2/2020 |

OTHER PUBLICATIONS

International Search Report from corresponding International Application No. PCT/CN2020/121656, mailed on Jan. 4, 2021, 4 pages.

* cited by examiner

*Primary Examiner* — Robert S Loewe
(74) *Attorney, Agent, or Firm* — Tucker Ellis LLP

(57) ABSTRACT

The present application provides a nitrogen-containing compounds represented by formula I-A, electronic elements and electronic devices. The application relates to the field of organic material. The nitrogen-containing compounds can improve the performance of electronic elements.

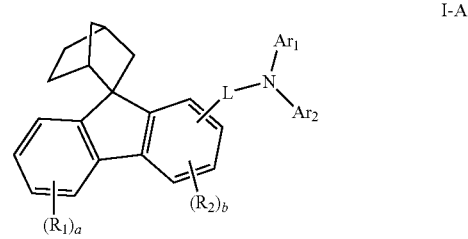

I-A

15 Claims, 2 Drawing Sheets

NITROGEN-CONTAINING COMPOUNDS, ELECTRONIC ELEMENTS AND ELECTRONIC DEVICES

CROSS REFERENCE TO RELATED APPLICATIONS

The present application claims priority to Chinese patent application No. CN2019110549766 filed on Oct. 31, 2019, and Chinese patent application No. CN2020110252907 filed on Sep. 25, 2020, which are incorporated herein by reference in their entirety.

TECHNICAL FIELD

The present application relates to the field of organic material, particularly to a nitrogen-containing compounds, electronic elements and electronic devices.

BACKGROUND

With the development of electronic techniques and the advancement of material sciences, the present application range of electronic components for realizing electroluminescence or photoelectric conversion becomes more and more extensive. Such electronic component usually includes a cathode and an anode disposed opposite to each other, and a functional layer disposed between the cathode and the anode. The functional layer is composed of multiple organic or inorganic film layers, and generally includes an energy conversion layer, a hole transporting layer disposed between the energy conversion layer and the anode, and an electron transporting layer disposed between the energy conversion layer and the cathode.

For example, when the electronic component is an organic electroluminescent device, it generally includes an anode, a hole transporting layer, an electroluminescent layer as an energy conversion layer, an electron transporting layer and a cathode, which are sequentially stacked. When a voltage is applied to between anode and cathode, the two electrodes generate an electric field. Under the action of the electric field, the electrons on the cathode side move to the electroluminescent layer, while the holes on the anode side move to the electroluminescent layer, so the electrons and the holes combine in the electroluminescent layer to form excitons, and the excitons are in an excited state and release energy outwards, which in turn makes the electroluminescent layer emit light outward. In order to improve the performance of electronic components that realize electroluminescence or photoelectric conversion, an electron blocking layer may also be provided between the energy conversion layer and the hole transporting layer.

In the prior art, CN201710407382.3 and the like disclosed materials available for preparing hole transport layers in organic electroluminescent devices. However, it is still necessary to continue to develop new materials in order to further improve the performance of electronic elements.

The information disclosed above in the background is only used to strengthen the understanding of the background of the present application, so it may include information that does not constitute the prior art known to those skilled in the art.

SUMMARY

The application is intended to provide nitrogen-containing compounds, electronic elements and electronic devices to improve the performance of electronic elements.

The following technical solution is used for the application in order to achieve the above disclosed purpose:

According to a first aspect of the present application, there is provided nitrogen-containing compounds, having a structure represented by formula I-A:

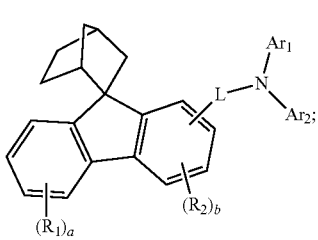

Formula I-A wherein L is selected from a single bond, a substituted or unsubstituted arylene with 6-30 carbon atoms, or a substituted or unsubstituted heteroarylene with 1-30 carbon atoms;

$Ar_1$ and $Ar_2$ are the same or different, and independently selected from: a substituted or unsubstituted alkyl with 1-20 carbon atoms, a substituted or unsubstituted cycloalkyl with 3-20 carbon atoms, a substituted or unsubstituted aryl with 6-30 carbon atoms or a substituted or unsubstituted heteroaryl with 1-30 carbon atoms, and neither the $Ar_1$ nor the $Ar_2$ is 9,9-diphenylfluorene;

$R_1$ and $R_2$ are independently selected from deuterium, halogen group, cyano, heteroaryl with 3~20 carbon atoms, aryl with 6~20 carbon atoms, trialkylsilyl with 3~12 carbon atoms, arylsilyl with 8~12 carbon atoms, alkyl with 1~10 carbon atoms, haloalkyl with 1~10 carbon atoms, alkenyl with 2~6 carbon atoms, alkynyl with 2~6 carbon atoms, cycloalkyl with 3~20 carbon atoms, heterocyclic alkyl with 2~10 carbon atoms, cycloalkenyl with 5~10 carbon atoms, heterocyclic alkenyl with 4~10 carbon atoms, alkoxyl with 1~10 carbon atoms, alkylthio with 1~10 carbon atoms, aryloxy with 6~18 carbon atoms, arylthio with 6~18 carbon atoms or triarylsilyl with 18~24 carbon atoms;

a is selected from 0, 1, 2, 3 or 4; when a is greater than 1, any two $R_1$ are the same or different;

b is selected from 0, 1, 2 or 3; when b is greater than 1, any two $R_2$ are the same or different;

the substituents of the $Ar_1$, $Ar_2$ and L are independently selected from deuterium, halogen group, cyano, heteroaryl with 3~20 carbon atoms, aryl with 6~20 carbon atoms which can be substituted with 0, 1, 2, 3, 4 or 5 substituents independently selected from deuterium, fluorine, chlorine, cyano, methyl and tertiary butyl, alkyl with 1~10 carbon atoms, haloalkyl with 1~10 carbon atoms, alkenyl with 2~6 carbon atoms, alkynyl with 2~6 carbon atoms, cycloalkyl with 3~10 carbon atoms, heterocyclic alkyl with 2~10 carbon atoms, cycloalkenyl with 5~10 carbon atoms, heterocyclic alkenyl with 4~10 carbon atoms, alkoxyl with 1~10 carbon atoms, alkylthio with 1~10 carbon atoms, aryloxy with 6~18 carbon atoms, arylthio with 6~18 carbon atoms or phosphinoxy with 6~18 carbon atoms.

According to a second aspect of the present application, there is provided electronic elements, including a cathode and an anode oppositely disposed, and a functional layer disposed between the anode and the cathode; the functional layer contains the above nitrogen-containing compounds.

According to a third aspect of the present application, there is provided electronic devices, comprising the above electronic elements.

The nitrogen-containing compounds provided by the present application, a bicycloalkyl structure at the 9th position of a fluorene ring, and the electron density of the fluorene ring and a whole conjugated system is improved through a hyperconjugation effect, which can enhance the hole conductivity and electron tolerance of the nitrogen-containing compounds, it can improve the luminescence efficiency and lifetime of the organic electroluminescent devices, and improve the lifetime of the photoelectric conversion devices, that is, improve the lifetime of the electronic elements used for photoelectric conversion or electrooptic conversion. Moreover, the nitrogen-containing compounds of the present application introduce a bulky sterically hindered groups between branches of triarylamine which is originally a near plane structure, rather than branch ends of triarylamine, so that the bond angle and conjugated degree between amine and each aryl can be regulated more finely, therefore the HOMO (highest occupied molecular orbital) value of the nitrogen-containing compounds can be adjusted more effectively, and the HOMO value of the nitrogen-containing compounds can be reduced effectively to improve the degree of coordination with adjacent materials in the organic electroluminescent devices, and the driving voltage of the organic electroluminescent devices is reduced, and the open circuit voltage of the photoelectric conversion device is increased. In addition, norborneol group introduced on the fluorene ring of the nitrogen-containing compounds in the present application is dicyclic hydrocarbyl group, with a relatively small rotation motion, vibration motion and the like for the group, so that the heat resistance of the nitrogen-containing compounds can be improved, and energy losses brought by the molecular motion of the nitrogen-containing compounds can be reduced. Moreover, the nitrogen-containing compounds of the application reduce the molecular symmetry, improve the glass transition temperature, reduce the deposition temperature and lower the crystallinity. Therefore, the nitrogen-containing compounds can show better physical and thermal stability when used to prepare the organic electroluminescent devices.

Norborneol spirofluorenyl is selected as a parent nucleu for the compounds of the present application; the compounds with this parent nucleus have a lower molecular weight, a smaller intermolecular force and a lower deposition temperature than those of compounds with an adamantane spirofluorenyl group as a parent nucleus when other substituents are the same; the compounds are less liable to decompose and show more excellent thermostability during device preparation, so the devices have a longer lifetime.

BRIEF DESCRIPTION OF THE DRAWINGS

The above-mentioned and other characteristics and advantages of the present application will become more apparent by describing the example embodiments in detail in combination with the drawings.

Figure 1:
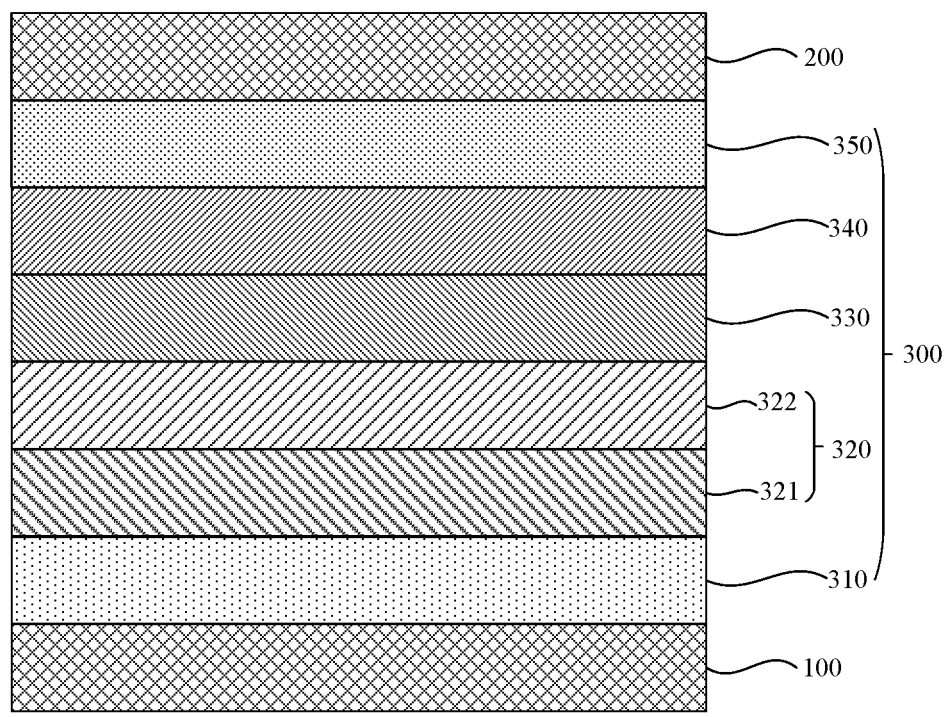
FIG. 1 illustrates a structural view of an organic electroluminescent device in accordance with the embodiment of the present application.

The reference numerals of main elements in the drawings are described as follows:

100. anode; 200. cathode; 300. functional layer; 310. hole injection layer; 320. hole transport layer; 321. first hole transport layer; 322. second hole transport layer; 330. organic light-emitting layer; 340. electron transport layer; 350. electron injection layer; 360. photoelectric conversion layer; 400. first electronic device; 500. second electronic device.

DETAILED DESCRIPTION OF THE EMBODIMENTS

The example embodiments are now described more thoroughly in combination with the drawings. However, the example embodiments can be implemented in multiple forms and shall not be construed as limitations to the examples set forth herein; on the contrary, these embodiments are provided to make the present application more comprehensive and complete, and fully convey the concept of the example embodiments to those skilled in the art. The described characteristics, structures or features may be integrated into one or more embodiments in any suitable manner. In the following description, many specific details are provided to give a full understanding of the embodiments of the present application.

There is provided a nitrogen-containing compound, having a structure represented by formula I-A:

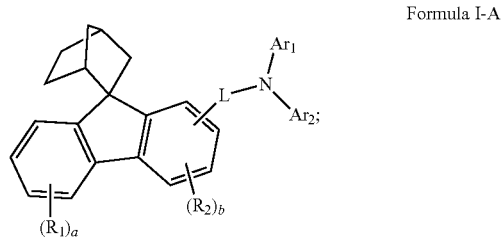

Formula I-A wherein L is selected from a single bond, a substituted or unsubstituted arylene with 6~30 carbon atoms, or a substituted or unsubstituted heteroarylene with 1-30 carbon atoms;

$Ar_1$ and $Ar_2$ are the same or different, and independently selected from: a substituted or unsubstituted alkyl with 1-20 carbon atoms, a substituted or unsubstituted cycloalkyl with 3-20 carbon atoms, a substituted or unsubstituted aryl with 6-30 carbon atoms or a substituted or unsubstituted heteroaryl with 1-30 carbon atoms, and neither the $Ar_1$ nor the $Ar_2$ is 9,9-diphenylfluorene;

$R_1$ and $R_2$ are independently selected from deuterium, halogen group, cyano, heteroaryl with 3~20 carbon atoms, aryl with 6~20 carbon atoms, trialkylsilyl with 3~12 carbon atoms, arylsilyl with 8~12 carbon atoms, alkyl with 1~10 carbon atoms, haloalkyl with 1~10 carbon atoms, alkenyl with 2~6 carbon atoms, alkynyl with 2~6 carbon atoms, cycloalkyl with 3~20 carbon atoms, heterocyclic alkyl with 2~10 carbon atoms, cycloalkenyl with 5~10 carbon atoms, heterocyclic alkenyl with 4~10 carbon atoms, alkoxyl with 1~10 carbon atoms, alkylthio with 1~10 carbon atoms, aryloxy with 6~18 carbon atoms, arylthio with 6~18 carbon atoms or triarylsilyl with 18~24 carbon atoms;

a is selected from 0, 1, 2, 3 or 4; when a is greater than 1, any two $R_1$ are the same or different;

b is selected from 0, 1, 2 or 3; when b is greater than 1, any two $R_2$ are the same or different;

the substituents of the $Ar_1$, $Ar_2$ and L are independently selected from deuterium, halogen group, cyano, heteroaryl with 3~20 carbon atoms, aryl with 6~20 carbon atoms which can be substituted with 0, 1, 2, 3, 4 or 5 substituents independently selected from deuterium, fluorine, chlorine, cyano, methyl and tertiary butyl, alkyl with 1~10 carbon atoms, haloalkyl with 1~10 carbon atoms, alkenyl with 2~6 carbon atoms, alkynyl with 2~6 carbon atoms, cycloalkyl with 3~10 carbon atoms, heterocyclic alkyl with 2~10 carbon atoms, cycloalkenyl with 5~10 carbon atoms, heterocyclic alkenyl with 4~10 carbon atoms, alkoxyl with 1~10 carbon atoms, alkylthio with 1~10 carbon atoms, aryloxy with 6~18 carbon atoms, arylthio with 6~18 carbon atoms or phosphinoxy with 6~18 carbon atoms.

In the present disclosure, aryl with 6~20 carbon atoms which can be substituted with 0, 1, 2, 3, 4 or 5 substituents independently selected from deuterium, fluorine, chlorine, cyano, methyl and tertiary butyl" means that the aryl may be substituted by one or more of deuterium, fluorine, chlorine, cyano, methyl and tertiary butyl, or may not be substituted by deuterium, fluorine, chlorine, cyano, methyl and tertiary butyl; when the number of substituents on the aryl is greater than or equal to 2, the substituents may be the same or different.

In the present disclosure, norborneol can present different shapes due to different drawing angles in a compound structure view because norborneol is of a three-dimensional structure.

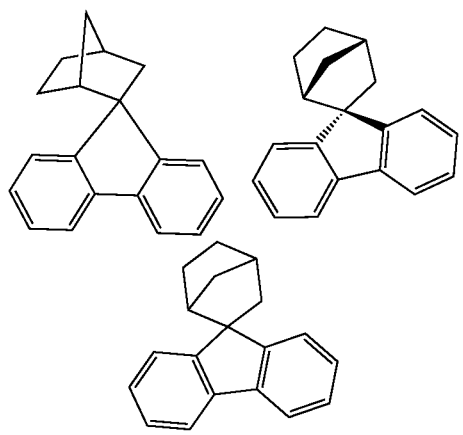

are of the same structure in the present application.

The nitrogen-containing compounds of the present application can be applied in organic electroluminescent devices and photoelectric conversion devices as a transport hole material as they have a good hole transport efficiency. For example, the nitrogen-containing compounds of the present application can be applied between the anode and the organic electroluminescent layer of an organic electroluminescent device in order to transport holes on the anode to the organic electroluminescent layer. Optionally, the nitrogen-containing compounds of the present application can be applied to one or more of the hole injection layer, hole transport layer and electron blocking layer of an organic electroluminescent device. In another example, the nitrogen-containing compounds of the present application can be applied between the anode and the photoelectric conversion layer of a photoelectric conversion device in order to transport holes on the photoelectric conversion layer to the anode.

In the present disclosure, as a way of description in use, "each . . . is independently" is interchangeable with " . . . are separately and independently" and " . . . is independently selected from", all of which shall be understood in a broad sense; it can mean that the specific options expressed between the same symbols in different groups do not affect each other, and can also indicate that the specific options expressed between the same symbols in the same group do not affect each other. For example, "

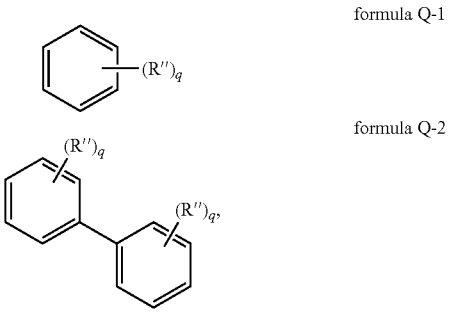

wherein each q is independently 0, 1, 2 or 3, and each R" is independently selected from hydrogen, deuterium, fluorine and chlorine", means that: formula Q-1 indicates that there are q substituents R" on a benzene ring, R"s may be the same or different, and the options of R"s do not affect each other; formula Q-2 indicates that there are q substituents R" on each benzene ring of biphenyl, the number q of R" substituents on the two benzene rings may be the same or different, R"s may be the same or different, and the options of R"s do not affect each other.

In one embodiment of the present disclosure, the nitrogen-containing compounds are selected from a structure represented by formula I:

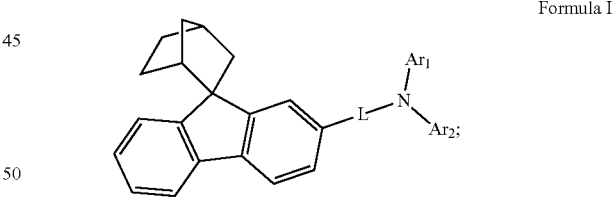

wherein L is selected from a single bond, a substituted or unsubstituted arylene with 6-30 carbon atoms, or a substituted or unsubstituted heteroarylene with 1-30 carbon atoms;

$Ar_1$ and $Ar_2$ are the same or different, and are independently selected from: a substituted or unsubstituted aryl with 6-20 carbon atoms, or a substituted or unsubstituted heteroaryl with 1-20 carbon atoms;

The substituents of the $Ar_1$, $Ar_2$ and L are the same or different, and are independently selected from deuterium, cyano, nitryl, halogen group, hydroxyl, alkyl with 1-20 carbon atoms, cycloalkyl with 3-20 carbon atoms, alkenyl with 2-20 carbon atoms, alkynyl with 2-24 carbon atoms, heterocyclic alkyl with 2-20 carbon atoms, alkoxy with 1-33 carbon atoms, alkylthio with 1-33 carbon atoms or arylsilyl with 6-33 carbon atoms.

In one embodiment of the present disclosure, the nitrogen-containing compound is selected from the compounds represented by the following formula:

Formula II

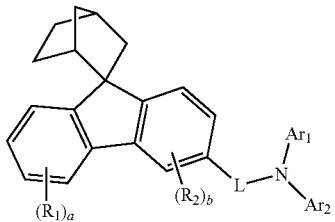

Formula III

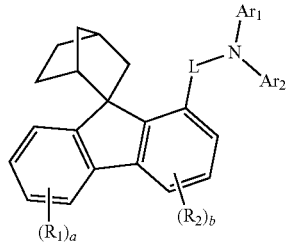

Formula IV

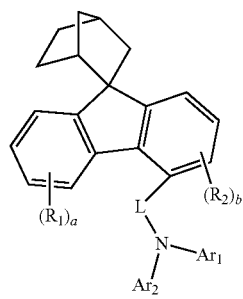

In the present disclosure, the number of carbon atoms of L, $Ar_1$ and $Ar_2$ refers to the number of all carbon atoms of L, $Ar_1$ and $Ar_2$. For example, if L is selected from substituted arylene with 12 carbon atoms, the number of all carbon atoms of the arylene and its substituent thereon is 12. For example: $Ar_1$ is

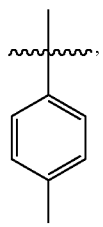

and the number of carbon atoms is 7; L is

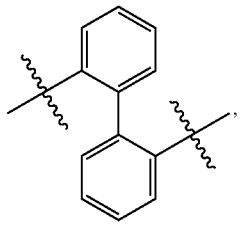 [SMILES: *c1ccccc1-c1ccccc1*]

and the number of carbon atoms is 12.

In the present disclosure, when no specific definition is additionally provided otherwise, "hetero" means that one functional group contains 1 to 3 heteroatoms selected from a group consisting of B, N, O, S, Si, Se and P, and the remaining atoms are carbon and hydrogen.

In the present disclosure, "alkyl" or "alkyl group" means a saturated linear or branched monovalent hydrocarbyl group containing 1 to 20 carbon atoms, wherein the alkyl group can be optionally substituted by one or more substituents described herein. Unless otherwise specified, the alkyl group contains 1-20 carbon atoms. Examples of the alkyl group include, but are not limited to, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tertiary butyl (t-Bu, —$C(CH_3)_3$) and the like. The alkyl may have 1 to 10 carbon atoms. And a numerical range such as "1 to 20" refers to integers in a given range in the present application; for example, "1 to 10 carbon atoms" refers to the alkyl that can contain 1 carbon atom, 2 carbon atoms, 3 carbon atoms, 4 carbon atoms, 5 carbon atoms, 6 carbon atoms, 7 carbon atoms, 8 carbon atoms, 9 carbon atoms or 10 carbon atoms. The alkyl may also be lower alkyl with 1 to 6 carbon atoms. In addition, the alkyl may be a substituted or unsubstituted. Unsubstituted alkyl may be a "saturated alkyl group" without any double or triple bond.

Optionally, the alkyl is selected from alkyl with 1-6 carbon atoms, and specific examples include, but are not limited to, methyl, ethyl, n-propyl, isopropyl, n-butyl, isobutyl, sec-butyl, tertiary butyl, amyl or hexyl.

In the present disclosure, the aryl refers to an optional functional group or substituent derived from an aromatic hydrocarbon ring. The aryl may be a monocyclic aryl or a polycyclic aryl, in other words, the aryl may be a monocyclic aryl, or a fused ring aryl group, a polycyclic aryl, which is formed by two or more monocyclic aryls conjugatedly connected through carbon-carbon bonds, formed by a monocyclic aryl and a fused ring aryl conjugatedly connected by a carbon-carbon bond, or formed by two or more fused ring aryl groups conjugatedly connected by a carbon-carbon bond. That is, two or more aryl groups conjugatedly connected through carbon-carbon bonds can also be regarded as the aryl groups in the present application. Wherein the aryl does not contain heteroatoms such as B, N, O, S or P. For example, biphenyl, triphenyl, and the like aryl in the present application. Examples of aryl groups may include, but are not limited thereto, phenyl, naphthyl, fluorenyl, anthracyl, phenanthryl, biphenyl, triphenyl, benzo [9,10] phenanthryl, pyrenyl, dimethyl fluorenyl and the like. The "aryl" of the present application may contain 6-30 carbon atoms, in some embodiments, the number of carbon atoms in the aryl may be 6-25, in other embodiments, the number of carbon atoms in the aryl may be 6-18, and in other embodiments, the number of carbon atoms in the aryl may be 6-13. For example, the number of carbon atoms may be 6, 12, 13, 14, 15, 18, 20, 25 or 30. Of course, the number of carbon atoms can also be other numbers, which will not be listed one by one here.

In the present disclosure, substituted aryl refers to one or more hydrogen atoms in the aryl group are substituted by other groups. For example, at least one hydrogen atom is substituted by a deuterium atom, F, Cl, I, CN, hydroxyl, nitro, branched alkyl, linear alkyl, cycloalkyl, alkoxyaryl, heteroaryl or other groups. It should be understood that the substitutedaryl with 18 carbon atoms means that the total number of carbon atoms of the aryl and the substituents on the aryl is 18. For example, the number of carbon atoms of 9,9-diphenylfluorene is 25. Specific examples of the substituted aryl include, but are not limited to: phenyl substituted phenanthryl, phenanthryl substituted phenyl, phenyl substituted naphthyl, naphthyl substituted phenyl, phenyl substituted biphenyl, phenyl substituted dimethylfluorenyl, dimethylfluorenyl substituted phenyl, dibenzothiophenyl substituted phenyl, dibenzofuranyl substituted phenyl, N-phenylcarbazolyl substituted phenyl, carbazolyl substituted phenyl and the like, and phenanthrolinyl substituted phenyl.

In the present disclosure, specific examples of aryl as a substituent include, but are not limited to: phenyl, naphthyl, biphenyl, triphenyl, anthracyl, phenanthryl or dimethylfluorenyl.

In the present disclosure, the fluorenyl may be substituted, and the two substitutes of fluorenyl group can be combined with each other to form a spiral structure, and specific examples include, but are not limited to, the following structure:

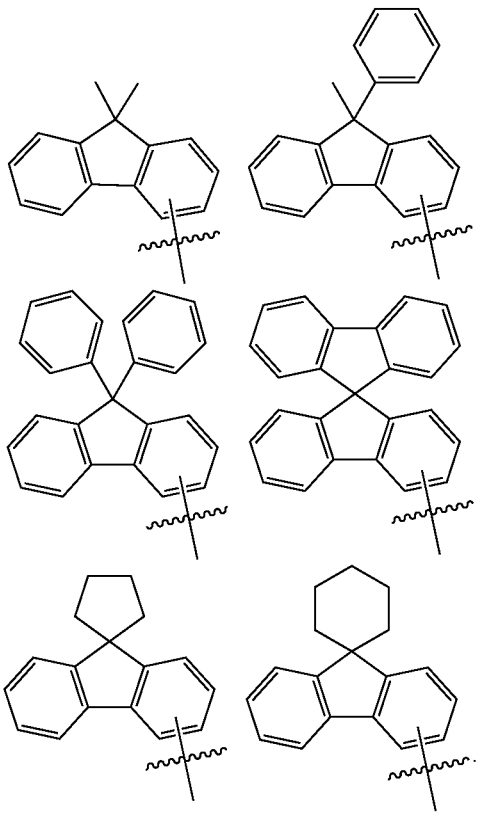

In the present disclosure, particularly, Ar₁ is not

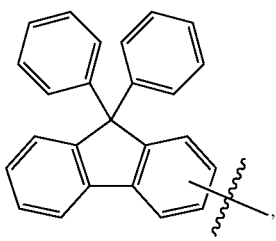

and Ar₂ is not

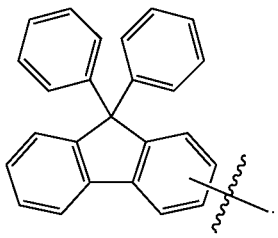

In the present disclosure, the "heteroaryl" refers to a heteroaryl group including at least one of B, O, N, P, Si, Se and S as a hetero atom. The heteroaryl may be monocyclic or polycyclic heteroaryl. In other words, the heteroaryl group may be a single aromatic ring system or a polycyclic ring system formed by more aromatic rings conjugatedly connected through a carbon-carbon bond where any aromatic ring is an aromatic monocyclic ring or an aromatic fused ring. Exemplarily, the heteroaryl may include, but is not limited to, thienyl, furyl, pyrrolyl, imidazolyl, thiazolyl, oxazolyl, oxadiazole, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridopyrimidyl, pyridopyrazinyl, pyrazinopyrazinyl, isoquinolinyl, indolyl, carbazolyl, N-arylcarbazolyl (e.g., N-phenylcarbazolyl), N-heteroarylcarbazolyl, N-alkylcarbazolyl, benzoxazolyl, benzimidazolyl, benzothiazolyl, benzocarbazolyl, benzothiophenyl, dibenzothiophenyl, thienothiophenyl, benzofuranyl, phenanthrolinyl, isoxazolyl, thiadiazolyl, benzothiazolyl, phenothiazinyl, dibenzofuranyl, phenyl substituted dibenzofuranyl, phenyl substituted dibenzothiophenyl, N-phenylcarbazolyl and the like. Wherein thienyl, furyl, phenanthrolinyl and the like are heteroaryls of a single aromatic ring system, and N-arylcarbazolyl, N-heteroarylcarbazolyl, phenyl substituted dibenzofuranyl and other heteroaryl groups of a plurality of aromatic ring systems conjugated by carbon-carbon bonds. The "heteroaryl" of the present application may contain 1-30 carbon atoms, in some embodiments, the number of carbon atoms in the heteroaryl may be 3-25, in other embodiments, the number of carbon atoms in the aryl may be 3-20, and in other embodiments, the number of carbon atoms in the aryl may be 12-20. For example, the number of carbon atoms may be 3, 4, 5, 7, 12, 13, 18, 20, 24, 25 or 30. Of course, the number of carbon atoms can also be other figures, which will not be listed one by one here.

In the present disclosure, specific examples of heteroaryl as a substituent include, but are not limited to: pyridyl, quinolinyl, quinazolinyl, dibenzofuranyl, dibenzothiophenyl, carbazolyl, N-phenylcarbazolyl and phenanthrolinyl.

In the present disclosure, the interpretation of aryl can be applied to arylene, and the interpretation of heteroaryl can also be applied to heteroarylene.

In the present disclosure, halogen groups include fluorine, chlorine, bromine and iodine.

In the present disclosure, the a and b are separately and independently selected from 0.

According to one embodiment, L is selected from a single bond, a substituted or unsubstituted arylene with 6-20 carbon atoms, and a substituted or unsubstituted heteroarylene with 3-20 carbon atoms.

Preferably, the L is selected from a single bond, a substituted or unsubstituted aryl with 6-18 carbon atoms, or a substituted or unsubstituted heteroarylene with 12-18 carbon atoms.

Optionally, the substituents of L include, but are not limited to, deuterium, halogen groups, cyano, alkyl with 1-5 carbon atoms, aryl with 6-20 carbon atoms, cycloalkyl with 3-10 carbon atoms, or heteroaryl with 3-12 carbon atoms.

Preferably, the substituents of L include, but are not limited to, deuterium, halogen groups, alkyl with 1-4 carbon atoms, and aryl with 6-12 carbon atoms. Specifically, the substituents of L include, but are not limited to, deuterium, fluorine, cyano, methyl, ethyl, n-propyl, isopropyl, tertiary butyl, phenyl, naphthyl, phenanthryl or biphenyl.

In one embodiment of the present disclosure, the L is selected from a single bond, a substituted or unsubstituted phenylene, a substituted or unsubstituted naphthylene, a substituted or unsubstituted biphenylene, a substituted or unsubstituted terphenylene, or a substituted or unsubstituted dimethylfluorene.

In one embodiment of the present disclosure, the L is selected from a single bond, a substituted or unsubstituted anthrylene, a substituted or unsubstituted phenanthrylene, a substituted or unsubstituted dibenzofurylene, a substituted or unsubstituted dibenzothienylidene, or a substituted or unsubstituted N-phenylcarbazolylidene.

Optionally, the L is selected from a single bond or the group consisting of the following groups: the L is selected from a single bond or a substituted or unsubstituted group W, and the unsubstituted W is selected from the group consisting of the following groups:

wherein

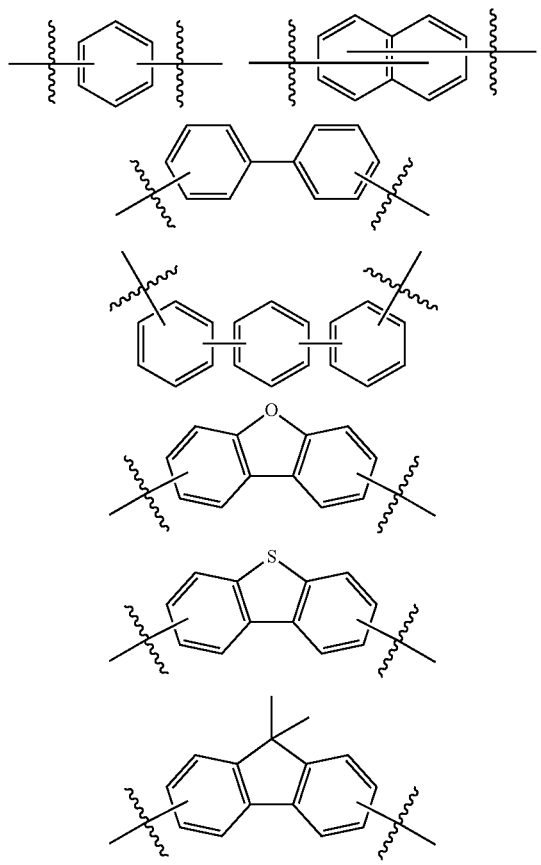

-continued

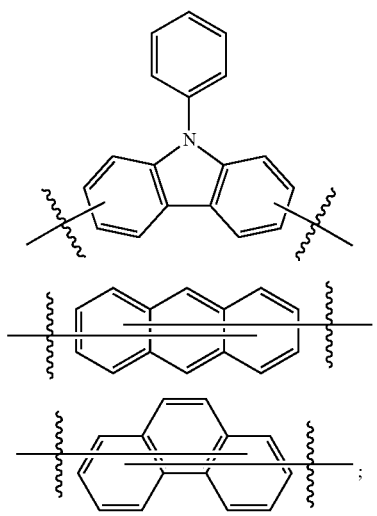

⁂ represents a chemical bond; there is one or more substituents on the group W, and the substituents are independently selected from: deuterium, cyano, halogen groups, methyl, ethyl, n-propyl, isopropyl, tertiary butyl, phenyl, naphthyl, phenanthryl or biphenyl; when the number of substituents of W is greater than 1, the substituents are the same or different.

Preferably, the L is selected from a single bond or from the group consisting of the following groups,

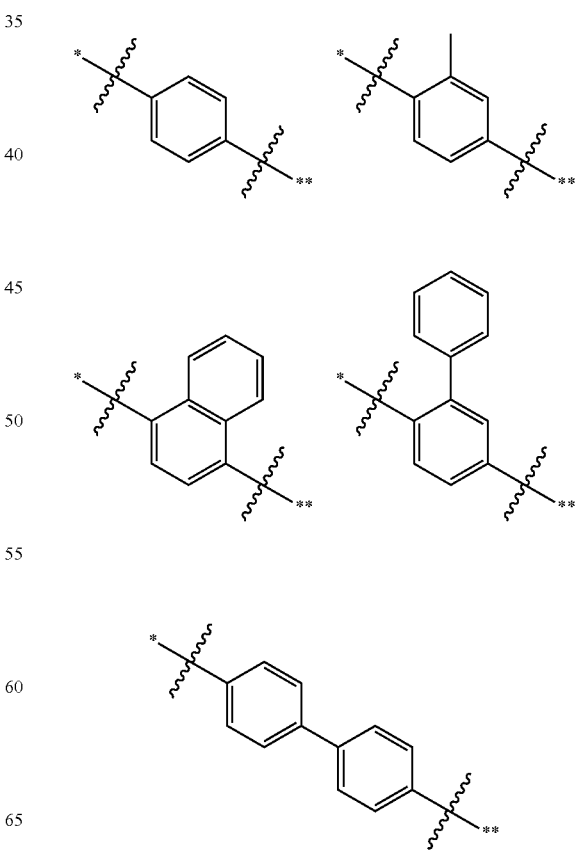

-continued
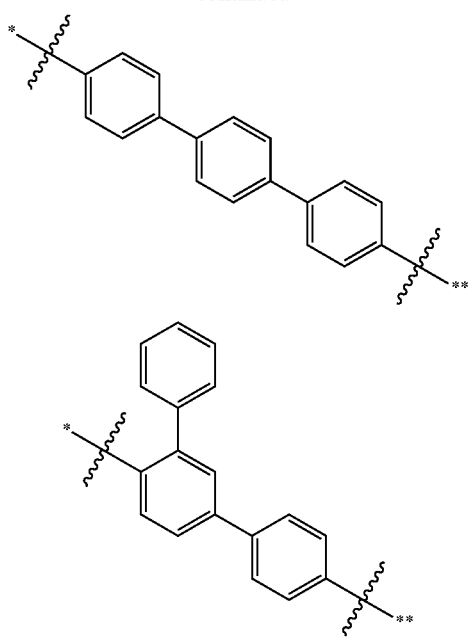
* is a linking point of the above groups connected to
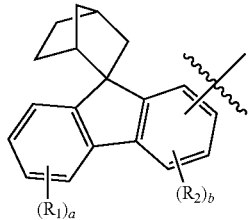
in formula I-A or
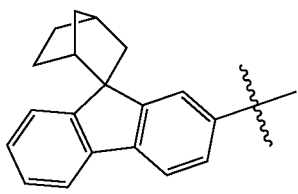 [SMILES: *c1ccc2c(c1)C1(CC3CCC1C3)c1ccccc1-2]
in formula I;
** is a linking point of the above groups connected to
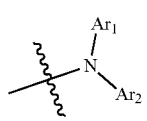
in formula I.
Optionally, the L is selected from a single bond or from the group consisting of the following groups,
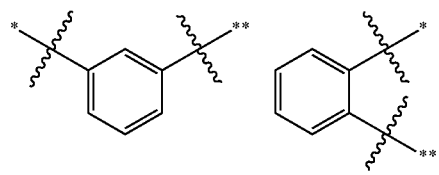
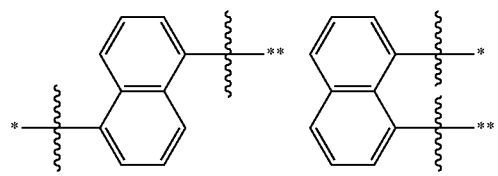
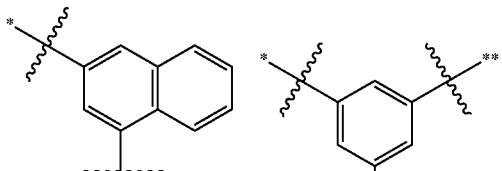
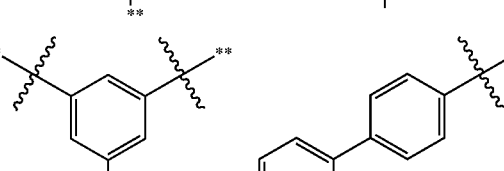
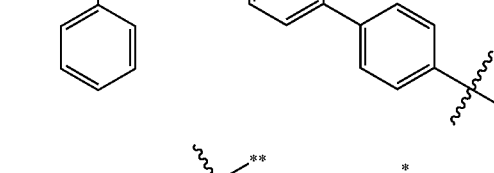
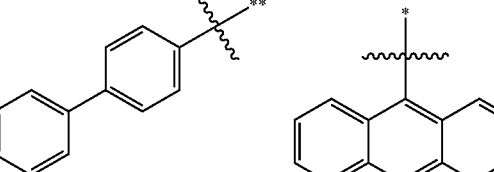
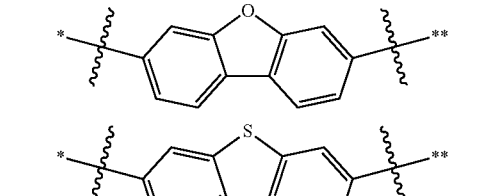
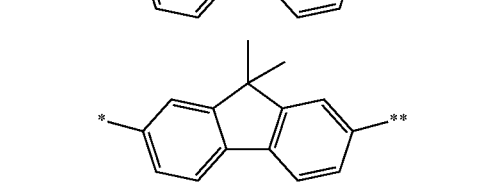

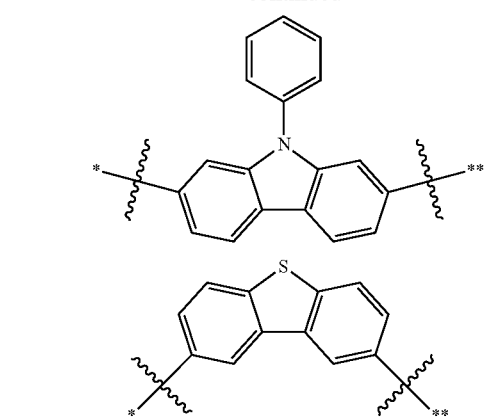
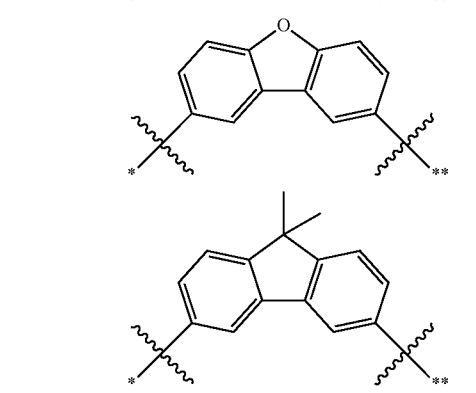
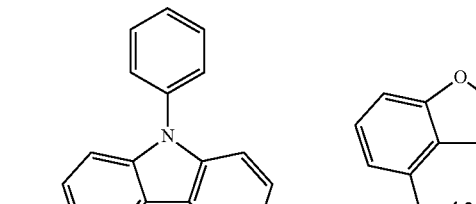
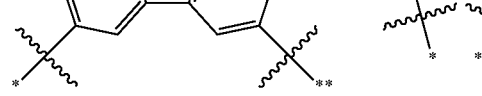
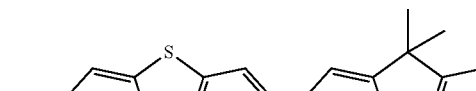
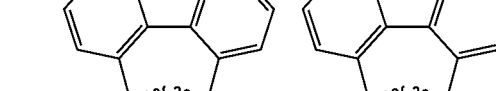

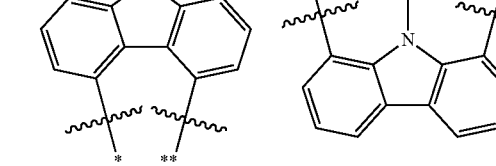
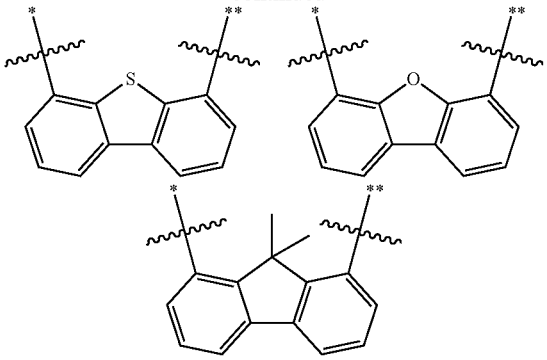
\* is a linking point of the above groups connected to
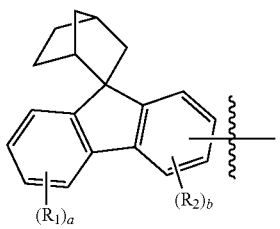
in formula I-A,
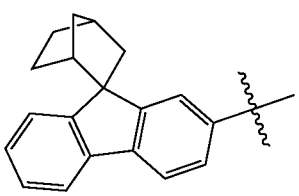
in formula I,
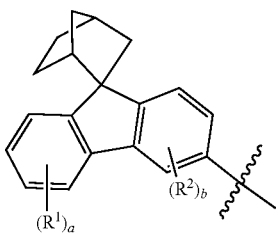
in formula II,
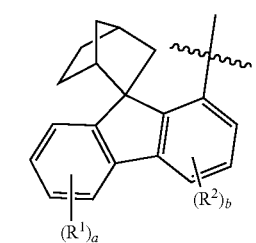

in formula III and

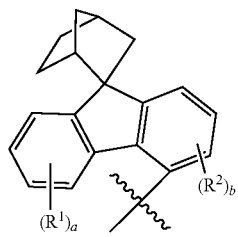

in formula IV;

** is a linking point of the above groups connected to

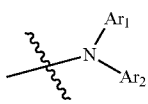

in formula I-A, formula I, formula II, formula III and formula IV.

In some embodiments of present disclosure, the $Ar_1$ and $Ar_2$ are the same or different, and are independently selected from a substituted or unsubstituted aryl with 6-24 carbon atoms, or a substituted or unsubstituted heteroaryl with 12-20 carbon atoms.

In some other embodiments of present disclosure, the $Ar_1$ and $Ar_2$ are the same or different, and are independently selected from: a substituted or unsubstituted aryl with 6-20 carbon atoms, or a substituted or unsubstituted heteroaryl with 1-20 carbon atoms.

Preferably, the $Ar_1$ and $Ar_2$ are the same or different, and are independently selected from a substituted or unsubstituted aryl with 6-18 carbon atoms, or a substituted or unsubstituted heteroaryl with 12-18 carbon atoms.

Optionally, the substituents of the $Ar_1$, $Ar_2$ and L are the same or different, and are independently selected from deuterium, fluorine, cyano, alkyl with 1-5 carbon atoms, cycloalkyl with 3-10 carbon atoms, aryl with 6-18 carbon atoms or heteroaryl with 3-18 carbon atoms.

Preferably, the substituents of $Ar_1$ and $Ar_2$ are the same or different, and are independently selected from deuterium, cyano, fluorine, substituted or unsubstituted aryl with 6-15 carbon atoms, heteroaryl with 12-18 carbon atoms, and alkyl with 1-4 carbon atoms. Specifically, the substituents of $Ar_1$ and $Ar_2$ include, but are not limited to: deuterium, fluorine, cyano, phenyl, naphthyl, phenanthryl, anthryl, biphenyl, dimethylfluorenyl, methyl, ethyl, n-propyl, isopropyl, tertiary butyl, pyridyl, quinolyl, pyrimidinyl, phenanthrolinyl, dibenzofuranyl, dibenzothiophenyl, N-phenylcarbazolyl, carbazolyl and the like.

In another embodiment of the present disclosure, the $Ar_1$ and $Ar_2$ are the same or different, and are independently selected from a substituted or unsubstituted group V, and the unsubstituted group V is selected from the group consisting of the following groups:

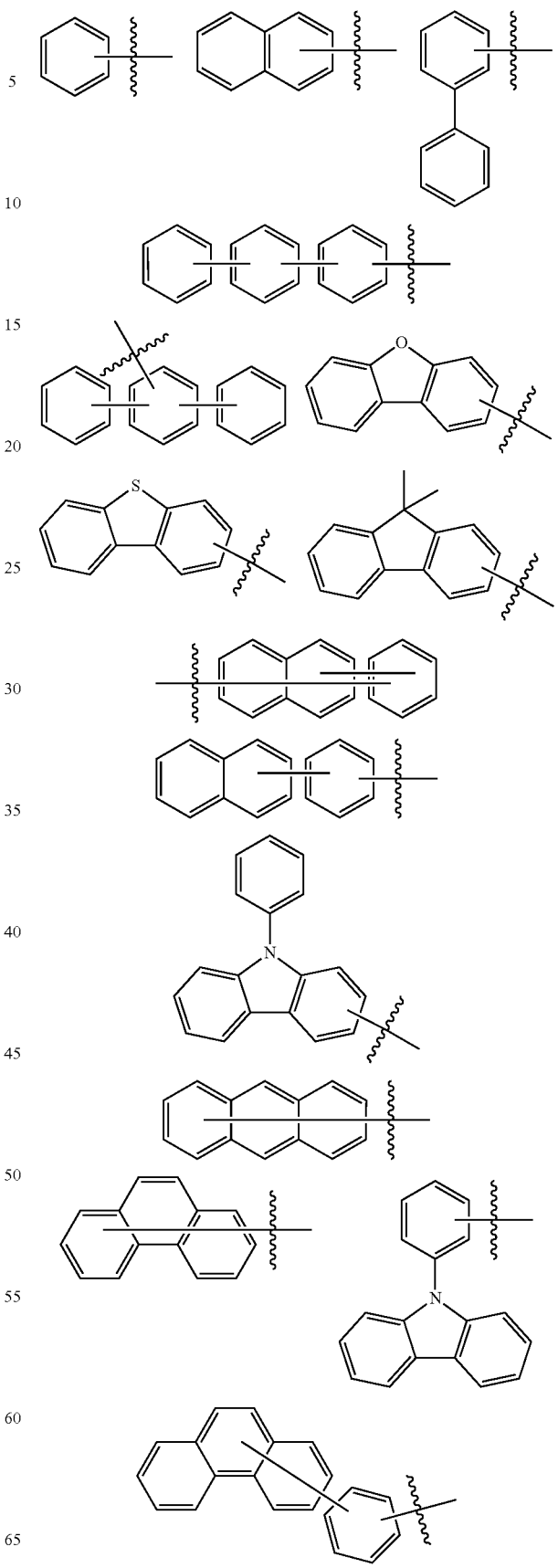

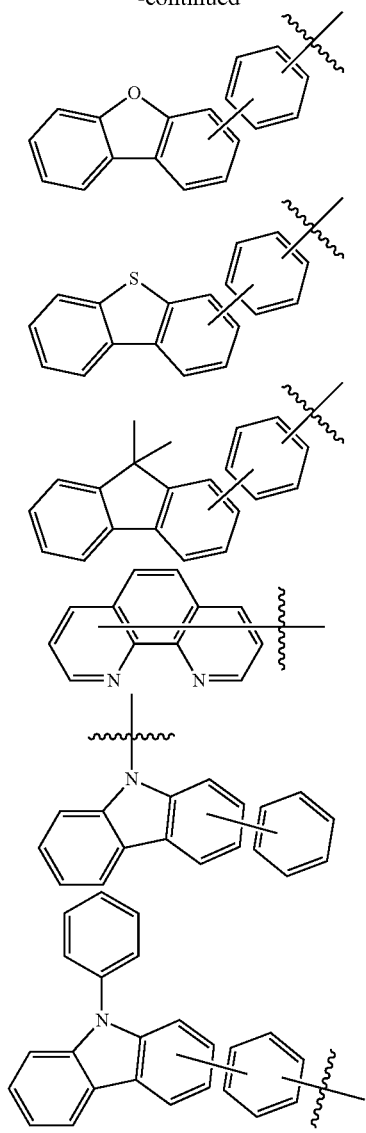

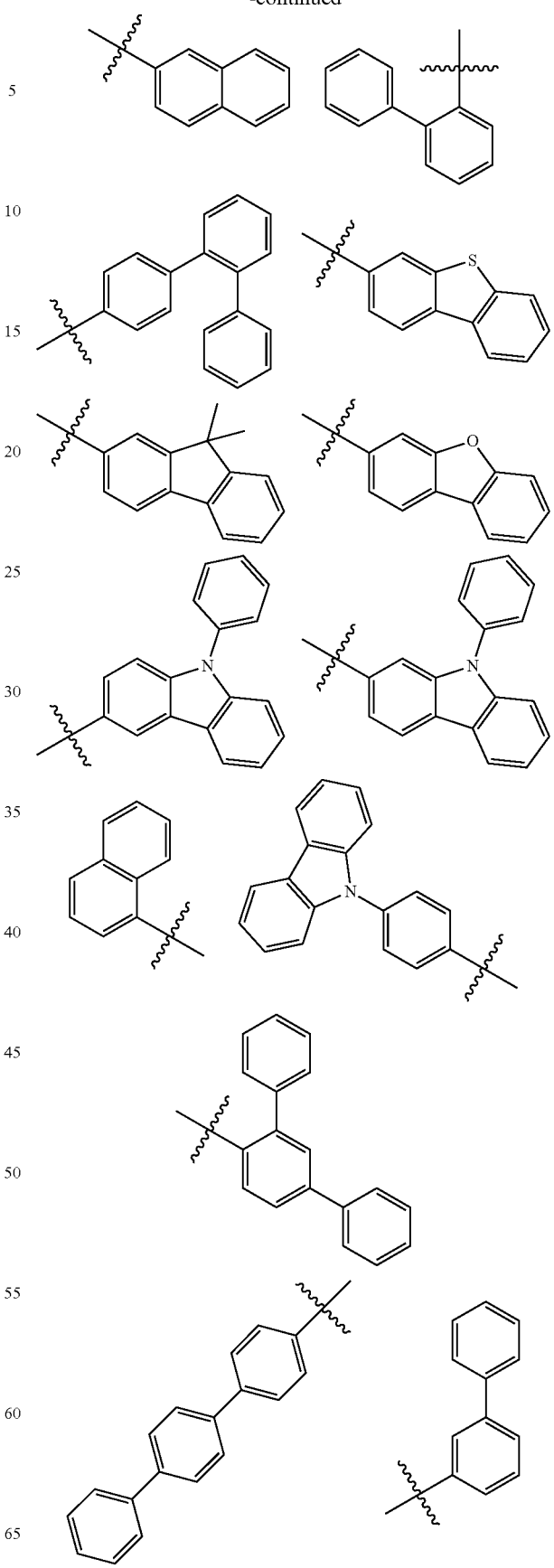

wherein ✦ represents a chemical bond; there is one or more substituents on the ✦ substituted V, and the substituents are respectively and independently selected from: deuterium, cyano, halogen groups, methyl, ethyl, n-propyl, isopropyl, tertiary butyl, phenyl, naphthyl, biphenyl or phenanthryl; when the number of substituents of V is greater than 1, the substituents are the same or different.

Optionally, the Ar$_1$ and Ar$_2$ are the same or different, and are independently selected from the group consisting of the following groups:

-continued
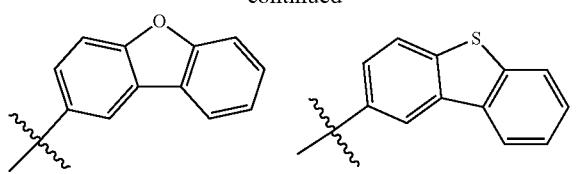
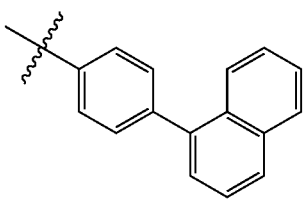
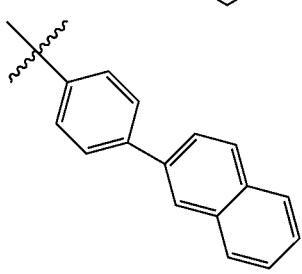
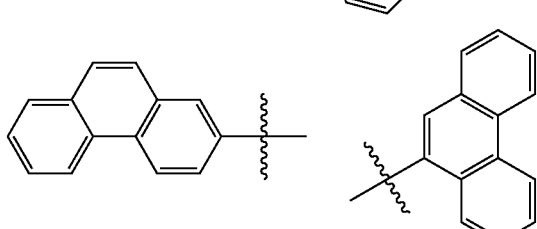
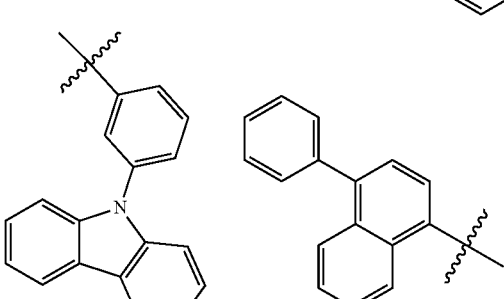
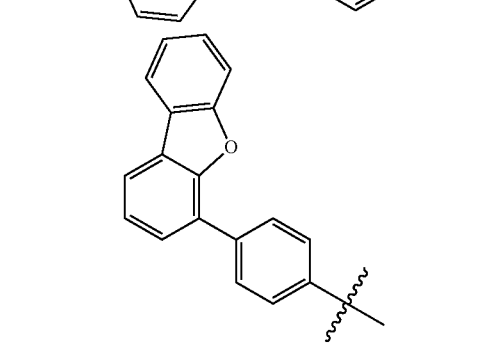
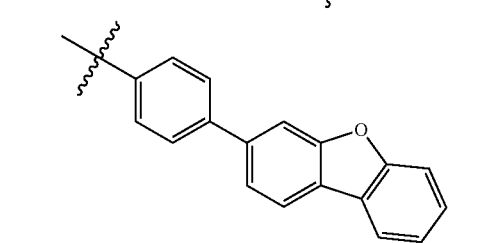
-continued
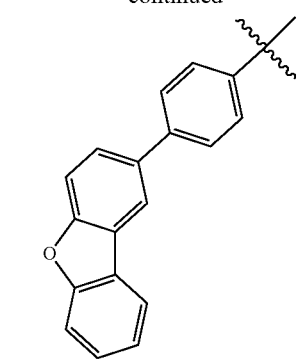
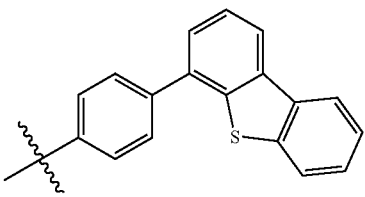
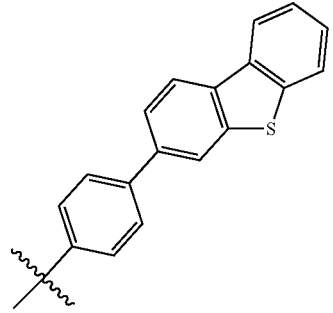
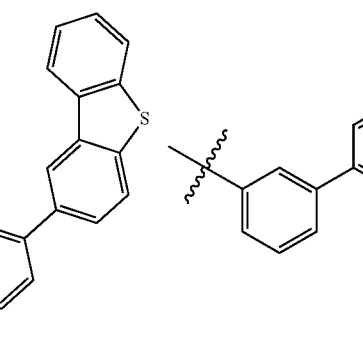
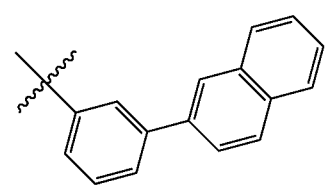
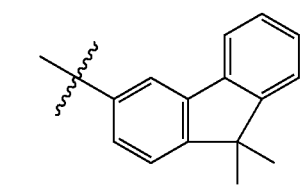

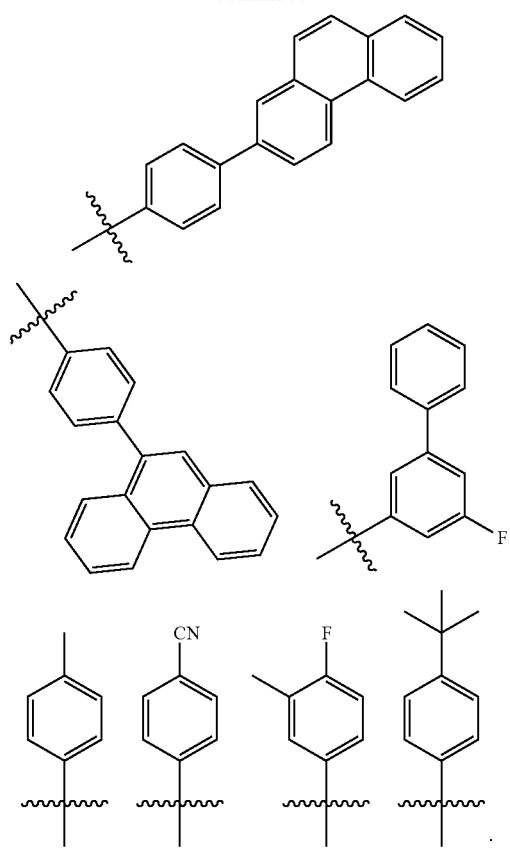
Optionally, the $Ar_1$ and $Ar_2$ are the same or different, and are independently selected from the group consisting of the following groups.
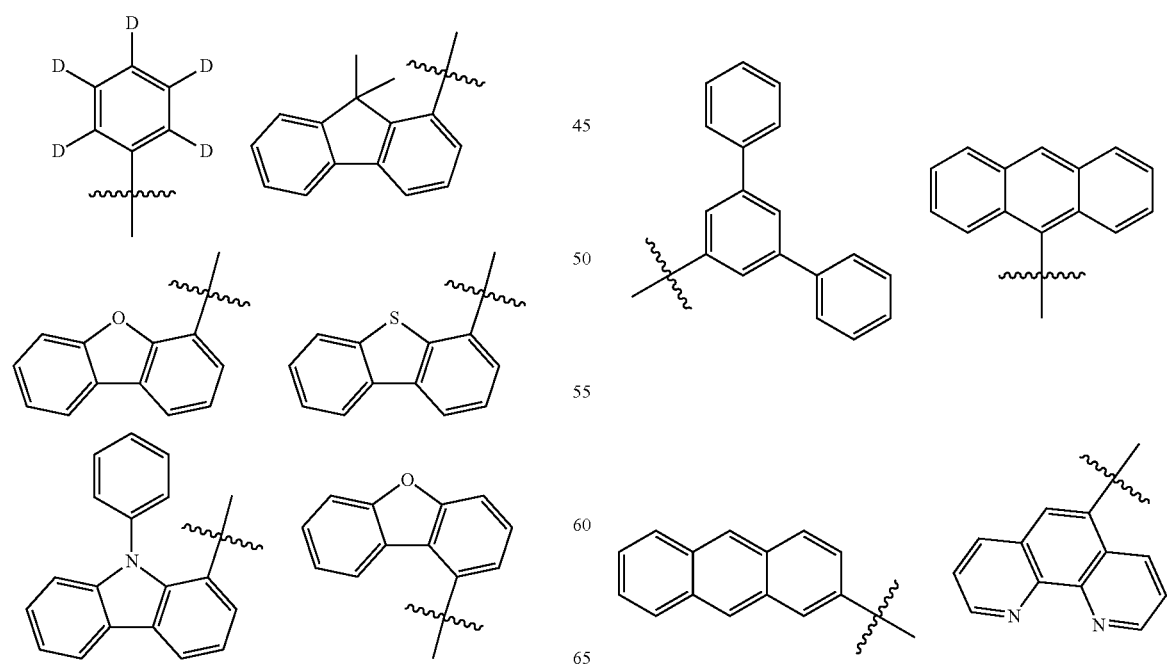
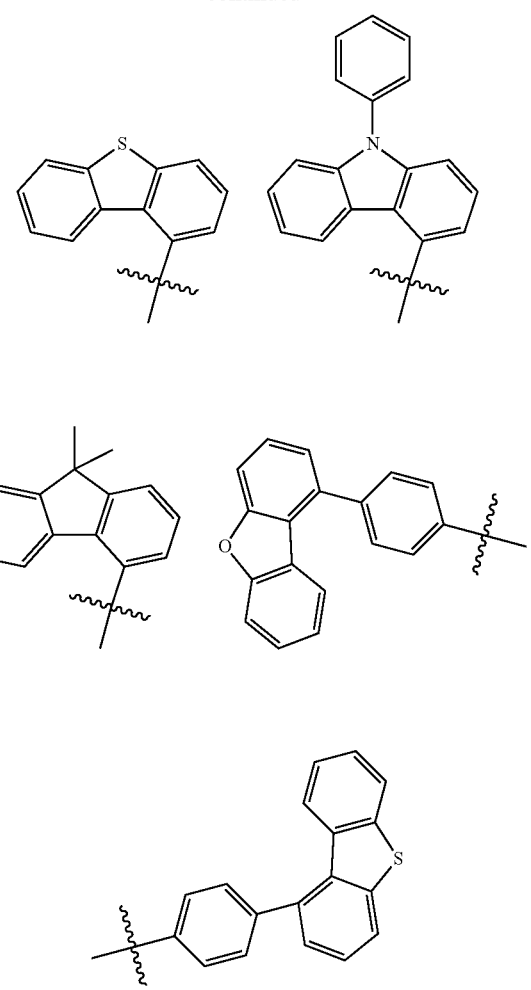

25
-continued
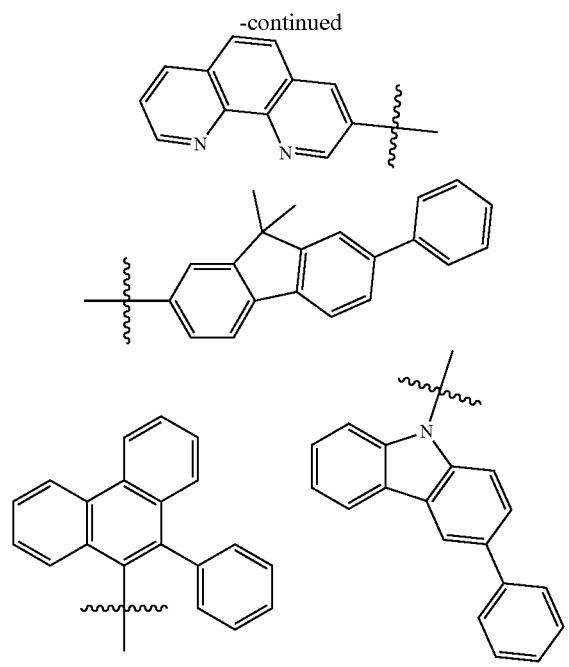
26
-continued
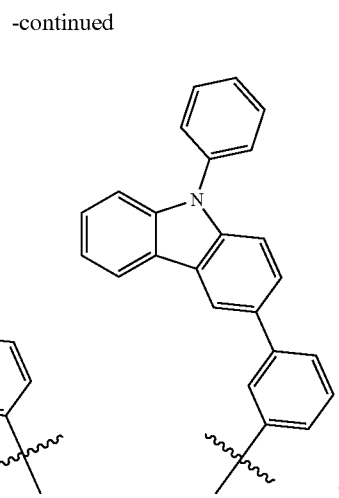
Optionally, the nitrogen-containing compound is selected from the group consisting of the following compounds:
1
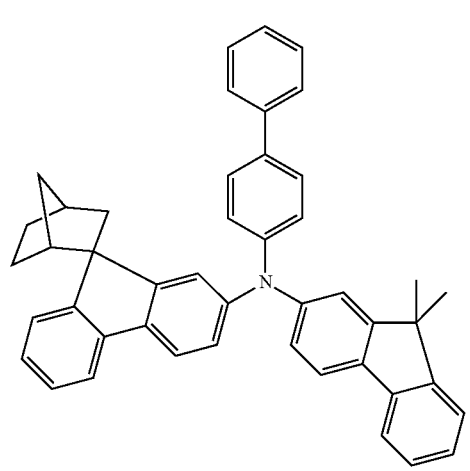
2
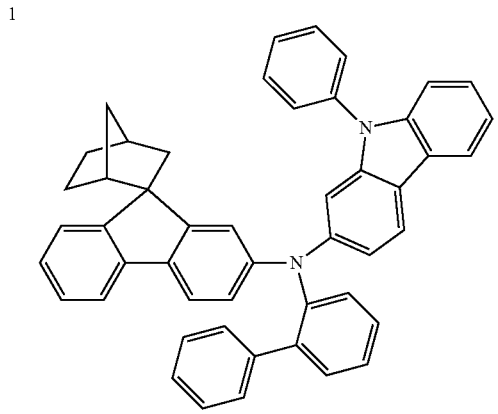
3
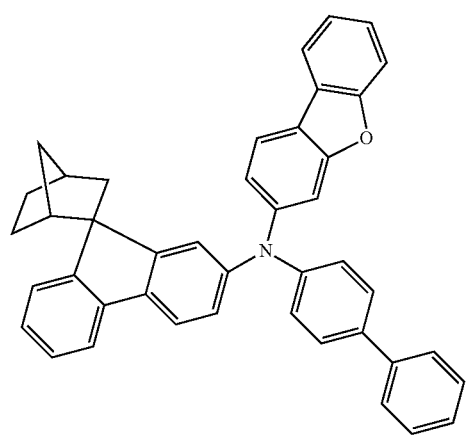
4
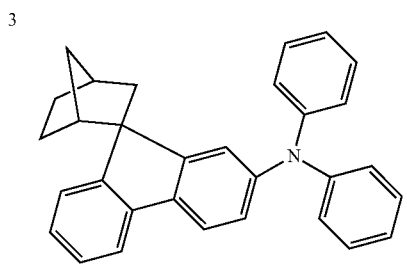

-continued
5
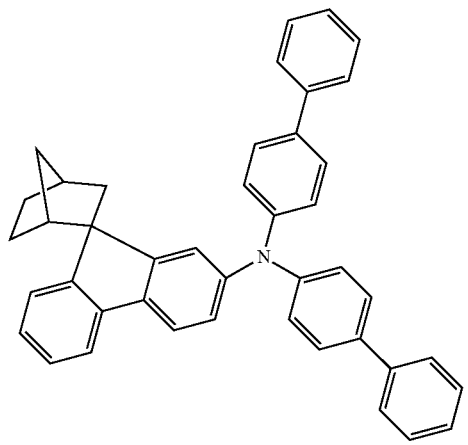
6
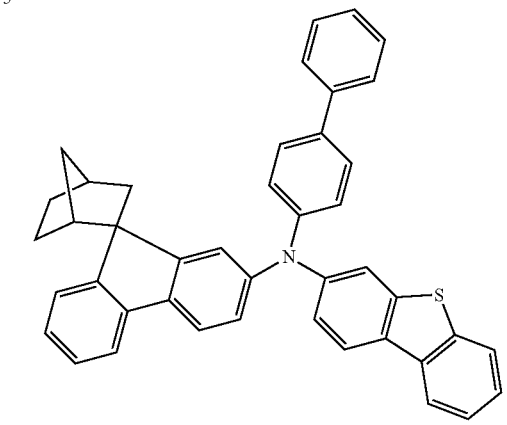
7
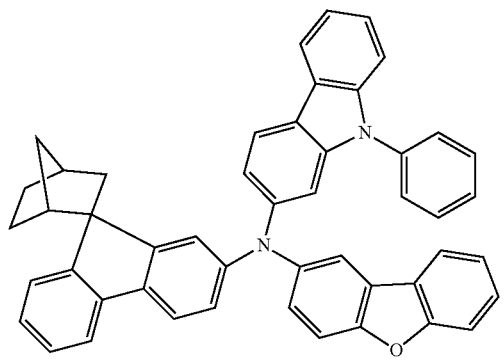
8
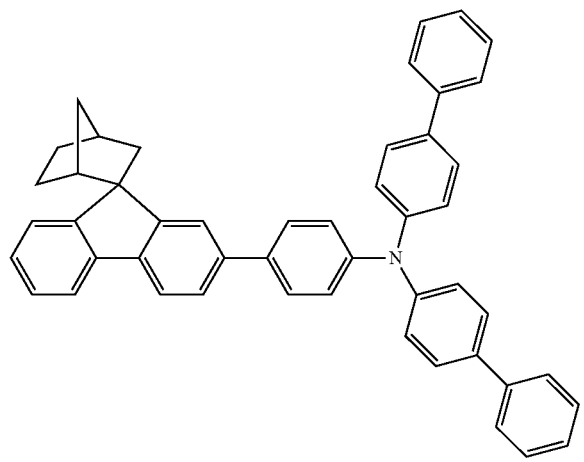
9
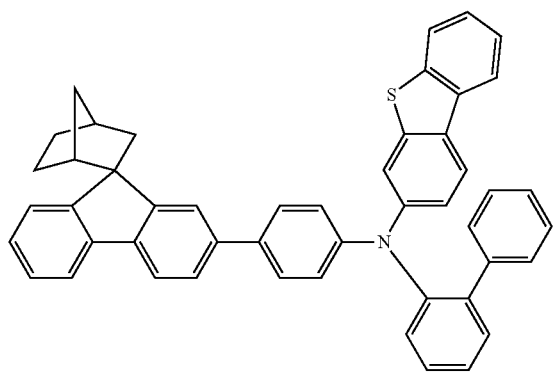
10
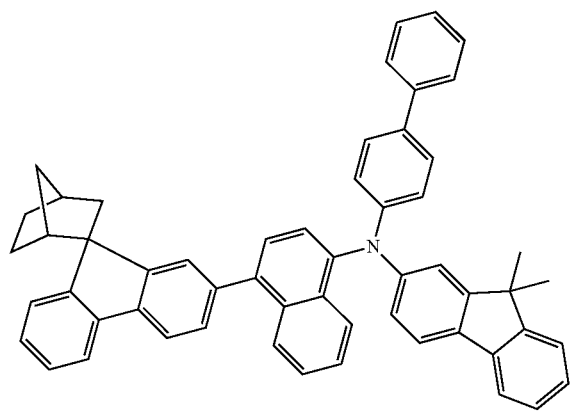

-continued
11
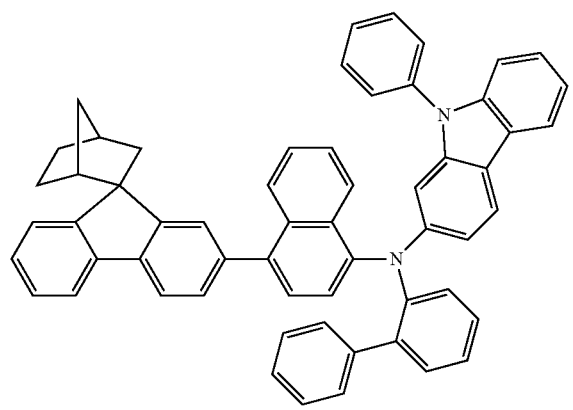
12
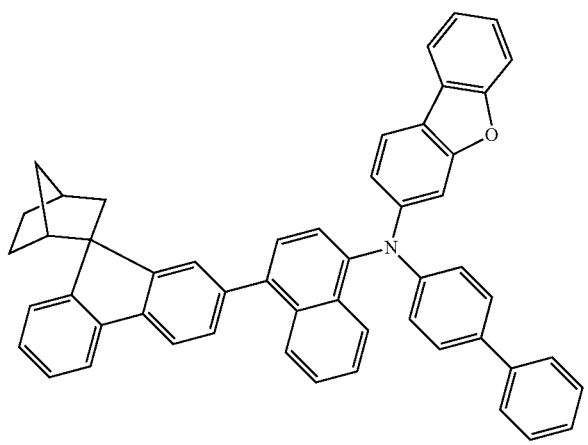
13
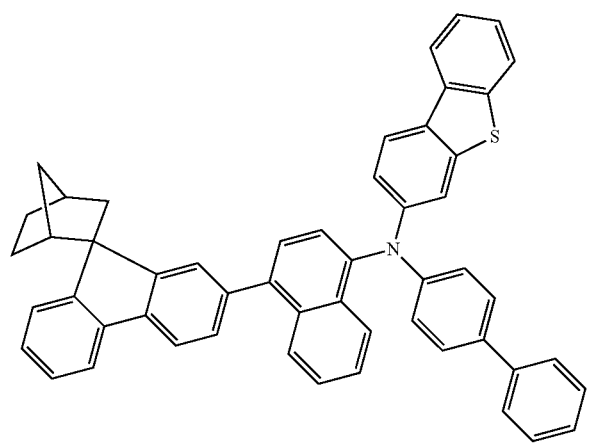
14
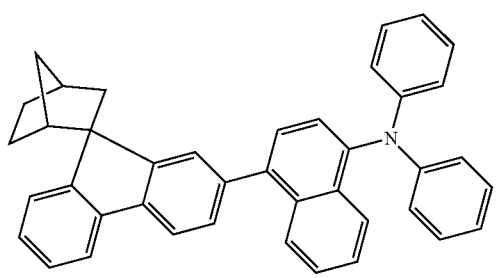
16
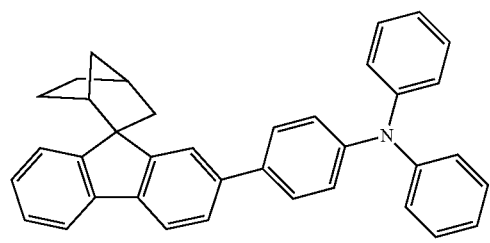
17
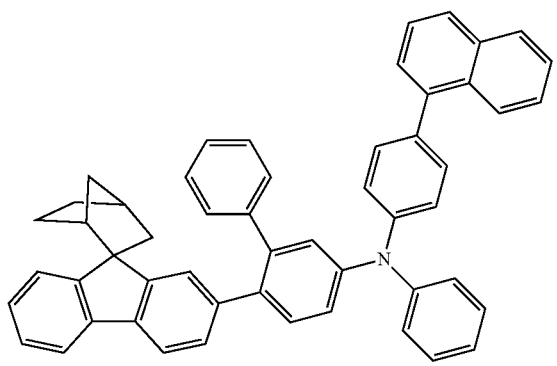

-continued
18
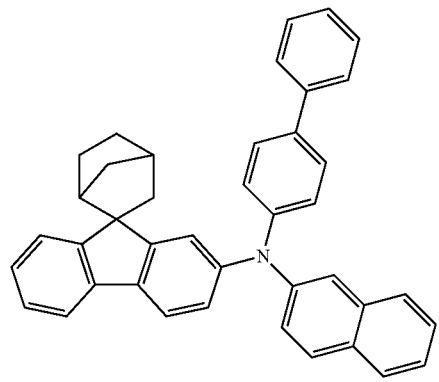
19
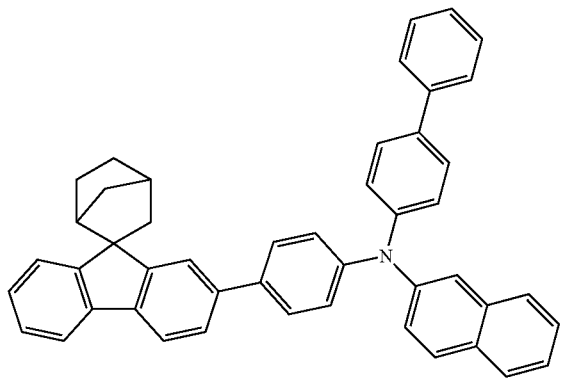
20
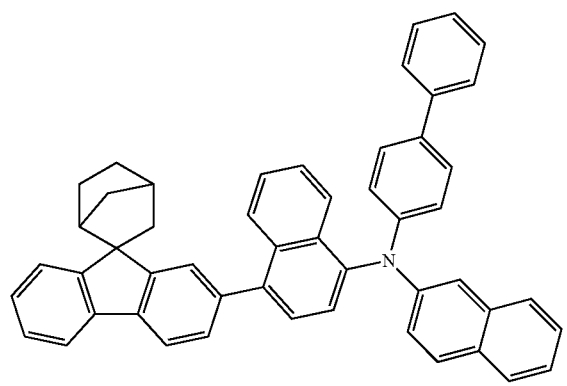
21
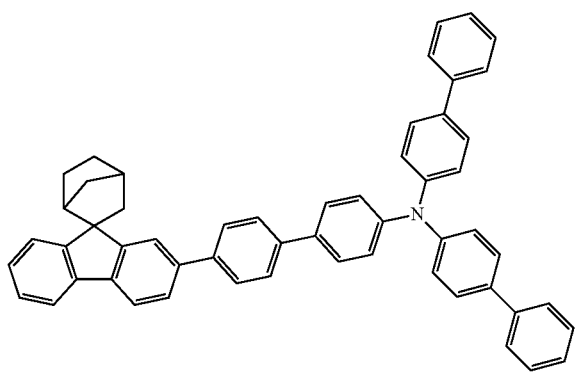
22
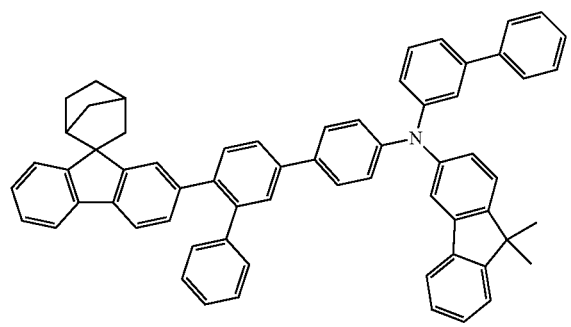
23
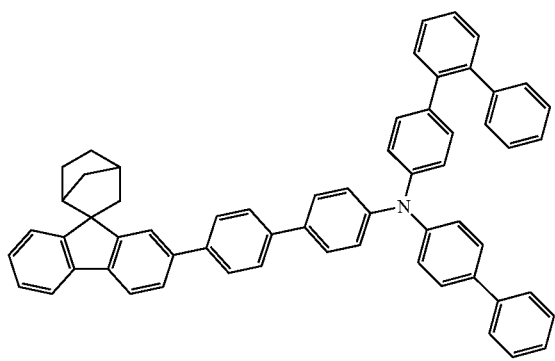
24
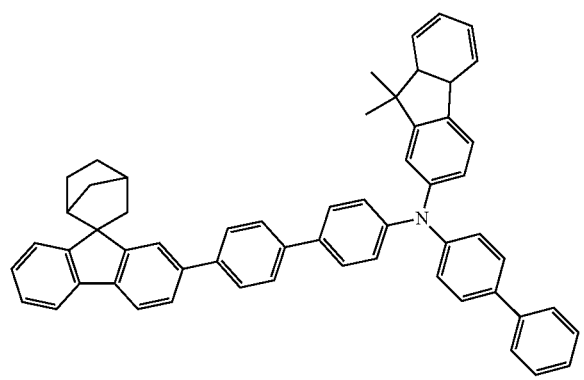
25
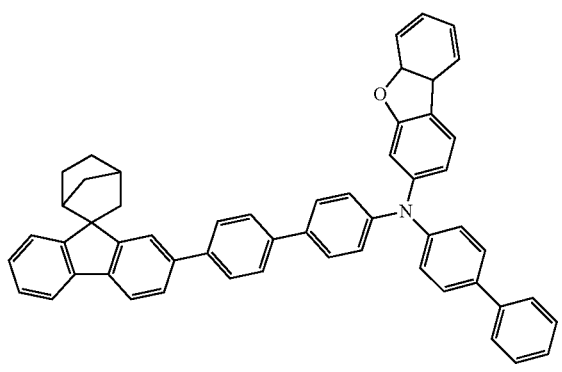

-continued
26
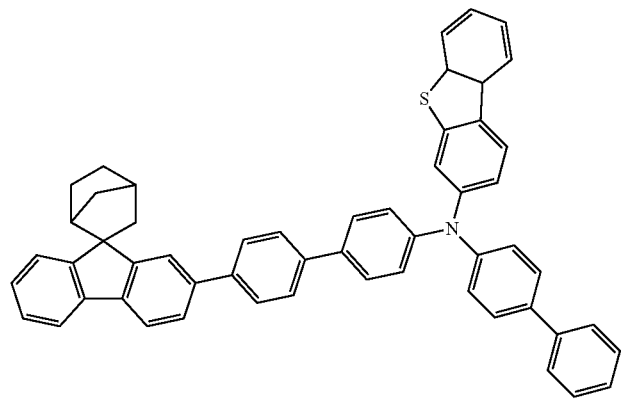
27
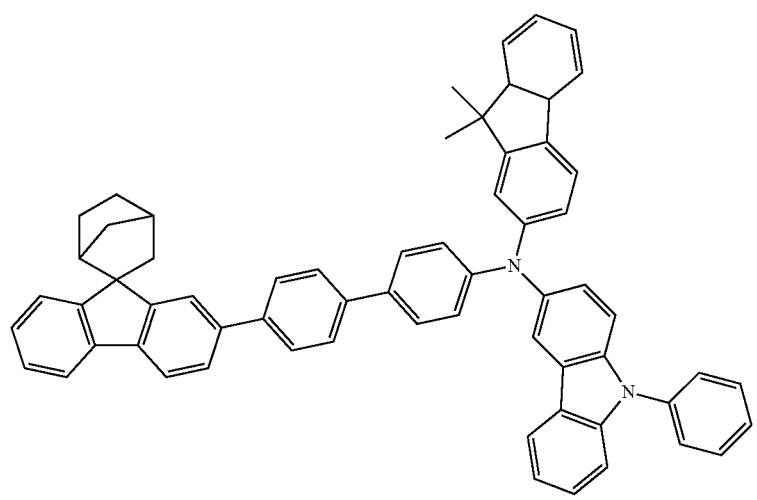
28
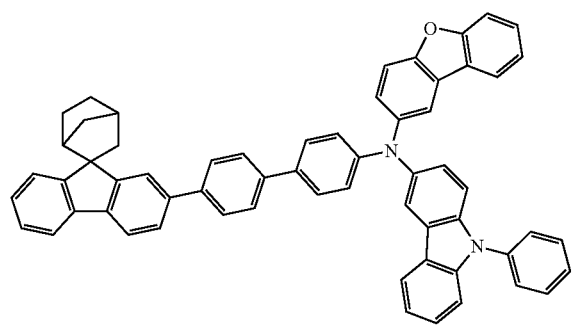
29
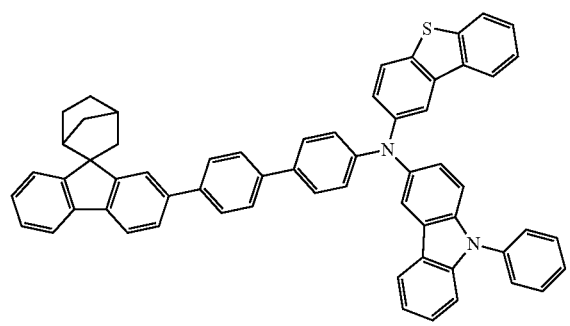
30
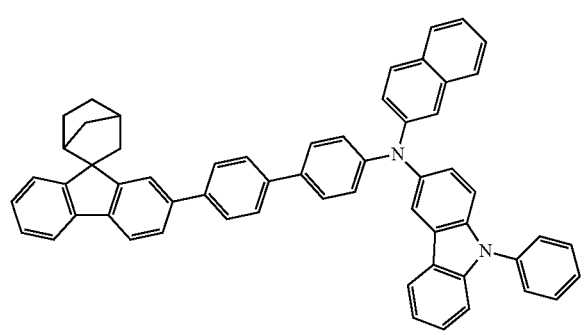
31
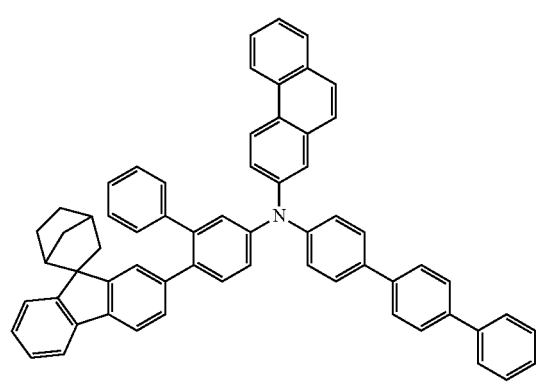

-continued
32
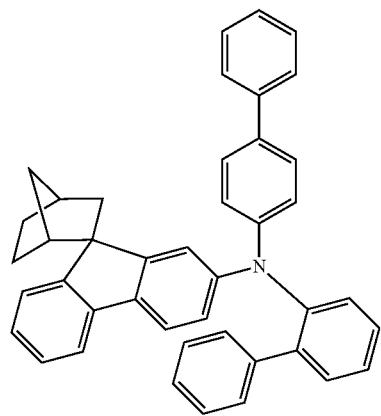
33
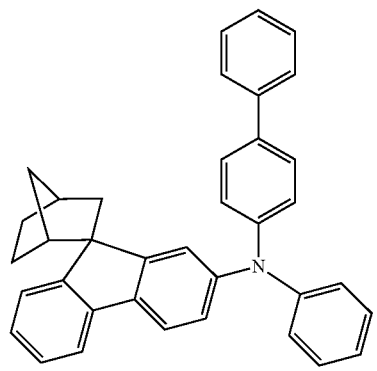
34
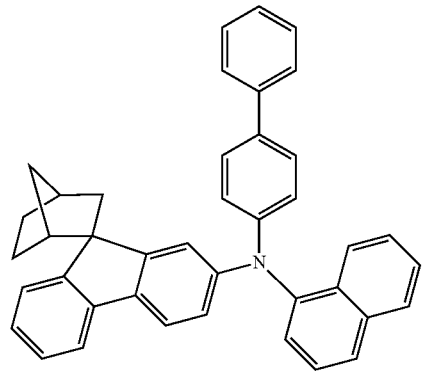
35
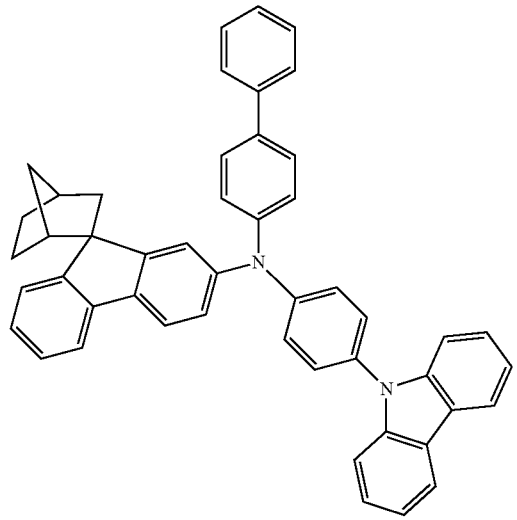
36
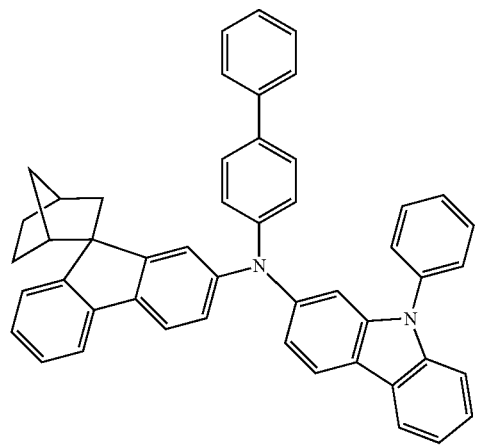
37
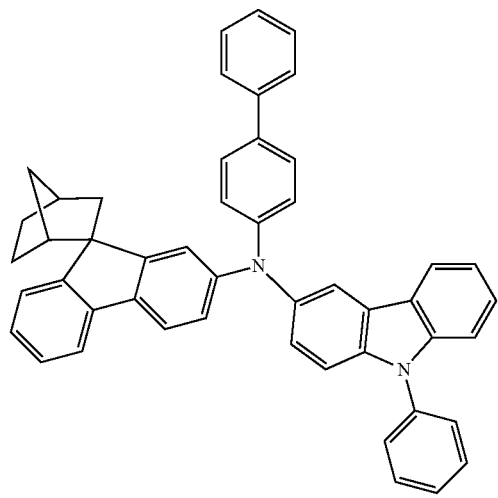

-continued
38
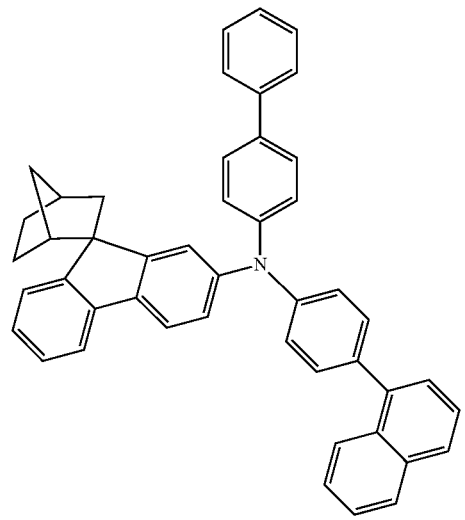
39
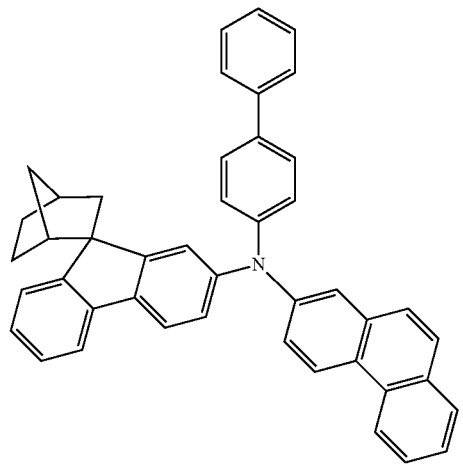
40
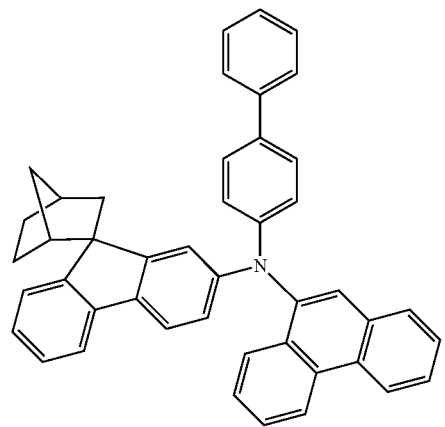
41
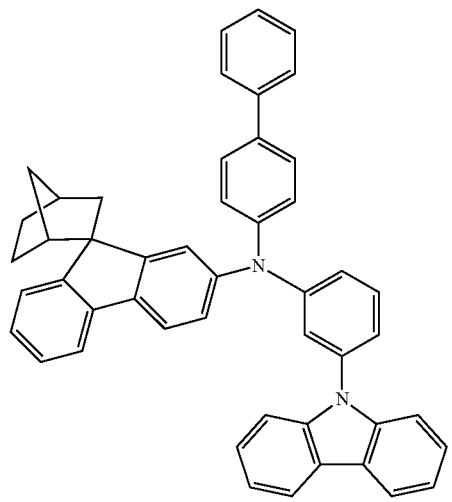
42
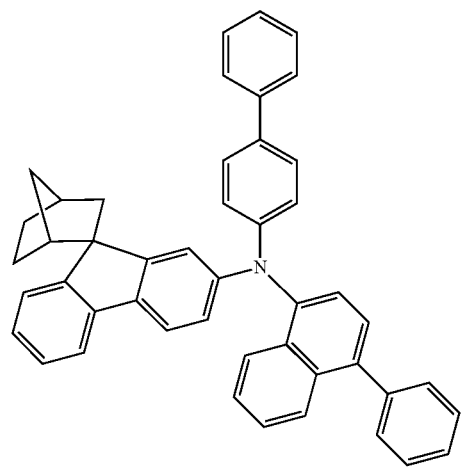
43
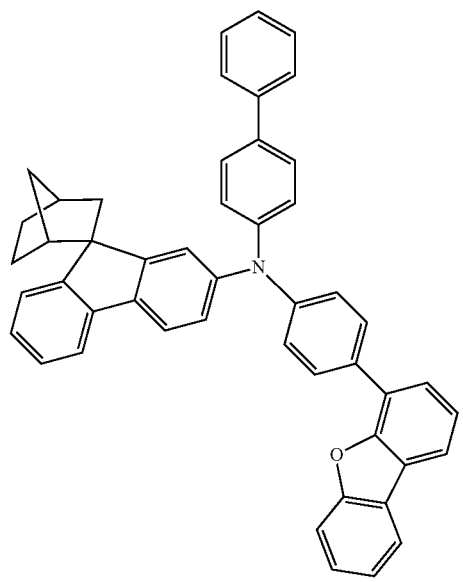

44
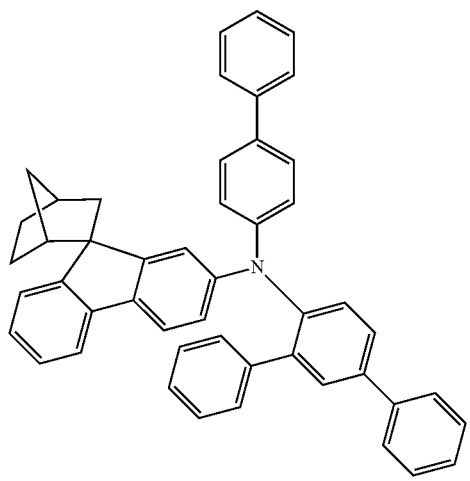
45
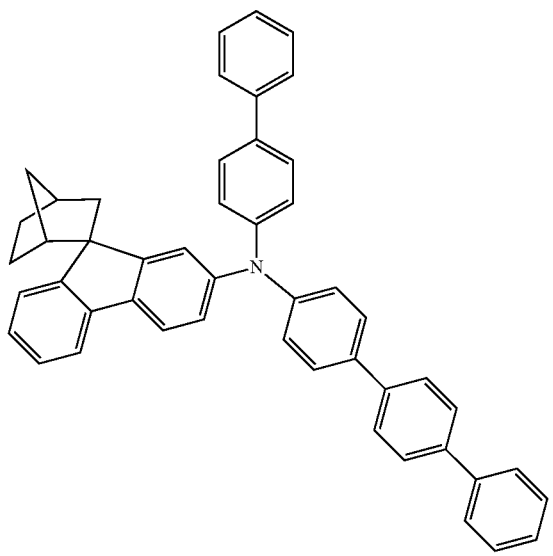
46
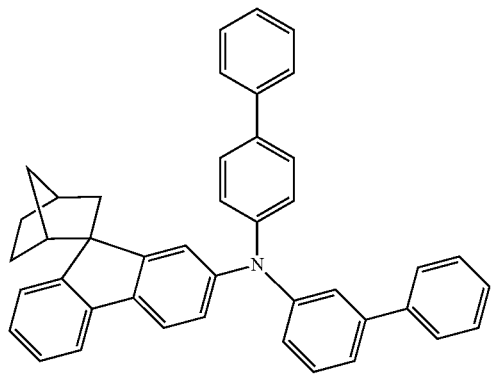
47
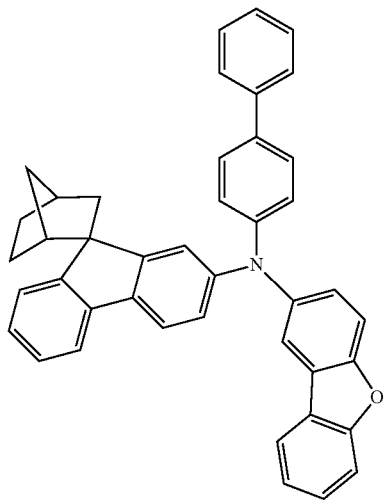
48
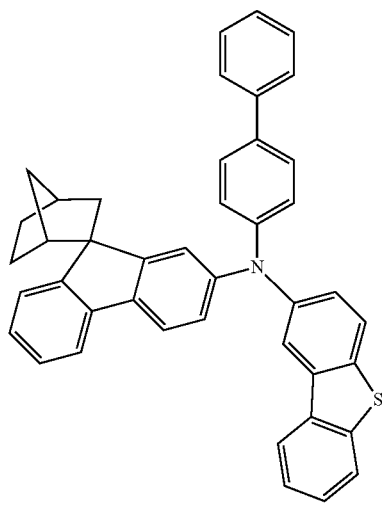
49
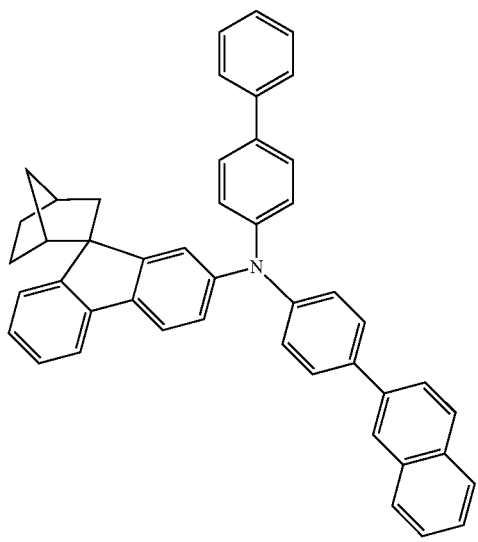

50
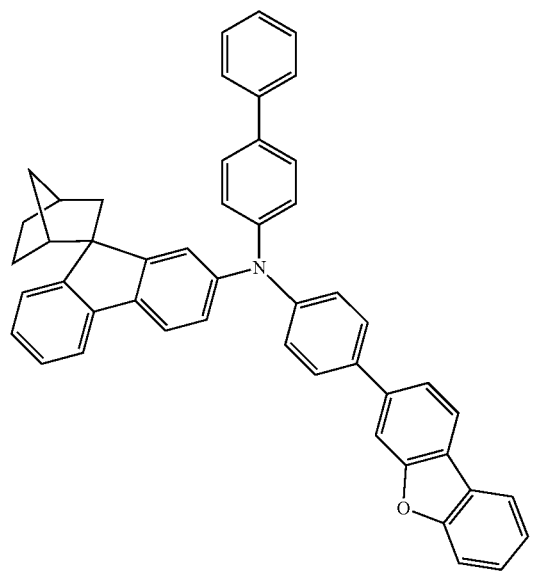
51
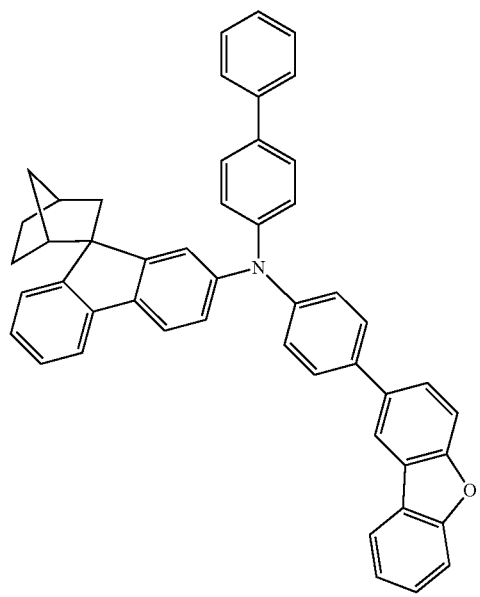
52
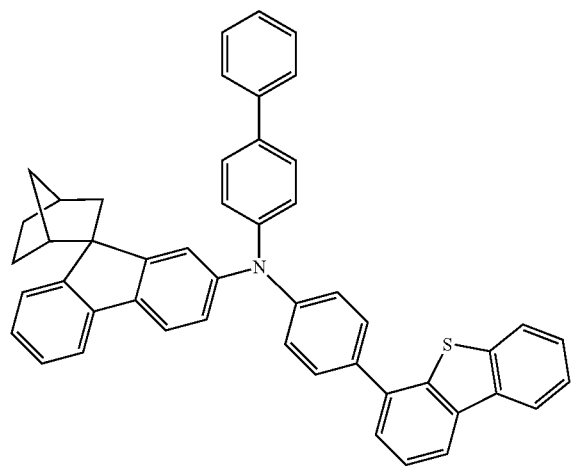
53
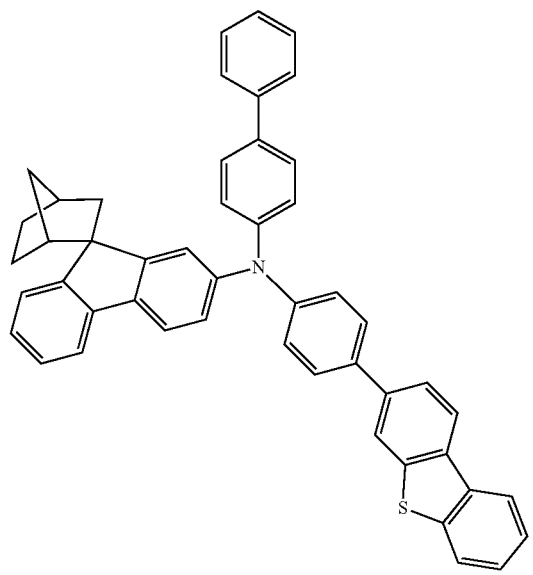

-continued
54
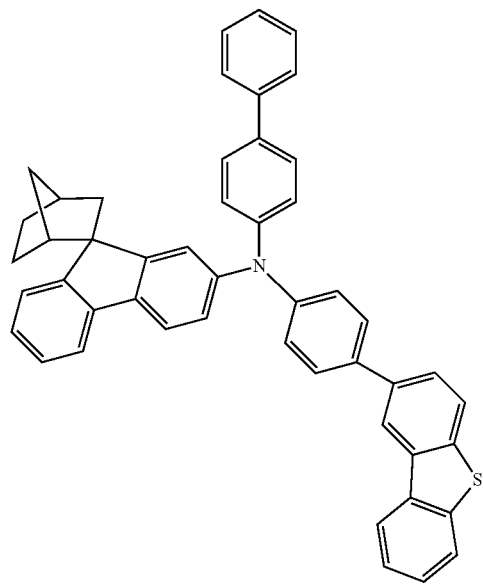
15
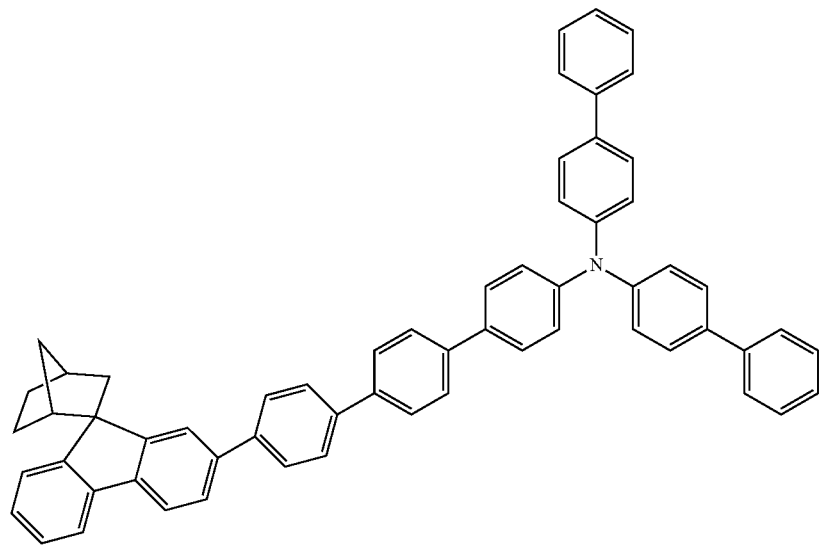
55
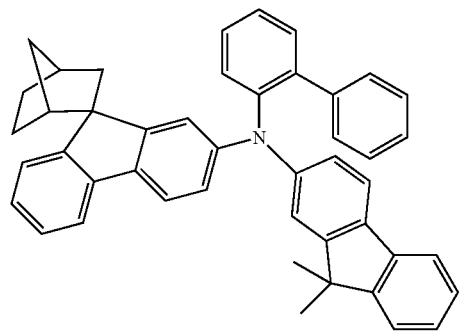
56
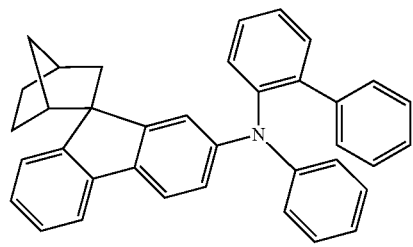

-continued
57
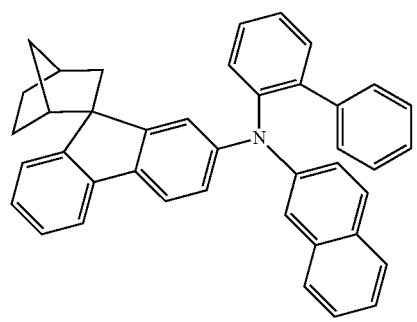
58
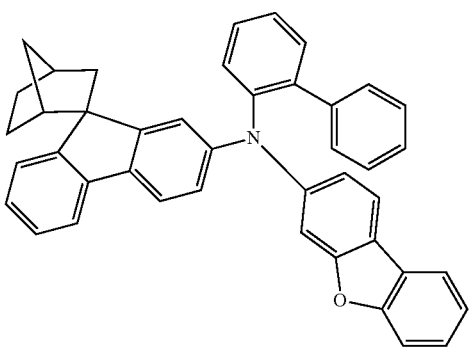
59
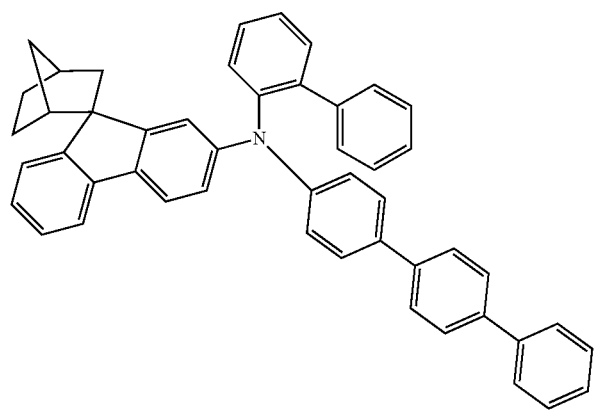
60
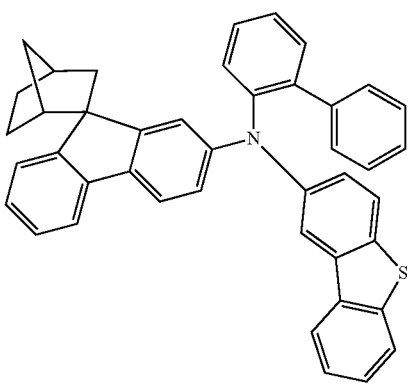
61
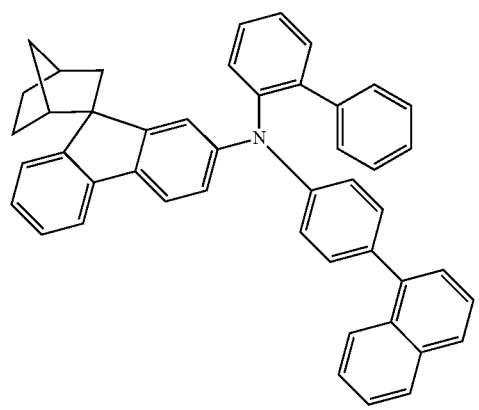
62
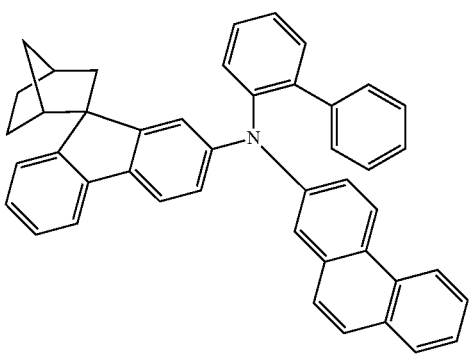
63
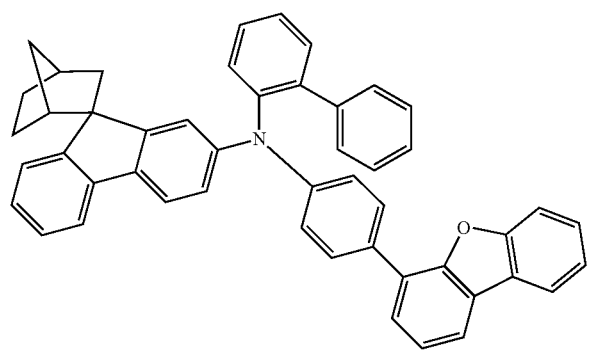
64
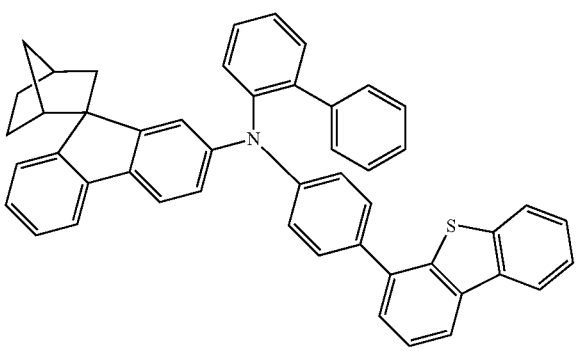

-continued
65
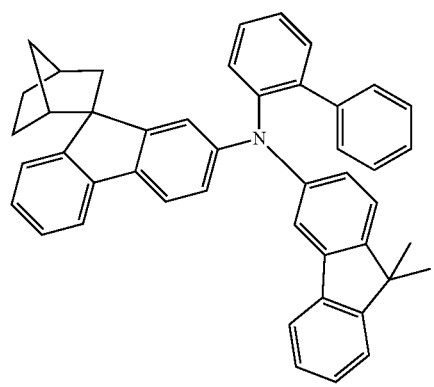
66
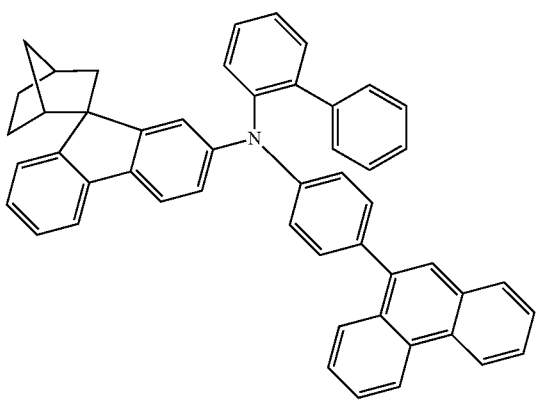
67
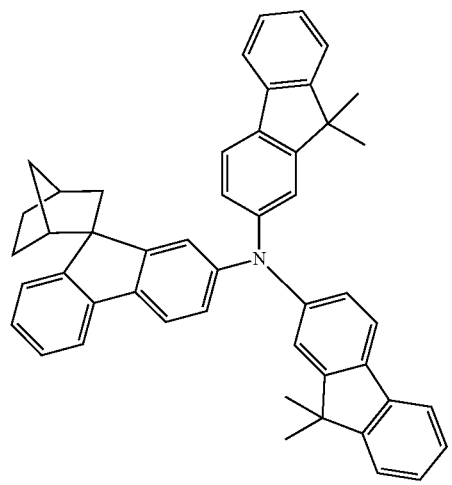
68
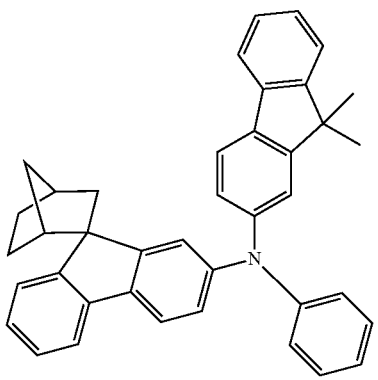
69
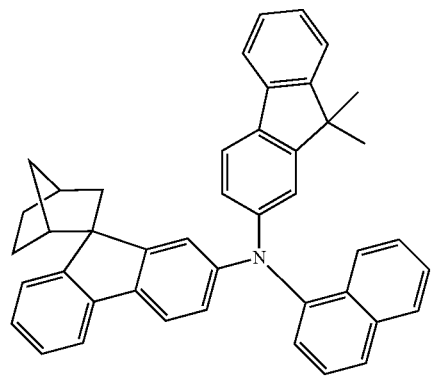
70
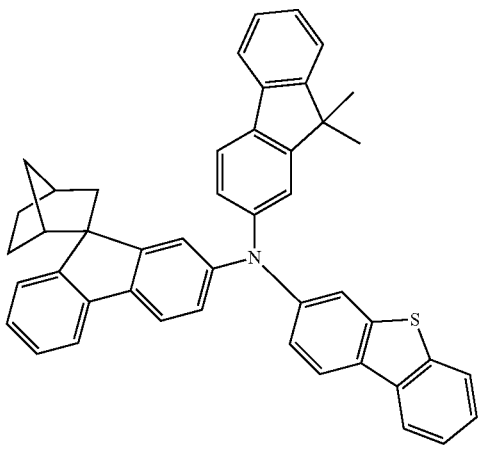

71
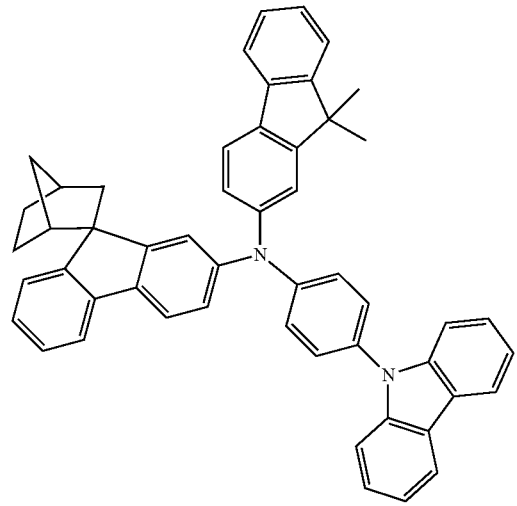
72
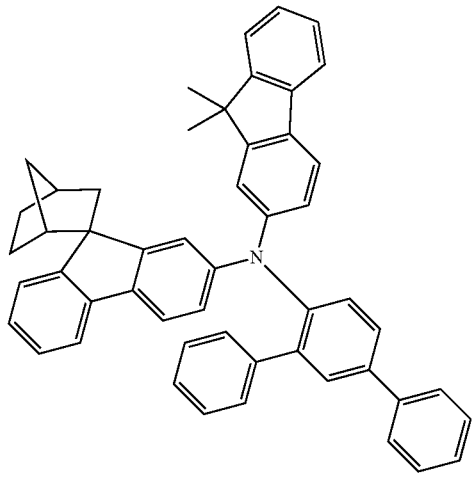
73
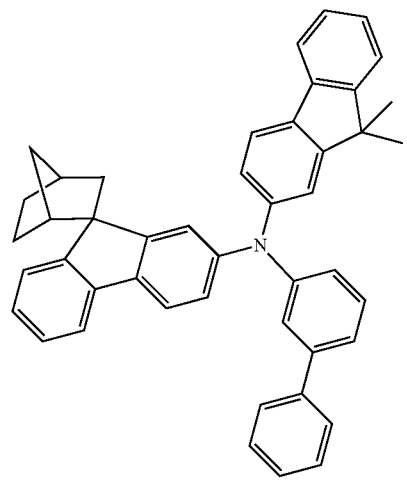
74
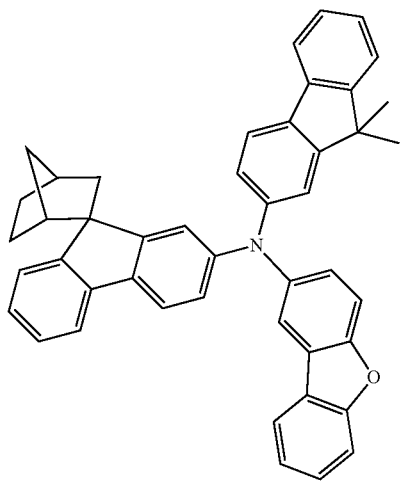
75
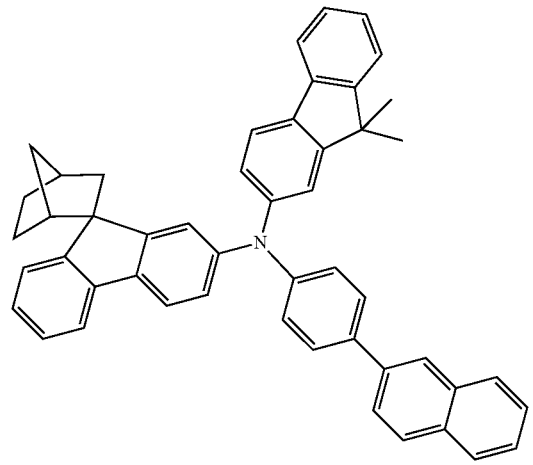
76
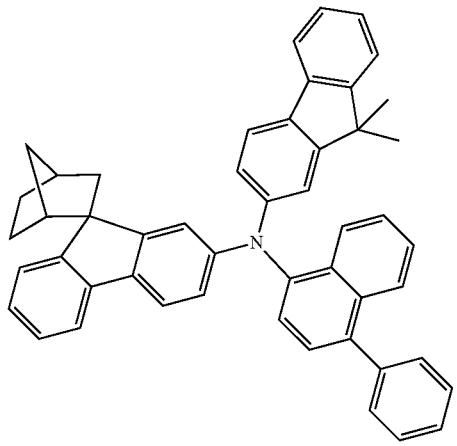

77
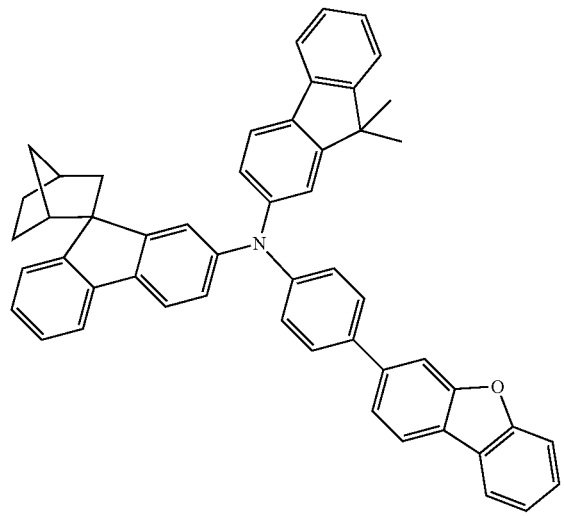
78
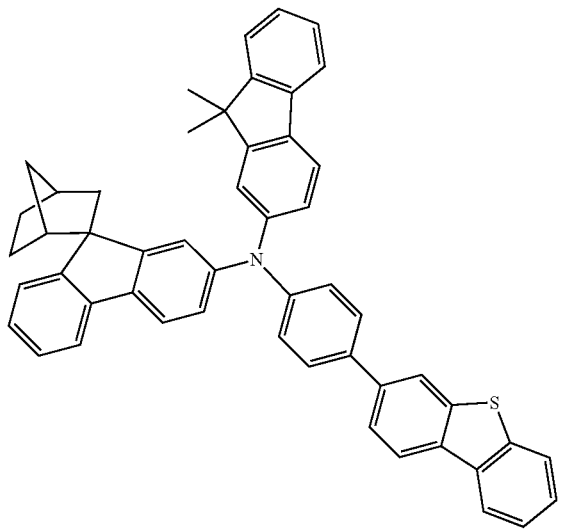
79
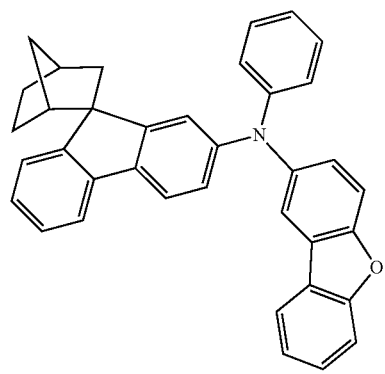
80
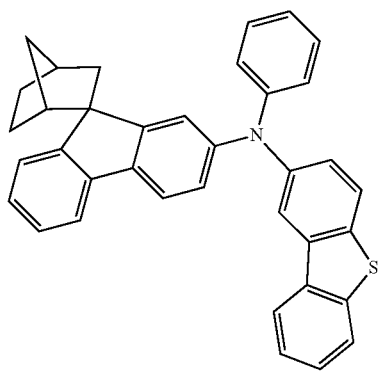
81
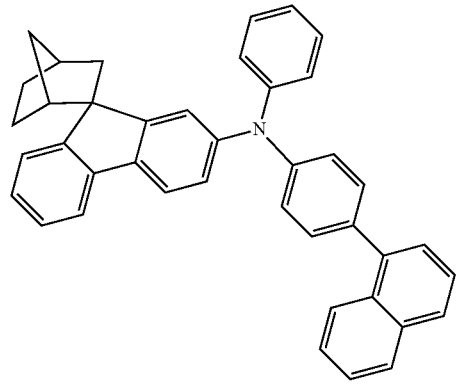
82
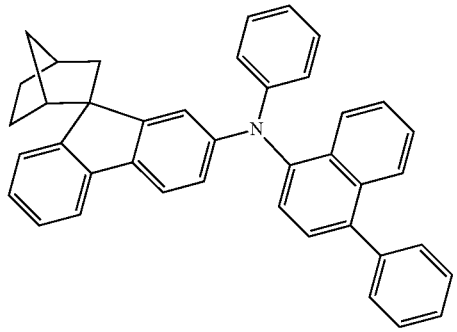
83
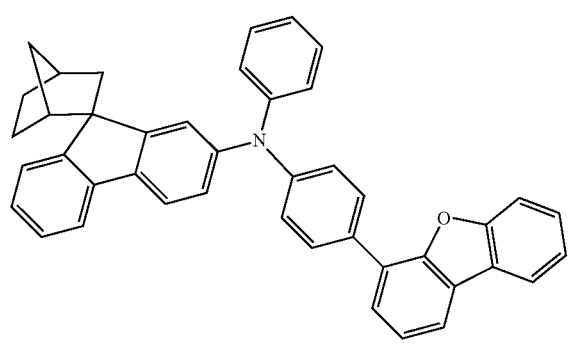
84
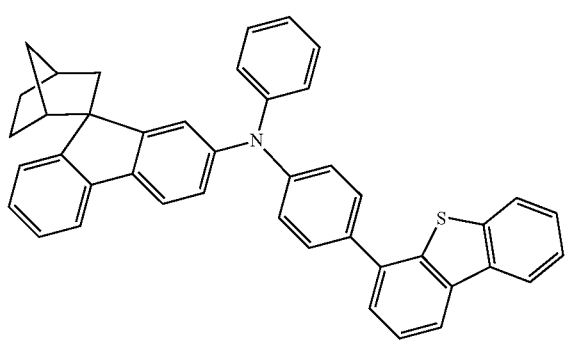

-continued
85
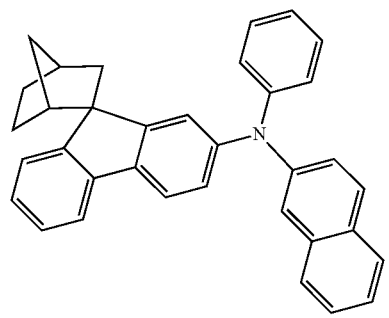
86
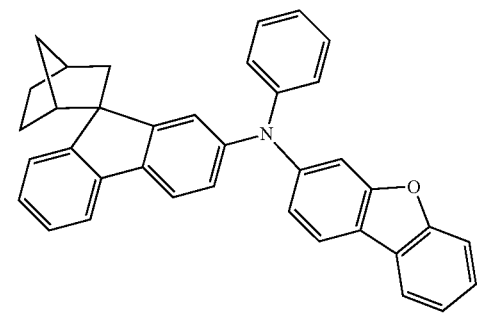
87
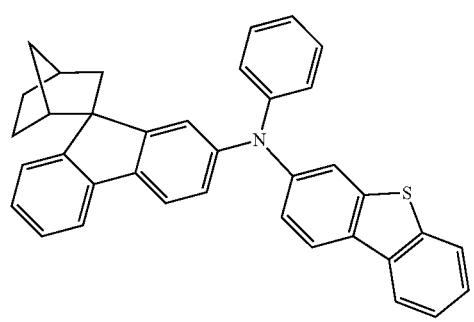
88
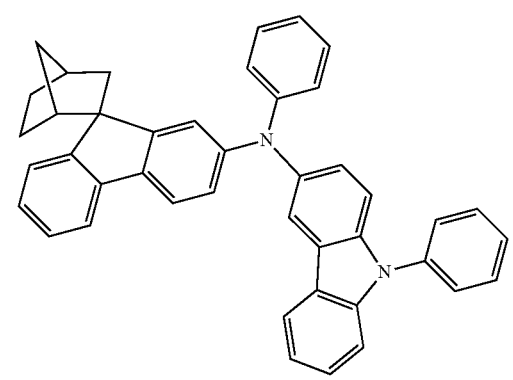
89
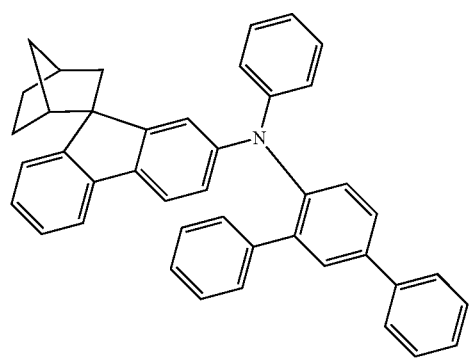
90
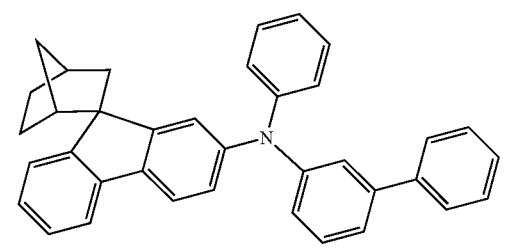
91
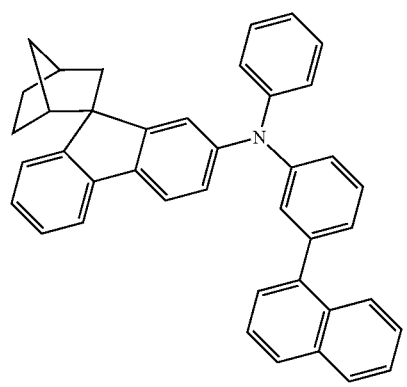
92
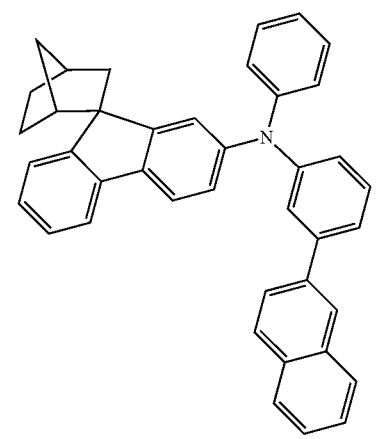

-continued
93
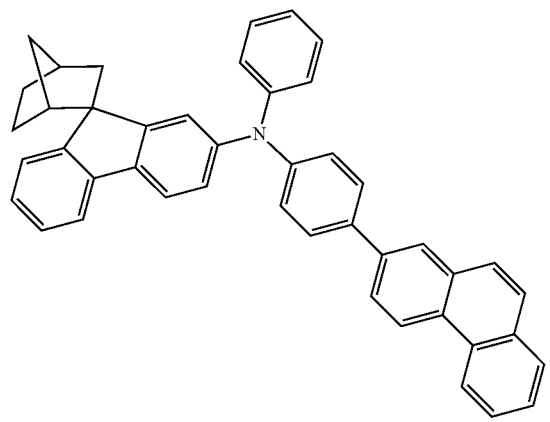
94
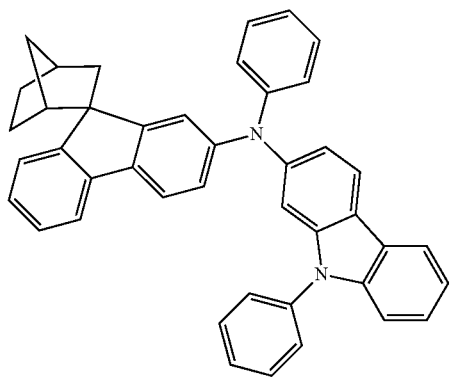
95
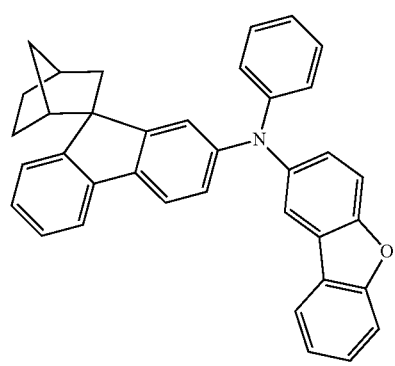
96
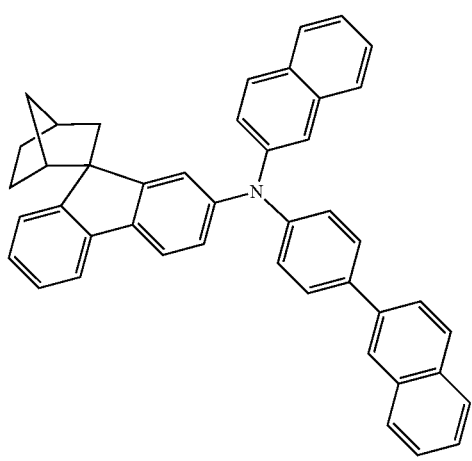
97
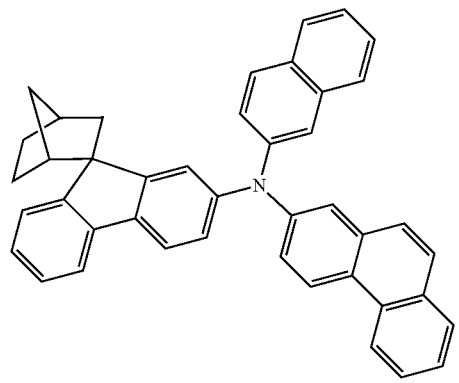
98
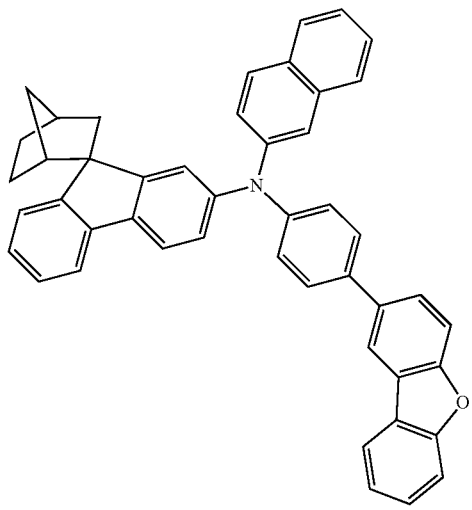

-continued
99
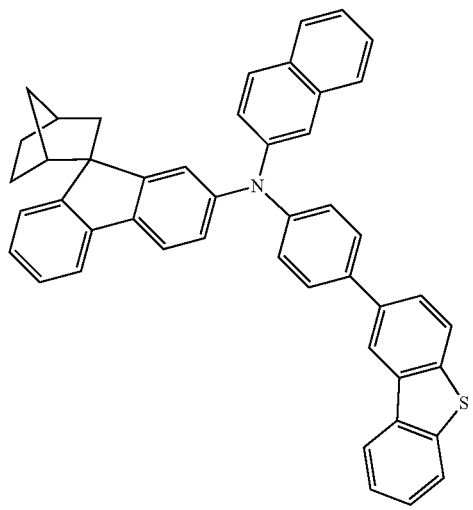
100
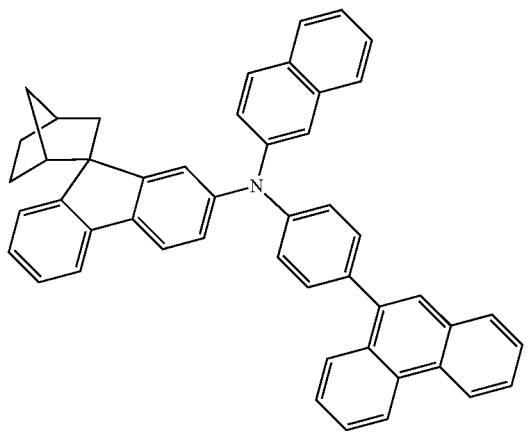
101
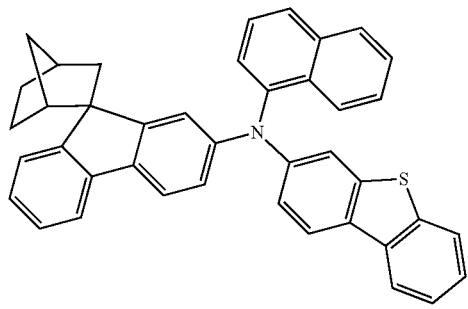
102
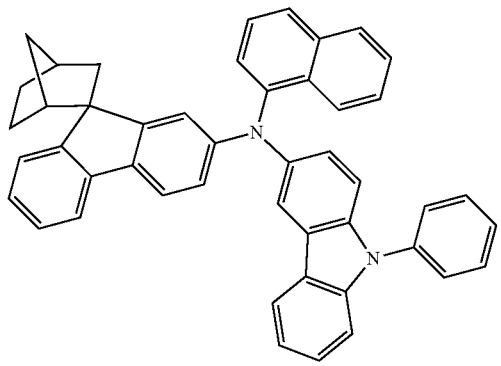
103
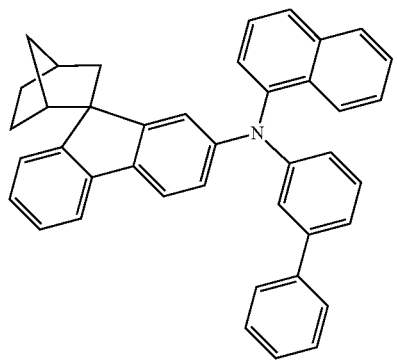
104
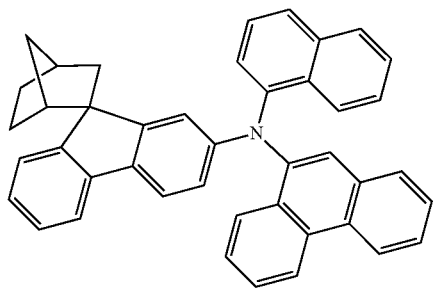
105
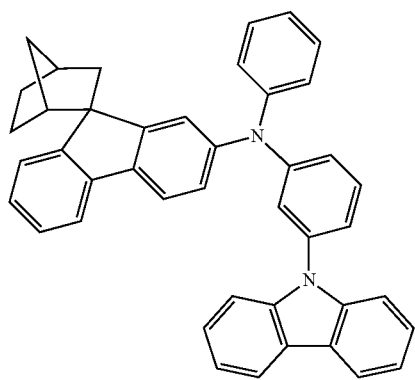
106
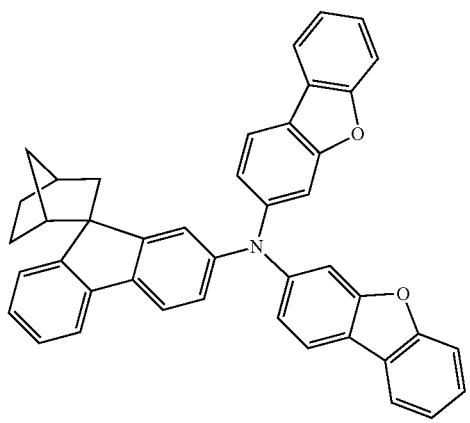

-continued
107
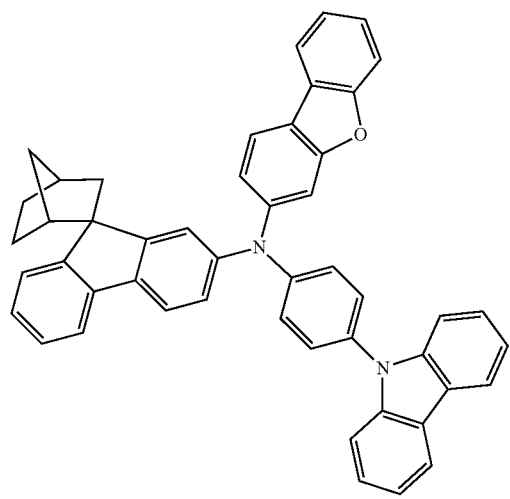
108
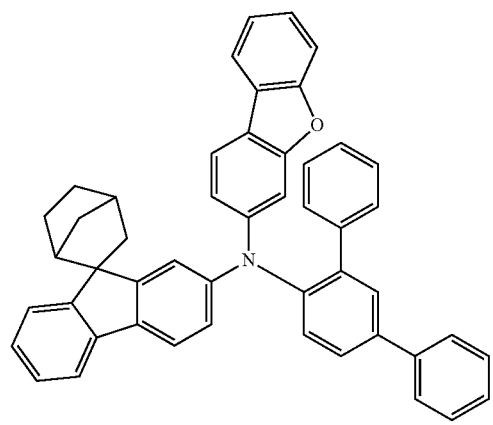
109
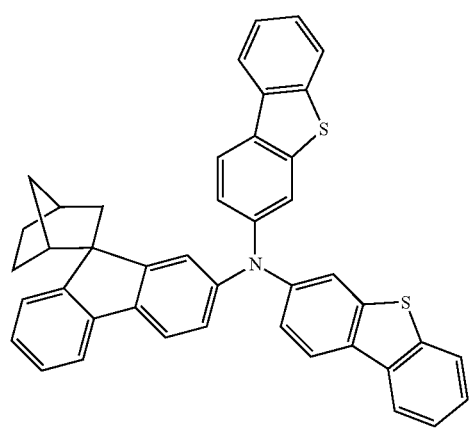
110
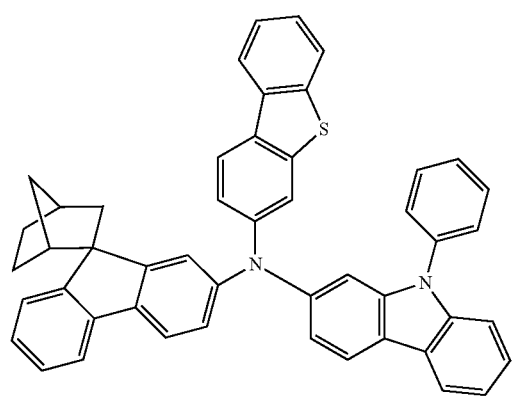
111
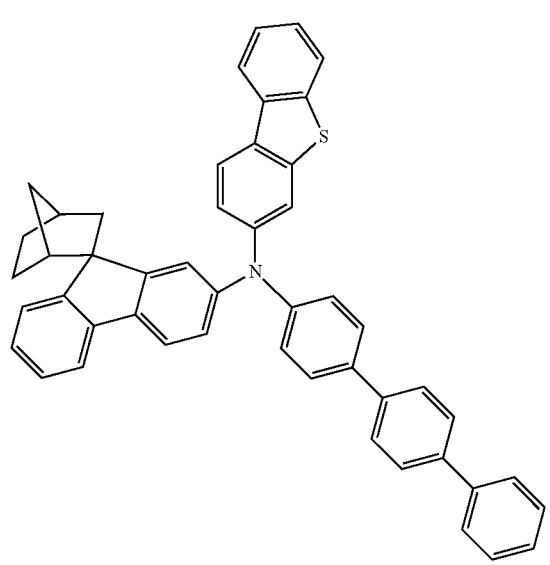
112
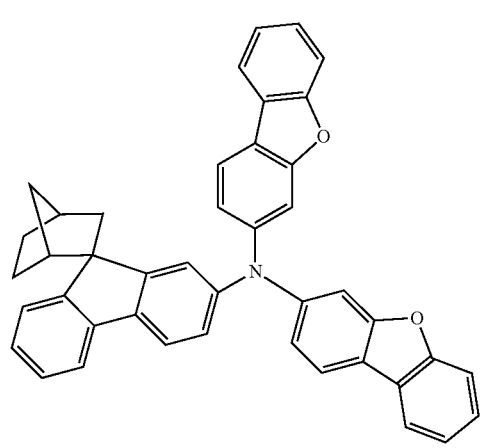

-continued
113
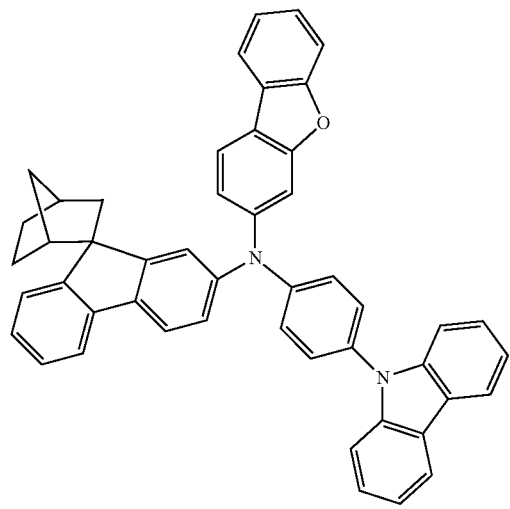
114
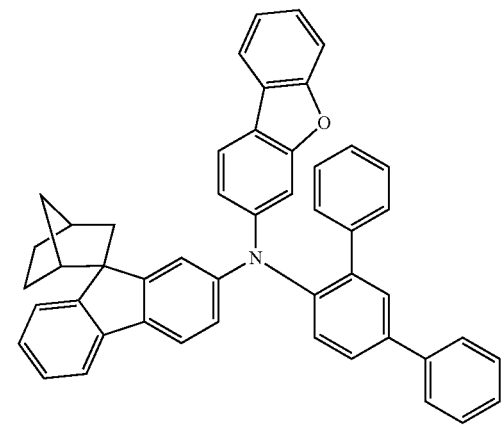
115
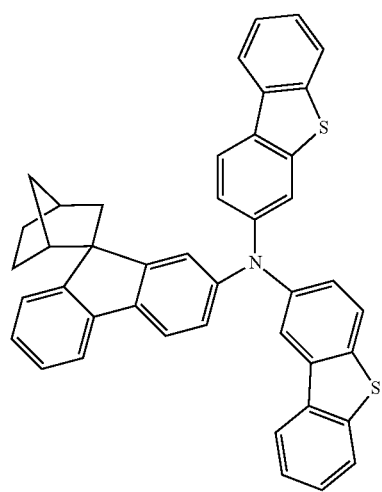
116
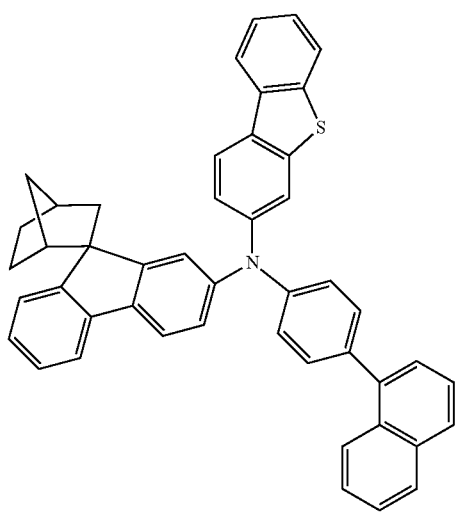
117
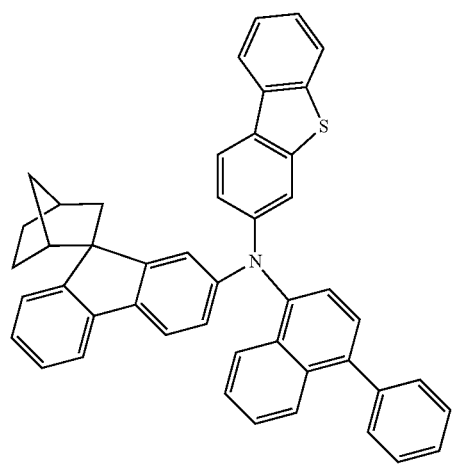
118
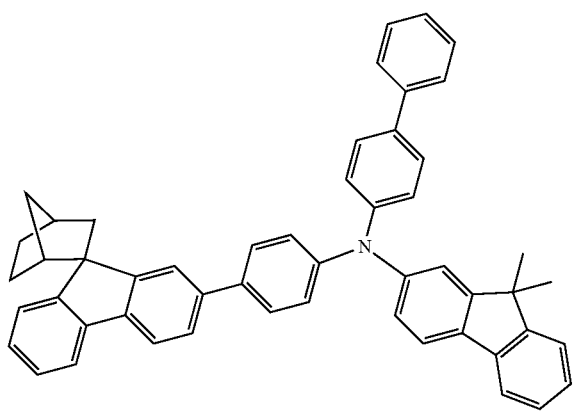

-continued
119
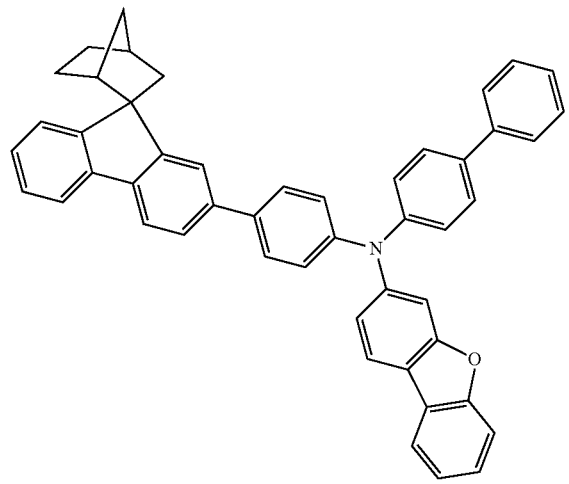
121
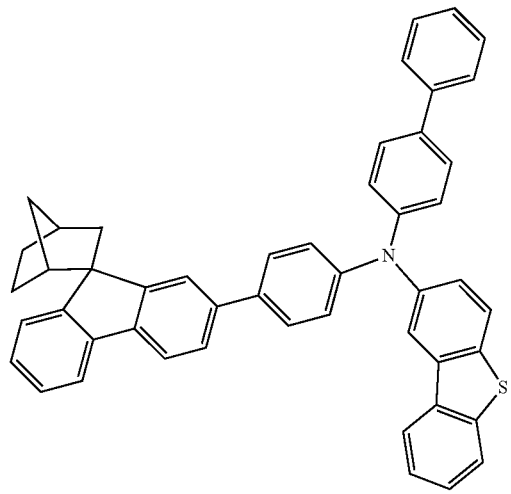
122
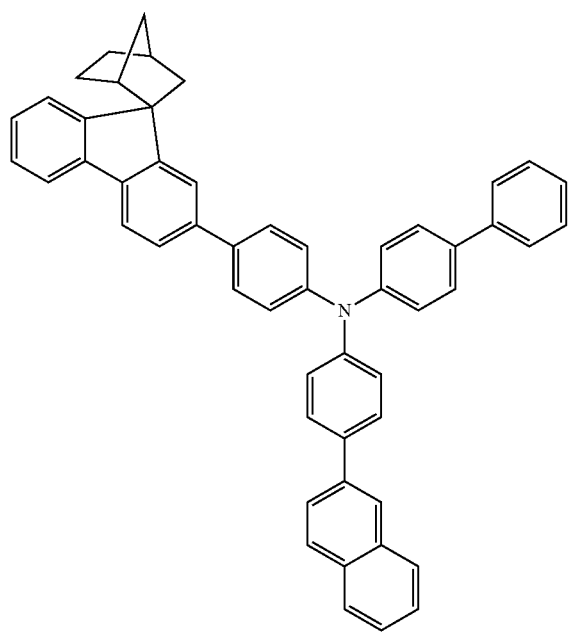
123
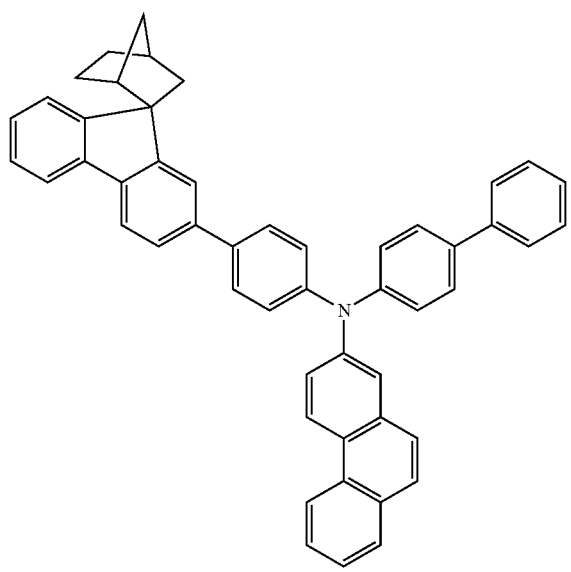
120
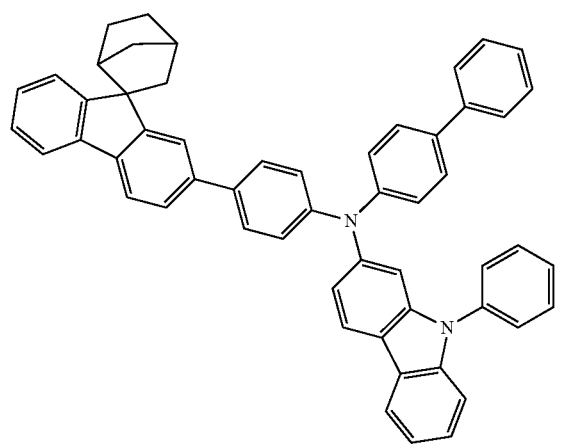
124
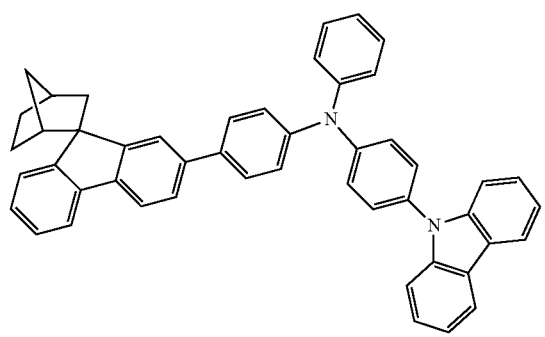

-continued
125
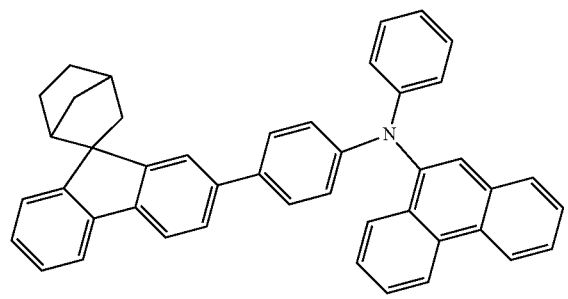
126
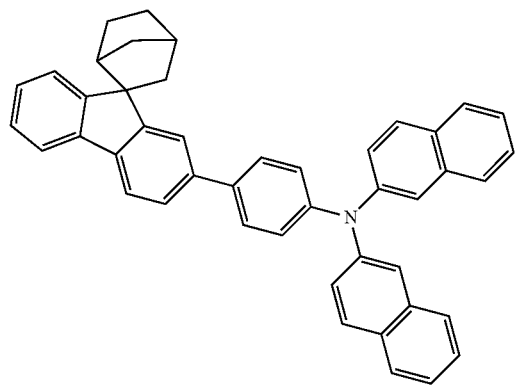
127
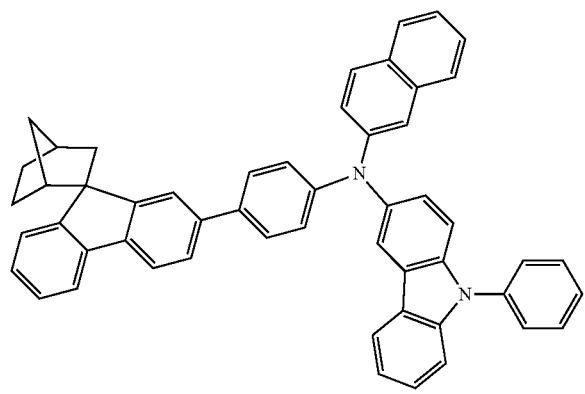
128
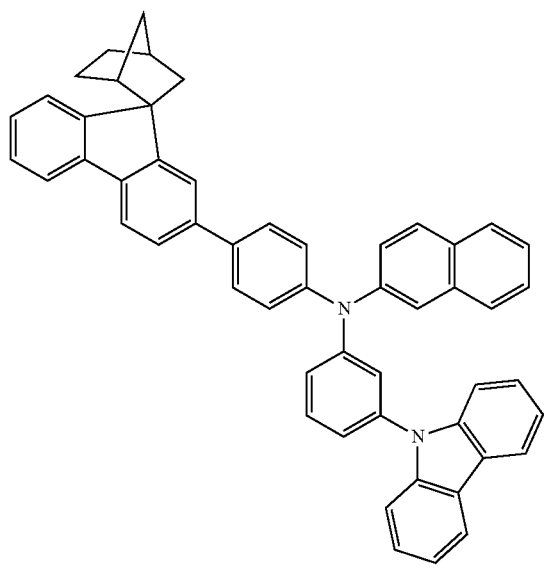
129
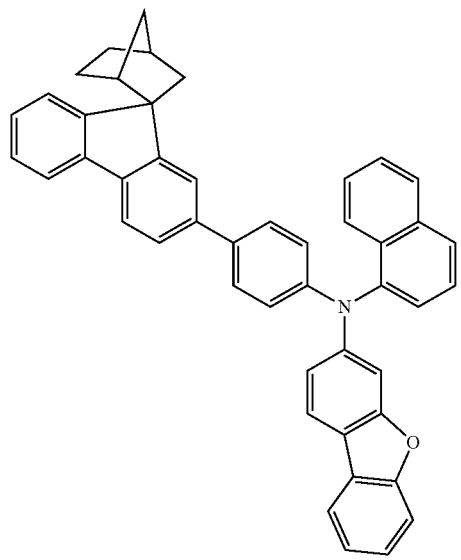
130
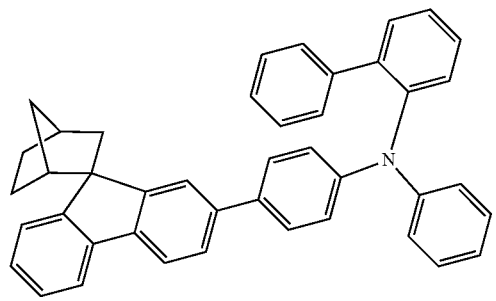

-continued
131
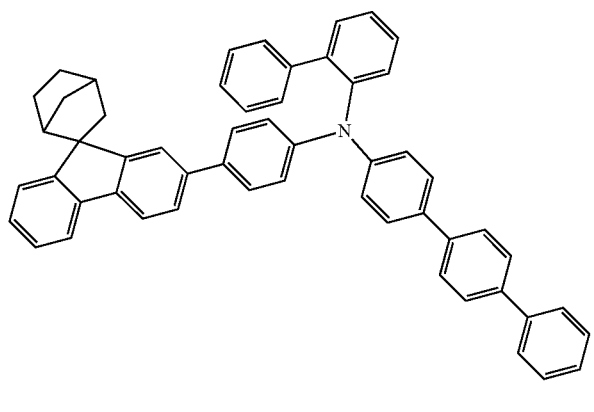
132
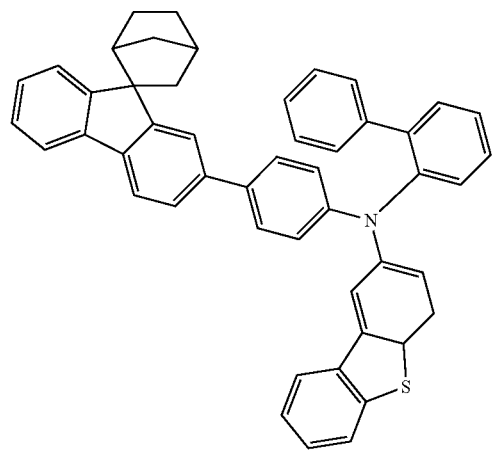
133
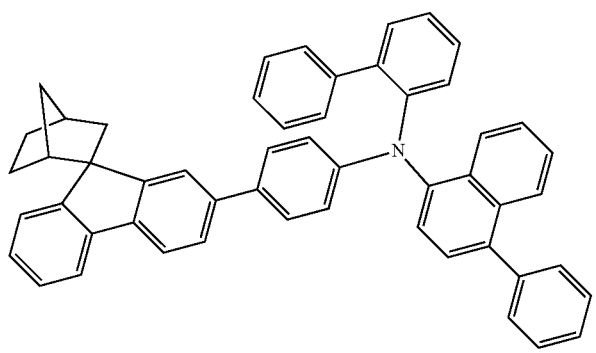
134
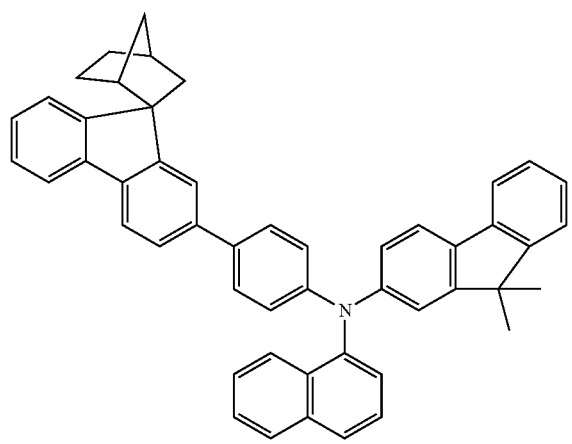
135
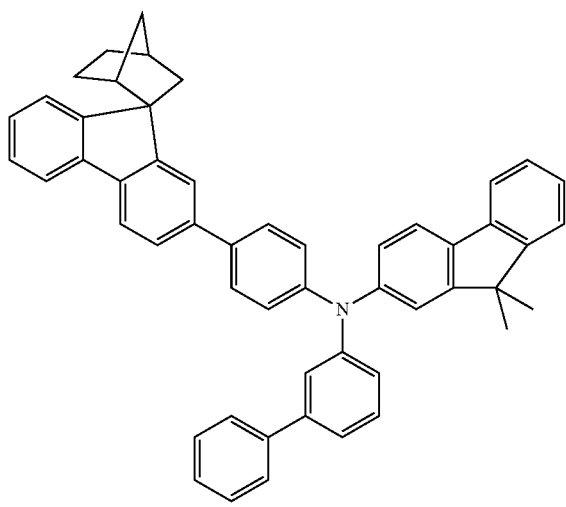
136
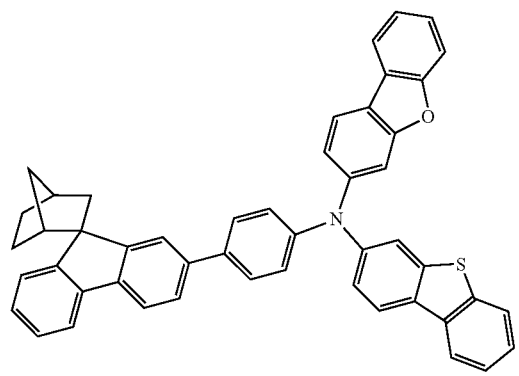

-continued
137 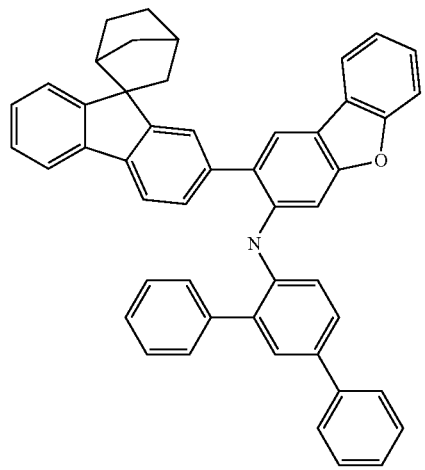
138 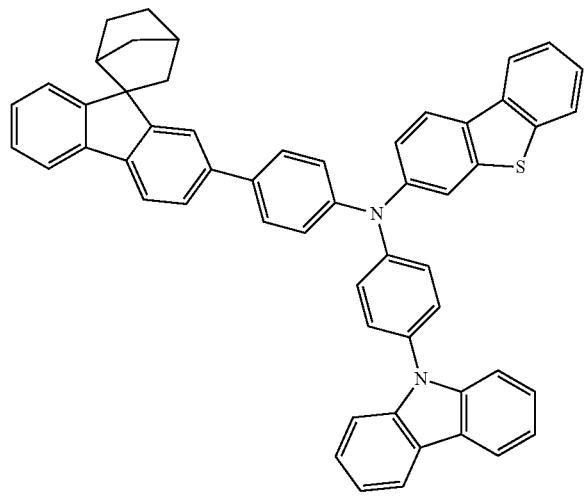
139 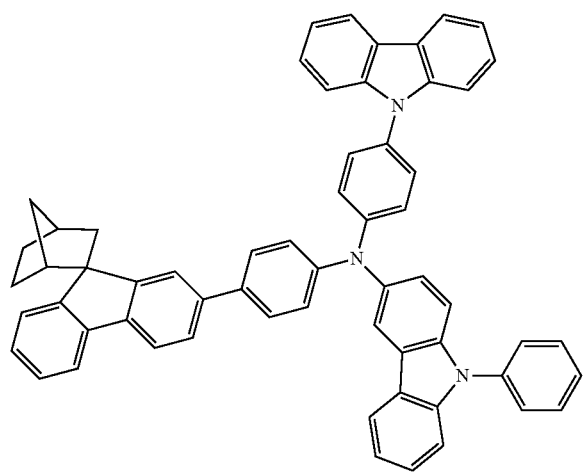
140 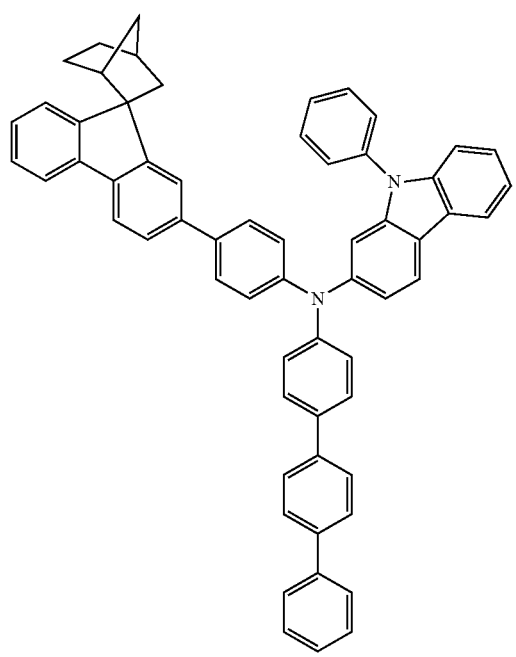

141 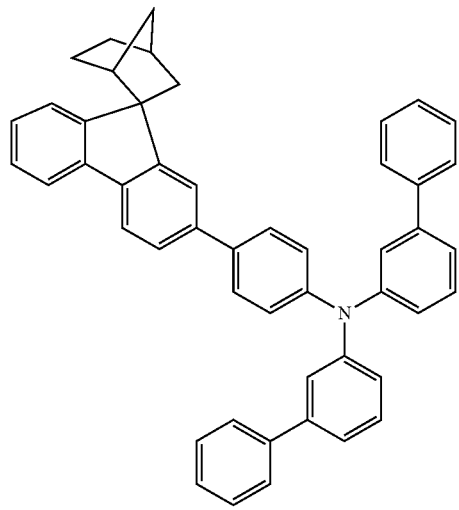
142 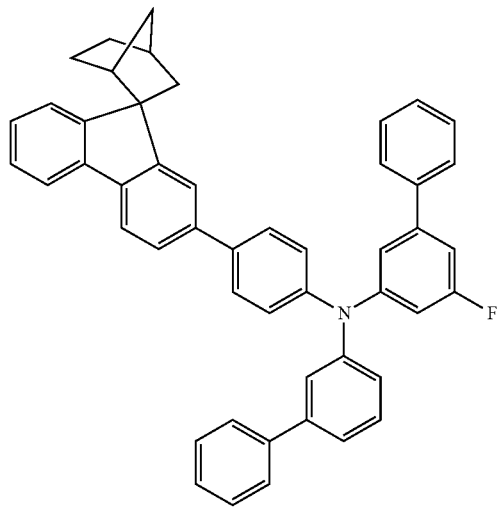
144 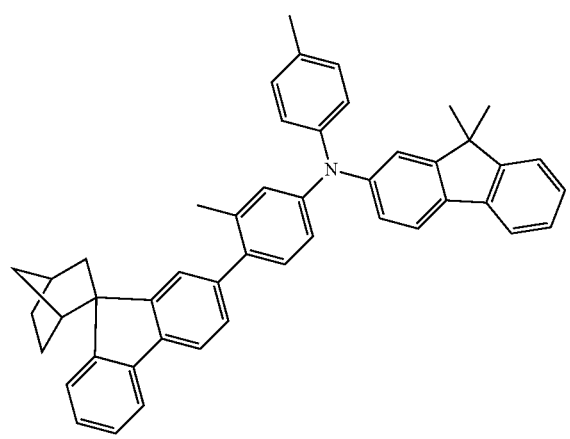
143 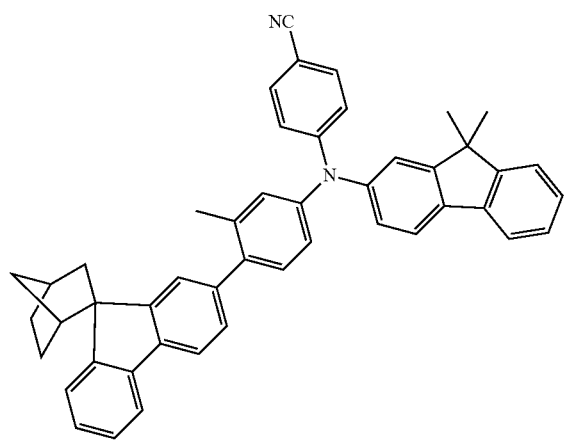
145 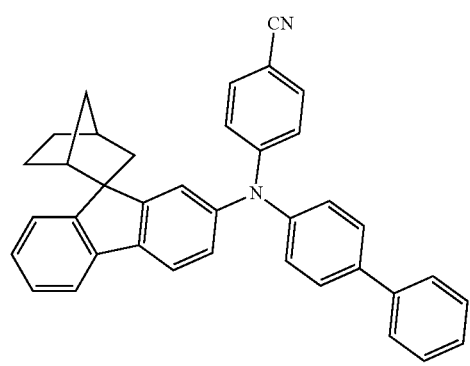

146 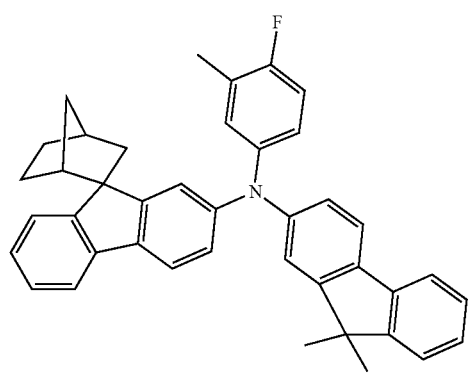
147 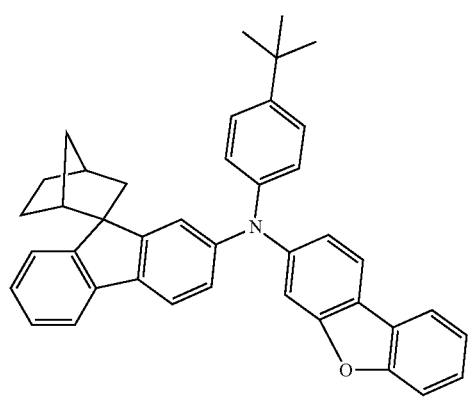
148 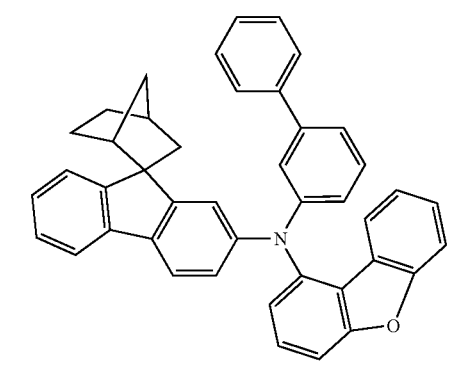
149 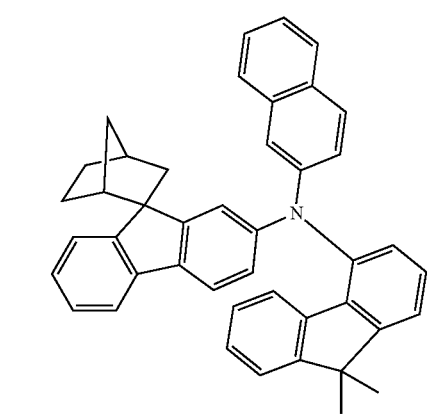
150 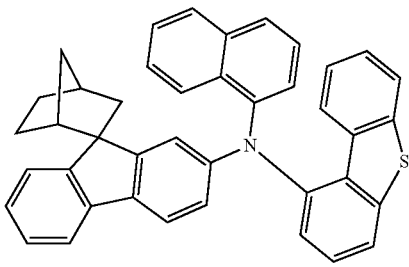
151 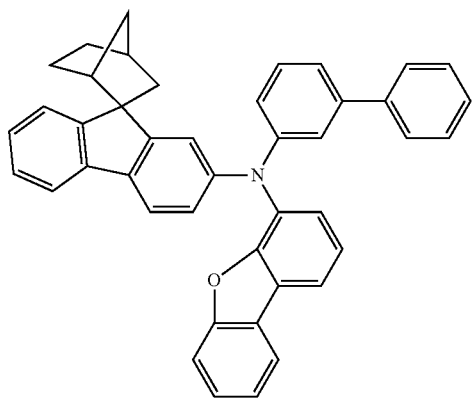
152 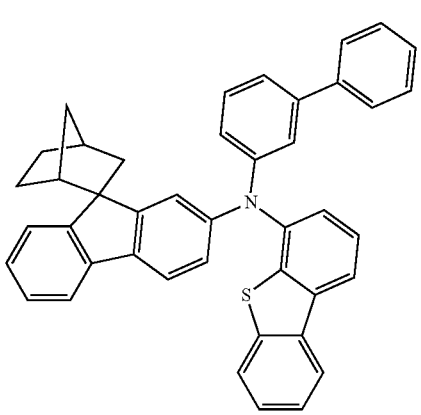
153 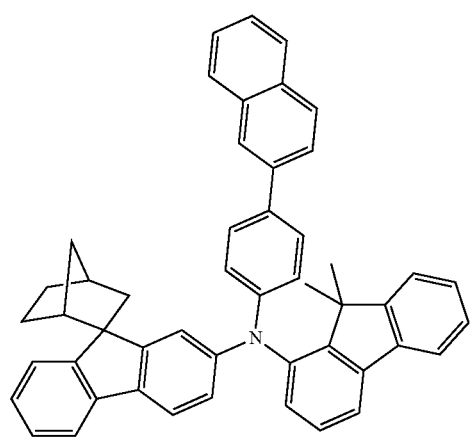

154
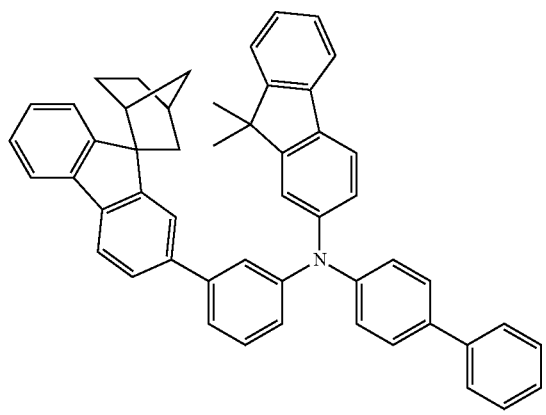
155
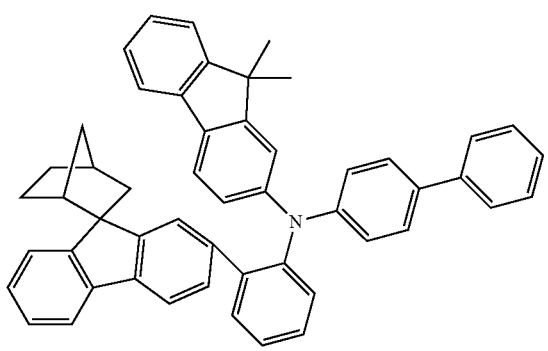
156
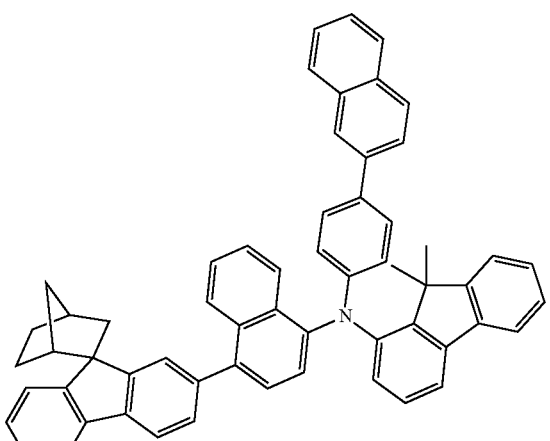
157
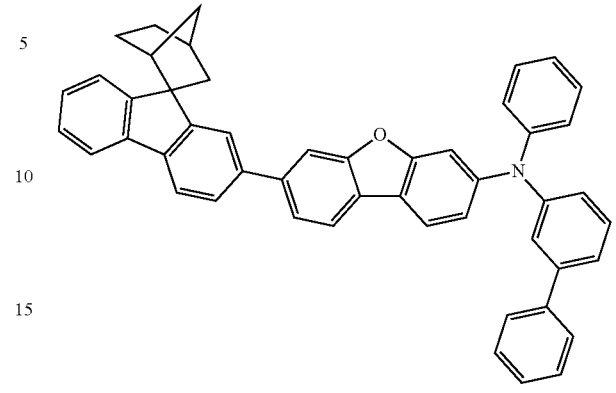
158
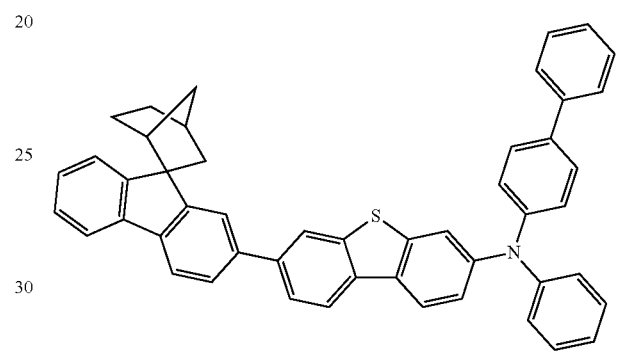
159
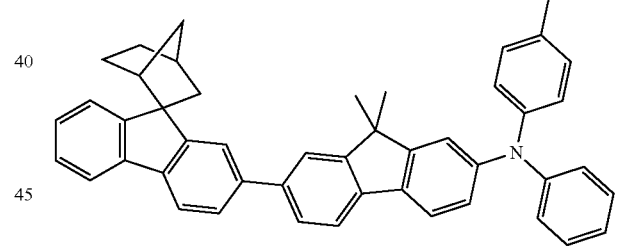
160
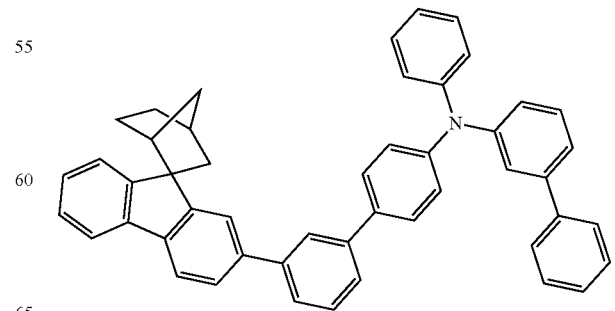

161
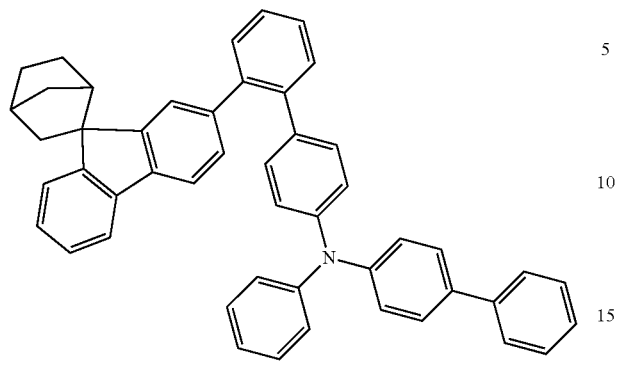
162
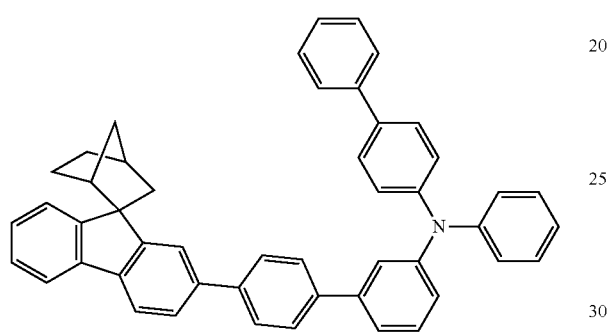
164
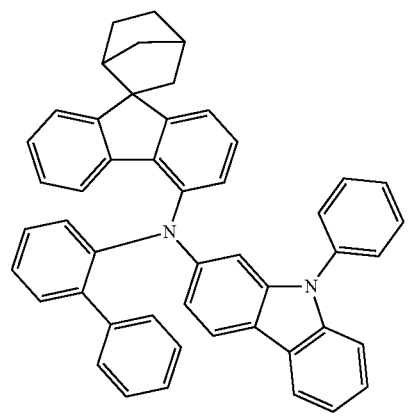
165
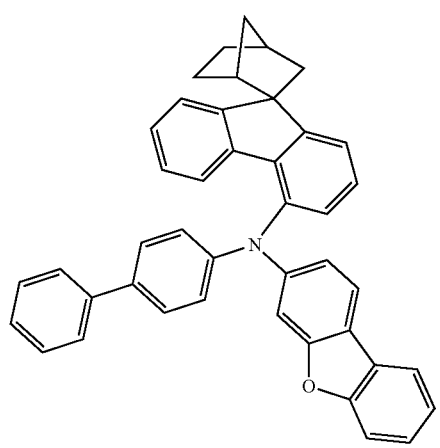
166
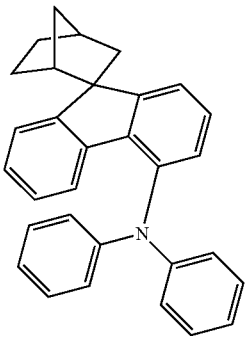
167
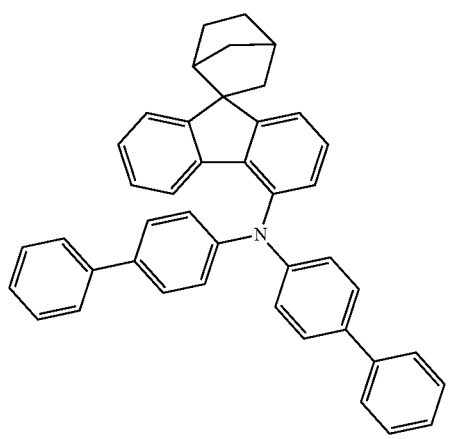
168
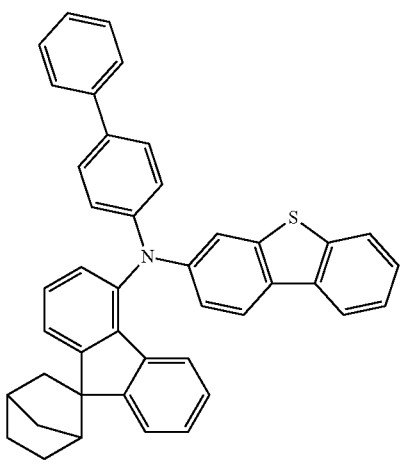
169
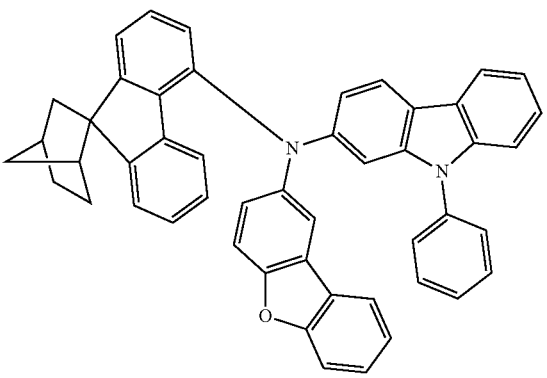

170
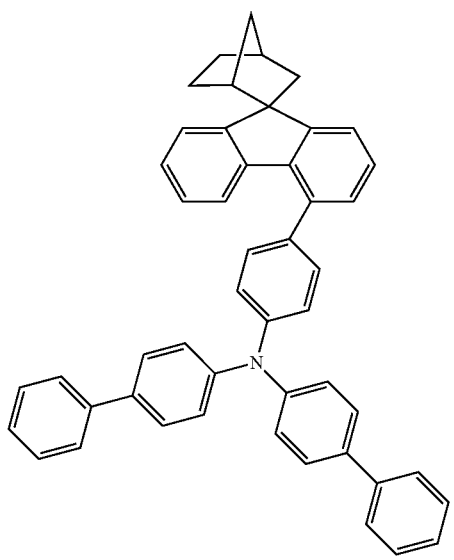
171
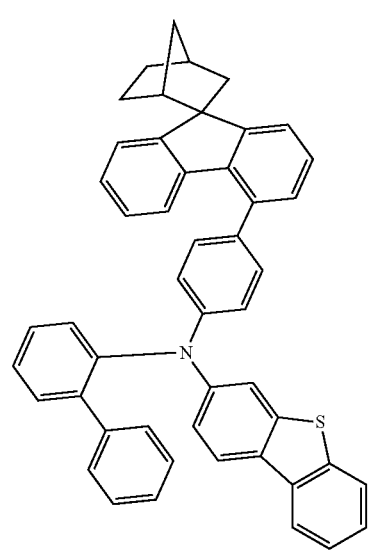
172
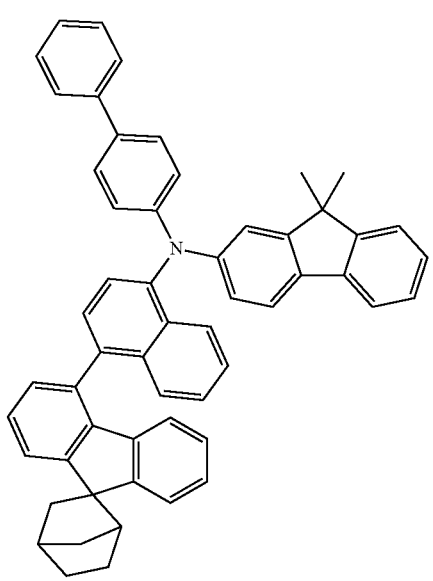
173
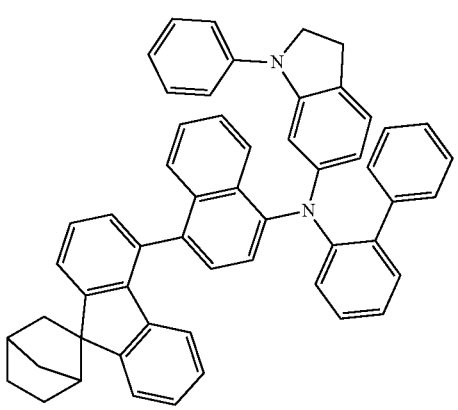
174
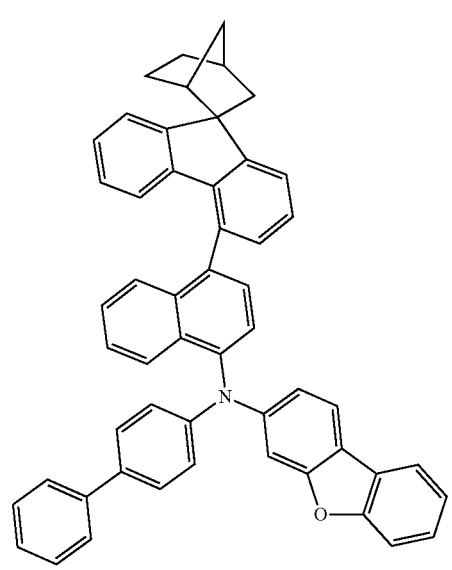
175
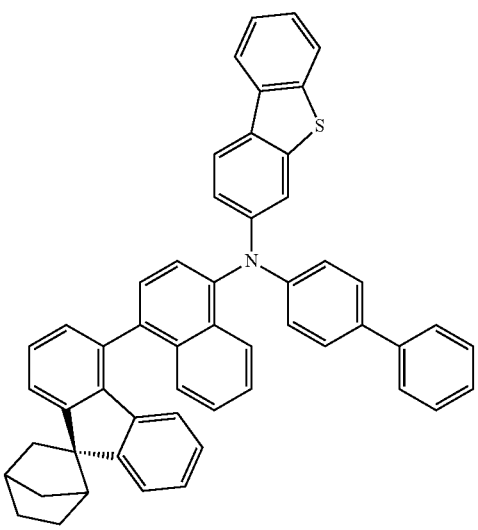

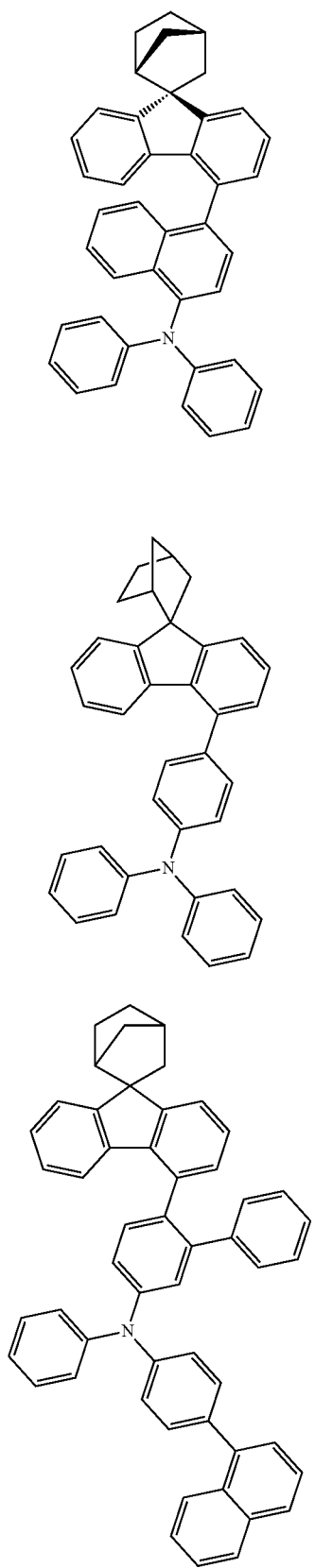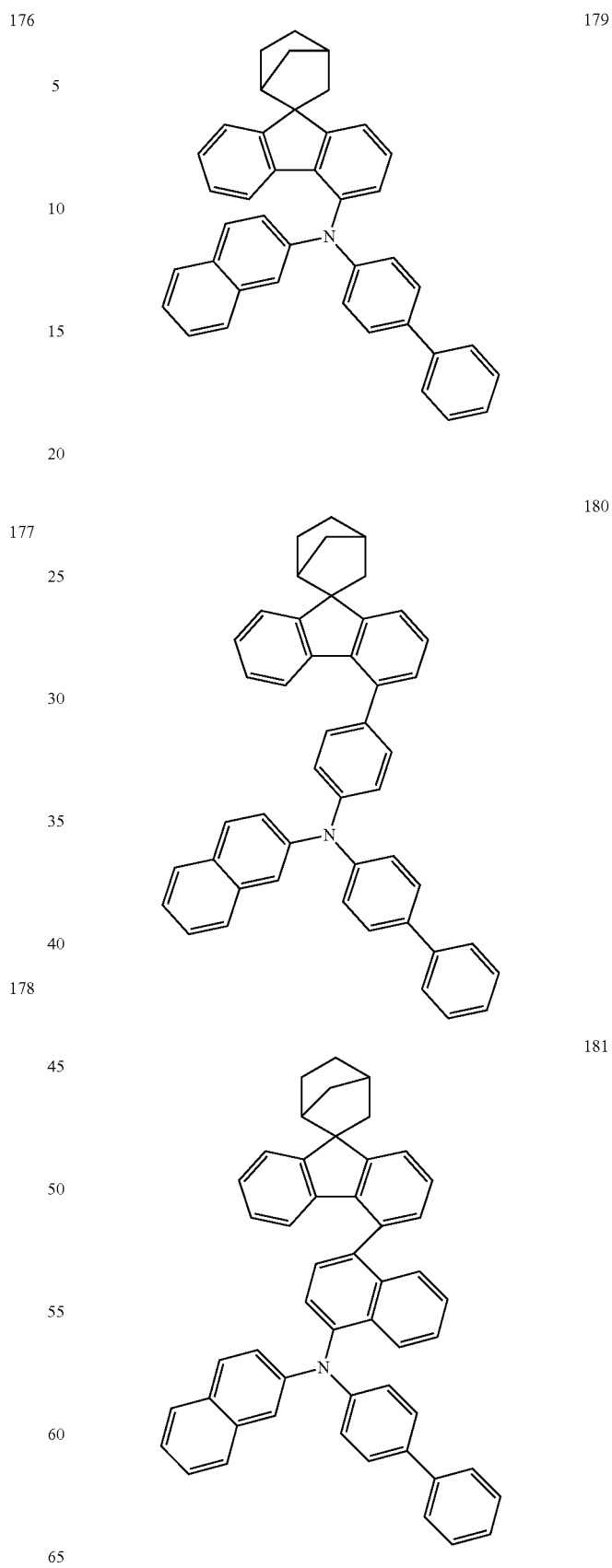

182
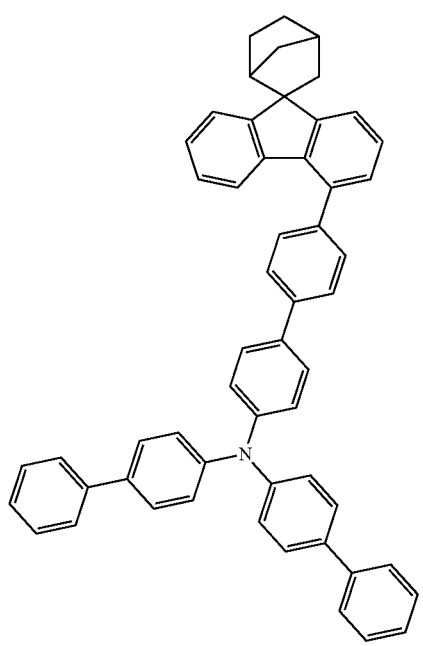
183
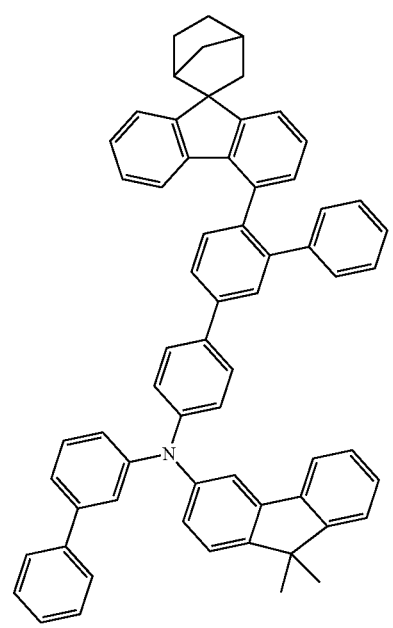
184
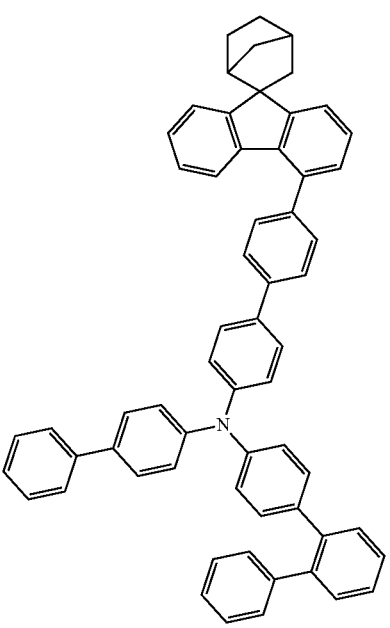
185
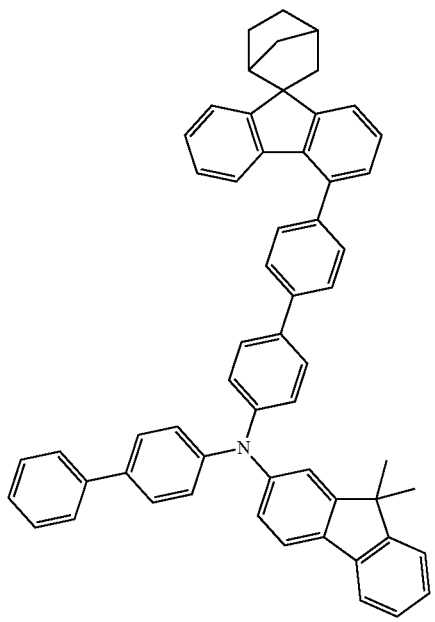

186
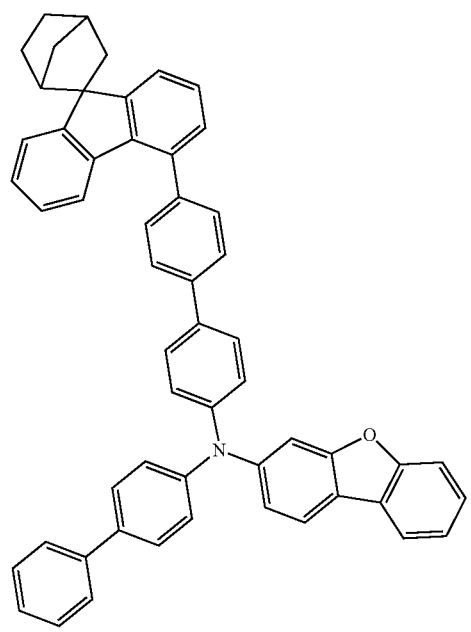
187
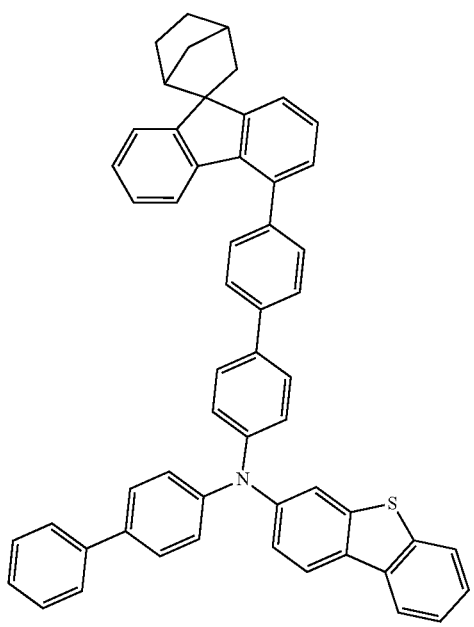
188
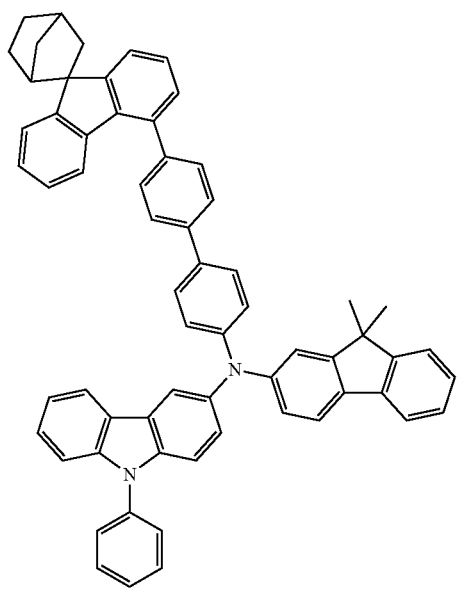
189
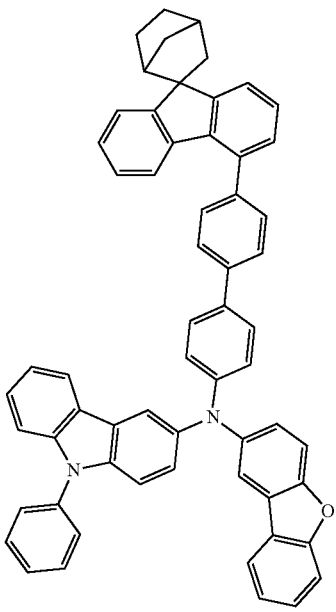

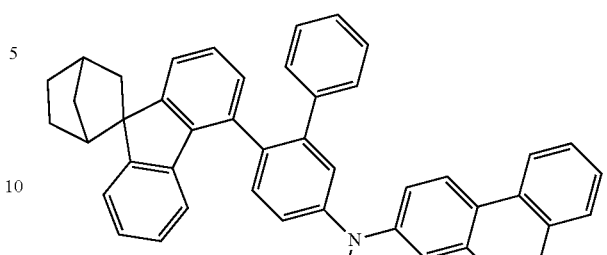
190
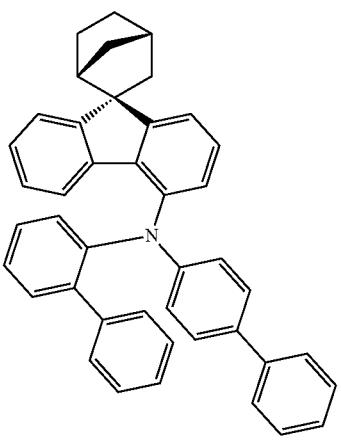
192
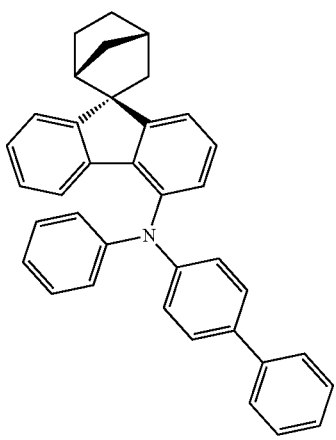
193
194

195
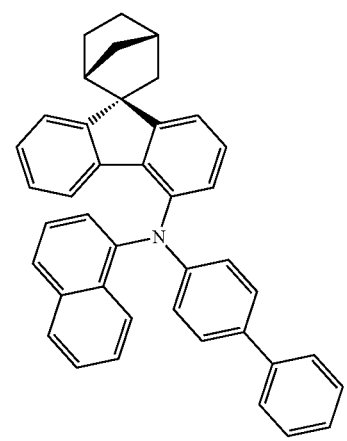
196
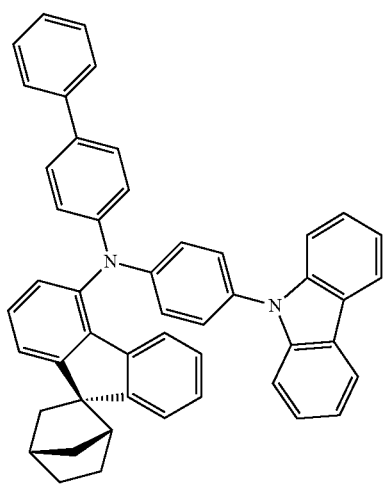
197
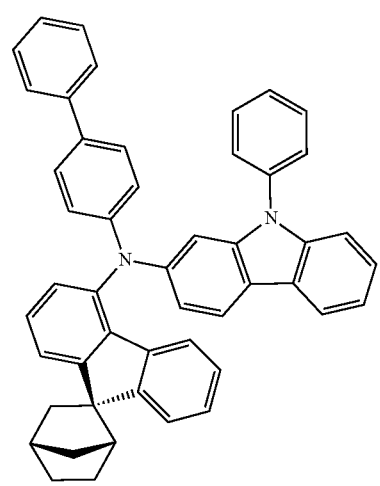
198
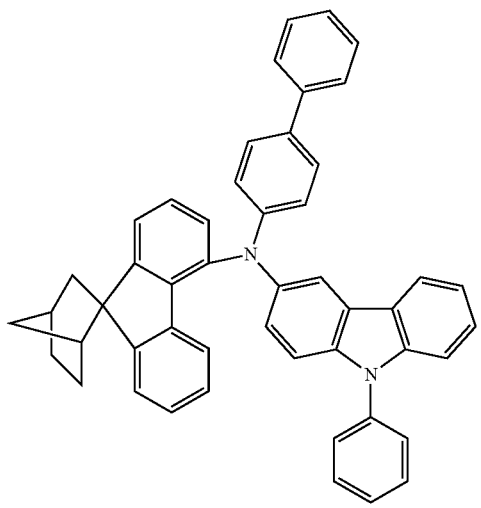
199
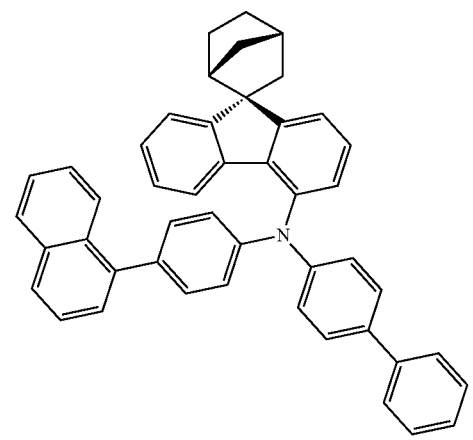
200
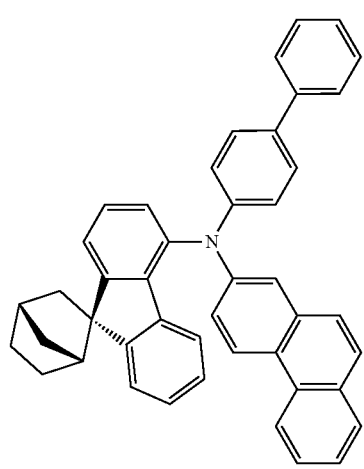

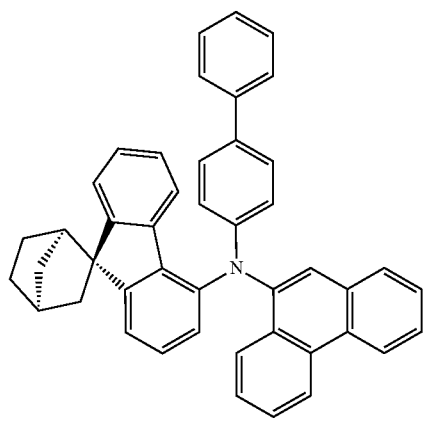
201
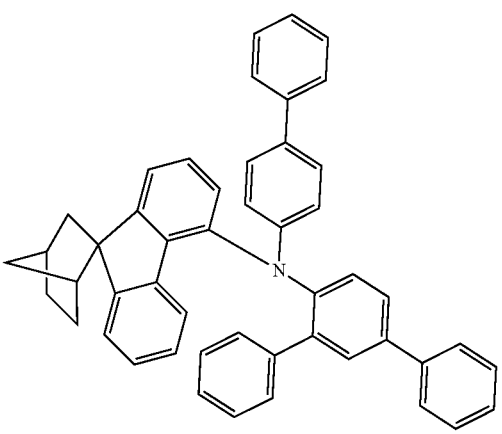
205
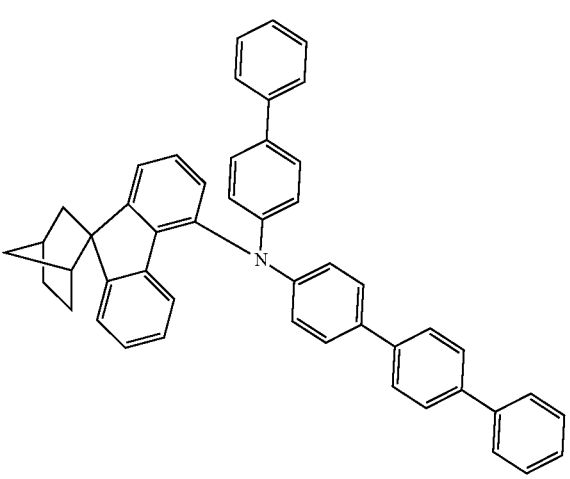
202
206
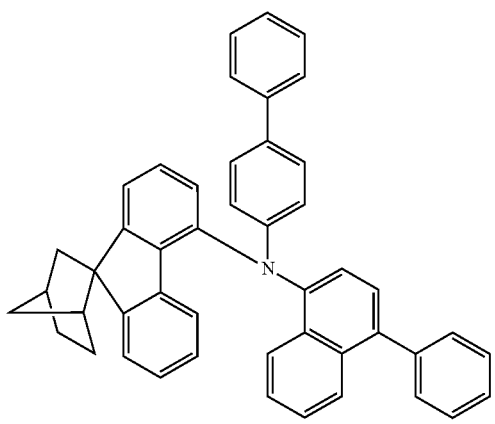
203
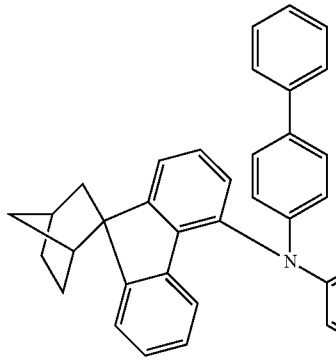
207

204
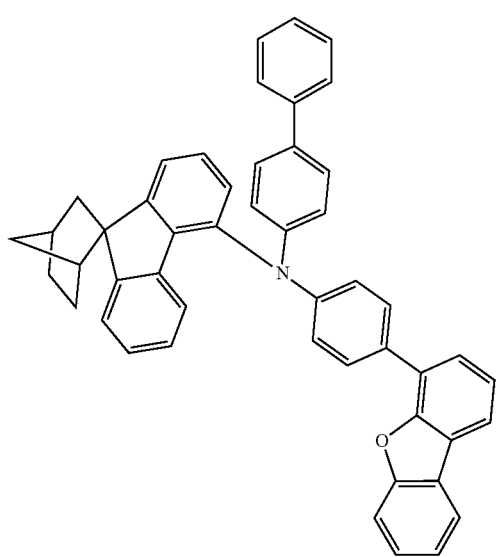
208
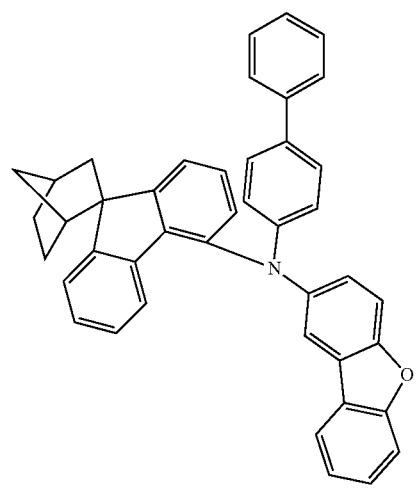
209
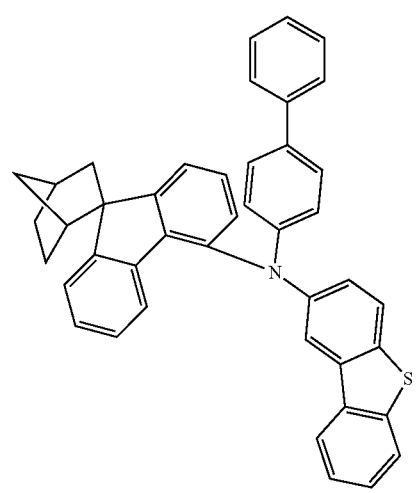
210
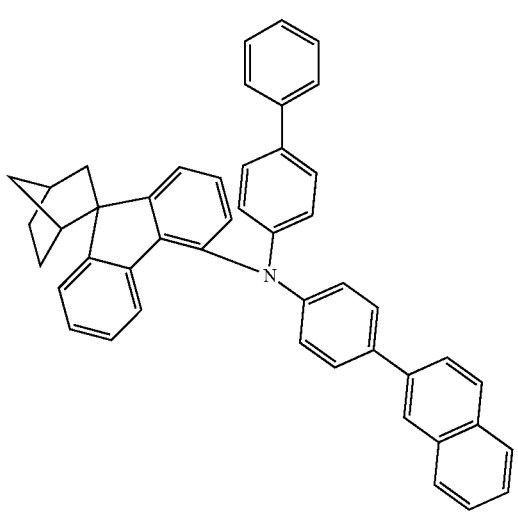
211
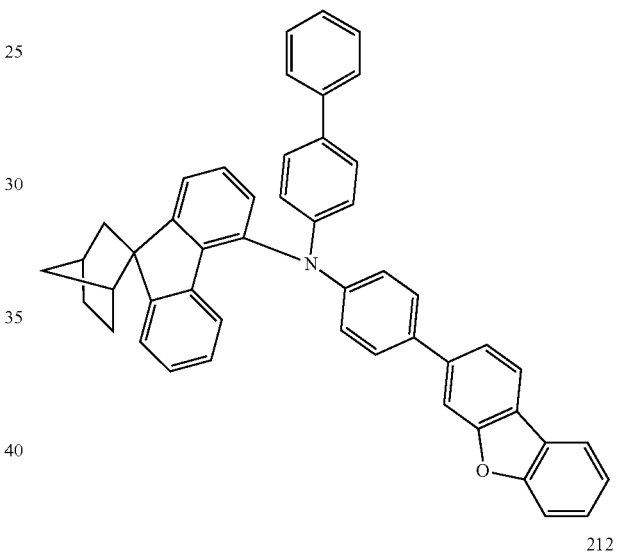
212
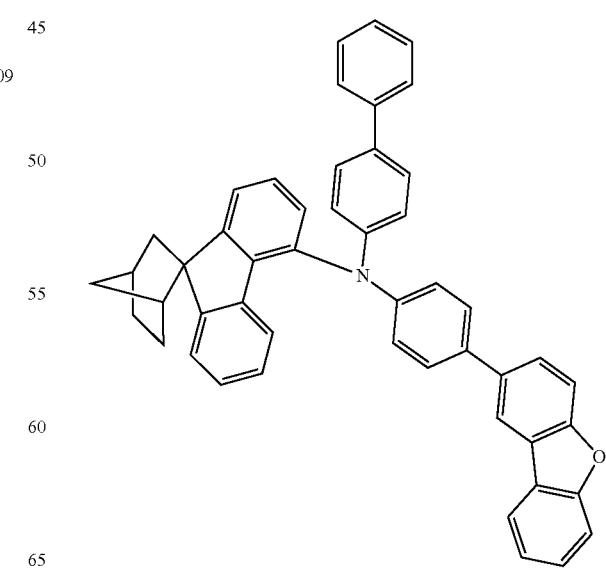

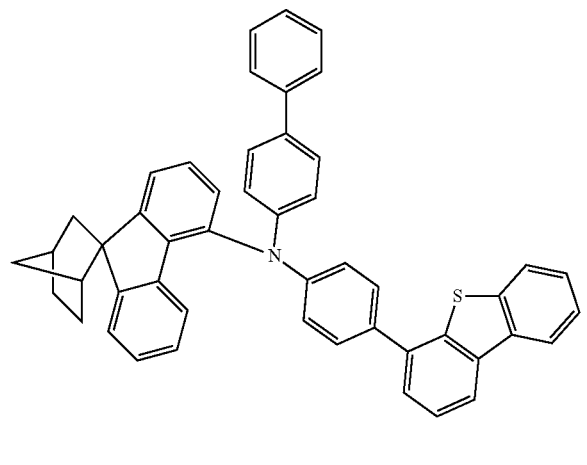
213
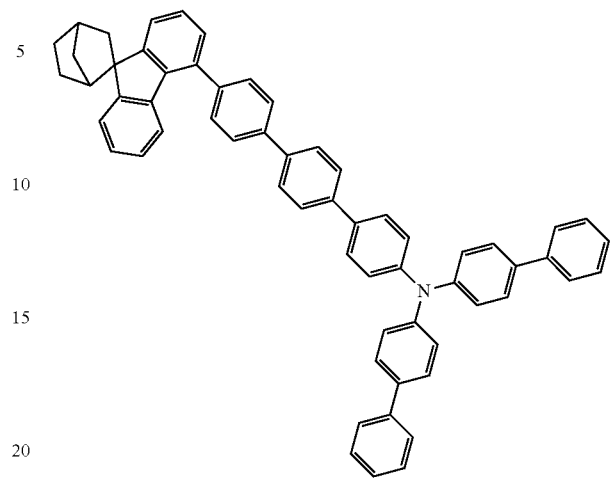
216
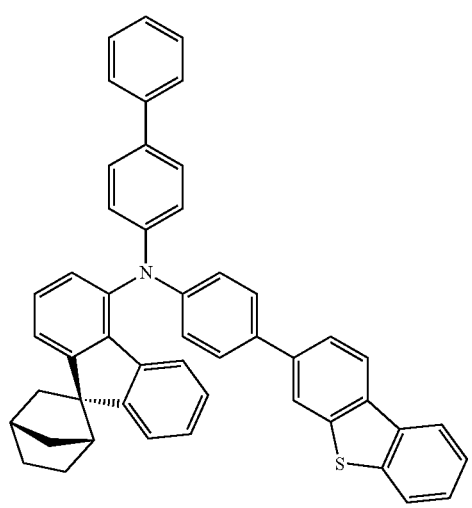
214
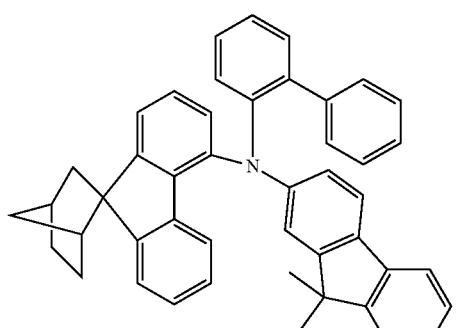
217
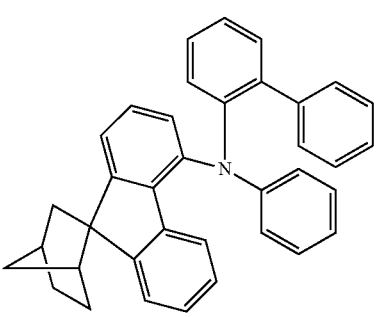
218
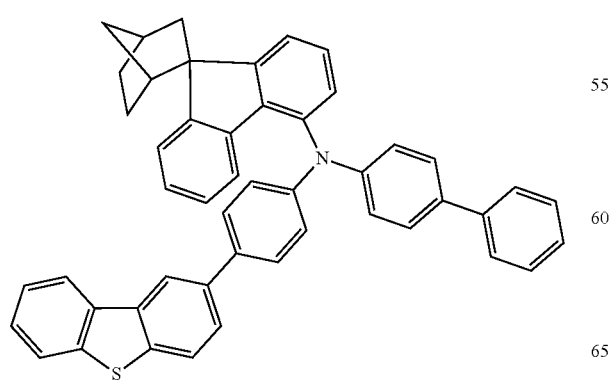
215
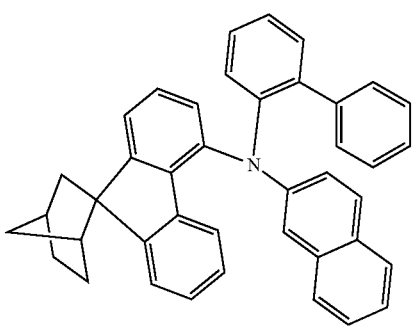
219

220
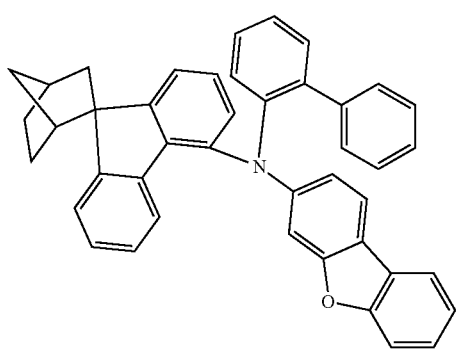
221
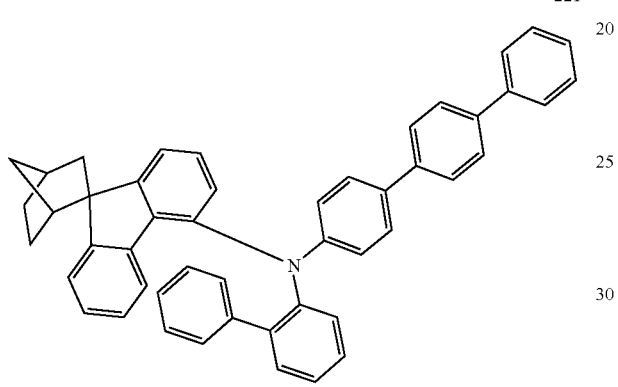
222
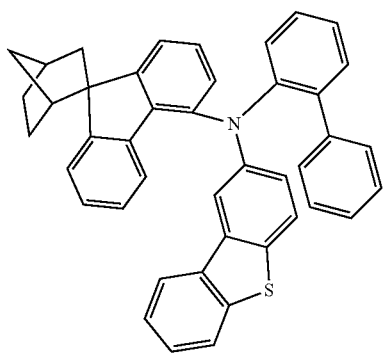
223
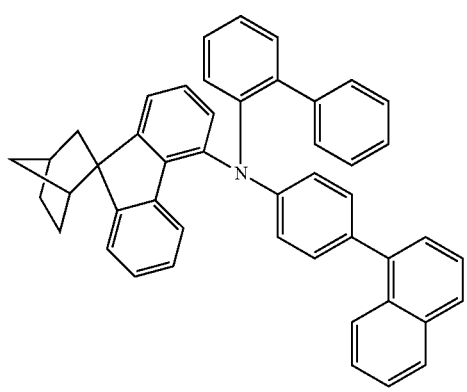
224
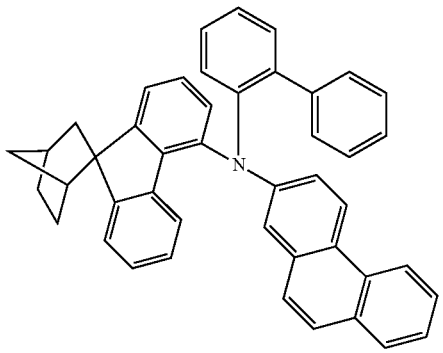
225
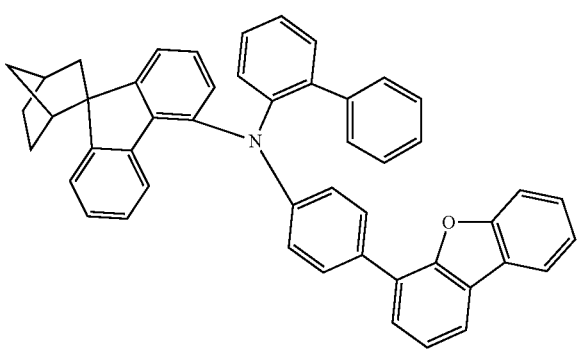
226
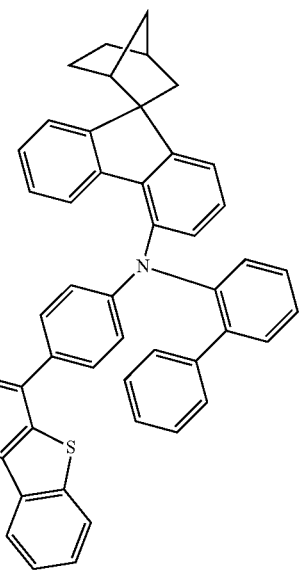

227 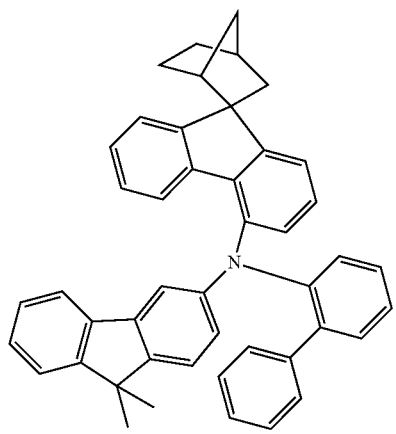
228 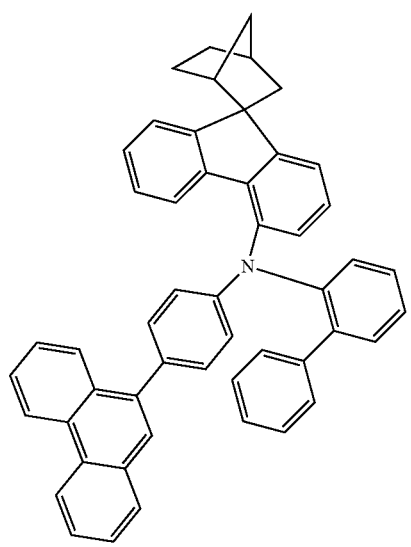
229 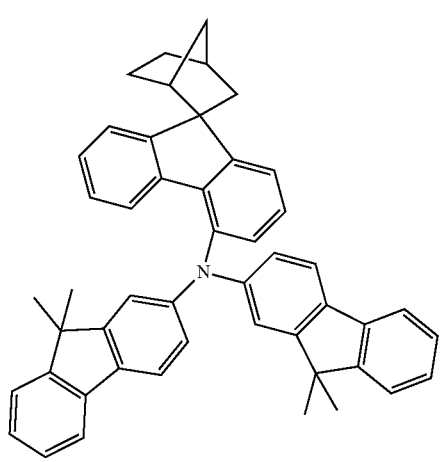
230 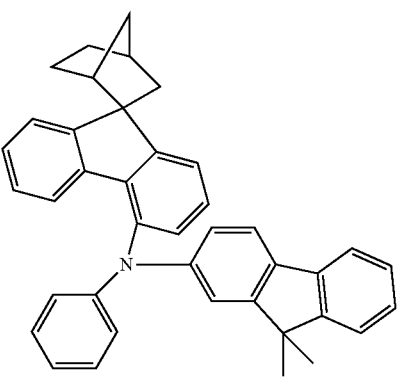
231 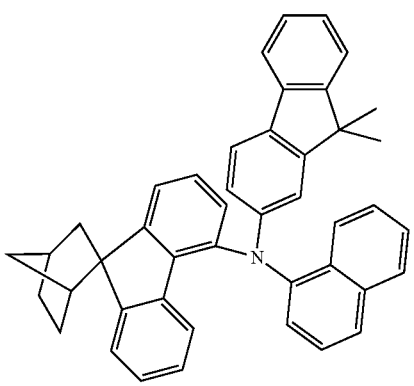
232 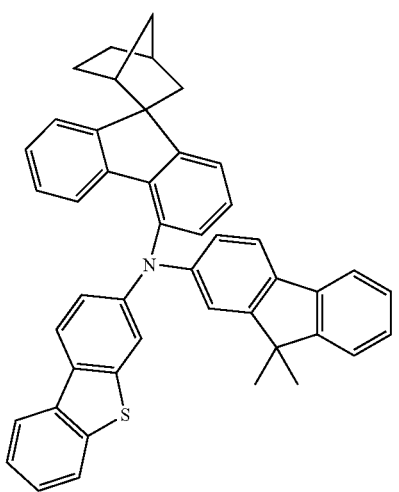

233
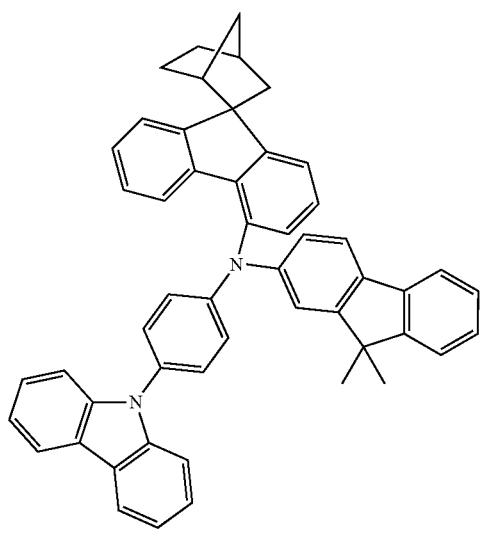
236
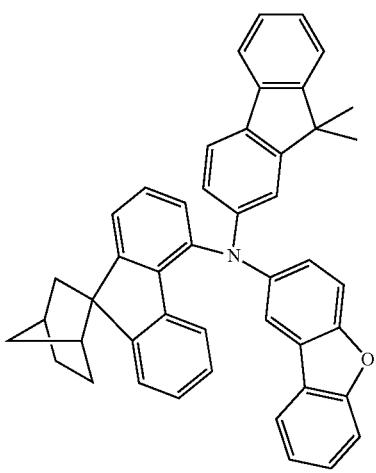
234
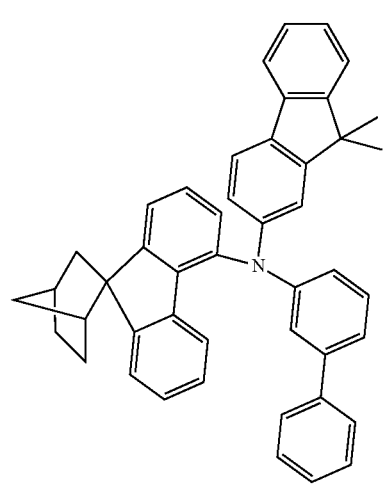
237
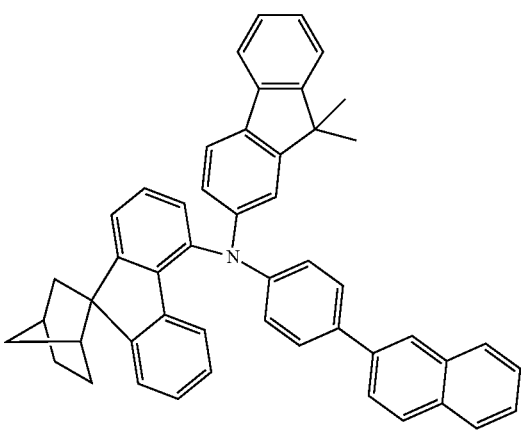
235
238
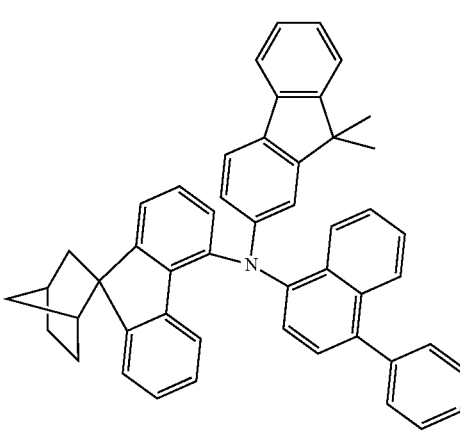

-continued
239
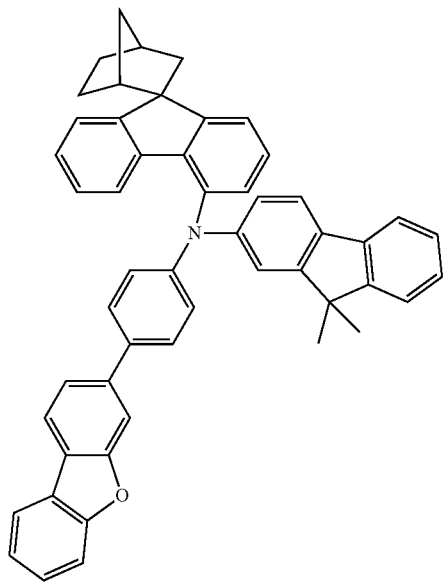
240
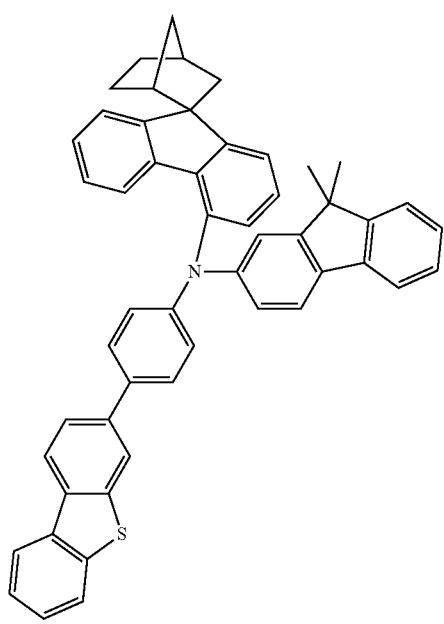
241
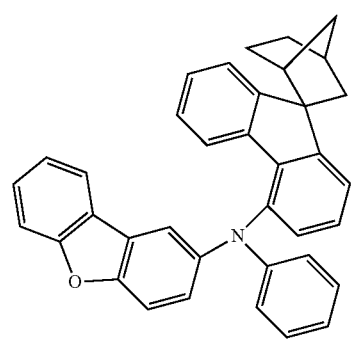
-continued
242
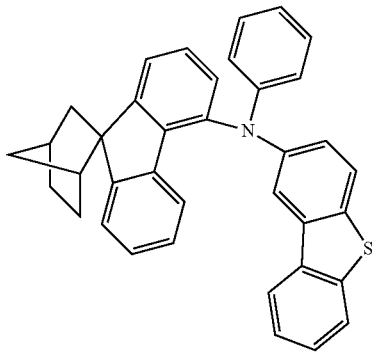
243
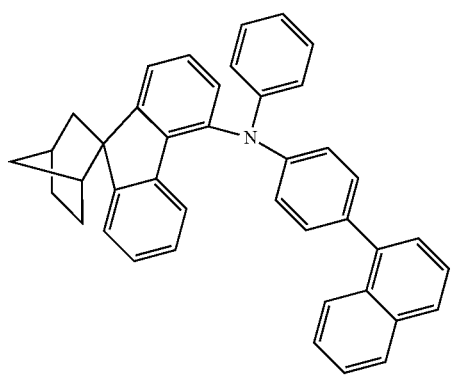
244
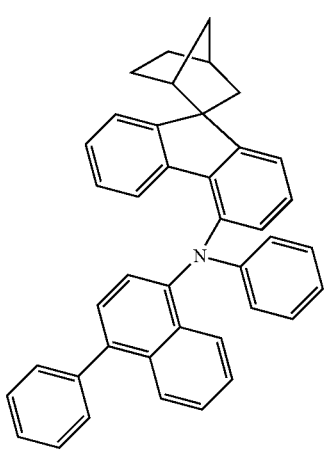

245
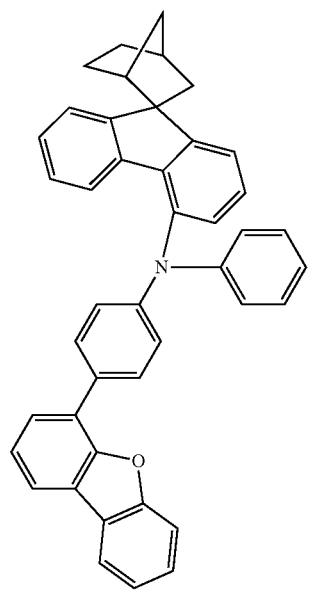
246
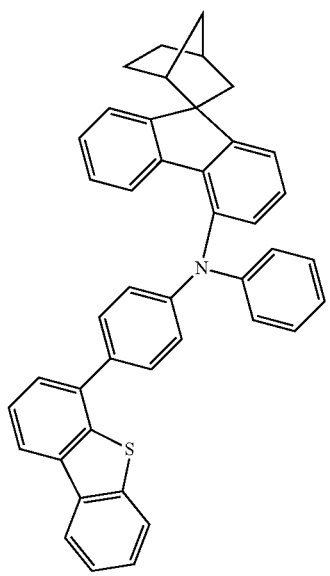
247
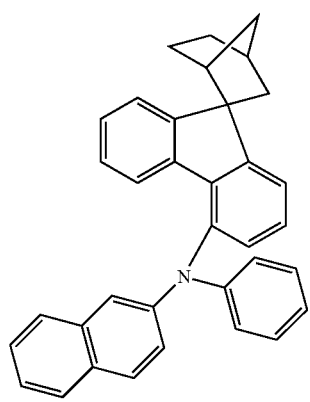
248
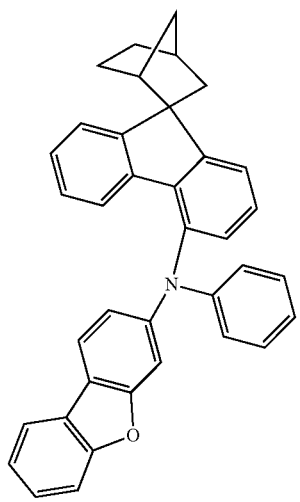
249
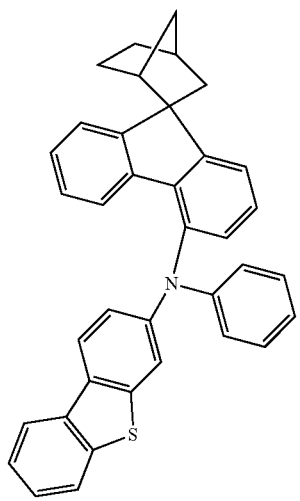
250
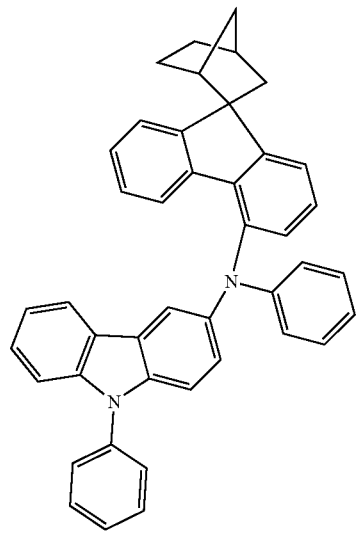

251
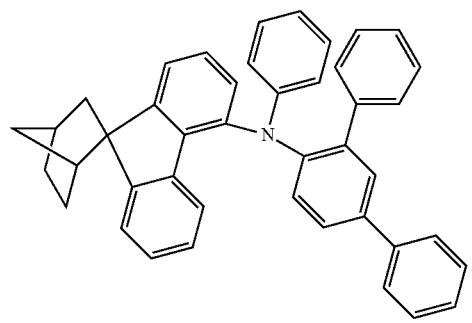
252
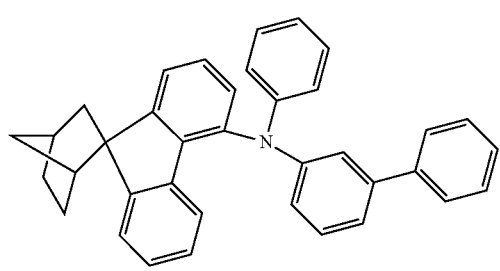
253
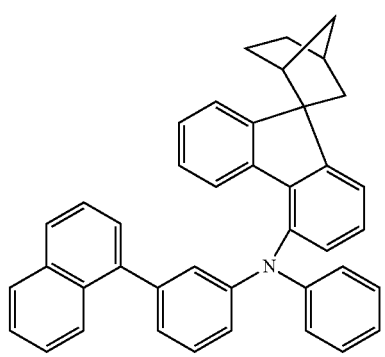
254
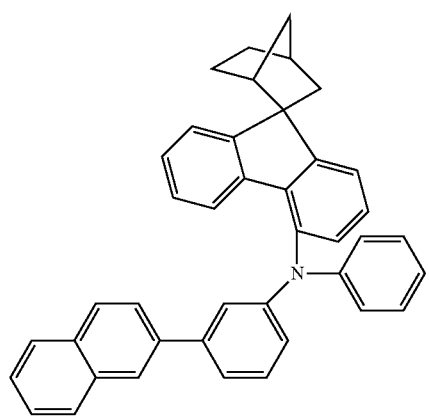
255
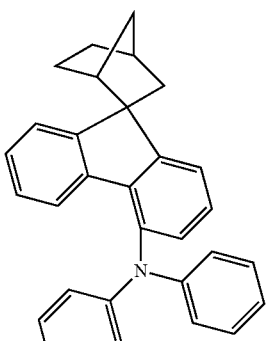
256
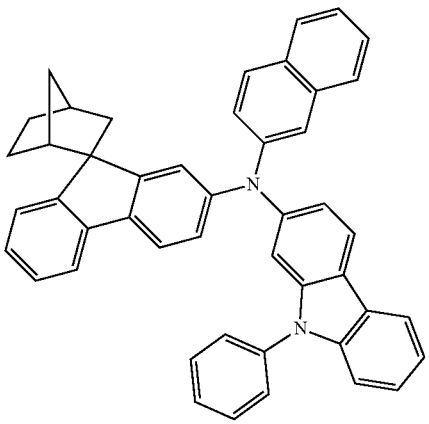
257
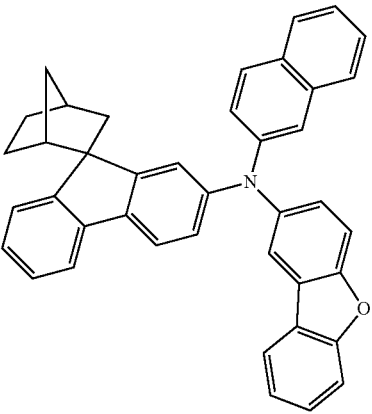

-continued
258
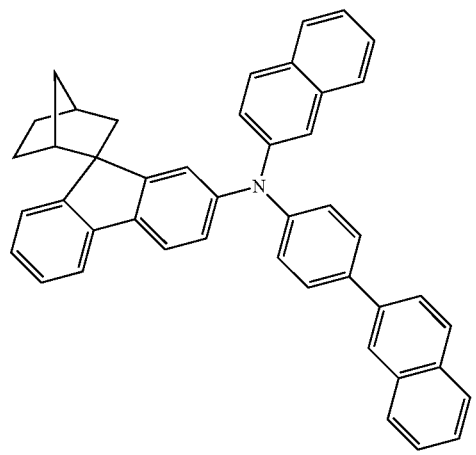
259
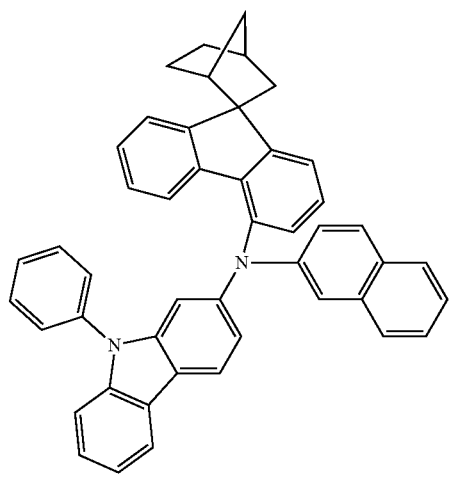
260
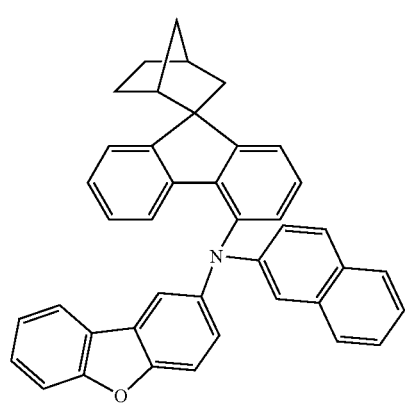
-continued
261
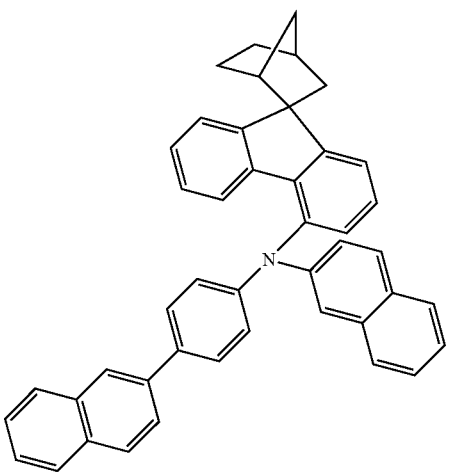
262
263
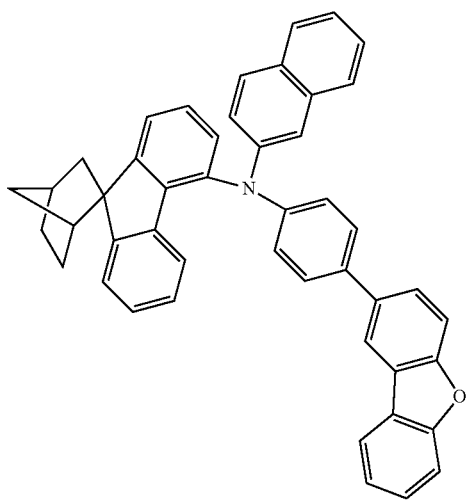

111
-continued
264
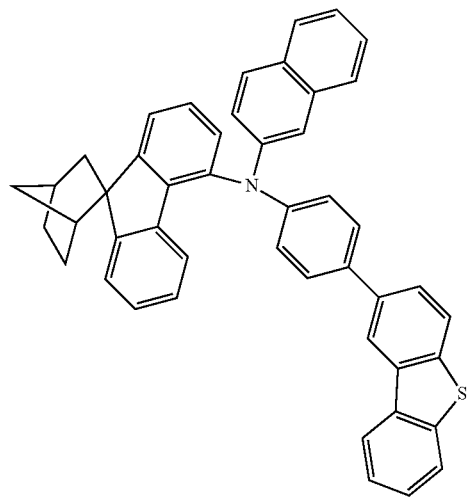
265
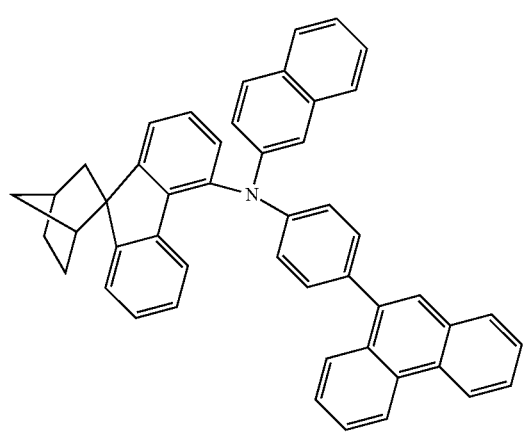
266
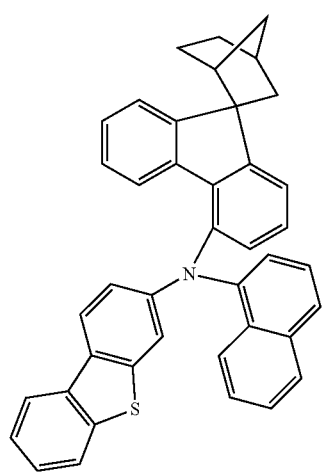
112
-continued
267
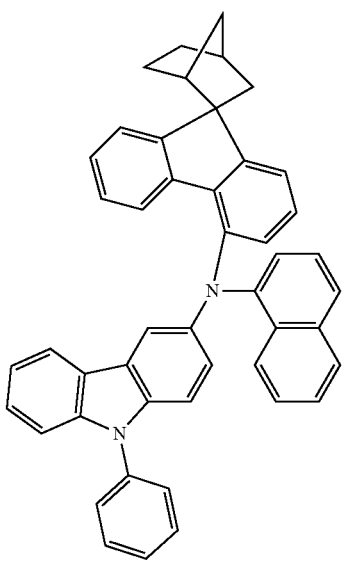
268
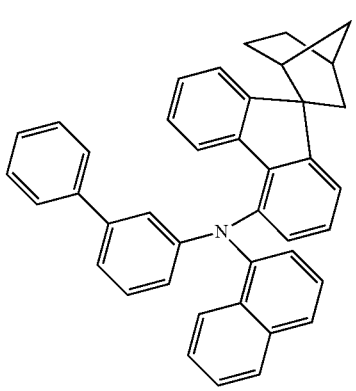
269

-continued
270
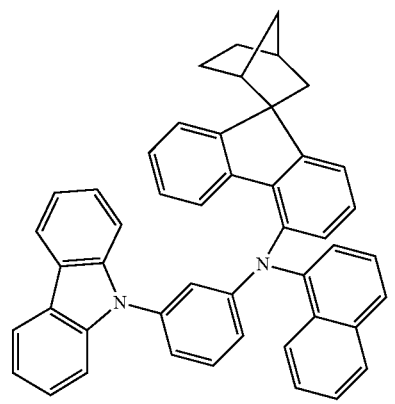
271
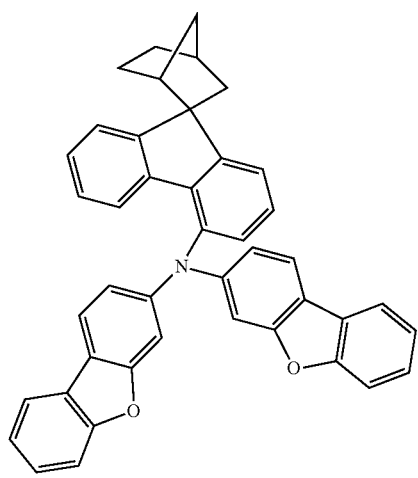
272
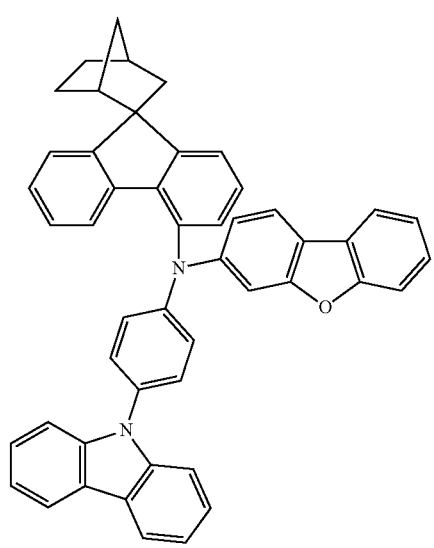
-continued
273
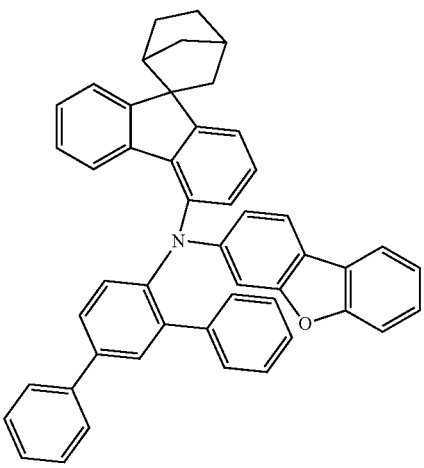
274
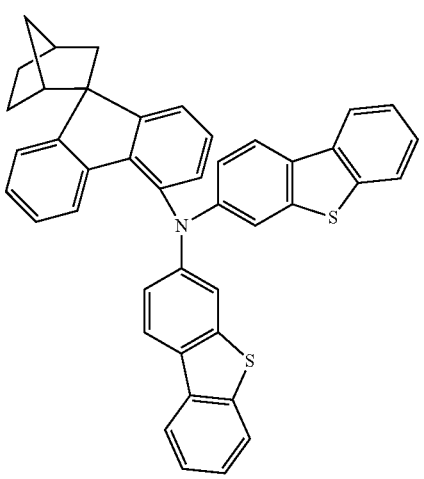
275
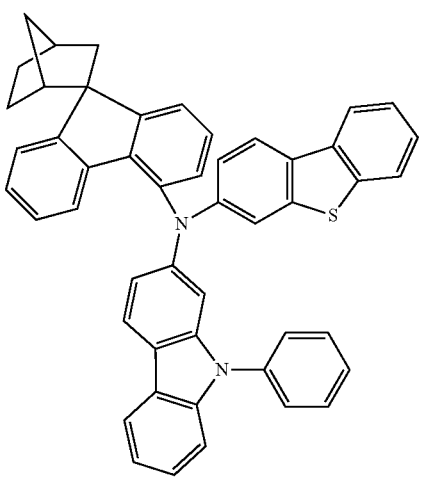

277
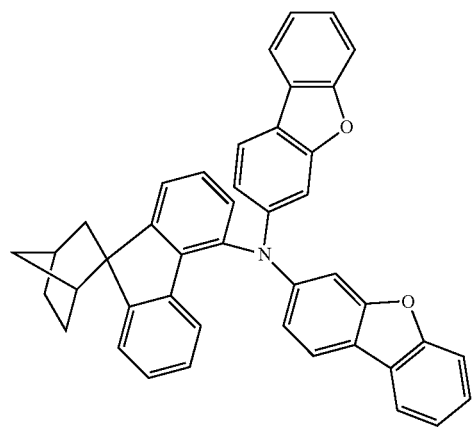
278
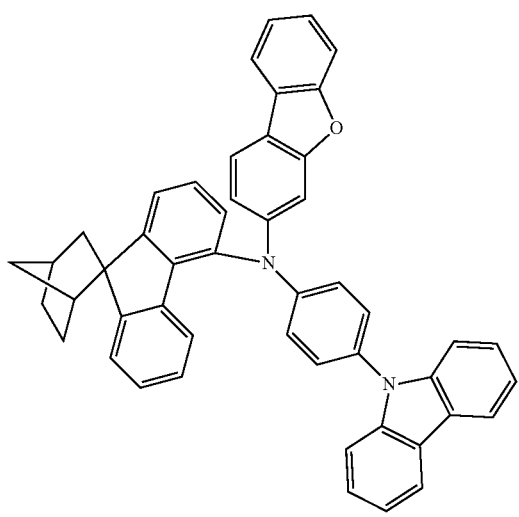
279
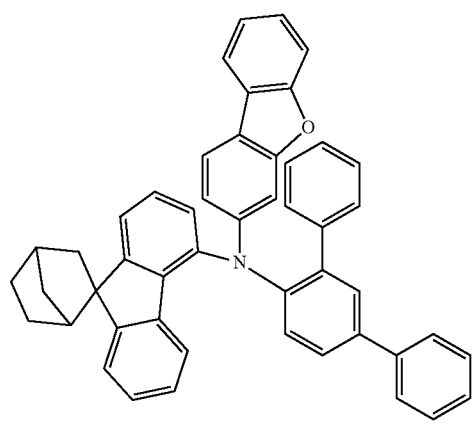
276
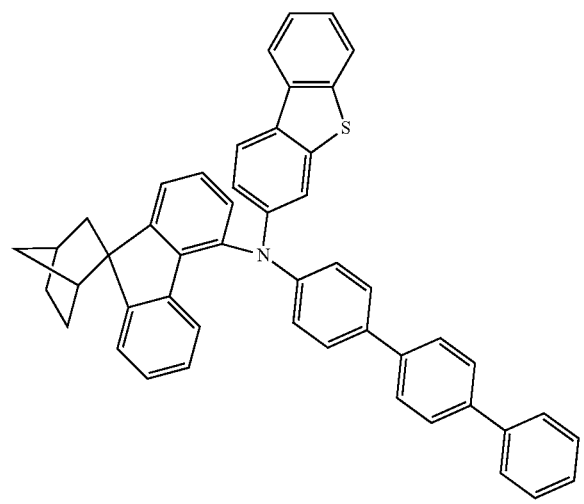
280
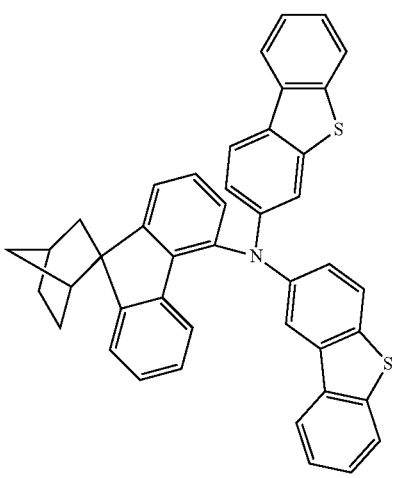
281
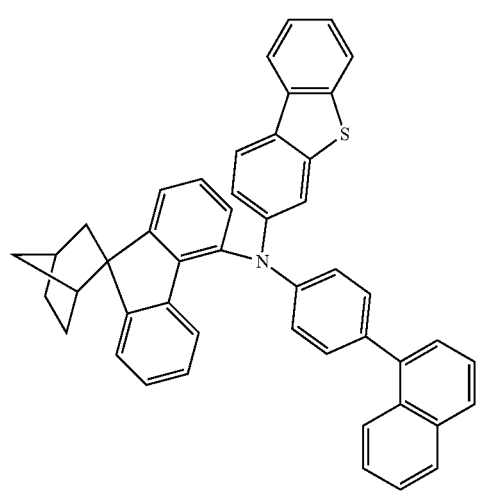

282
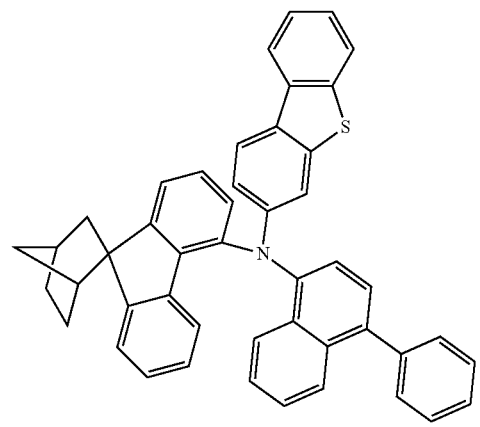
283
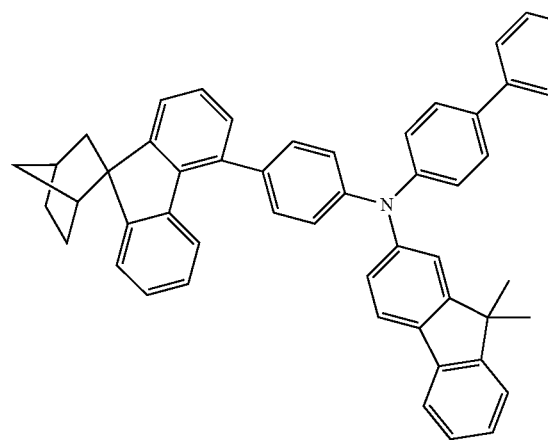
284
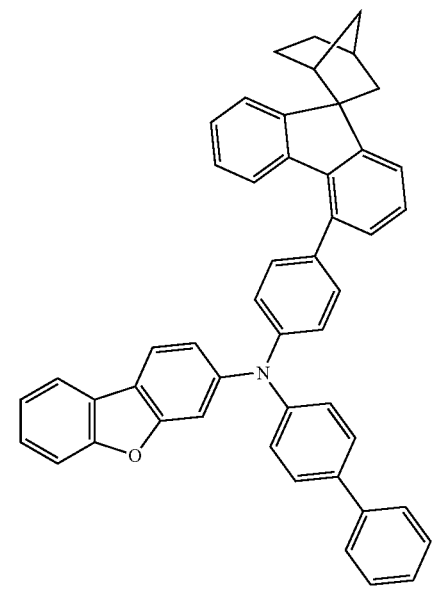
285
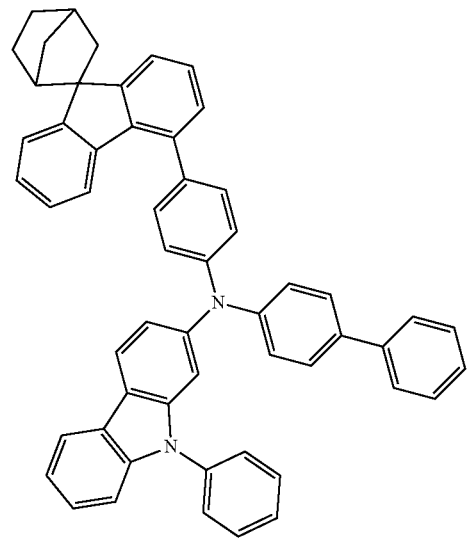
286
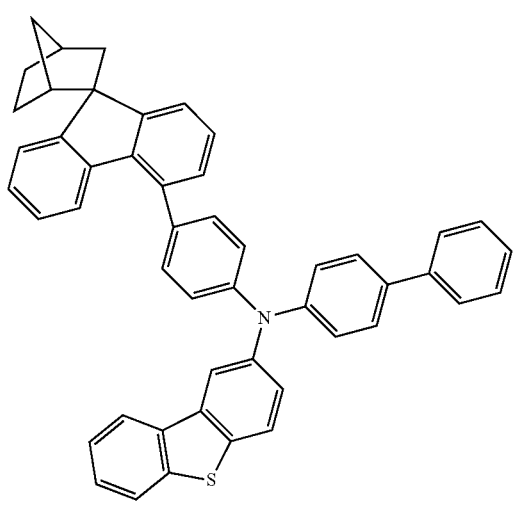
287
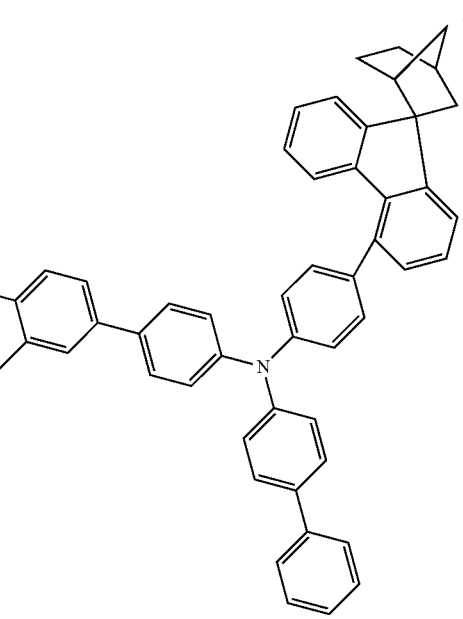

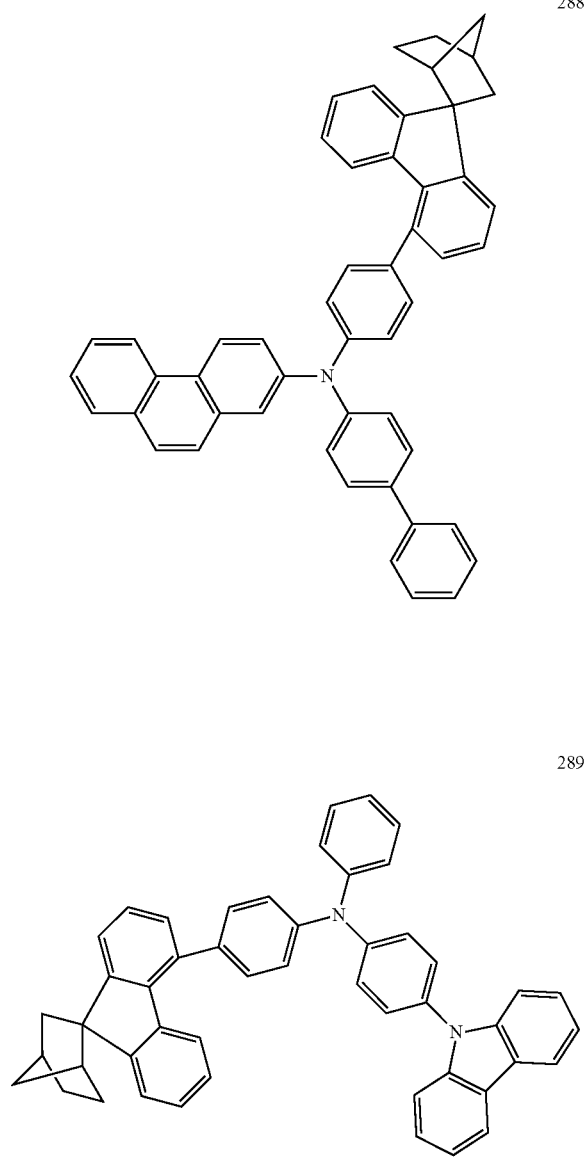
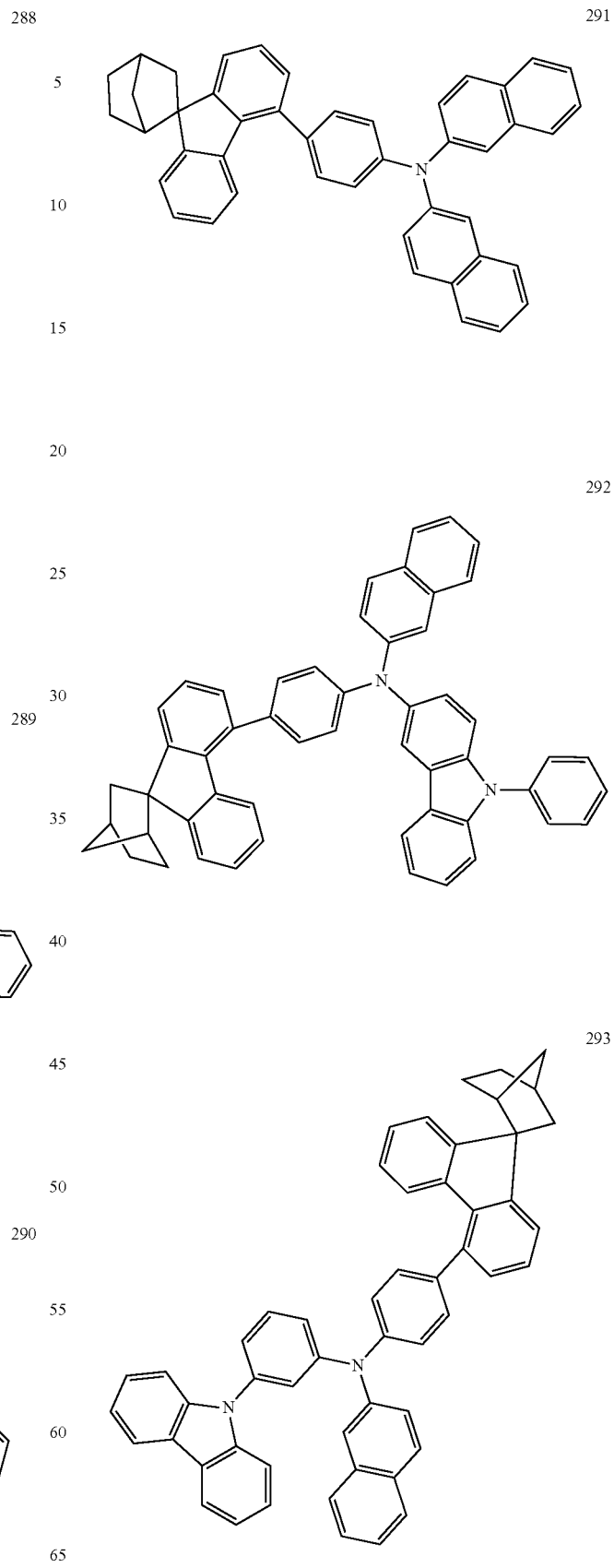

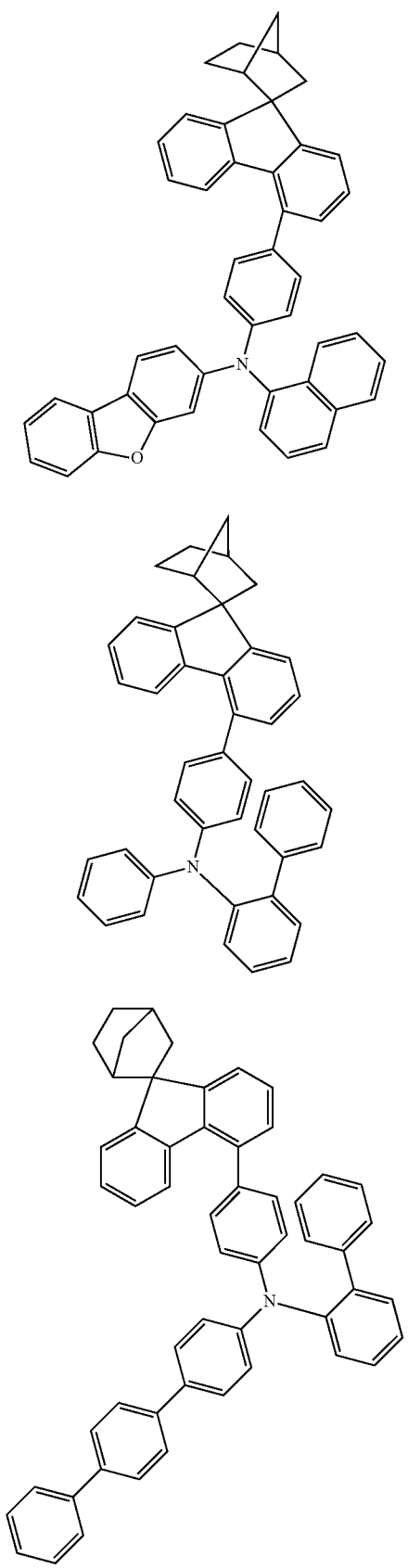
294
295
296
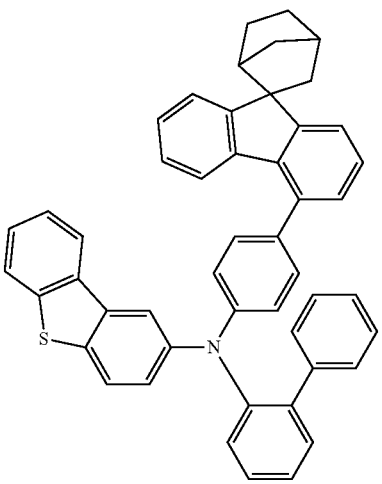
297
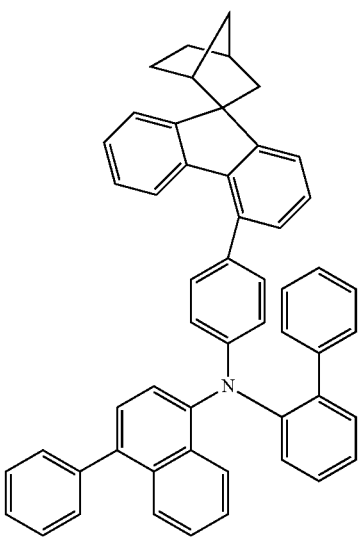
298
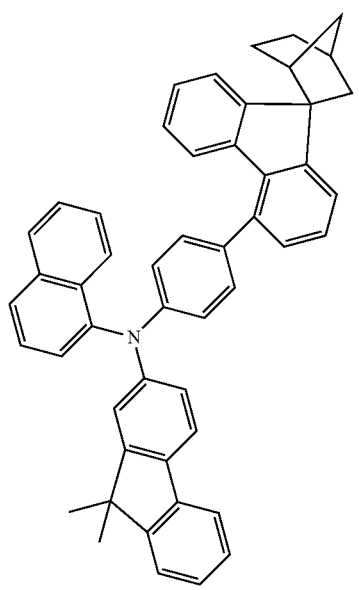
299

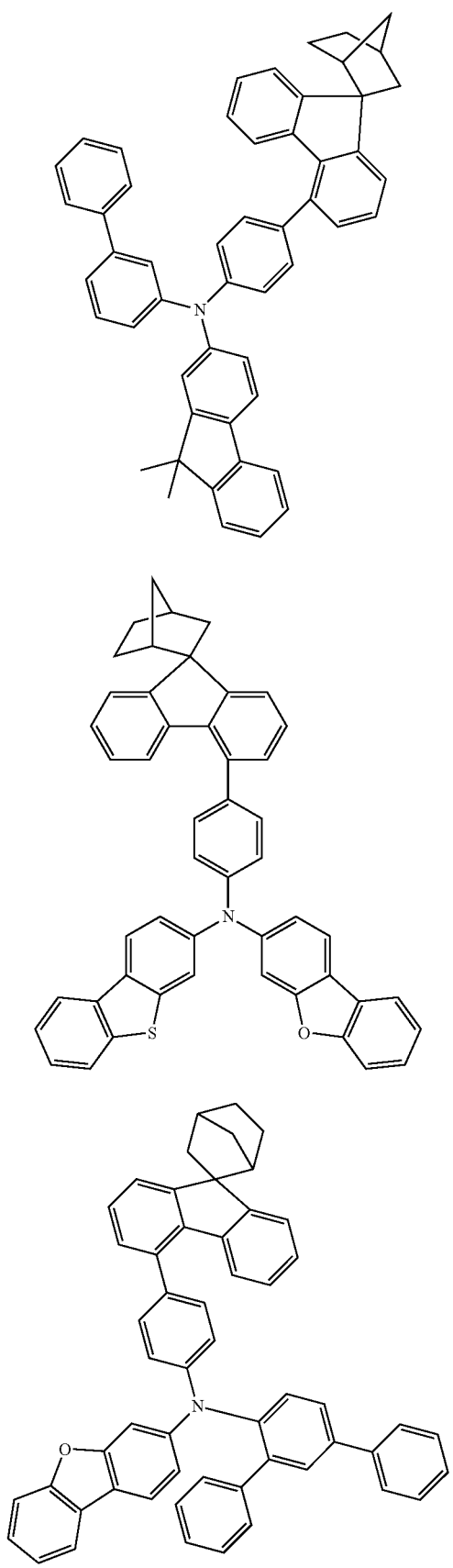
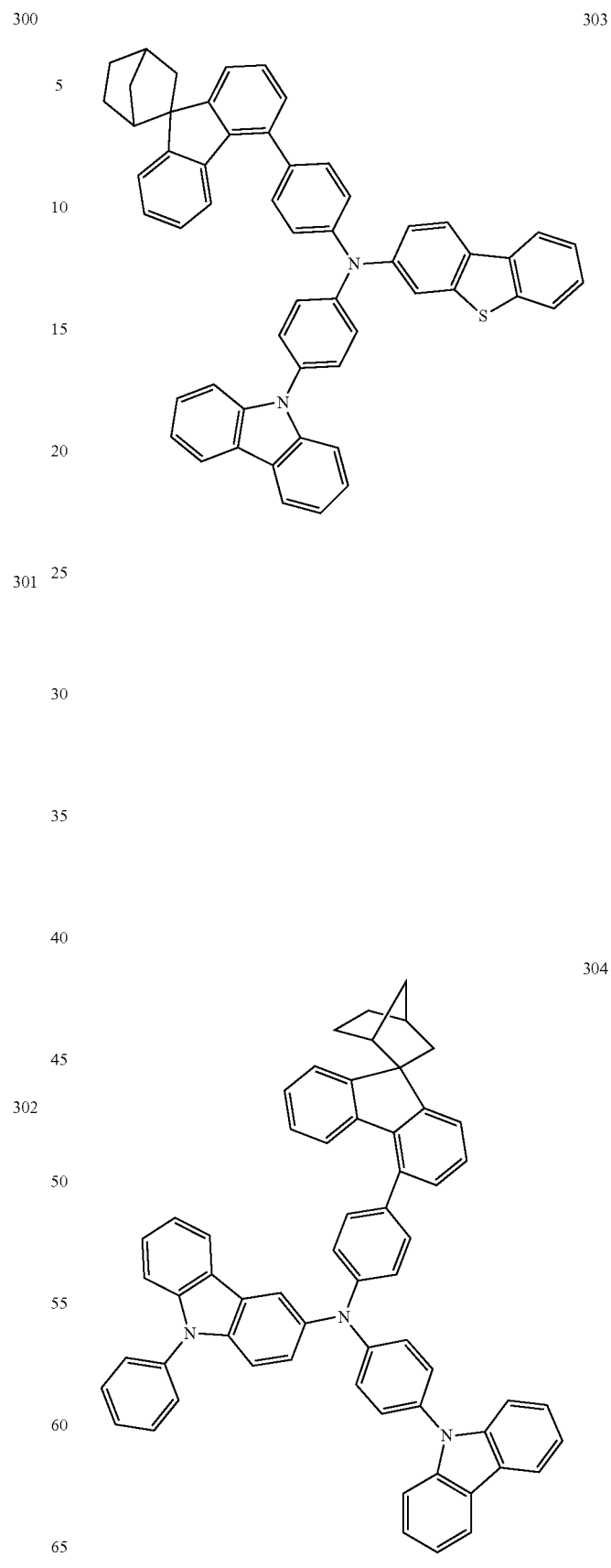

125
-continued
305
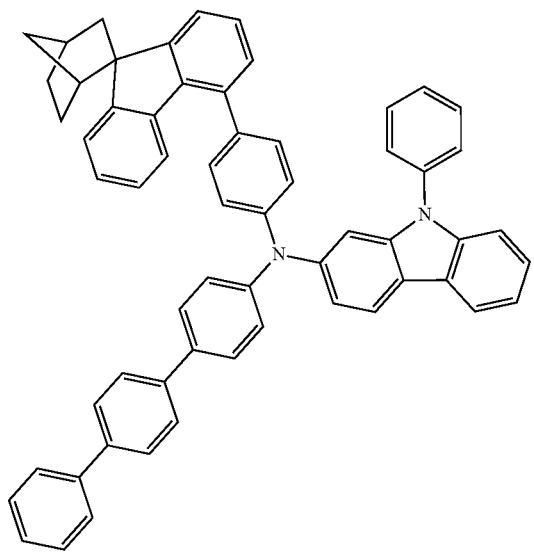
306
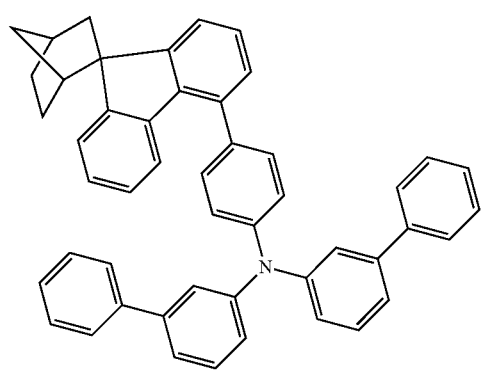
307
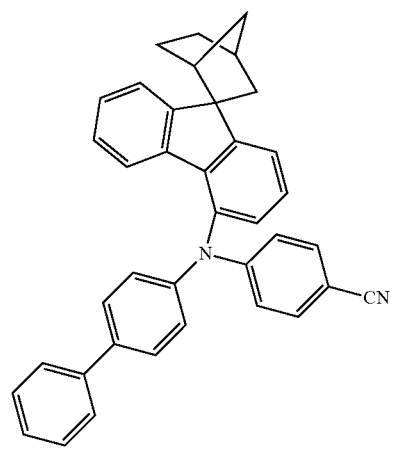
126
-continued
308
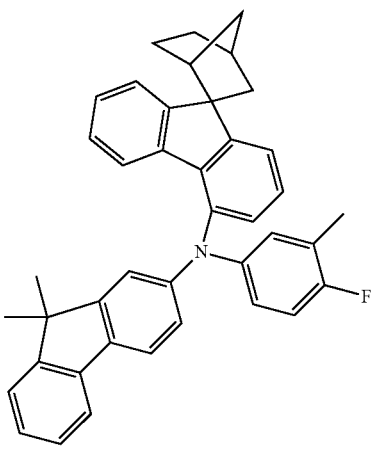
309
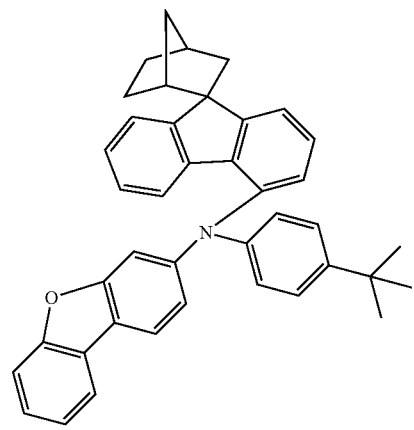
310
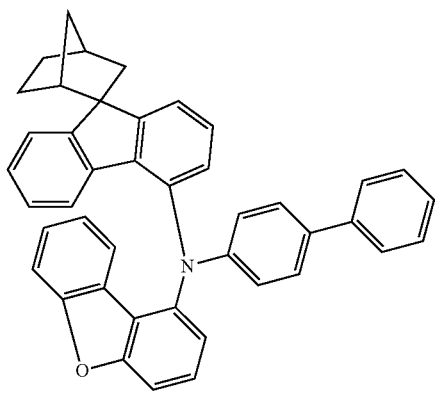

127
-continued
128
-continued
311
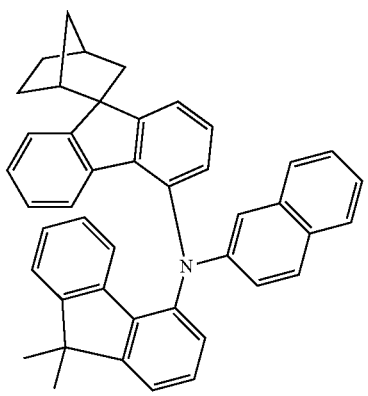
314
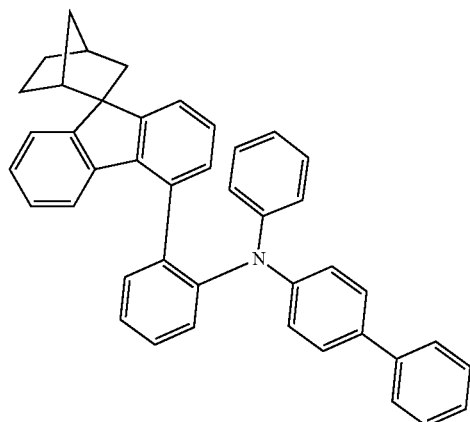
312
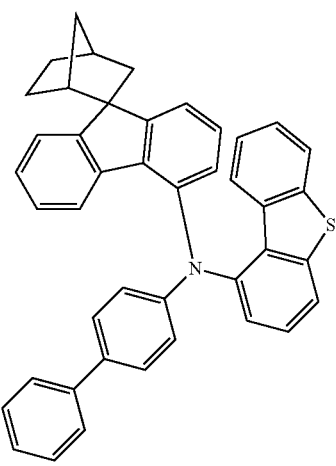
315
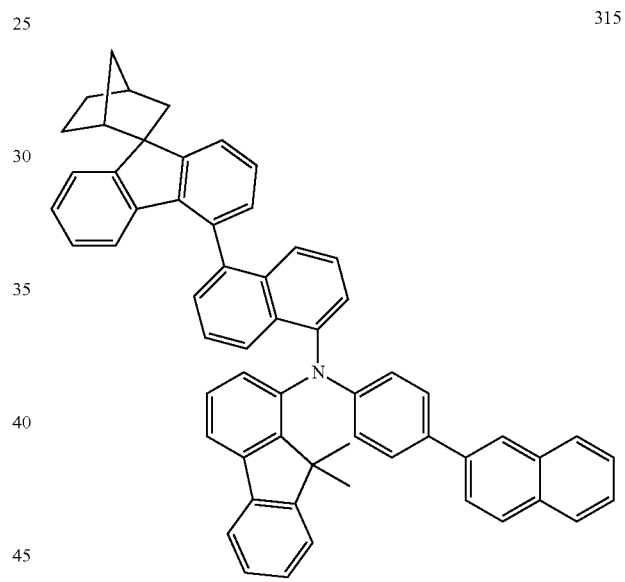
313
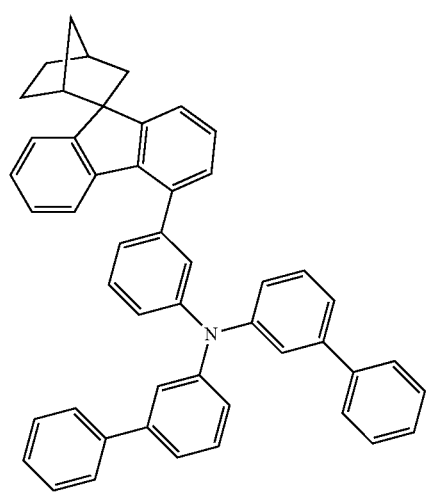
316
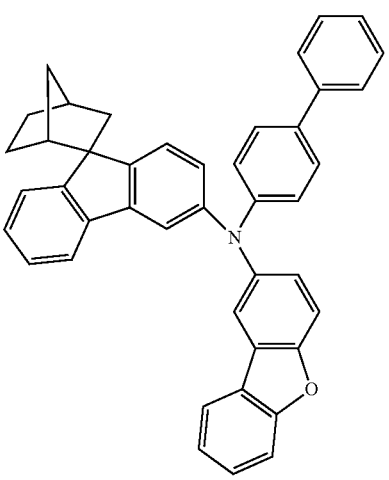

317
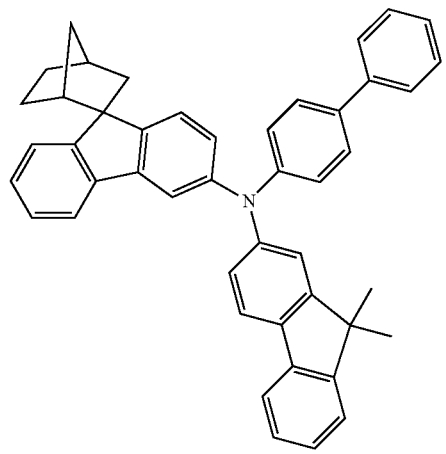
320
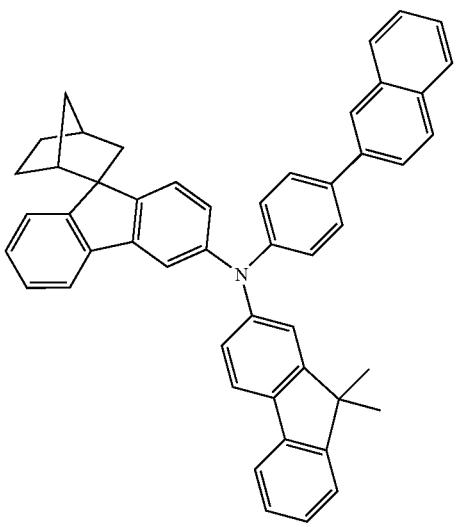
318
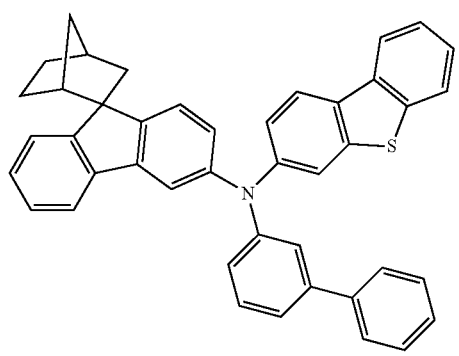
321
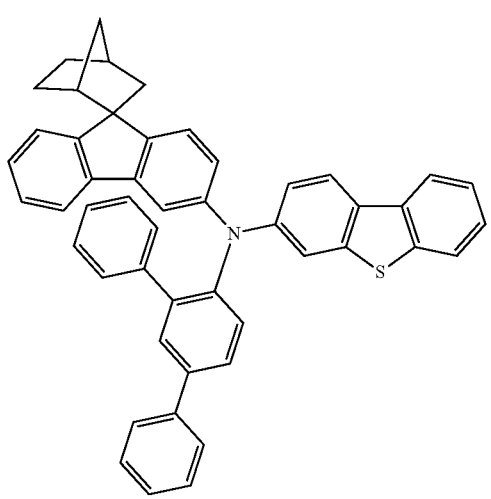
319
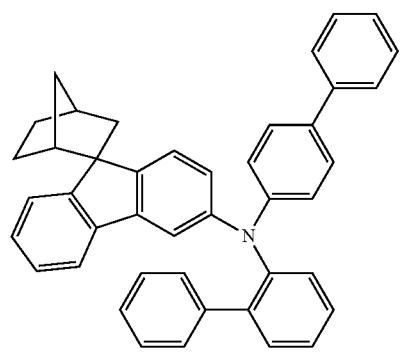
322
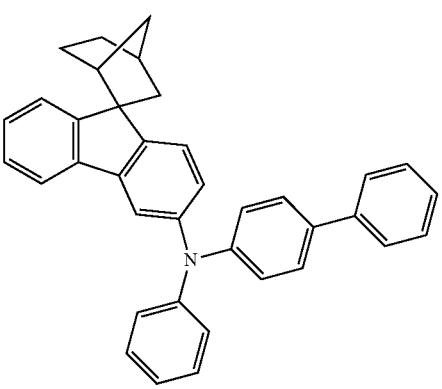

323
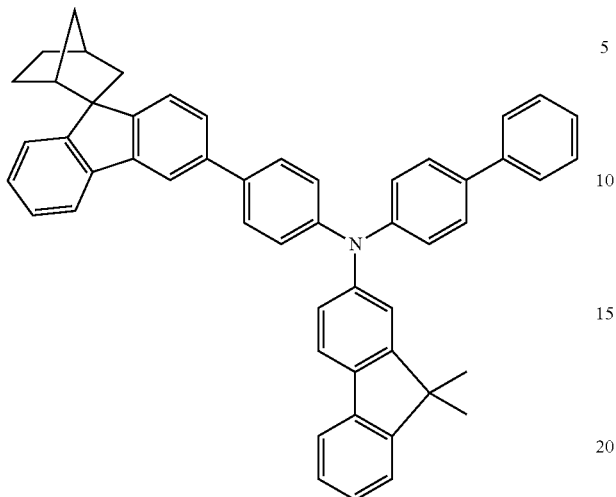
324
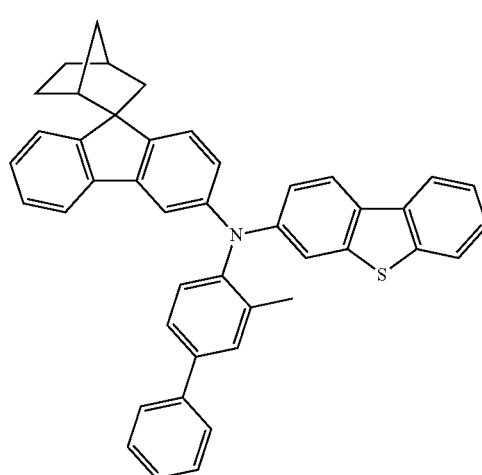
325
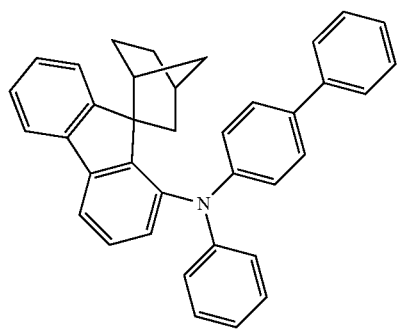
326
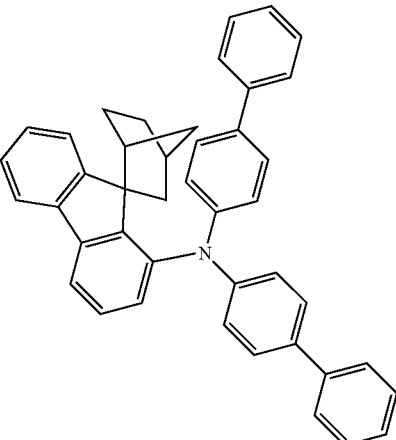
327
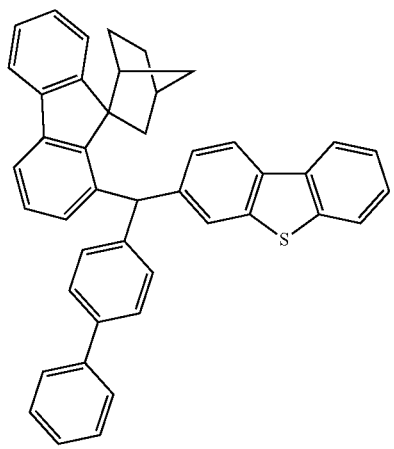
328
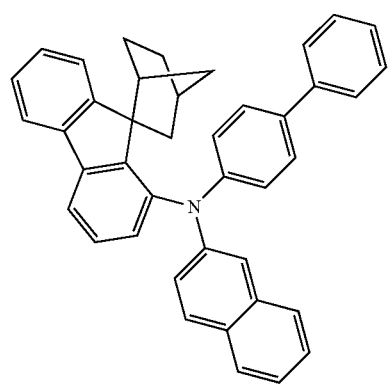

133
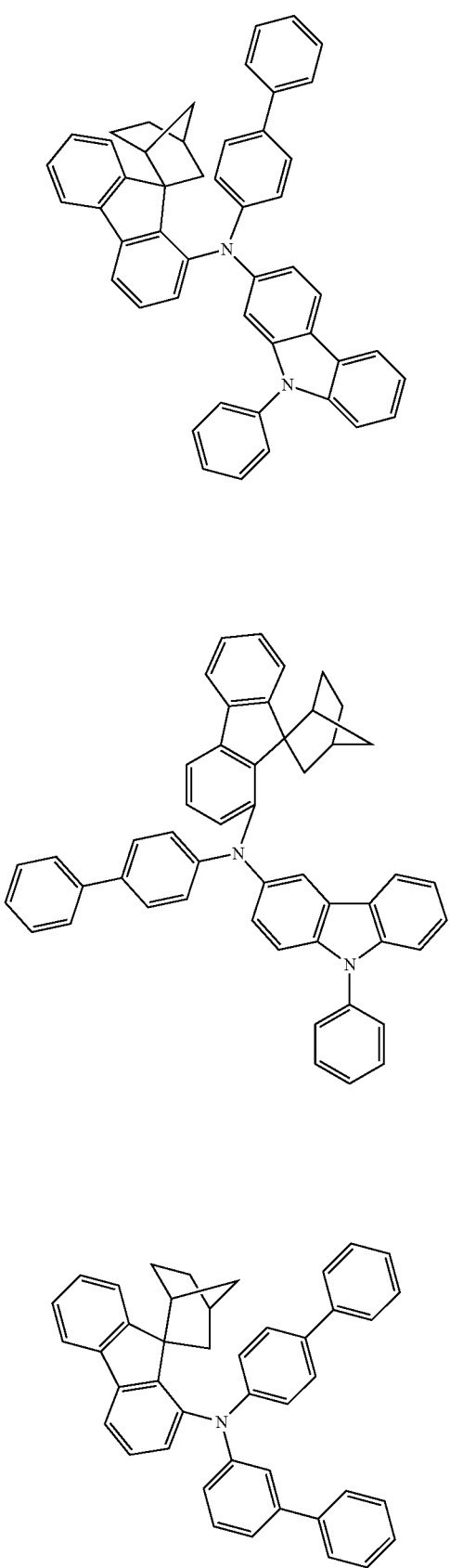
134
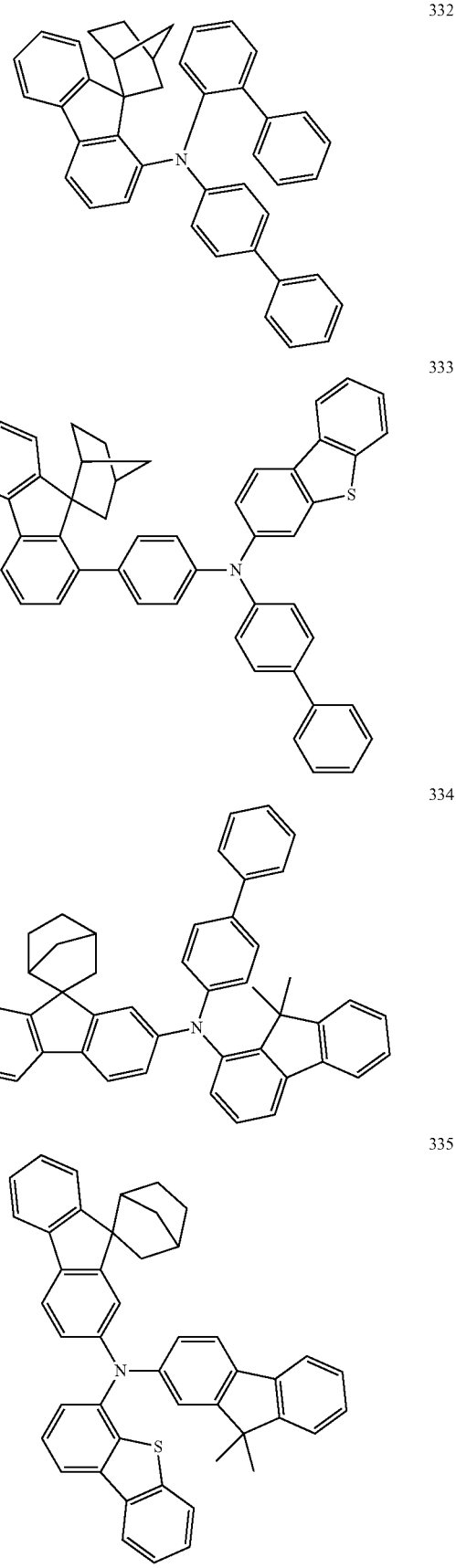

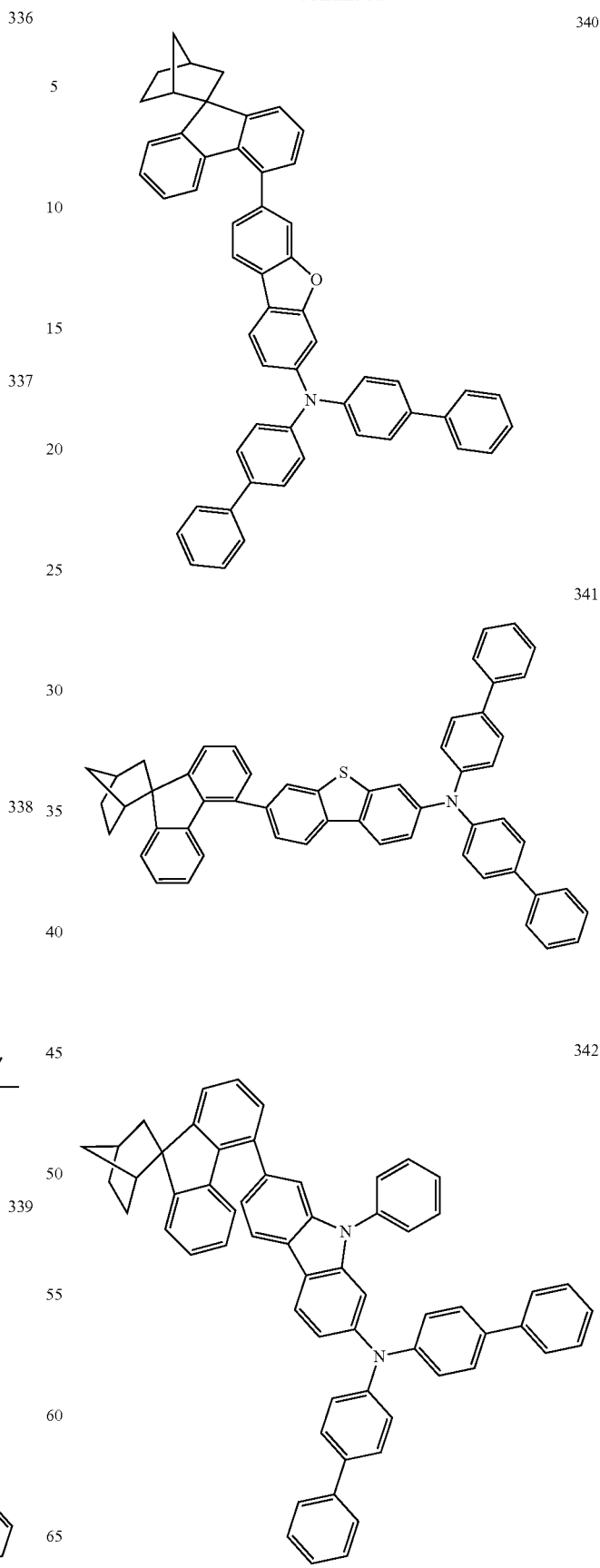

343
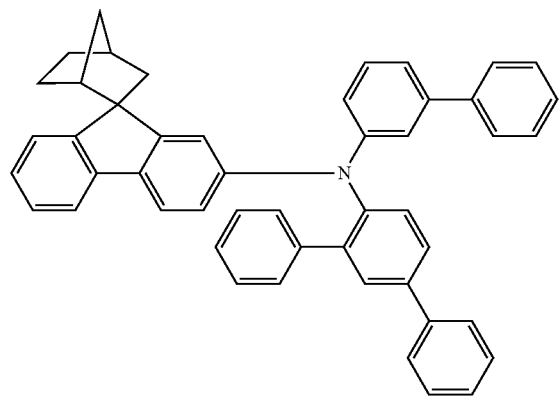
344
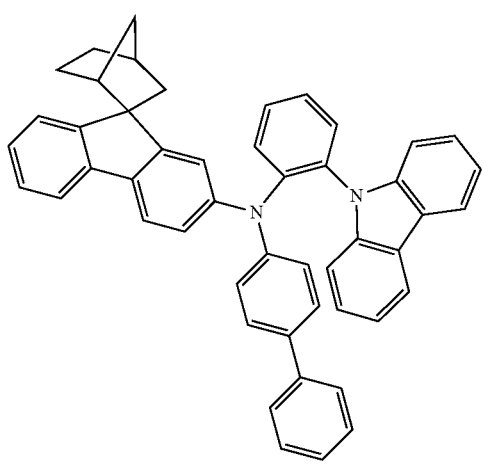
345
347
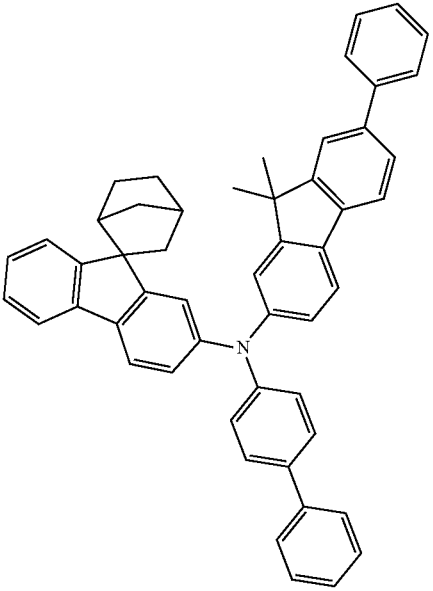
348
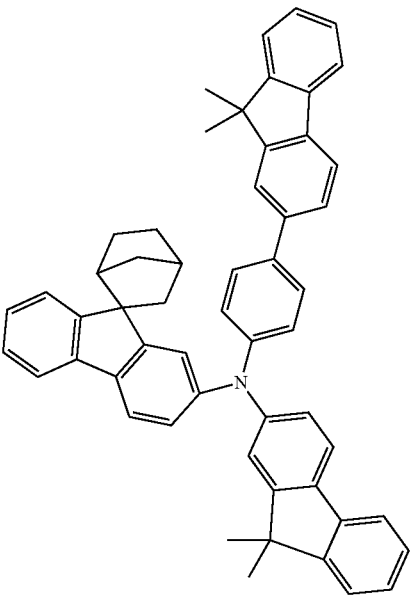

351
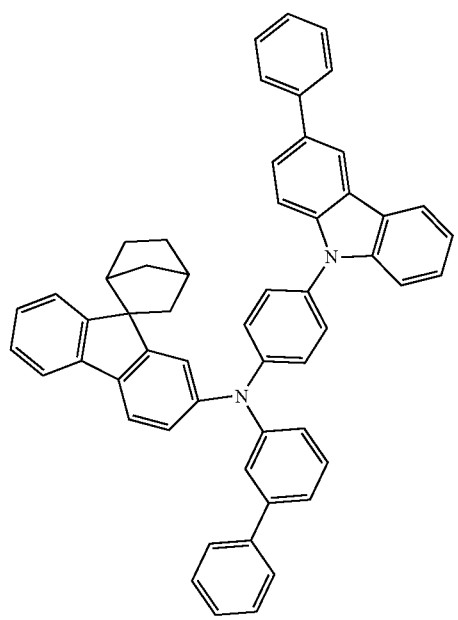
352
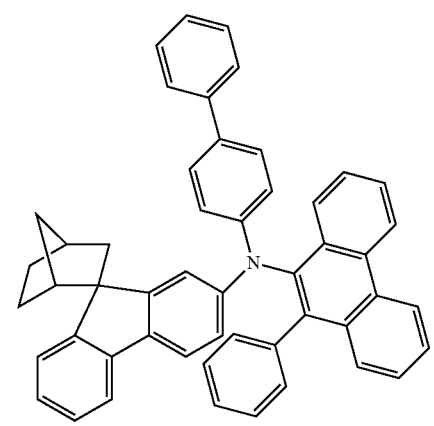
346
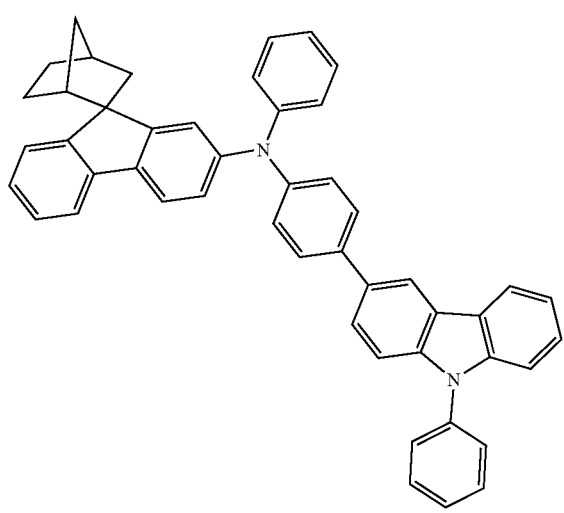
349
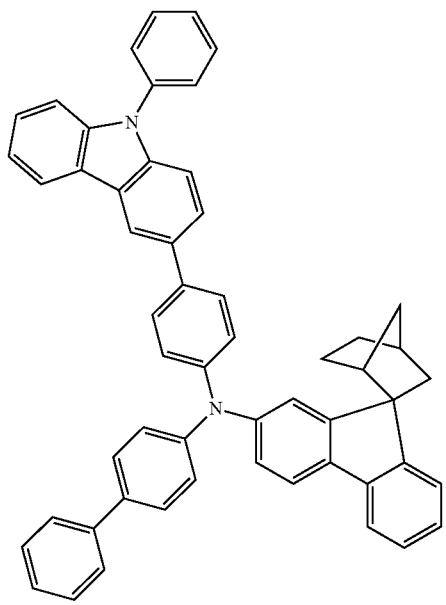
350
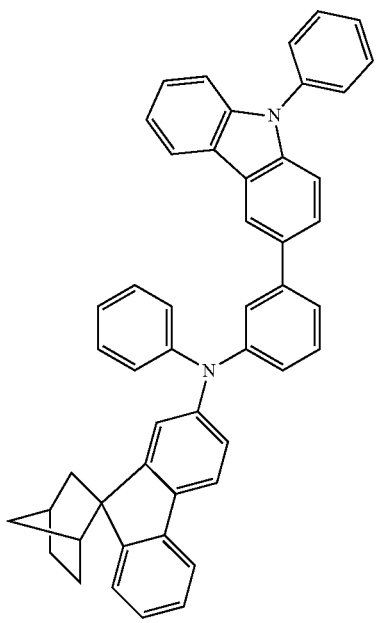

-continued

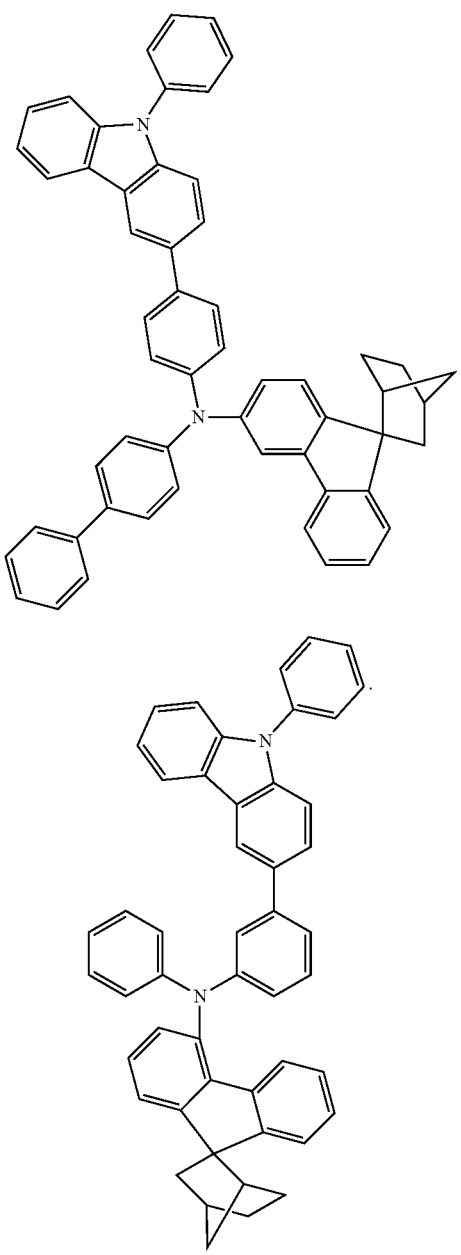

353

354

Also there is provided electronic elements, comprising an anode and a cathode oppositely disposed, and a functional layer disposed between the anode and the cathode; the functional layer contains the above nitrogen-containing compounds.

The nitrogen-containing compounds provided by the present application can be used to form at least one organic membrane layer in the functional layer to improve the voltage, efficiency and lifetime of the electronic elements. Optionally, the organic film layer of the electronic elements containing the nitrogen-containing compound of the present application is located between the anode and the energy conversion layer of the electronic elements, in order to improve the transmission of electrons between the anode and the energy conversion layer. Further, the functional layer contains a hole transport layer, the hole transport layer contains the above nitrogen-containing compounds.

The electronic elements of the present application may be, for example, organic electroluminescent devices or photo-electric conversion devices.

According to one embodiment, the electronic elements are organic electroluminescent devices. The organic electroluminescent devices may be, for example, red organic electroluminescent devices or blue organic electroluminescent devices.

As shown in FIG. 1, the organic electroluminescent device contains an anode 100 and a cathode 200 oppositely disposed, and a functional layer 300 disposed between the anode 100 and the cathode 200; the functional layer 300 contains the nitrogen-containing compounds provided by the present application.

Optionally, the functional layer 300 contains a second hole transport layer 322.

Optionally, the functional layer 300 contains a first hole transport layer 321.

In a specific embodiment of present disclosure, the second hole transport layer 322 contains the nitrogen-containing compounds provided by the present application. Wherein the second hole transport layer 322 may either comprise the nitrogen-containing compounds provided by the present application, or comprise the nitrogen-containing compounds provided by the present application and other materials together. Optionally, the organic electroluminescent devices are red organic electroluminescent devices.

In another specific embodiment of present disclosure, the first hole transport layer 321 contains the nitrogen-containing compounds provided by the present application to improve the hole transport capability in electronic elements. Optionally, the organic electroluminescent devices are blue organic electroluminescent devices.

In a specific embodiment of present disclosure, as shown in FIG. 1, the organic electroluminescent device contains an anode 100 and a cathode 200 oppositely disposed, and a functional layer 300 disposed between the anode 100 and the cathode 200; the functional layer 300 contains the nitrogen-containing compounds provided by the present application.

Optionally, the nitrogen-containing compounds provided by the present application can be used to form at least one organic film layer in the functional layer 300 to improve the lifetime and efficiency of the organic electroluminescent devices and reduce the driving voltage. In some embodiments, the nitrogen-containing compounds can also improve the electrochemical stability and thermostability of organic electroluminescent devices and improve the uniformity and stability of the organic electroluminescent device in mass production.

Optionally, the functional layer 300 contains a hole transport layer 320, the hole transport layer 320 contains the nitrogen-containing compounds provided by the present application. Wherein, the hole transport layer 320 may be composed of the nitrogen-containing compounds provided by the present application, and also may be composed of the nitrogen-containing compounds provided by the present application and other materials.

Optionally, the hole transport layer 320 contains a first hole transport layer 321 and a second hole transport layer 322, wherein the first hole transport layer 321 is disposed on a surface of the second hole transport layer 322 close to the anode 100; the first hole transport layer 321 or the second hole transport layer 322 contains the nitrogen-containing compounds by the present present application. Wherein either the first hole transport layer 321 or the second hole transport layer 322 contains the nitrogen-containing compounds provided by the present application, or both the first hole transport layer 321 and the second hole transport layer 322 contain the nitrogen-containing compounds provided by the present present application. It is understood that the first hole transport layer 321 or the second hole transport layer 322 may or may not contain other materials. It is understood that in another embodiment of the present application, the second hole transport layer 322 can be used as an electron blocking layer of the organic electroluminescent device.

In one embodiment of present disclosure, as shown in FIG. 1, the organic electroluminescent device may comprise an anode 100, a first hole transport layer 321, a second hole transport layer 322, an organic light emitting layer 330, an electron transport layer 340 and a cathode 200 which are stacked in turn. The nitrogen-containing compounds provided by the present application can be applied to the first hole transport layer 321 or the second hole transport layer 322 of the organic electroluminescent device, and can effectively improve the hole characteristic of the organic electroluminescent device. Wherein the hole characteristic means that the holes formed in the anode 100 are easily injected into the organic electroluminescent layer 330 and transmitted in the organic electroluminescent layer 330 according to the conduction characteristic at the HOMO level.

Optionally, the anode 100 contains the following anode materials, which are preferably materials with great escape work (work function) that facilitates hole injection into the functional layer. Specific examples of anode materials include, but are not limited to: metals such as nickel, platinum, vanadium, chromium, copper, zinc and gold or alloys thereof, metal oxides, such as zinc oxide, indium oxide, indium tin oxide (ITO) and indium zinc oxide (IZO), combined metals and oxides, such as ZnO:Al or $SnO_2$:Sb, or conducting polymers such as poly (3-methylthiophene), poly [3,4-(ethylidene-1,2-dioxyl) thiophene] (PEDT), polypyrrole and polyaniline. Preferably, the specific examples of anode materials include a transparent electrode containing indium tin oxide (ITO) as an anode.

Optionally, the organic electroluminescent layer 330 may comprise a single light emitting material, or comprise a host material and an guest material. Optionally, the organic electroluminescent layer 330 contains a host material and a guest material; the holes injected into the organic light-emitting layer 330 and the electrons injected into the organic light-emitting layer 330 can be recombined at the organic light-emitting layer 330 to generate excitons. The excitons transfer energy to the host material, and the host material transfers energy to the guest material, so that the guest material can emit light.

The host material of the organic light-emitting layer 330 may be a metal chelate compound, a diphenyl-vinyl derivative, an aromatic amine derivative, a dibenzofuran derivative or other types of materials, which is not specially restricted in the present application. In one embodiment of the present application, the host material of the organic light-emitting layer 330 may be CBP. In another embodiment of the present application, the host material of the organic light-emitting layer 330 may be $\alpha,\beta$-ADN.

The guest material of the organic light-emitting layer 330 may be a compound with a condensed aryl ring or a derivative, a compound with a heteroaryl ring or a derivative, an aromatic amine derivative or other materials, which is not specially limited in the present present application. In one embodiment of the present application, the guest material of the organic light-emitting layer 330 may be $Ir(piq)_2$ (acac). In another embodiment of the present application, the guest material of the organic light-emitting layer 330 may be BD-1.

The electron transport layer 340 is either a single-layer structure or a multi-layer structure, the electron transport layer 340 may comprise one or more electron transport materials, the electron transport material may be selected from benzimidazole derivatives, oxadiazole derivatives, quinoxaline derivatives or other electron transport materials, which is not specially limited in the present application. For example, in one embodiment of the present application, the electron transport layer 340 may consist of DBimiBphen and LiQ.

Optionally, the cathode 200 contains the following cathode materials, which are materials with a small work that facilitates electron injection into the functional layer. Specific examples of cathode materials include, but are not limited to: metals such as magnesium, calcium, sodium, potassium, titanium, indium, yttrium, lithium, gadolinium, aluminum, silver, tin and lead or alloys thereof; or multilayer materials such as LiF/Al, Liq/Al, $LiO_2$/Al, LiF/Ca, LiF/Al and $BaF_2$/Ca. Preferably, the specific examples of cathode materials include a Mg—Ag alloy containing metal electrode as a cathode.

Optionally, as shown in FIG. 1, a hole injection layer 310 may also be disposed between the anode 100 and the first hole transport layer 321 to enhance the capability of injecting holes into the first hole transport layer 321. Benzidine derivatives, starburst arylamine compounds, phthalocyanine derivatives or other materials are options for the hole injection layer 310, which is not specially restricted in the present application. In one embodiment of the present application, the hole injection layer 310 may composed of m-MTDATA.

Optionally, as shown in FIG. 1, an electron injection layer 350 may also be disposed between the cathode 200 and the electron transport layer 340 to enhance the capability of injecting electrons into the electron transport layer 340. The electron injection layer 350 may comprise either inorganic materials such as alkali sulfides and alkali halides, or a complex of alkali metal and organic substances. In one embodiment of the present application, the electron injection layer 350 may comprise Yb.

Optionally, an electron injection layer 350 may also be disposed between the cathode 200 and the electron transport layer 340.

Figure 3:
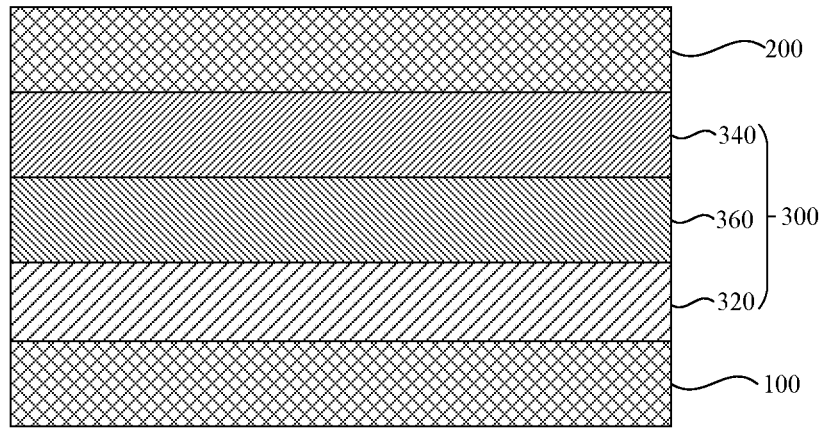
FIG. 3 illustrates a structural view of an photoelectric conversion device in accordance with the embodiment of the application.

In another embodiment of present disclosure, the electronic elements may be photoelectric conversion devices, as shown in FIG. 3. The photoelectric conversion device may comprise an anode 100 and a cathode 200 oppositely disposed, and a functional layer 300 disposed between the anode 100 and the cathode 200. The functional layer 300 contains the nitrogen-containing compounds provided by the present application.

Optionally, the nitrogen-containing compounds provided by the present application can be used to form at least one organic film layer in the functional layer 300 to improve the performance of the photoelectric conversion device, particularly improve the lifetime of the photoelectric conversion devices, increase the open circuit voltage of the photoelectric conversion devices, or improve the performance uniformity and stability of mass-produced photoelectric conversion devices.

Optionally, the functional layer 300 contains a hole transport layer 320 which contains the nitrogen-containing compounds in the present application. Wherein the hole transport layer 320 may either comprise the nitrogen-containing compounds provided by the present application, or comprise the nitrogen-containing compounds provided by the present application and other materials together.

Optionally, the hole transport layer 320 contains a first hole transport layer 321 and a second hole transport layer 322 (the second hole transport layer 322 as an electron blocking layer of the photoelectric conversion devices), wherein the first hole transport layer 321 is disposed on a surface of the second hole transport layer 322 close to the anode 100; the first hole transport layer 321 or the second hole transport layer 322 contains the nitrogen-containing compounds provided by the present application. Wherein either the first hole transport layer 321 or the second hole transport layer 322 contains the nitrogen-containing compounds provided by the present application, or both the first hole transport layer 321 and the second hole transport layer 322 contain the nitrogen-containing compounds provided by the present application. It is understood that the first hole transport layer 321 or the second hole transport layer 322 may or may not contain other materials.

Optionally, the hole transport layer 320 may also comprise inorganic doped materials to improve the hole transport performance of the hole transport layer 320.

In one embodiment of the present disclosure, as shown in FIG. 3, the photoelectric conversion devices may comprise an anode 100, a hole transport layer 320 (as an electron blocking layer of the photoelectric conversion devices), a photoelectric conversion layer 360 as an energy conversion layer, an electron transport layer 340 and a cathode 200 which are stacked in turn.

Optionally, the photoelectric conversion device may be a solar cell, particularly an organic thin film solar cell. For example, in one embodiment of the present application, the solar cell contains an anode 100, a first hole transport layer 321, a second hole transport layer 322 (a second hole transport layer 322 as an electron blocking layer of a photoelectric conversion device), a photoelectric conversion layer 360, an electron transport layer 340 and a cathode 200 which are stacked in turn, wherein the second hole transport layer 322 contains the nitrogen-containing compounds of the present application.

Also there is provided electronic devices, comprising the above electronic elements.

Figure 2:
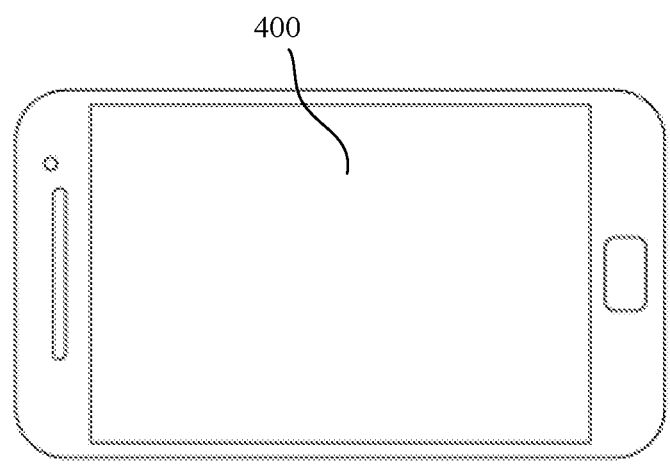
FIG. 2 illustrates a structural view of an electronic device in accordance with the embodiment of the present application.

In one embodiment of the present disclosure, as shown in FIG. 2, the electronic device provided by the present present application is a first electronic device 400, comprising the above organic electroluminescent devices. The electronic device may be, for example, a display device, a lighting device, an optical communication device or other types of electronic devices, for example, including but not limited to a computer screen, a mobile phone screen, a television, electronic paper, an emergency lighting lamp, an optical module and the like. The electronic device has the above organic electroluminescent devices, so it has the same beneficial effect, which will not be repeated here.

Figure 4:
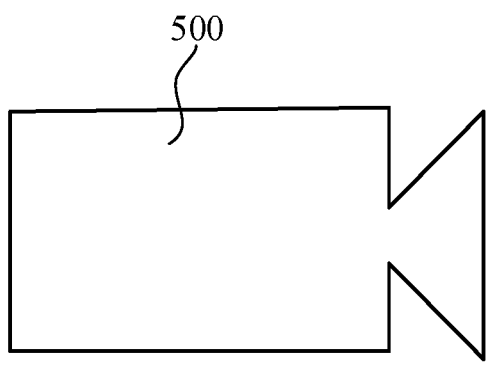
FIG. 4 illustrates a structural view of an electronic device in accordance with the embodiment of the present application.

In another embodiment of the present disclosure, as shown in FIG. 4, the electronic device provided by the present application is a second electronic device 500, comprising the above photoelectric conversion devices. The electronic device may be, for example, solar power generation equipment, an optical detector, fingerprint identification equipment, an optical module, a CCD camera or other types of electronic devices. The electronic device has the above photoelectric conversion devices, so it has the same beneficial effect, which will not be repeated here.

Unless otherwise specified, MC refers to dichloromethane, and rt refers to a room temperature thereinafter.

The present disclosure will be described in further details below by embodiments.

However, the following embodiments are only examples of the present application, not intended to limit the present application.

SYNTHESIS EMBODIMENTS

Synthesis of Compound 1

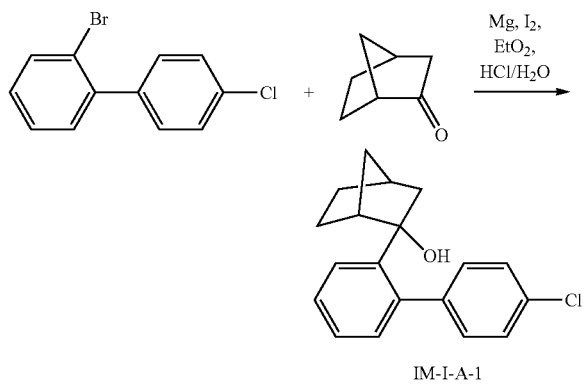

IM-I-A-1

A magnesium ribbon (13.54 g, 564 mmol) and diethyl ether (100 mL) were placed in a dry round-bottom flask under the protection of nitrogen gas, and iodine (100 mg) was added. Then, 2-bromo-4-chlorobiphenyl (50.00 g, 188.0 mmol) was dissolved in diethyl ether (200 mL) was slowly dropped into the flask, the temperature was raised to 35° C. after dropping was completed, and the solution was stirred for 3 hours. The temperature of the reaction solution was cooled to 0° C., the solution of 2-norbornanone (42.36 g, 384 mmol) was dissolved in diethyl ether (200 mL) was slowly dropped into the reaction solution, the temperature was raised to 35° C. after dropping was completed, and the reaction solution was stirred for 6 hours.

The reaction solution was cooled to room temperature, 5% hydrochloric acid was added into the reaction solution until pH<7, the reaction solution was stirred for 1 hour, diethyl ether (200 mL) was added into the reaction solution for extraction, organic phases were combined, the reaction solution was dried with anhydrous magnesium sulfate, filtered, and the solvent was removed under reduced pressure. The crude product was purified by silica gel column chromatography with ethyl acetate/n-heptane (1:2) as a mobile phase to obtain a white solid intermediate IM-I-A-1 (43 g, yield was 77%).

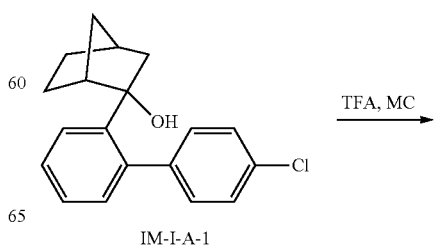

IM-I-A-1

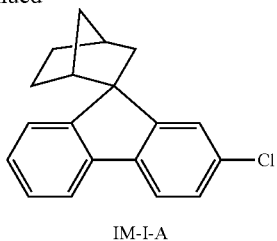

IM-I-A

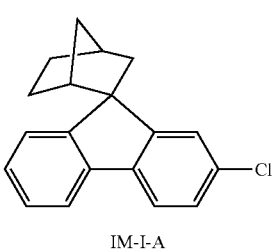

IM-I-A

The intermediate IM-I-A-1 (43 g, 143.9 mmol), trifluoroacetic acid (36.93 g, 380.6 mmol) and dichloromethane (300 mL) were added into a round-bottom flask, and stirred for 2 hours under the protection of nitrogen gas; then, an aqueous solution of sodium hydroxide was added into the reaction solution until pH=8, followed by liquid separation, the organic phase was dried with anhydrous magnesium sulfate, filtered, and the solvent was removed under reduced pressure. The crude product was purified by silica gel column chromatography with dichloromethane/n-heptane (1:2) to obtain a white solid intermediate IM-I-A (39.2 g, yield was 96.3%).

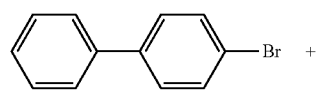

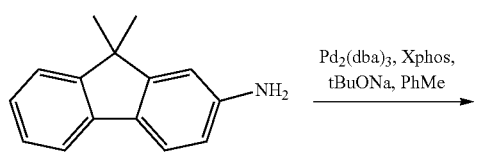

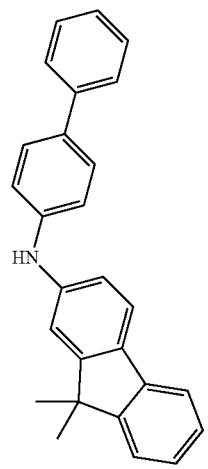

IM-II-A

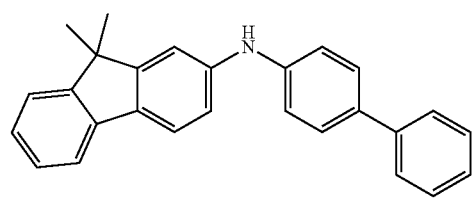

IM-II-A

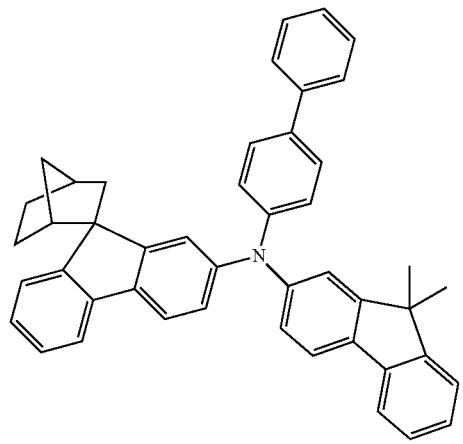

1

4-bromobiphenyl (10.0 g, 10.9 mmol), 2-amino-9,9-dimethylfluorene (9.88 g, 47.2 mmol), tris (dibenzylidenacetone) dipalladium (0.39 g, 0.43 mmol), 2-dicyclohexylphosphino-2',4',6'-triisopropylbiphenyl (0.41 g, 0.86 mmol) and sodium tert-butoxide (6.18 g, 64.3 mmol) were added into toluene (80 mL), the reaction solution was heated to 108° C. under the protection of nitrogen and stirred for 2 h. Then the reaction solution was cooled to room temperature, after the reaction solution was washed with water, magnesium sulfate was added to dry the reaction solution was dried and filtered, after filtered, the solvent from the filtrate was removed under reduced pressure; the crude product was recrystallized and purified by the dichloromethane/ethanol system to obtain intermediate IM-II-A (13.1 g, yield was 84%) as a light gray solid.

The intermediate IM-I-A (3.05 g, 10.9 mmol), the intermediate IM-II-A (3.94 g, 10.9 mmol), tris (dibenzylidenacetone) dipalladium (0.10 g, 0.11 mmol), 2-dicyclohexylphosphino-2', 6'-dimethoxybiphenyl (0.09 g, 0.22 mmol) and sodium tert-butoxide (1.57 g, 16.36 mmol) were added to toluene (30 mL), the reaction solution was heated to 108° C. under the protection of nitrogen and stirred for 1 h. Then the reaction solution was cooled to room temperature, after the reaction solution was washed with water, magnesium sulfate was added for drying the reaction solution, and the reaction solution was filtered, the filtrate was passed through a short silica gel column, the solvent removed under reduced pressure; the crude product was recrystallized and purified by the dichloromethane/n-heptane system to obtain a white solid compound 1(5.35 g, yield was 76%). Mass spectrum: m/z=606.3 [M+H]$^+$.

Synthesis of Compound 2

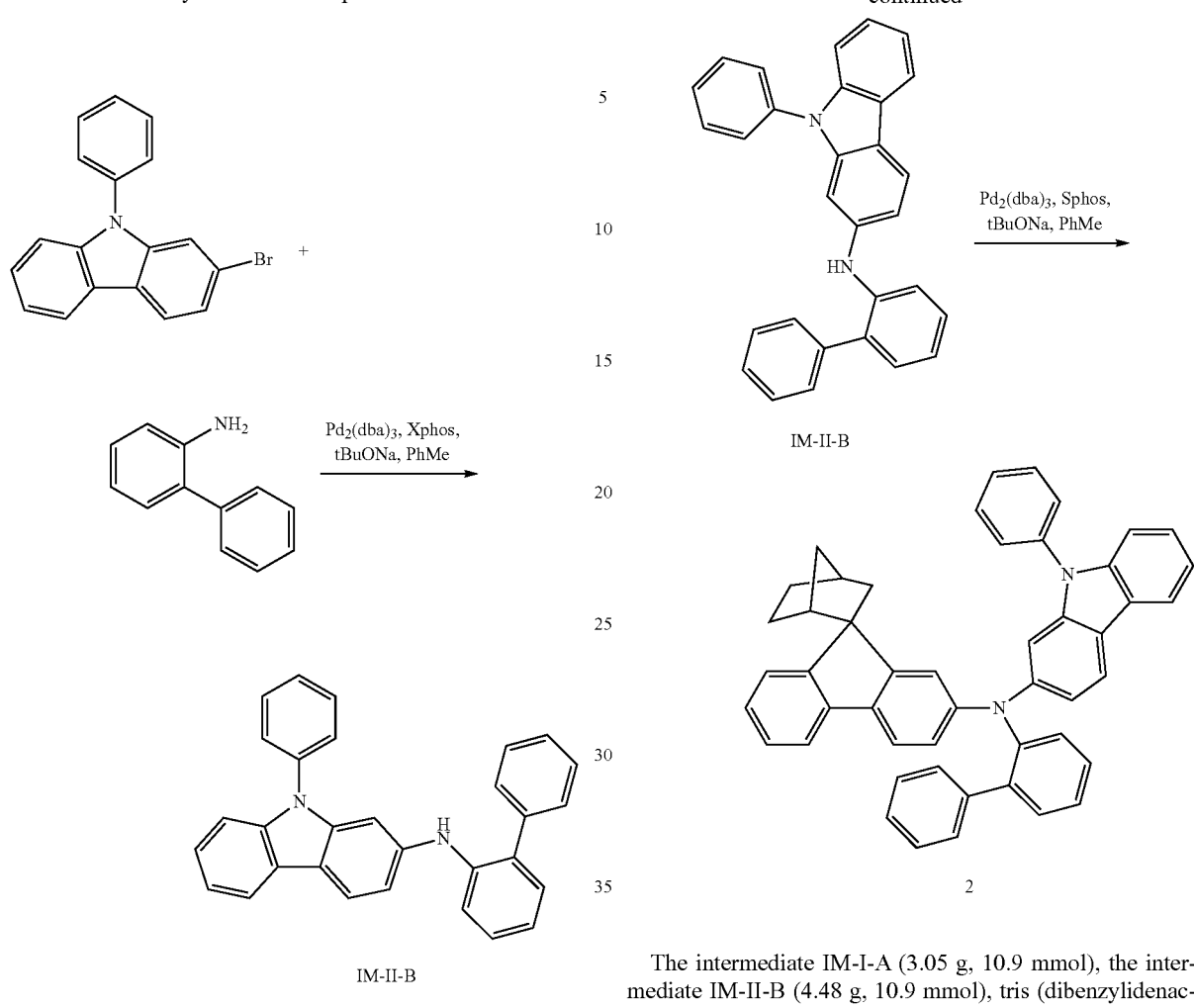

2-bromo-N-phenylcarbazole (10.0 g, 31.0 mmol), 2-aminobiphenyl (5.78 g, 34.1 mmol), tris (dibenzylideneacetone) dipalladium (0.28 g, 0.31 mmol), 2-dicyclohexylphosphino-2', 4', 6'-triisopropylbiphenyl (0.30 g, 0.62 mmol) and sodium tert-butoxide (4.47 g, 46.6 mmol) were added into toluene (80 mL), the reaction solution was heated to 108° C. under the protection of nitrogen and stirred for 4 h. Then the reaction solution was cooled to room temperature, after the reaction solution was washed with water, magnesium sulfate was added, the reaction solution was dried and filtered, after filtered, the solvent from the filtrate under reduced pressure; the crude product was recrystallized and purified by the dichloromethane/n-heptane system to obtain an orange solid intermediate IM-II-B (8.65 g, yield was 67.81%).

The intermediate IM-I-A (3.05 g, 10.9 mmol), the intermediate IM-II-B (4.48 g, 10.9 mmol), tris (dibenzylidenacetone) dipalladium (0.20 g, 0.22 mmol), 2-dicyclohexylphosphino-2', 6'-dimethoxybiphenyl (0.18 g, 0.44 mmol) and sodium tert-butoxide (1.57 g, 16.3 mmol) were added into toluene (30 mL), the reaction solution was heated to 105~110° C. under the protection of nitrogen and stirred for 10 h. Then the reaction solution was cooled to room temperature, after the reaction solution was washed with water, magnesium sulfate was added, the reaction solution was dried and filtered, the filtrate was passed through a silica gel column with dichloromethane/n-heptane (volume ratio was 1/5) as a mobile phase for purification by chromatography, pressure of the column passing solution was reduced to remove solvent; the crude product was recrystallized and purified by the dichloroethane system to obtain compound 2 (5.42 g, yield was 76.23%) as a white solid. Mass spectrum: m/z=655.3 [M+H]$^+$.

Synthesis of Compound 3

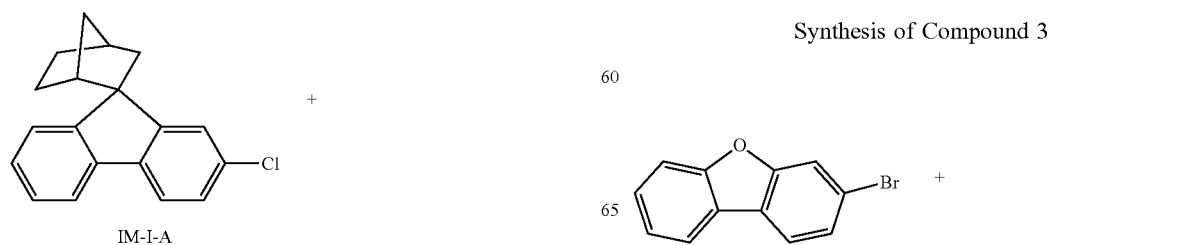

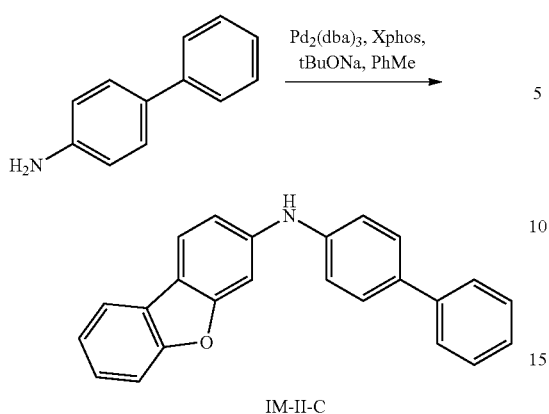

IM-II-C

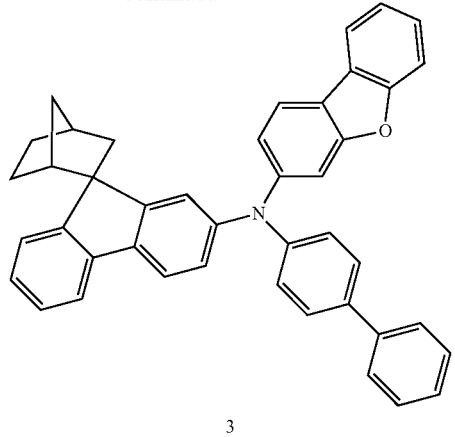

3

3-bromodibenzofuran (10.0 g, 40.5 mmol), 4-aminobiphenyl (7.53 g, 44.5 mmol), tris (dibenzylidenacetone) dipalladium (0.37 g, 0.40 mmol), 2-dicyclohexylphosphino-2', 4', 6'-triisopropylbiphenyl (0.39 g, 0.81 mmol) and sodium tert-butoxide (5.83 g, 60.7 mmol) were added into toluene (80 mL), the reaction solution was heated to 108° C. under the protection of nitrogen and stirred for 4 h. Then the reaction solution was cooled to room temperature, after the reaction solution was washed with water, magnesium sulfate was added, the reaction solution was dried and filtered, after filtered, the solvent from the filtrate under reduced pressure; the crude product was recrystallized and purified by the ethyl acetate/n-heptane system to obtain intermediate IM-II-C (11.8 g, yield was 87%) as a light gray solid.

The intermediate IM-I-A (3.05 g, 10.9 mmol), the intermediate IM-II-C (3.66 g, 10.9 mmol), tris (dibenzylidenacetone) dipalladium (0.20 g, 0.22 mmol), 2-dicyclohexylphosphino-2', 6'-dimethoxybiphenyl (0.18 g, 0.44 mmol) and sodium tert-butoxide (1.57 g, 16.4 mmol) were added into toluene (30 mL), the reaction solution was heated to 108° C. under the protection of nitrogen and stirred for 5 h. Then the reaction solution was cooled to room temperature, after the reaction solution was washed with water, magnesium sulfate was added, the reaction solution was dried and filtered, the filtrate was passed through a short silica gel column, the solvent was removed under reduced pressure; the crude product was recrystallized and purified by the dichloromethane/ethyl acetate system to obtain a white solid compound 3 (4.98 g, yield was 73.67%). Mass spectrum: m/z=580.3 [M+H]$^+$.

Synthesis of Compound 4

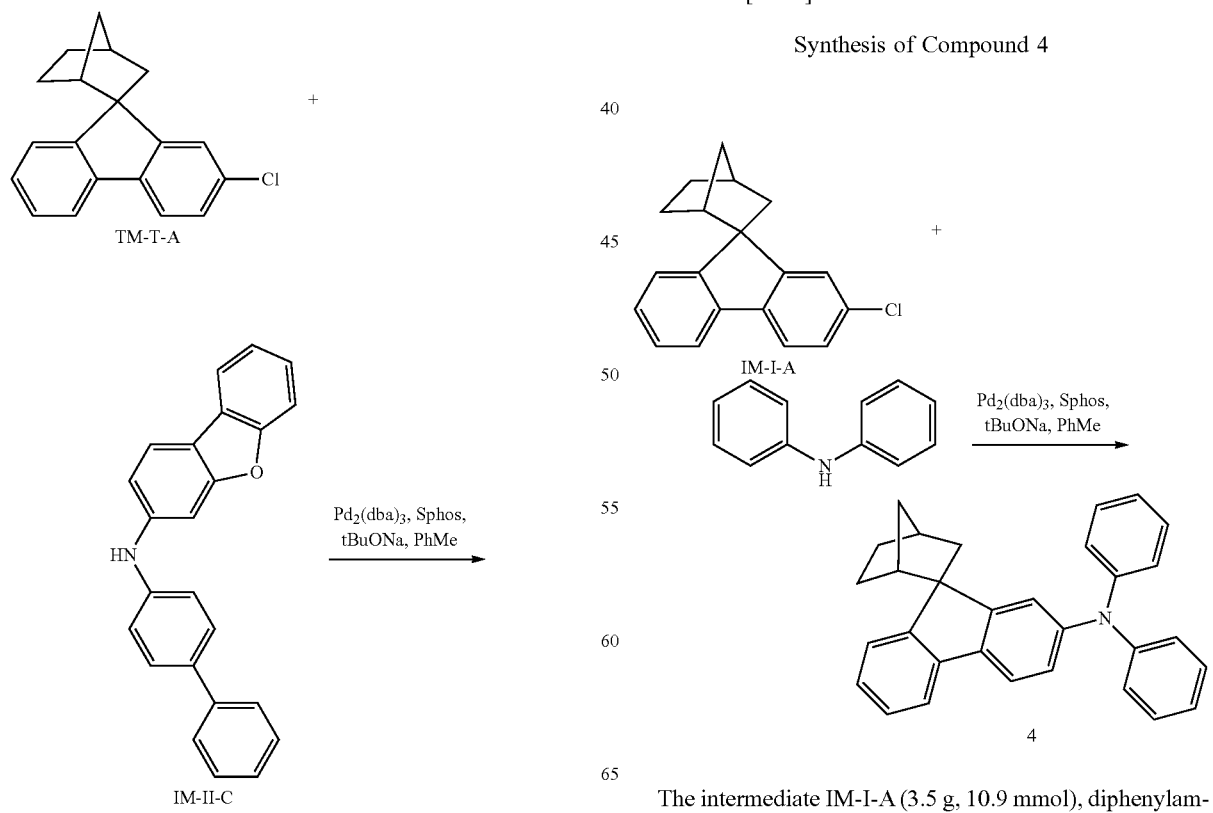

The intermediate IM-I-A (3.5 g, 10.9 mmol), diphenylamine (1.85 g, 10.9 mmol), tris (dibenzylidenacetone) dipalladium (0.20 g, 0.22 mmol), 2-dicyclohexylphosphino-2', 6'-dimethoxybiphenyl (0.18 g, 0.44 mmol) and sodium tert-butoxide (1.57 g, 16.4 mmol) were added into toluene (30 mL), the reaction solution was heated to 108° C. under the protection of nitrogen and stirred for 2 h. Then the reaction solution was cooled to room temperature, after the reaction solution was washed with water, magnesium sulfate was added, the reaction solution was dried and filtered, the filtrate was passed through a short silica gel column, the solvent was removed under reduced pressure; the crude product was recrystallized and purified by the dichloromethane/ethyl acetate system to obtain a white solid compound 4 (3.06 g, yield was 61.94%). Mass spectrum: m/z=414.2[M+H]$^+$.

Synthesis of Compound 5

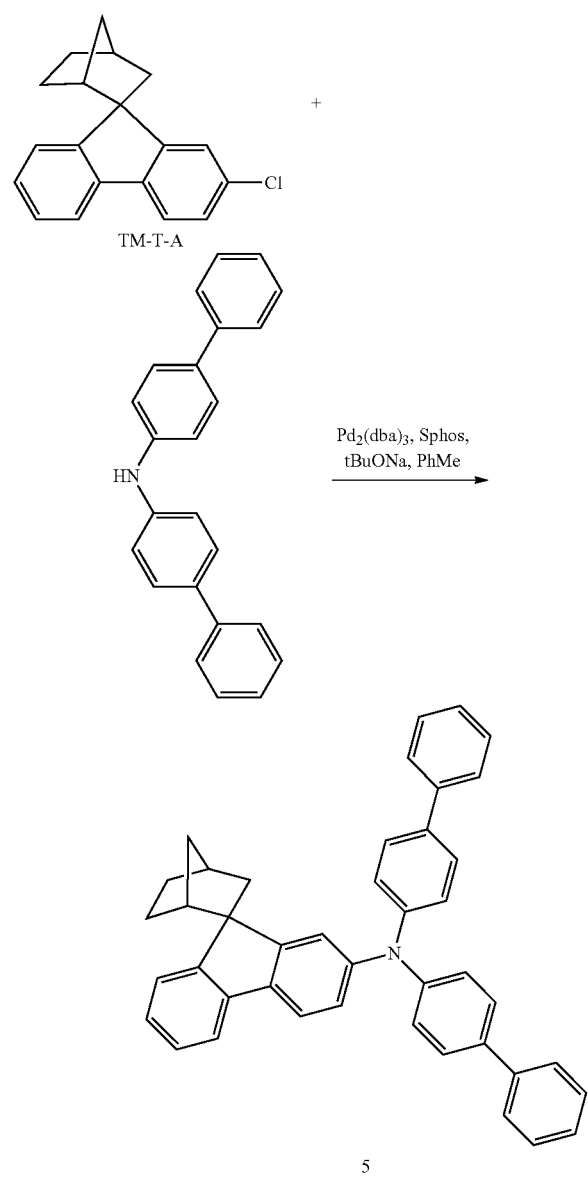

The intermediate IM-I-A (3.50 g, 10.9 mmol), bis-(4-biphenyl) amine (3.51 g, 10.9 mmol), tris (dibenzylidenac-etone) dipalladium (0.20 g, 0.22 mmol), 2-dicyclohexylphosphino-2', 6'-dimethoxybiphenyl (0.18 g, 0.44 mmol) and sodium tert-butoxide (1.58 g, 16.4 mmol) were added to toluene (30 mL), the reaction solution was heated to 108° C. under the protection of nitrogen and stirred for 8 h. Then the reaction solution was cooled to room temperature, after the reaction solution was washed with water, magnesium sulfate was added, the reaction solution was dried and filtered, after filtered, the solvent from the filtrate was removed under reduced pressure; the crude product was recrystallized and purified by the toluene system, so that a white solid compound 5 (4.35 g, yield was 65.81%) was obtained. Mass spectrum: m/z=566.3 [M+H]$^+$.

Synthesis of Compound 6

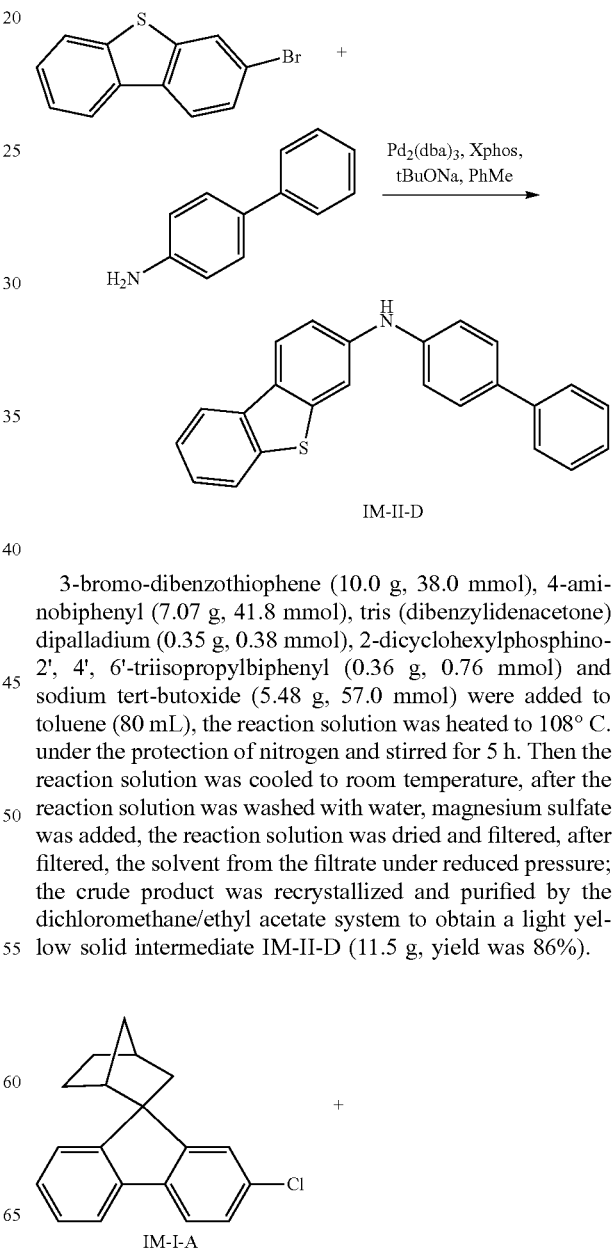

3-bromo-dibenzothiophene (10.0 g, 38.0 mmol), 4-aminobiphenyl (7.07 g, 41.8 mmol), tris (dibenzylidenacetone) dipalladium (0.35 g, 0.38 mmol), 2-dicyclohexylphosphino-2', 4', 6'-triisopropylbiphenyl (0.36 g, 0.76 mmol) and sodium tert-butoxide (5.48 g, 57.0 mmol) were added to toluene (80 mL), the reaction solution was heated to 108° C. under the protection of nitrogen and stirred for 5 h. Then the reaction solution was cooled to room temperature, after the reaction solution was washed with water, magnesium sulfate was added, the reaction solution was dried and filtered, after filtered, the solvent from the filtrate under reduced pressure; the crude product was recrystallized and purified by the dichloromethane/ethyl acetate system to obtain a light yellow solid intermediate IM-II-D (11.5 g, yield was 86%).

Synthesis of Compound 7

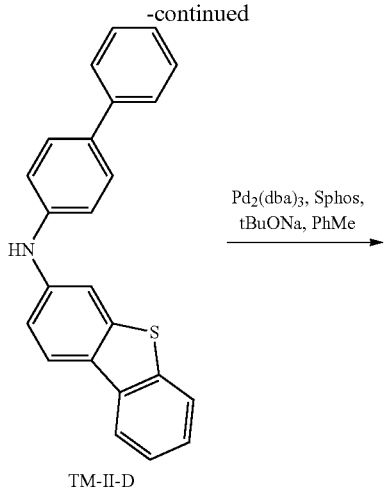

TM-II-D

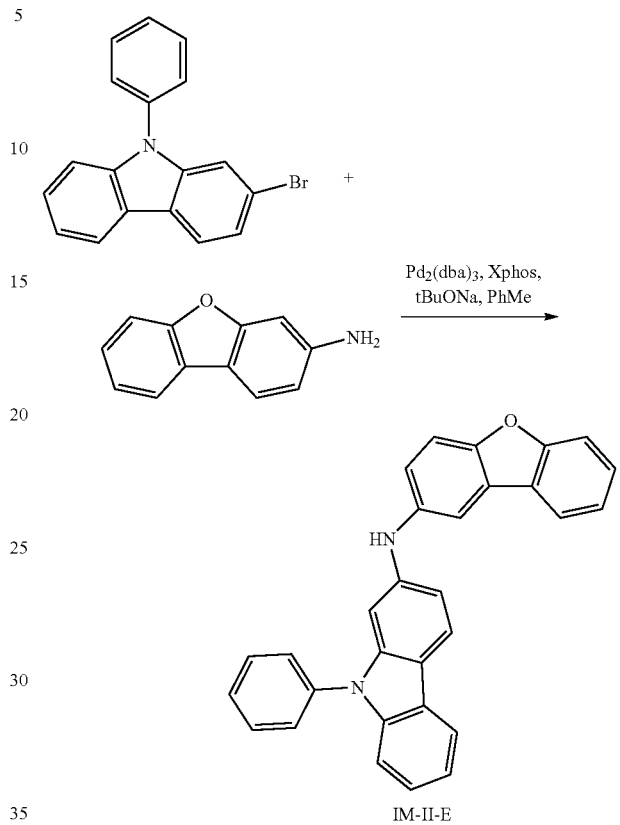

IM-II-E 2-bromo-N-phenylcarbazole (10.0 g, 31.0 mmol), 2-bromodibenzofuran (6.25 g, 34.1 mmol), tris (dibenzylidenacetone) dipalladium (0.28 g, 0.31 mmol), 2-dicyclohexylphosphino-2', 4', 6'-triisopropylbiphenyl (0.30 g, 0.62 mmol) and sodium tert-butoxide (4.47 g, 46.6 mmol) were added to toluene (80 mL), heated to 108° C. under the protection of nitrogen and stirred for 5 h. Then the reaction solution was cooled to room temperature, after the reaction solution was washed with water, magnesium sulfate was added, the reaction solution was filtered and passed through a short silica gel column, the solvent was removed under reduced pressure; the crude product was recrystallized and purified by the dichloromethane/n-heptane system to obtain a white solid intermediate IM-II-E (9.76 g, yield was 74.7%).

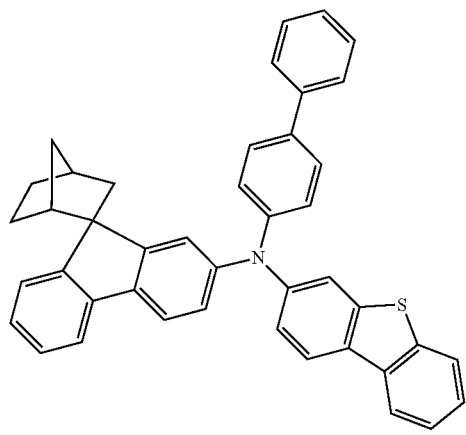

6

The intermediate IM-I-A (3.5 g, 10.9 mmol), the intermediate IM-II-D (3.83 g, 10.9 mmol), tris (dibenzylidenacetone) dipalladium (0.20 g, 0.22 mmol), 2-dicyclohexylphosphino-2', 6'-dimethoxybiphenyl (0.18 g, 0.44 mmol) and sodium tert-butoxide (1.58 g, 16.4 mmol) were added into toluene (30 mL), the reaction solution was heated to 108° C. under the protection of nitrogen and stirred for 6 h. Then the reaction solution was cooled to room temperature, after the reaction solution was washed with water, magnesium sulfate was added, the reaction solution was dried and filtered, the filtrate was passed through a silica gel column with dichloromethane/n-heptane (⅓) as a mobile phase for purification by chromatography, pressure of the column passing solution was reduced to remove the solvent; the crude product was recrystallized and purified by the toluene system to obtain a white solid compound 6 (3.35 g, yield was 51.5%). Mass spectrum: m/z=596.3 [M+H]⁺.

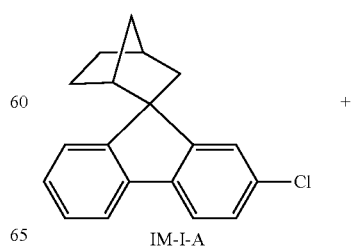

IM-I-A

-continued

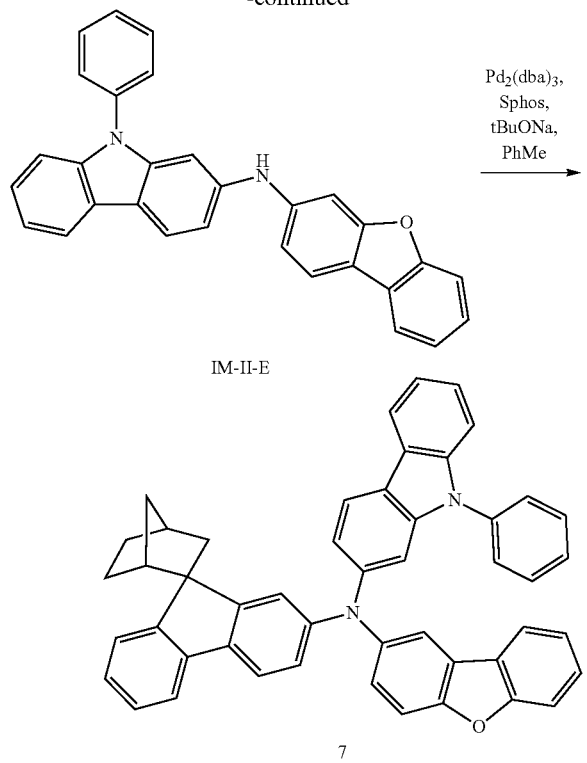

The intermediate IM-I-A (3.05 g, 10.9 mmol), the intermediate IM-II-E (5.07 g, 11.9 mmol), tris (dibenzylidenacetone) dipalladium (0.20 g, 0.22 mmol), 2-dicyclohexylphosphino-2', 6'-dimethoxybiphenyl (0.18 g, 0.44 mmol) and sodium tert-butoxide (1.58 g, 16.4 mmol) were added into toluene (40 mL), the reaction solution was heated to 108° C. under the protection of nitrogen and stirred for 8 h. Then the reaction solution was cooled to room temperature, after the reaction solution was washed with water, magnesium sulfate was added, the reaction solution was dried, filtered and passed through a short silica gel column, the solvent was removed under reduced pressure; the crude product was recrystallized and purified by the toluene system to obtain a white solid compound 7 (6.42 g, yield was 88%). Mass spectrum: m/z=669.3 [M+H]$^+$.

Referring to the synthesis method of compound 1, the intermediate in Column 4, Table 1 was synthetized from a raw material 1 instead of 2-amino-9,9-dimethylfluorene and a raw material 2 instead of 4-bromobiphenyl, and other compounds in Table 1 were prepared from the intermediate in Column 4 instead of the intermediate IM-II-A and the intermediate IM-I-A. The specific compound numbers, structures, raw materials, synthesis yield in the last step, characterization data and the like are shown in Table 1.

TABLE 1

Structures, Preparation and Characterization Data of Compounds

| Compound Number | Raw material 1 | Raw material 2 | Intermediate | Compound Structure | Yield (%) | Mass spectrum (m/z) [M + H]$^+$ |
|---|---|---|---|---|---|---|
| 334 | 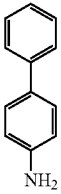 | 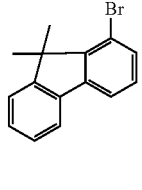 [SMILES: CC1(C)c2ccccc2-c2cccc(Br)c21] | 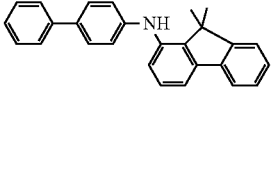 [SMILES: CC1(C)c2ccccc2-c2cccc(Nc3ccc(-c4ccccc4)cc3)c21] | 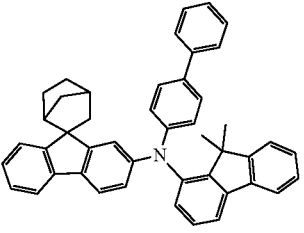 [SMILES: CC1(C)c2ccccc2-c2cccc(N(c3ccc(-c4ccccc4)cc3)c3ccc4c(c3)C3(CC5CCC3C5)c3ccccc3-4)c21] | 67 | 606.3 |
| 148 | 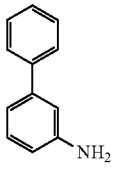 |  | 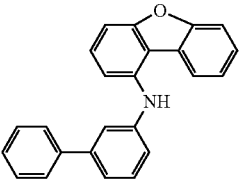 [SMILES: c1ccc(-c2cccc(Nc3cccc4oc5ccccc5c34)c2)cc1] | 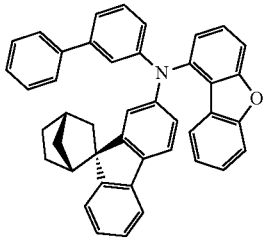 [SMILES: c1ccc(-c2cccc(N(c3ccc4c(c3)[C@@]3(C[C@H]5CC[C@@H]3C5)c3ccccc3-4)c3cccc4oc5ccccc5c34)c2)cc1] | 69 | 580.3 |

TABLE 1-continued
Structures, Preparation and Characterization Data of Compounds
| Compound Number | Raw material 1 | Raw material 2 | Intermediate | Compound Structure | Yield (%) | Mass spectrum (m/z) [M + H]+ |
|---|---|---|---|---|---|---|
| 335 | 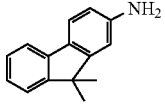 | 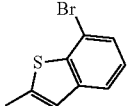 | 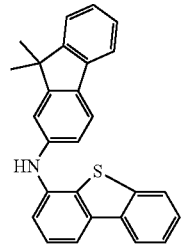 [SMILES: CC1(C)c2ccccc2-c2ccc(Nc3cccc4c3sc3ccccc34)cc21] | 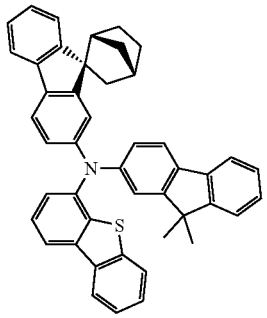 [SMILES: CC1(C)c2ccccc2-c2ccc(N(c3ccc4c(c3)[C@@]3(C[C@H]5CC[C@@H]3C5)c3ccccc3-4)c3cccc4c3sc3ccccc34)cc21] | 72 | 636.3 |
| 336 | 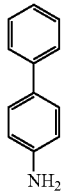 | 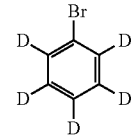 | 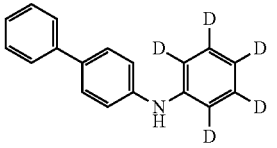 [SMILES: [2H]c1c([2H])c([2H])c(Nc2ccc(-c3ccccc3)cc2)c([2H])c1[2H]] | 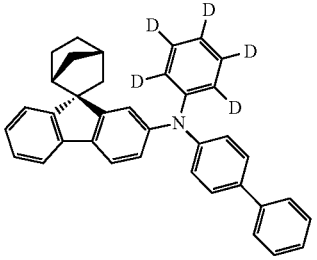 [SMILES: [2H]c1c([2H])c([2H])c(N(c2ccc(-c3ccccc3)cc2)c2ccc3c(c2)[C@@]2(C[C@H]4CC[C@@H]2C4)c2ccccc2-3)c([2H])c1[2H]] | 54 | 696.3 |
| 337 | 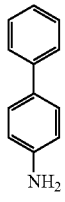 | 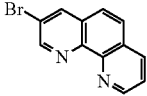 | 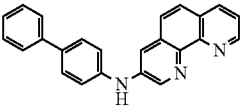 [SMILES: c1ccc(-c2ccc(Nc3cnc4c(ccc5cccnc54)c3)cc2)cc1] | 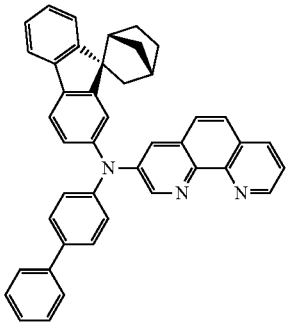 [SMILES: c1ccc(-c2ccc(N(c3ccc4c(c3)[C@@]3(C[C@H]5CC[C@@H]3C5)c3ccccc3-4)c3cnc4c(ccc5cccnc54)c3)cc2)cc1] | 53 | 592.3 |
| 343 | 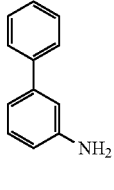 | 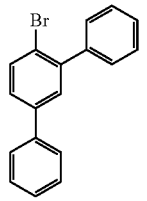 | 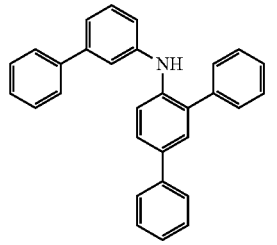 [SMILES: c1ccc(-c2cccc(Nc3ccc(-c4ccccc4)cc3-c3ccccc3)c2)cc1] | 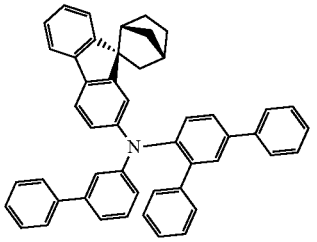 [SMILES: c1ccc(-c2cccc(N(c3ccc4c(c3)[C@@]3(C[C@H]5CC[C@@H]3C5)c3ccccc3-4)c3ccc(-c4ccccc4)cc3-c3ccccc3)c2)cc1] | 55 | 642.4 |
| 41 | 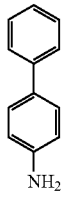 | 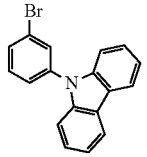 [SMILES: Brc1cccc(-n2c3ccccc3c3ccccc32)c1] | 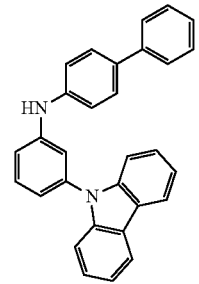 [SMILES: c1ccc(-c2ccc(Nc3cccc(-n4c5ccccc5c5ccccc54)c3)cc2)cc1] | 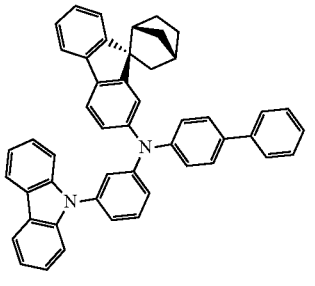 [SMILES: c1ccc(-c2ccc(N(c3cccc(-n4c5ccccc5c5ccccc54)c3)c3ccc4c(c3)[C@@]3(C[C@H]5CC[C@@H]3C5)c3ccccc3-4)cc2)cc1] | 66 | 655.3 |

TABLE 1-continued

Structures, Preparation and Characterization Data of Compounds

| Compound Number | Raw material 1 | Raw material 2 | Intermediate | Compound Structure | Yield (%) | Mass spectrum (m/z) [M + H]+ |
|---|---|---|---|---|---|---|
| 344 | | | | 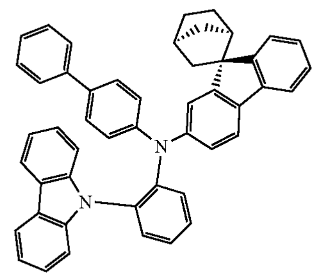 [SMILES: c1ccc(-c2ccc(N(c3ccc4c(c3)[C@@]3(C[C@H]5CC[C@@H]3C5)c3ccccc3-4)c3ccccc3-n3c4ccccc4c4ccccc43)cc2)cc1] | 59 | 655.3 |
| 345 | | | | 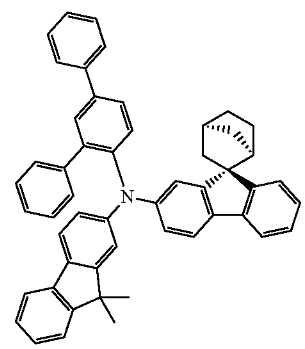 [SMILES: CC1(C)c2ccccc2-c2ccc(N(c3ccc4c(c3)[C@@]3(C[C@H]5CC[C@@H]3C5)c3ccccc3-4)c3ccc(-c4ccccc4)cc3-c3ccccc3)cc21] | 65 | 682.4 |
| 346 | | | | 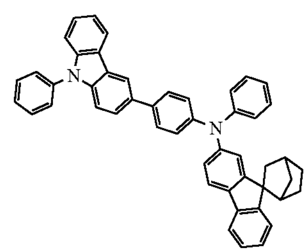 [SMILES: c1ccc(N(c2ccc(-c3ccc4c(c3)c3ccccc3n4-c3ccccc3)cc2)c2ccc3c(c2)C2(CC4CCC2C4)c2ccccc2-3)cc1] | 71 | 655.2 |

Synthesis of Compound 8

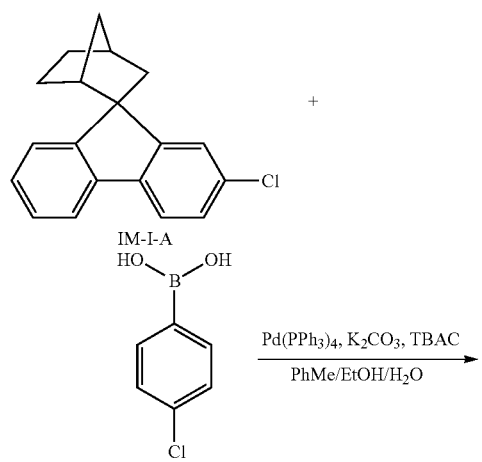

IM-I-A

Pd(PPh₃)₄, K₂CO₃, TBAC
PhMe/EtOH/H₂O

-continued

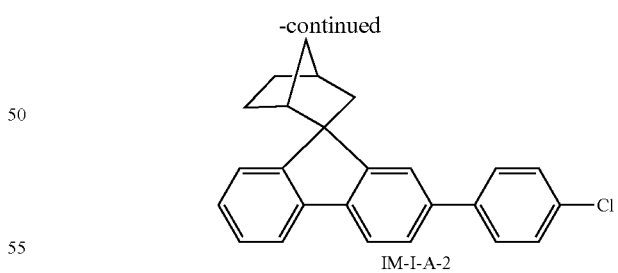

IM-I-A-2

The intermediate IM-J-A (10 g, 35.6 mmol), 4-chlorophenylboronic acid (3.23 g, 20.7 mmol), tetrakis (triphenylphosphine) palladium (1.19 g, 1.03 mmol), potassium carbonate (5.71 g, 41.38 mmol), tetrabutyl ammonium chloride (0.28 g, 1.03 mmol), toluene (80 mL), ethanol (20 mL) and deionized water (20 mL) were added into a round-bottom flask, the reaction solution was heated to 78° C. under the protection of nitrogen and stirred for 8 hours. The reaction solution was cooled to room temperature, toluene (100 mL) was added for extraction, organic phases were combined the reaction solution was dried with anhydrous magnesium sulfate, the reaction solution was filtered, the solvent was removed under reduced pressure; the crude product was purified by silica gel column chromatography with n-heptane as a mobile phase, then recrystallized and purified by dichloromethane/ethyl acetate system to obtain a white solid intermediate IM-I-A-2 (6.78 g, yield was 92%).

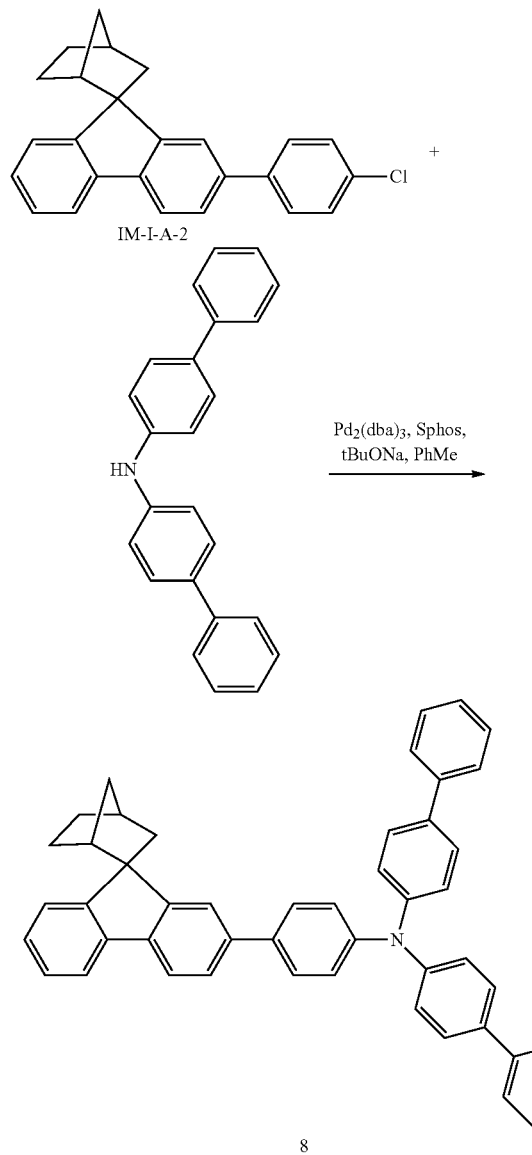

The intermediate IM-I-A-2 (2.7 g, 7.6 mmol), bis-(4-biphenyl) amine (2.43 g, 7.6 mmol), tris (dibenzylidenacetone) dipalladium (0.14 g, 0.15 mmol), 2-dicyclohexylphosphino-2', 6'-dimethoxybiphenyl (0.12 g, 0.30 mmol) and sodium tert-butoxide (1.09 g, 11.33 mmol) were added into toluene (25 mL), the reaction solution was heated to 108° C. under the protection of nitrogen and stirred for 2 h. Then the reaction solution was cooled to room temperature, after the reaction solution was washed with water, magnesium sulfate was added, the reaction solution was dried, the reaction solution was filtered and passed through a short silica gel column, the solvent was removed under reduced pressure; the crude product was recrystallized and purified by the toluene system to obtain a white solid compound 8 (2.53 g, yield was 52%). Mass spectrum: m/z=642.3 [M+H]$^+$.

Synthesis of Compound 9

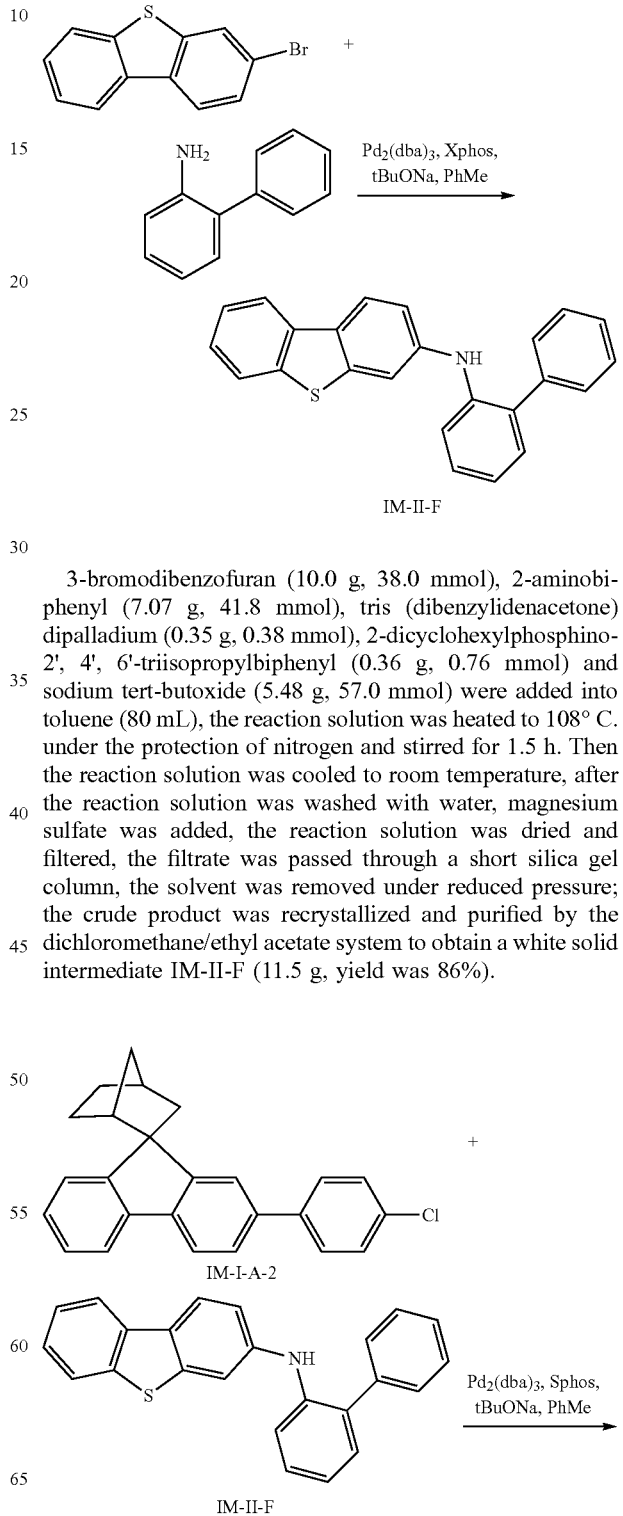

3-bromodibenzofuran (10.0 g, 38.0 mmol), 2-aminobiphenyl (7.07 g, 41.8 mmol), tris (dibenzylidenacetone) dipalladium (0.35 g, 0.38 mmol), 2-dicyclohexylphosphino-2', 4', 6'-triisopropylbiphenyl (0.36 g, 0.76 mmol) and sodium tert-butoxide (5.48 g, 57.0 mmol) were added into toluene (80 mL), the reaction solution was heated to 108° C. under the protection of nitrogen and stirred for 1.5 h. Then the reaction solution was cooled to room temperature, after the reaction solution was washed with water, magnesium sulfate was added, the reaction solution was dried and filtered, the filtrate was passed through a short silica gel column, the solvent was removed under reduced pressure; the crude product was recrystallized and purified by the dichloromethane/ethyl acetate system to obtain a white solid intermediate IM-II-F (11.5 g, yield was 86%).

-continued

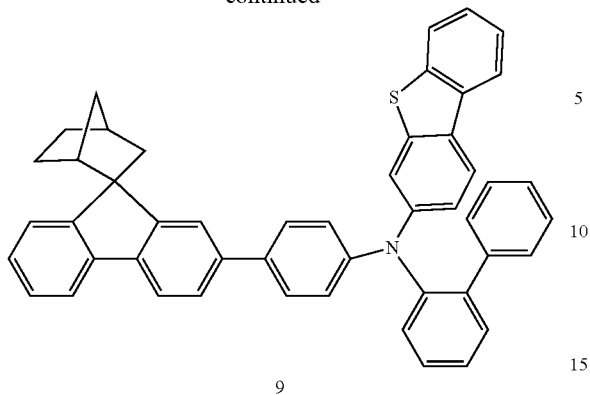

9

The intermediate IM-I-A-2 (3.0 g, 8.4 mmol), the intermediate IM-II-F (2.95 g, 8.4 mmol), tris (dibenzylidenacetone) dipalladium (0.14 g, 0.15 mmol), 2-dicyclohexylphosphino-2', 6'-dimethoxybiphenyl (0.12 g, 0.30 mmol) and sodium tert-butoxide (1.09 g, 11.33 mmol) were added into toluene (25 mL), the reaction solution was heated to 108° C. under the protection of nitrogen and stirred for 3 h. Then the reaction solution was cooled to room temperature, after the reaction solution was washed with water, magnesium sulfate was added, the reaction solution was dried, filtered and passed through a short silica gel column, the solvent was removed under reduced pressure; the crude product was recrystallized and purified by the toluene system, so that a white solid compound 9 (2.37 g, yield was 42%) was obtained. Mass spectrum: m/z=672.3 [M+H]$^+$.

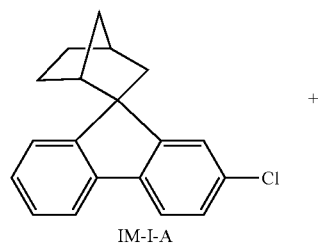

IM-I-A

+

-continued

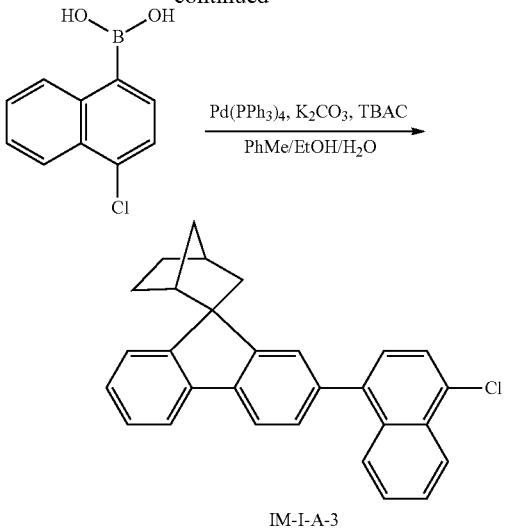

IM-I-A-3

The intermediate IM-I-A (3.0 g, 10.7 mmol), (4-chloronaphthalen-1-yl) boronic acid (1.3 g, 6.41 mmol), tetrakis (triphenylphosphine) palladium (0.15 g, 0.13 mmol), potassium carbonate (1.74 g, 12.6 mmol), tetrabutylammonium chloride (0.09 g, 0.31 mmol), toluene (25 mL), ethanol (6 mL) and deionized water (6 mL) were added into a round-bottom flask, the reaction solution was heated to 78° C. under the protection of nitrogen and stirred for 16 hours. The reaction solution was cooled to room temperature, toluene (30 mL) was added for extraction, organic phases were combined, the reaction solution was dried with anhydrous magnesium sulfate and filtered, the solvent was removed under reduced pressure The crude product was purified by silica gel column chromatography with n-heptane as a mobile phase, then recrystallized and purified by dichloromethane/ethyl acetate system to obtain a white solid intermediate IM-I-A-3 (1.89 g, yield was 72.4%).

Referring to the synthesis method of the intermediate IM-I-A-3, the difference was that the intermediate shown in Column 3 of the table below was synthesized from the raw material 1 in Column 2 in Table 1 below instead of (4-chloronaphthalen-1-yl) boronic acid:

TABLE 2

Raw Materials and Intermediates

| Intermediate Number | Raw material 3 | Intermediate Structure | Yield (%) |
|---|---|---|---|
| Intermediate IM-I-A-4 | ![Cl-phenyl-B(OH)2] | ![structure] | 37 |

TABLE 2-continued

Raw Materials and Intermediates

| Intermediate Number | Raw material 3 | Intermediate Structure | Yield (%) |
|---|---|---|---|
| Intermediate IM-I-A-5 | 2-chlorophenylboronic acid | fluorene-spirobicycloheptane with 2-chlorophenyl substituent | 41 |
| Intermediate IM-I-A-6 | 3'-chloro-[1,1'-biphenyl]-3-ylboronic acid | fluorene-spirobicycloheptane with 3'-chlorobiphenyl substituent | 39 |

Synthesis of Compound 10

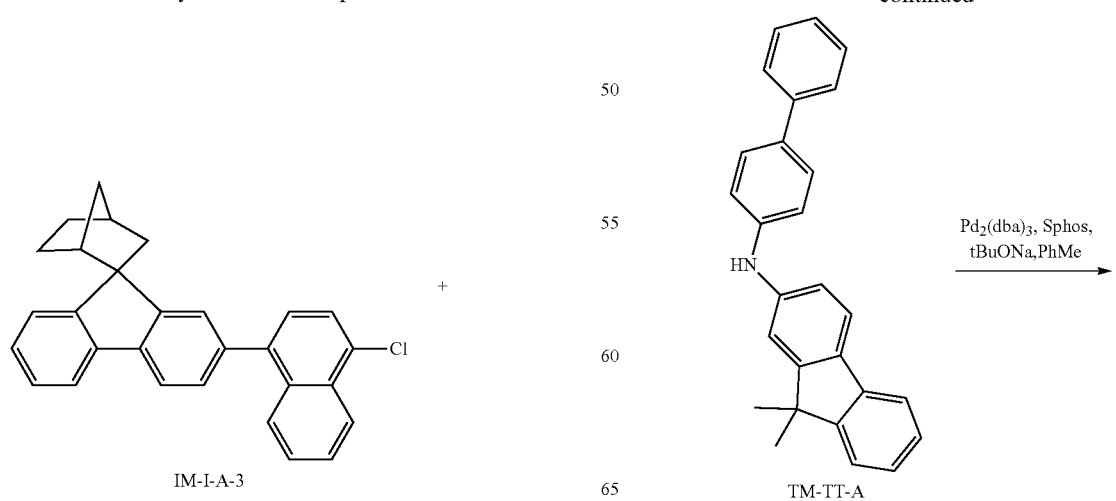

IM-I-A-3 + TM-TT-A →(Pd₂(dba)₃, Sphos, tBuONa, PhMe)

-continued

-continued

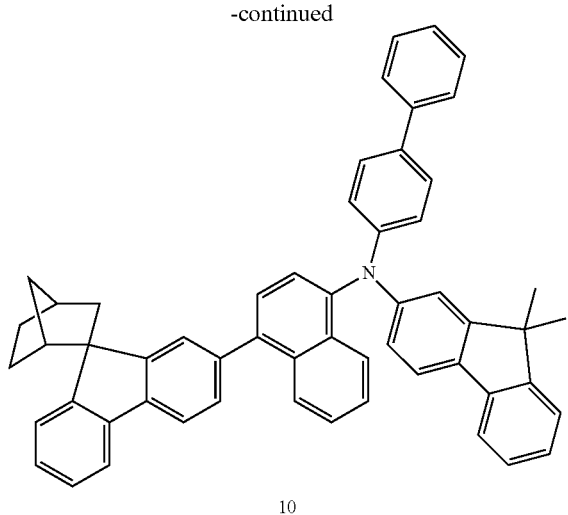

10

The intermediate IM-I-A-3 (1.18 g, 2.91 mmol), the intermediate IM-II-A (1.05 g, 2.91 mmol), tris (dibenzylide- nacetone) dipalladium (0.05 g, 0.06 mmol), 2-dicyclohex-ylphosphino-2', 6'-dimethoxybiphenyl (0.05 g, 0.12 mmol) and sodium tert-butoxide (0.42 g, 4.36 mmol) were added into toluene (20 mL), the reaction solution was heated to 108° C. under the protection of nitrogen and stirred for 2 h. Then the reaction solution was cooled to room temperature, after the reaction solution was washed with water, magnesium sulfate was added, the reaction solution was dried and filtered, the filtrate was passed through a short silica gel column, the solvent was removed under reduced pressure; the crude product was recrystallized and purified by the dichloromethane/ethyl acetate system to obtain a white solid compound 10 (2.05 g, yield was 96.7%). Mass spectrum: m/z=732.4 [M+H]$^+$.

Referring to the synthesis method of compound 10, the compound shown in Column in Table 3 was synthesized from the intermediate shown in Column 3 in Table 2 below instead of the intermediate IM-I-A, together with the intermediate IM-II-A, and the specific compound number, structure, raw materials, synthesis yield in the last step, characterization data and the like are shown in Table 3.

TABLE 3

Numbers, Structures, Preparation and Characterization Data of Compounds

| Compound Number | Intermediate Number | Intermediate Structure | Compound Structure | Yield (%) | Mass spectrum (m/z) [M + H]$^+$ |
|---|---|---|---|---|---|
| 154 | Intermediate IM-I-A-4 | | 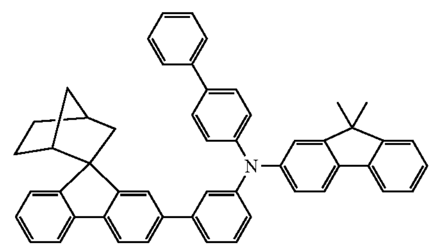 [SMILES: CC1(C)c2ccccc2-c2ccc(N(c3ccc(-c4ccccc4)cc3)c3cccc(-c4ccc5c(c4)C4(CC6CCC4C6)c4ccccc4-5)c3)cc21] | 61 | 682.3 |
| 155 | Intermediate IM-I-A-5 | | 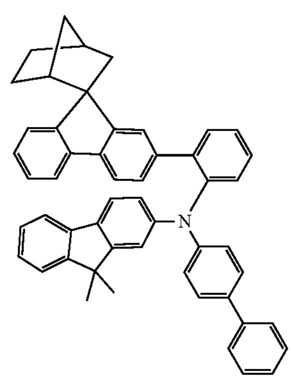 [SMILES: CC1(C)c2ccccc2-c2ccc(N(c3ccc(-c4ccccc4)cc3)c3ccccc3-c3ccc4c(c3)C3(CC5CCC3C5)c3ccccc3-4)cc21] | 57 | 682.3 |

TABLE 3-continued

Numbers, Structures, Preparation and Characterization Data of Compounds

| Compound Number | Intermediate Number | Intermediate Structure | Compound Structure | Yield (%) | Mass spectrum (m/z) [M + H]+ |
|---|---|---|---|---|---|
| 338 | Intermediate IM-I-A-6 | 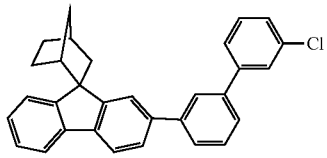 [SMILES: Clc1cccc(-c2cccc(-c3ccc4c(c3)C3(CC5CCC3C5)c3ccccc3-4)c2)c1] | 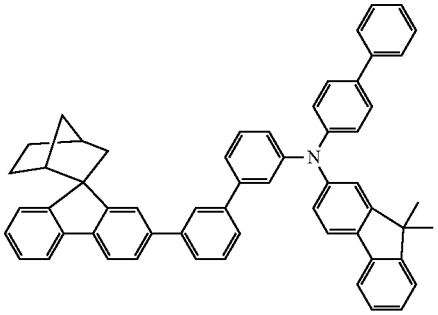 [SMILES: CC1(C)c2ccccc2-c2ccc(N(c3ccc(-c4ccccc4)cc3)c3cccc(-c4cccc(-c5ccc6c(c5)C5(CC7CCC5C7)c5ccccc5-6)c4)c3)cc21] | 54 | 758.4 |

Synthesis of Compound 11

Synthesis of Compound 13

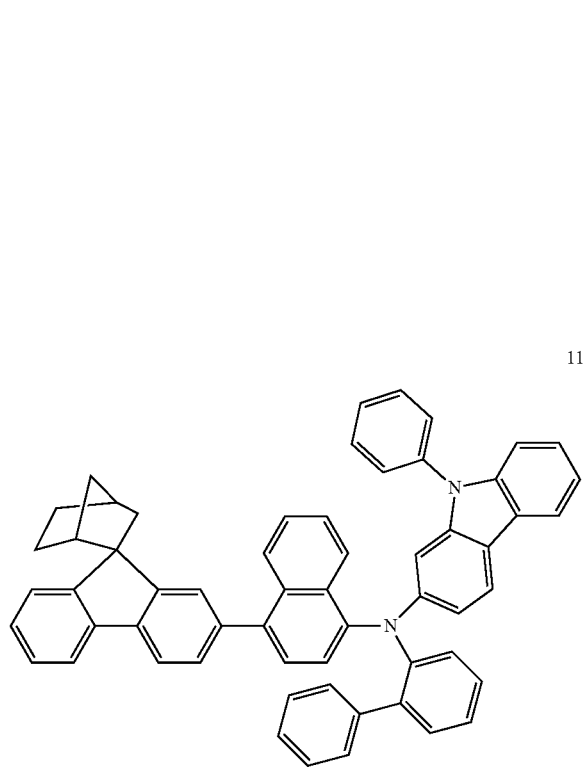 [SMILES: c1ccc(-c2ccccc2N(c2ccc3c4ccccc4n(-c4ccccc4)c3c2)c2ccc(-c3ccc4c(c3)C3(CC5CCC3C5)c3ccccc3-4)c3ccccc23)cc1]

11

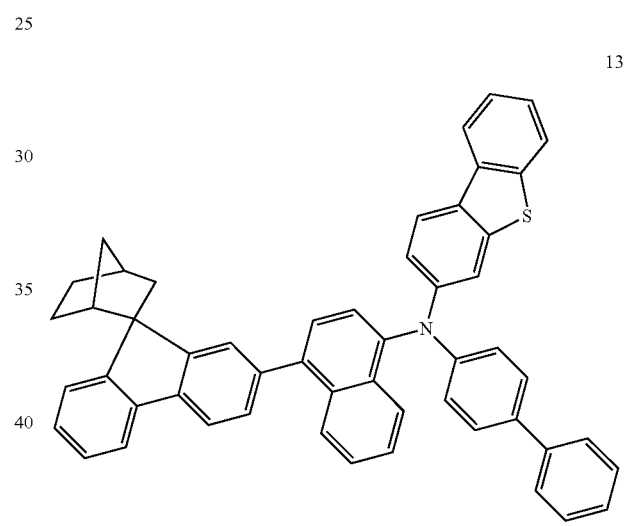

13

The compound 13 was synthesized from 3.11 g (15 mmol) of intermediate I-A-3 and 5.06 g (16.5 mmol) of intermediate IM-II-D by reference to the synthesis method of compound 1. Mass spectrum: m/z=722.3[M+H]+.

Synthesis of Compound 14

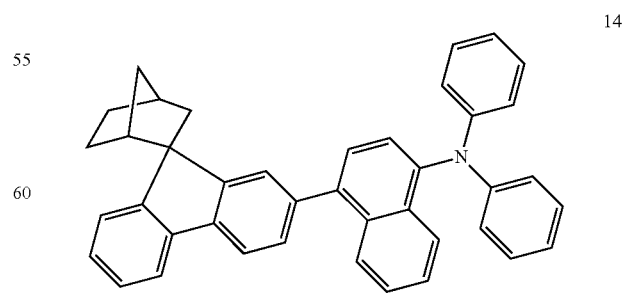

14

The compound 11 was synthesized from 5.64 g (15 mmol) of intermediate IM-I-A-3 and 4.96 g (15 mmol) of intermediate IM-II-B by reference to the synthesis method of compound 1. Mass spectrum: m/z=781.4[M+H]+.

The compound 14 was synthesized from 4.12 g (15 mmol) of intermediate I-A-3 by reference to the synthesis method of compound 4. Mass spectrum: m/z=540.3[M+H]+.

Synthesis of Compound 15

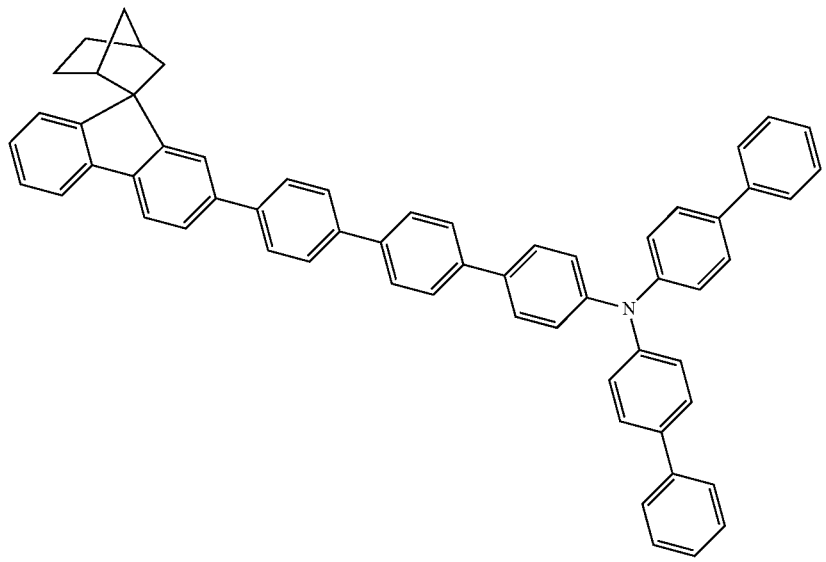

The compound 15 was synthesized from 4-chlorobiphenyl-4-boric acid instead of 4-chlorophenylboronic acid by reference to the synthesis method of compound 8. Mass spectrum: m/z=794.4[M+H]$^+$.

Synthesis of Compound 17

Synthesis of Compound 22

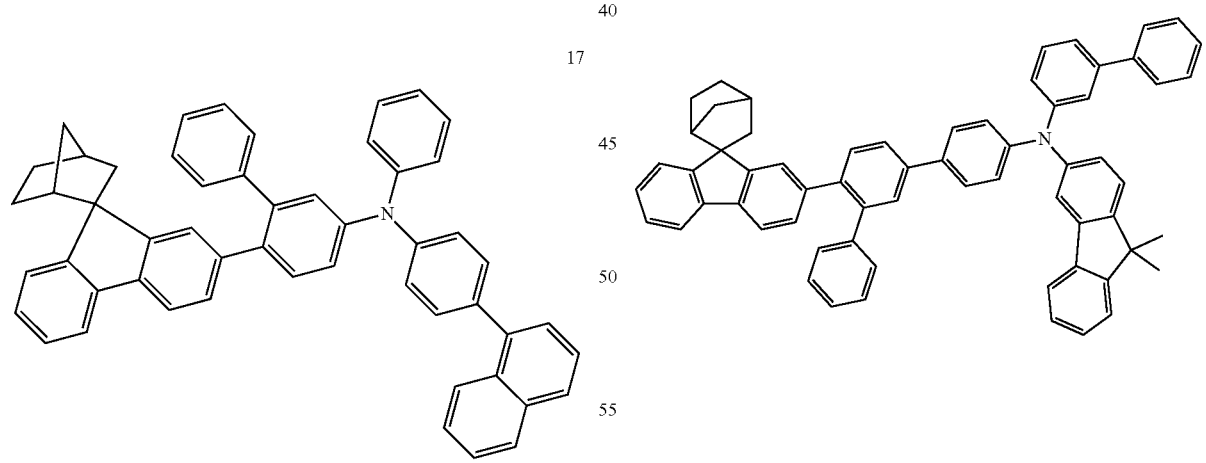

The compound 17 was synthesized from (6-chloro-[1,1'-biphenyl]-3-yl) boric acid instead of 4-chlorophenylboronic acid, and an intermediate synthesized from phenylamine and 1-(4-chlorophenyl) naphthalene instead of bis-(4-biphenyl) amine by reference to the synthesis method of compound 8. Mass spectrum: m/z=692.3[M+H]$^+$.

The compound 22 was synthesized from an intermediate synthesized from 2,5-dichloro-1,1'-biphenyl and 4-chlorophenylboronic acid instead of the intermediate IM-I-A-2, and an intermediate synthesized from 3-aminobiphenyl and 3-bromo-9,9-dimethylfluorene instead of bis-(4-biphenyl) amine by reference to the synthesis method of compound 8. Mass spectrum: m/z=834.4[M+H]$^+$.

Synthesis of Compound 26

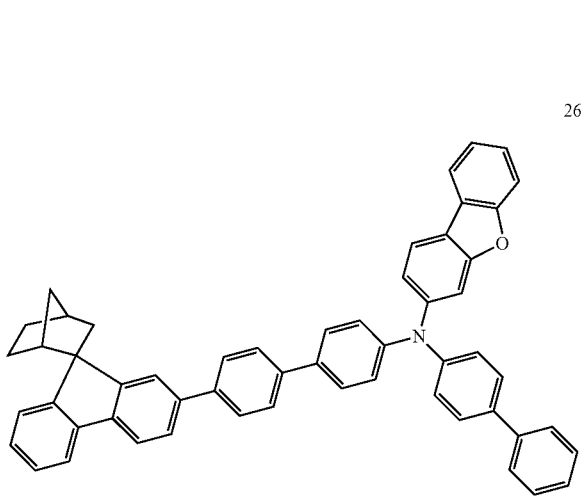 [SMILES: c1ccc(-c2ccc(N(c3ccc(-c4ccc(-c5ccc6c(c5)C5(CC7CCC5C7)c5ccccc5-6)cc4)cc3)c3ccc4c(c3)oc3ccccc34)cc2)cc1]

The compound 12 was synthesized from 4'-chlorobiphenyl-4-boric acid instead of (4-chloronaphthalen-1-yl) boronic acid, and 5.73 g (15 mmol) of intermediate IM-II-C instead of the intermediate IM-II-A by reference to the synthesis method of compound 10. Mass spectrum: m/z=732.3[M+H]$^+$.

Synthesis of Compound 29

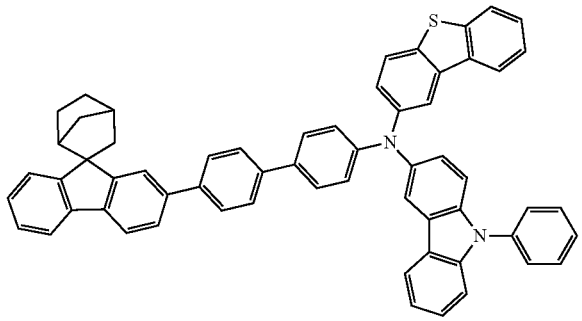

The compound 29 was synthesized from an intermediate synthesized from 2-aminodibenzothiophene and 3-bromo-9-phenyl-9H-carbazole instead of the intermediate IM-II-C by reference to the synthesis method of compound 26. Mass spectrum: m/z=837.3[M+H]$^+$.

Synthesis of Compound 30

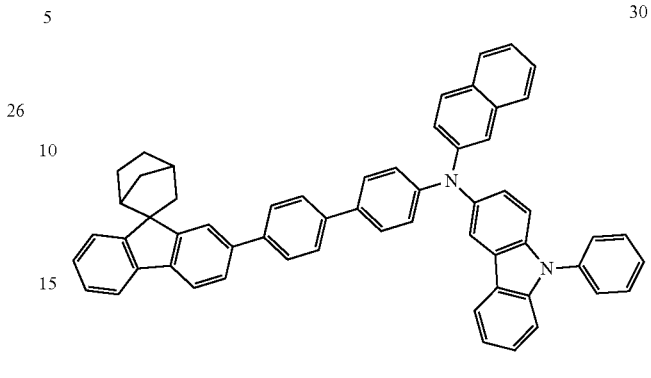

The compound 30 was synthesized from an intermediate synthesized from 2-naphthylamine and 3-bromo-9-phenyl-9H-carbazole instead of the intermediate IM-II-C by reference to the synthesis method of compound 8. Mass spectrum: m/z=781.4[M+H]$^+$.

Synthesis of Compound 31

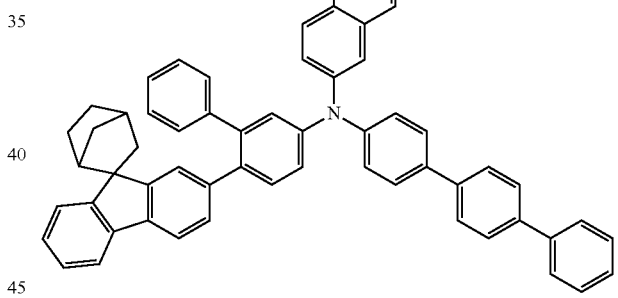

The compound 31 was synthesized from (6-chloro-[1,1'-biphenyl]-3-yl) boric acid instead of 4-chlorophenylboronic acid, and an intermediate synthesized from 2-aminophenanthrene and 4-bromo-p-terphenyl instead of bis-(4-biphenyl) amine by reference to the synthesis method of compound 8. Mass spectrum: m/z=818.4[M+H]$^+$.

Synthesis of Compound 143

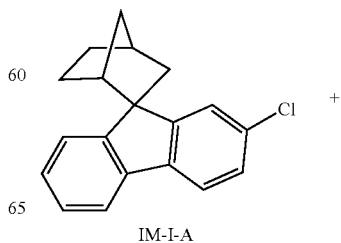

IM-I-A

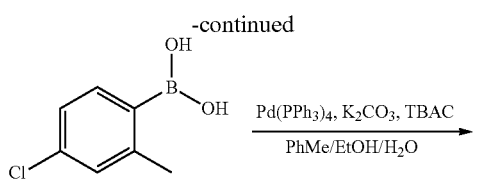

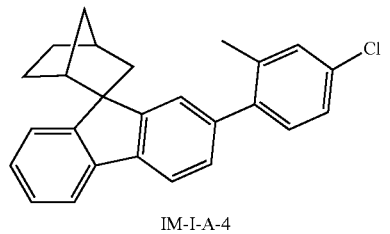

IM-I-A-4

The intermediate IM-I-A-4 was synthesized from 4-chloro-2-methylphenylboric acid instead of (4-chloronaphthalen-1-yl) boronic acid by reference to the synthesis method of intermediate IM-I-A-3.

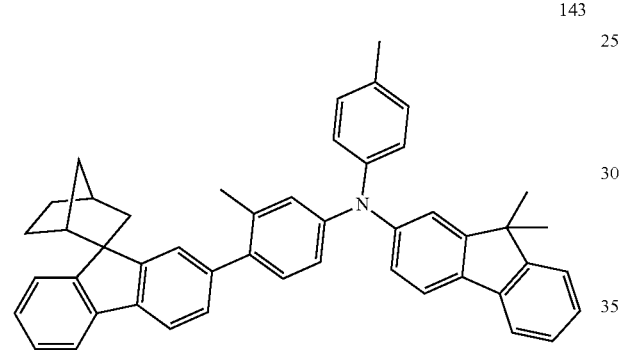

143

The compound 143 was synthesized from the intermediate IM-I-A-4 instead of the intermediate IM-I-A, and an intermediate synthesized from p-methylbromobenzene and 2-amino-9,9-dimethylfluorene instead of the intermediate IM-II-A by reference to the synthesis method of compound 1. Mass spectrum: m/z=634.3[M+H]$^+$.

Synthesis of Compound 145

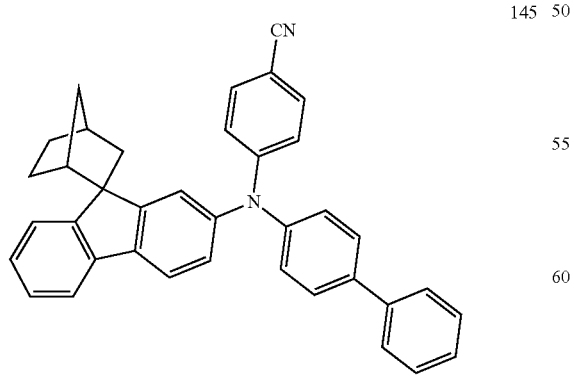

145

The compound 145 was synthesized from an intermediate synthesized from 4-bromobenzonitrile and 4-aminobiphenyl instead of the intermediate IM-II-A by reference to the synthesis method of compound 1. Mass spectrum: m/z=515.2[M+H]$^+$.

Synthesis of Compound 146

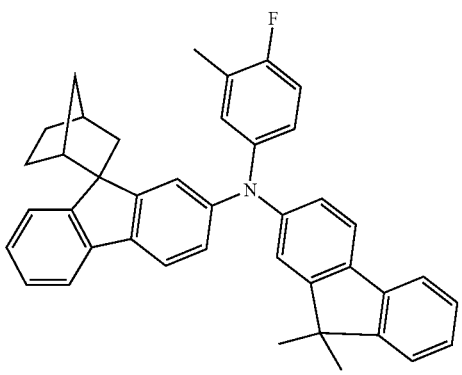

146

The compound 146 was synthesized from an intermediate synthesized from 5-bromo-2-fluorotoluene and 2-amino-9,9-dimethylfluorene instead of the intermediate IM-II-A by reference to the synthesis method of compound 1. Mass spectrum: m/z=562.2[M+H]$^+$.

Synthesis of Compound 147

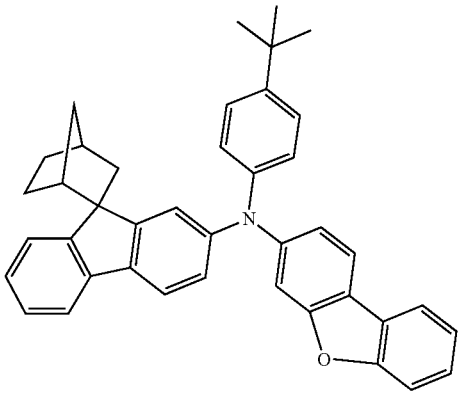 [SMILES: CC(C)(C)c1ccc(N(c2ccc3c(c2)C2(CC4CCC2C4)c2ccccc2-3)c2ccc3c(c2)oc2ccccc23)cc1]

The compound 147 was synthesized from an intermediate synthesized from 4-tert-butylbromobenzene and 3-aminodibenzofuran instead of the intermediate IM-II-A by reference to the synthesis method of compound 1. Mass spectrum: m/z=560.3[M+H]$^+$.

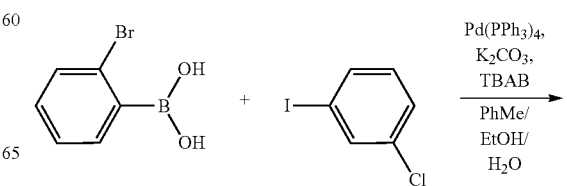

-continued

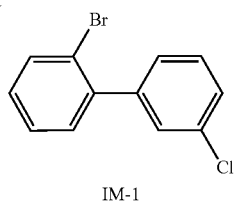

IM-1

2-bromophenylboronic acid (100.0 g, 500.0 mmol), 1-chloro-3 iodobenzene (142.6 g, 597.6 mmol), tetrakis (triphenylphosphine) palladium (11.5 g, 9.97 mmol), potassium carbonate (102 g, 746 mmol), tetrabutyl ammonium bromide (32.1 g, 99.6 mmol), toluene (800 mL), ethanol (200 mL) and deionized water (200 mL) were added into a round-bottom flask, the reaction solution was heated to 78° C. under the protection of nitrogen and stirred for 2 hours; the reaction solution was cooled to room temperature, toluene (500 mL) was added for extraction, organic phases were combined, the reaction solution was dried with anhydrous magnesium sulfate, filtered, the solvent was removed under reduced pressure; the crude product was purified by silica gel column chromatography with n-heptane as a mobile phase, then recrystallized and purified by dichloromethane/ethanol system to obtain a light yellow solid intermediate IM-I (64.0 g, yield was 48%).

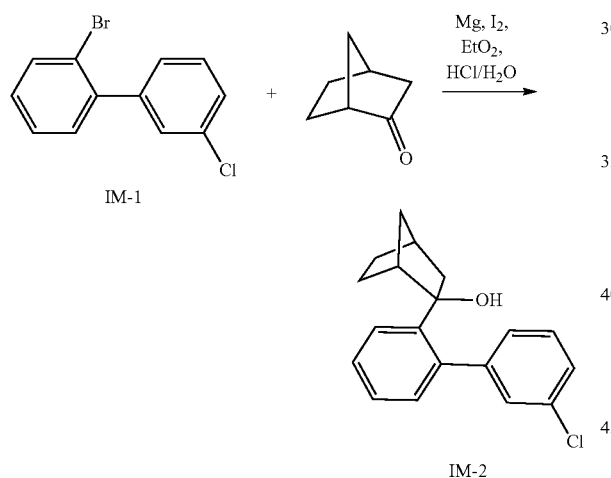

A magnesium ribbon (13.54 g, 564 mmol) and diethyl ether (100 mL) were placed in a dry round-bottom flask under protection of nitrogen gas, and iodine (100 mg) was added. Then the intermediate IM-1(64.00 g, 239.0 mmol) dissolved in diethyl ether (200 mL) was slowly dropped into the flask, the temperature was raised to 35° C. after dropping was completed, and the solution was stirred for 3 hours; the temperature of the reaction solution was cooled to 0° C., the solution of norbornanone (16.3 g, 149 mmol) dissolved in diethyl ether (200 mL) was slowly dropped into the reaction solution, the temperature was raised to 35° C. after dropping was completed, and the reaction solution was stirred for 6 hours; the reaction solution was cooled to room temperature, 5% hydrochloric acid was added into the reaction solution until pH<7, the reaction solution was stirred for 1 hour, diethyl ether (200 mL) was added for extraction, organic phases were combined, the reaction solution was dried with anhydrous magnesium sulfate and filtered, and the solvent was removed under reduced pressure; the crude product was purified by silica gel column chromatography with n-heptane as a mobile phase, and a solid intermediate IM-2 (24 g, yield was 54.16%) was obtained.

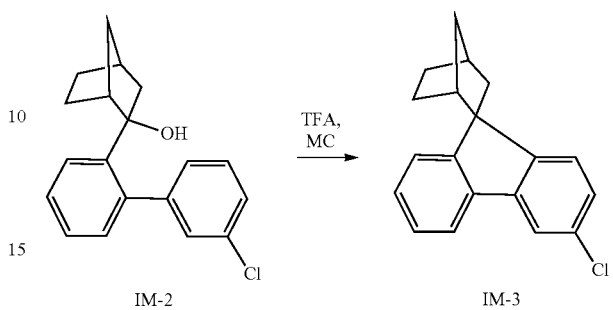

The intermediate IM-2 (24 g, 80.32 mmol), trifluoroacetic acid (40.48 g, 355.0 mmol) and dichloromethane (200 mL) were added into a round-bottom flask, and stirred for 2 hours under the protection of nitrogen; then, an aqueous solution of sodium hydroxide was added into the reaction solution until pH=8, followed by liquid separation, the organic phase was dried with anhydrous magnesium sulfate and filtered, and the solvent was removed under reduced; the crude product was recrystallized and purified by dichloromethane/n-heptane (1:2), and a white solid intermediate IM-3 (21 g, yield was 93.12%) was obtained.

Synthesis of Compound 317

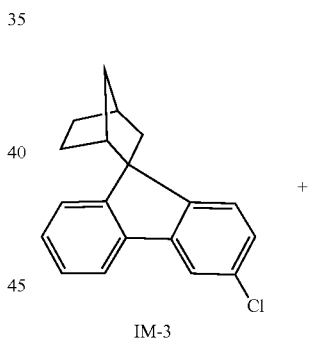

+

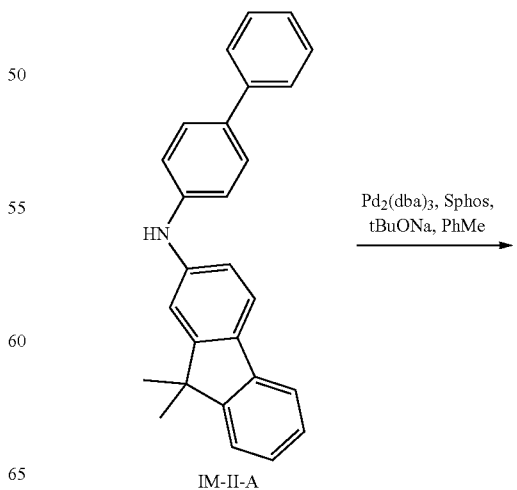

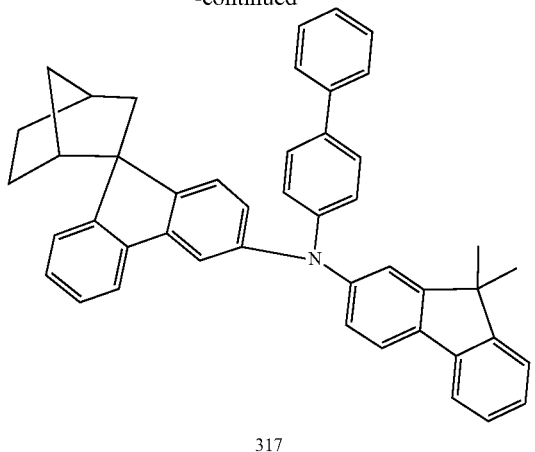

317

The compound 317 was synthesized from the intermediate IM-3 instead of the intermediate IM-I-A by reference to the synthesis method of compound 1. Mass spectrum: m/z=606.3 [M+H]⁺.

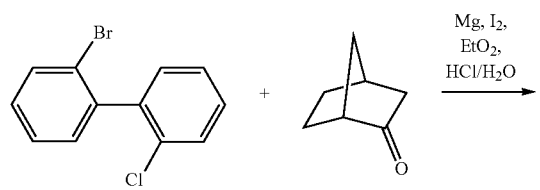

A magnesium ribbon (13.54 g, 564 mmol) and diethyl ether (100 mL) were placed in a dry round-bottom flask under the protection of nitrogen gas, and iodine (100 mg) was added.

Then, 2'-bromo-2-chlorobiphenyl (50.00 g, 187.0 mmol) dissolved in diethyl ether (200 mL) was slowly dropped into the flask, the temperature was raised to 35° C. after dropping was completed, and the solution was stirred for 3 hours; the temperature of the reaction solution was cooled to 0° C., the solution of norbornanone (16.4 g, 149 mmol) dissolved in diethyl ether (200 mL) was slowly dropped into the reaction solution, the temperature was raised to 35° C. after dropping was completed, and the reaction solution was stirred for 6 hours; the reaction solution was cooled to room temperature, 5% hydrochloric acid was added into the reaction solution until pH<7, the reaction solution was stirred for 1 hour, diethyl ether (200 mL) was added for extraction, organic phases were combined, the reaction solution was dried with anhydrous magnesium sulfate and filtered, the solvent was removed under reduce pressure; the crude product was purified by silica gel column chromatography with ethyl acetate/n-heptane (1:2) as a mobile phase, and a white solid intermediate IM-I-B (30.26 g, yield was 68%) was obtained.

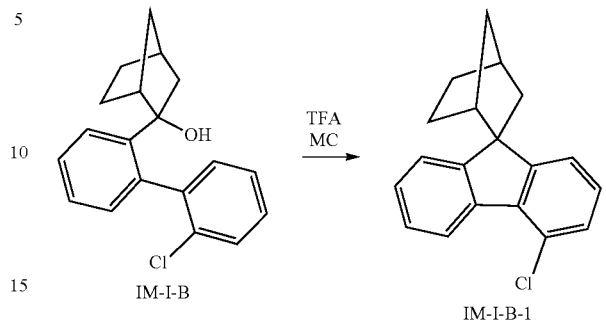

The intermediate IM-I-B (30.37 g, 101.6 mmol), trifluoroacetic acid (TFA) (36.93 g, 380.6 mmol) and dichloromethane (MC) (300 mL) were added into a round-bottom flask and stirred for 2 hours under the protection of nitrogen; then, an aqueous solution of sodium hydroxide was added into the reaction solution until pH=8, followed by liquid separation, the organic phase was dried with anhydrous magnesium sulfate and filtered, the solvent was removed under reduced pressure; the crude product was purified by silica gel column chromatography with dichloromethane/n-heptane (1:2), and a white solid intermediate IM-I-B-1 (27.51 g, 96.3%) was obtained.

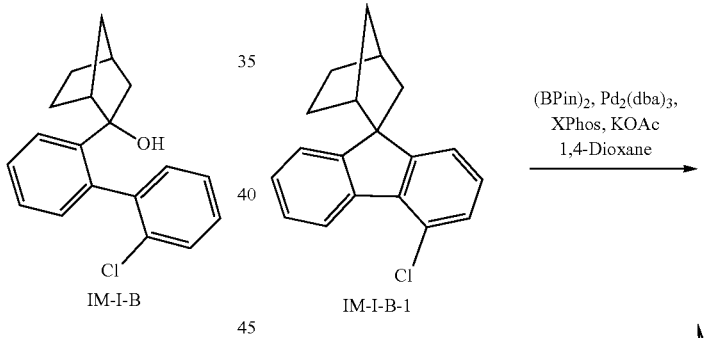

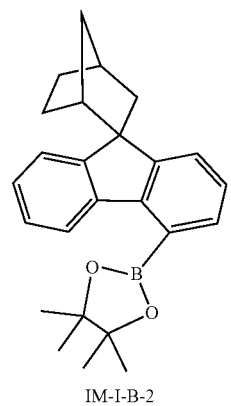

IM-I-B-2

The intermediate IM-I-B-1 (20.4 g; 72.6 mmol), bis(pinacolato) diboron (19.4 g; 76.5 mmol), tris (dibenzylideneacetone) dipalladium (0.6 g; 0.6 mmol), 2-(Dicyclohexylphosphino)-2',4',6'-triisopropylbiphenyl (0.6 g; 1.3 mmol), potassium acetate (12.5 g; 127.4 mmol) and 1,4-dioxane (150 mL) were added into a flask, and stirred at 100° C. with reflux for 16 under the protection nitrogen gas; the reaction solution was cooled to room temperature, dichloromethane and water were added into the reaction solution to separate, the organic phase was washed with water and dried with anhydrous magnesium sulfate, the solvent was removed under reduced pressure, and the crude product was obtained; the crude product was purified by silica gel column chromatography by dichloromethane/n-heptane system, and a white solid intermediate IM-I-B-2 (13.3 g; 51%) was obtained.

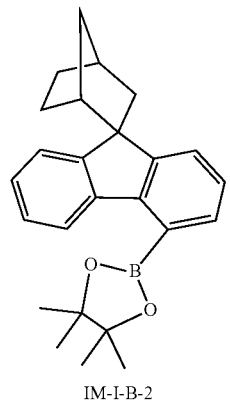

IM-I-B-2

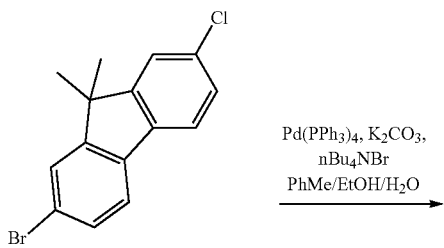

IM-I-B-3

The intermediate IM-I-B-2 (13.3 g; 35.7 mmol), 2-bromo-7-chloro-9,9-dimethyl fluorene (12.1 g; 39.3 mmol), tetrakis (triphenylphosphine) palladium (0.7 g; 0.6 mmol), potassium carbonate (11.1 g; 80.7 mmol) and tetrabutyl ammonium bromide (2.1 g; 6.5 mmol) were added into a flask, a mixed solvent of toluene (80 mL), ethanol (20 mL) and water (20 mL) was added, the temperature was raised to 80° C. and stirred for 24 hours maintaining the temperature under the protection of nitrogen; the solution was cooled to room temperature, the stirring was stopped, after the reaction solution was washed with water, the organic phase was separated, the reaction solution was dried with anhydrous magnesium sulfate, the solvent was removed under reduced pressure, and the crude product was obtained; the crude product was purified by silica gel column chromatography with dichloromethane/n-heptane as the mobile phase, and a white solid product intermediate IM-I-B-3 (9.0 g; 53.3%) was obtained.

Referring to the synthesis method of the intermediate IM-I-B-3, the difference was that the intermediates IM-I-B-4 to IM-I-B-6 shown in Column 3 of the table below were synthesized from the raw material 2 in Column 2 in Table 4 below instead of 2-bromo-7-chloro-9,9-dimethylfluorene:

TABLE 4

Raw Materials and Intermediates

| Intermediate Number | Raw material 2 | Intermediate Structure | Yield (%) |
|---|---|---|---|
| Intermediate IM-I-B-4 |  |  | 39 |

TABLE 4-continued

Raw Materials and Intermediates

| Intermediate Number | Raw material 2 | Intermediate Structure | Yield (%) |
|---|---|---|---|
| Intermediate IM-I-B-5 | | | 22 |
| Intermediate IM-I-B-6 | | | 31 |

Referring to the synthesis method of compound 5, the compounds 339~342 shown in Column 4 in Table 5 were synthesized from an intermediate shown in Column 3 in Table 5 below instead of the intermediate IM-I-A with bis-(4-biphenyl) amine, and the specific compound number, structure, raw materials, synthesis yield in the last step, characterization data and the like are shown in Table 5.

TABLE 5

Numbers, Structures, Preparation and Characterization Data of Compounds

| Compound Number | Intermediate Number | Intermediate Structure | Compound Structure | Yield (%) | Mass spectrum (m/z) [M + H]⁺ |
|---|---|---|---|---|---|
| 339 | Intermediate IM-I-B-3 | | 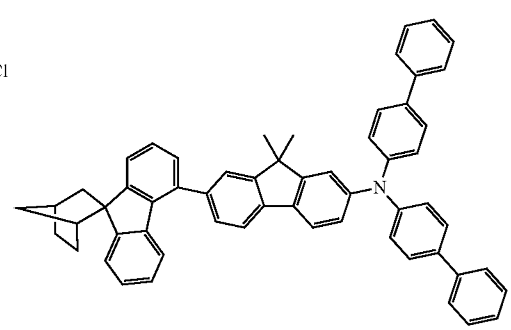 | 61 | 758.4 |

TABLE 5-continued

Numbers, Structures, Preparation and Characterization Data of Compounds

| Compound Number | Intermediate Number | Intermediate Structure | Compound Structure | Yield (%) | Mass spectrum (m/z) [M + H]+ |
|---|---|---|---|---|---|
| 340 | Intermediate IM-I-B-4 | | 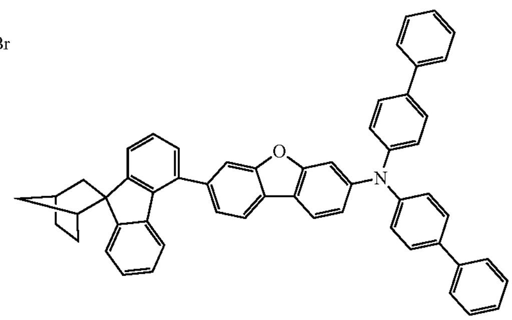 | 57 | 732.3 |
| 341 | Intermediate IM-I-B-5 | | 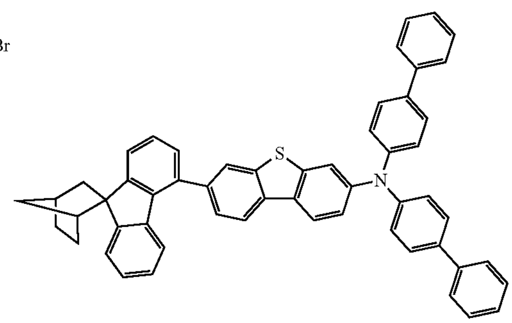 | 42 | 748.3 |
| 342 | Intermediate IM-I-B-6 | | 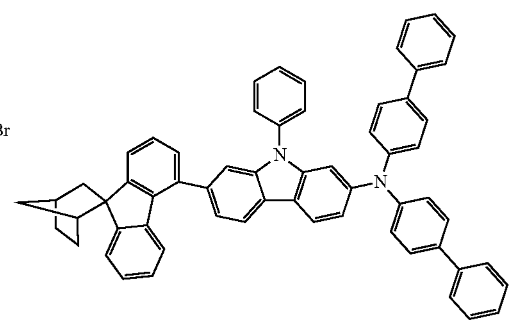 | 49 | 807.4 |

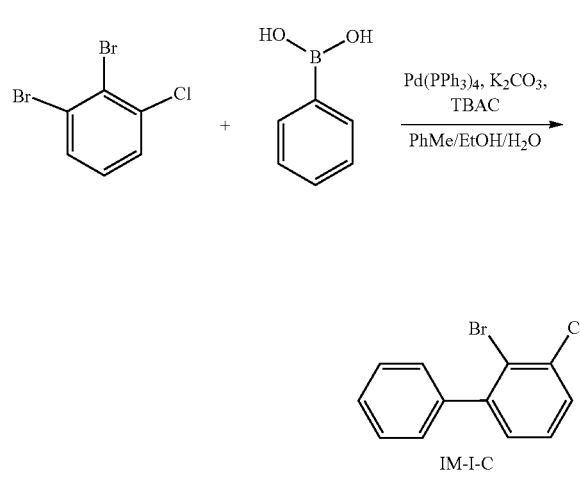

1,2-dibromo-3-chlorobenzene (80.8 g; 298.7 mmol), phenylboric acid (36.5 g; 298.7 mmol), tetrakis (triphenylphosphine) palladium (6.9 g; 6.0 mmol), potassium carbonate (103.2 g; 746.7 mmol), tetrabutyl ammonium bromide (19.2 g; 59.7 mmol) were added into a flask, a mixed solvent of toluene (600 mL), ethanol (150 mL) and water (150 mL) was added, the temperature was raised to 80° C. and stirred for 18 hours maintaining the temperature under the protection of nitrogen; the solution was cooled to room temperature, the stirring was stopped, after the reaction solution was washed with water, the organic phase was separated, the reaction solution was dried with anhydrous magnesium sulfate, the solvent was removed under reduced pressure, and the crude product was obtained; the crude product was purified by silica gel column chromatography with dichloromethane/n-heptane as the mobile phase, and a white solid product intermediate IM-I-C (42.0 g; yield 53%) was obtained.

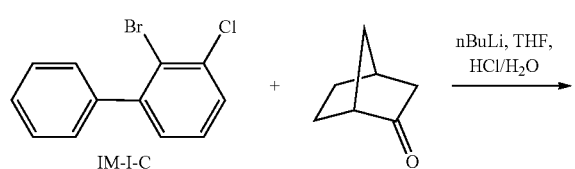

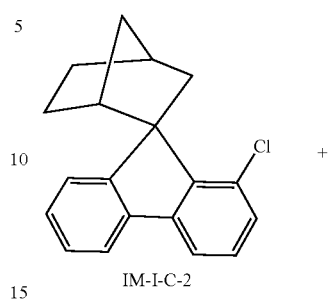

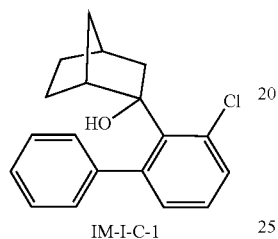

The intermediate IM-I-C (42.0 g; 157.9 mmol) and tetrahydrofuran (300 ml) were added into the flask, cooled to −78° C. under the protection of nitrogen, a tetrahydrofuran (2.5M) solution (95 mL; 236.9 mmol) of n-butyl lithium was dropped under the stirring condition, after dropping was completed, the temperature was maintained, the reaction solution was stirred for 1 hour, the temperature was kept at −78° C., a solution of norbornanone (19.0 g; 172.5 mmol) dissolved in tetrahydrofuran (100 mL) was dropped, after dropping was completed, the temperature was kept for 1 hour and raised to room temperature, and the solution was stirred for 24 hours; an aqueous (100 mL) solution of hydrochloric acid (12M) (26.3 mL; 315.8 mmol) was added into the reaction solution and stirred for 1 hour; after liquid separation, the organic phase was washed with water to neutral, anhydrous magnesium sulfate was added for drying, the solvent was removed under reduced pressure, and the crude product was obtained; the crude product was purified by silica gel column chromatography by ethyl acetate/n-heptane system, and a white solid product intermediate IM-I-C-1 (25.8 g; yield 54%) was obtained.

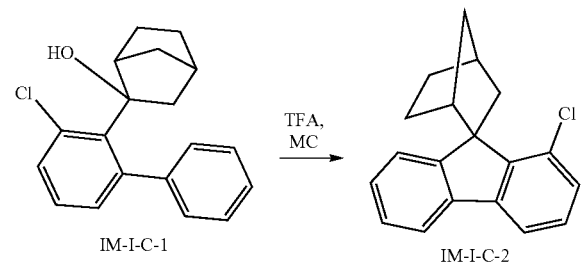 [SMILES: OC1(c2c(Cl)cccc2-c2ccccc2)CC2CCC1C2 ; Clc1cccc2c1C1(CC3CCC1C3)c1ccccc1-2]

The intermediate IM-I-C-2 was synthesized from the intermediate IM-I-C-1 instead of the intermediate IM-I-A-1 by reference to the synthesis method of the intermediate IM-I-A.

Synthesis of Compound 194

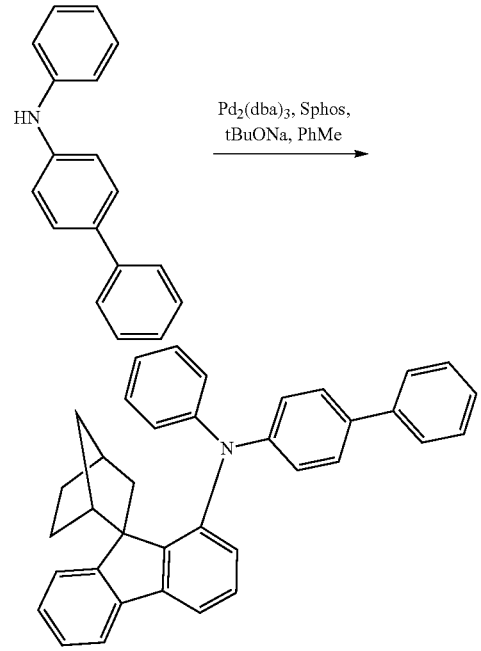

The intermediate IM-I-C-2 (3.06 g, 10.9 mmol), N-phenyl-4-benzidine (2.67 g, 10.9 mmol), tris (dibenzylidenacetone) dipalladium (0.20 g, 0.22 mmol), 2-dicyclohexylphosphino-2', 6'-dimethoxybiphenyl (0.18 g, 0.44 mmol) and sodium tert-butoxide (1.58 g, 16.4 mmol) were added into toluene (30 mL), the reaction solution was heated to 108° C. under the protection of nitrogen and stirred for 8 h. Then the reaction solution was cooled to room temperature, after the reaction solution was washed with water, magnesium sulfate was added, the reaction solution was dried and filtered, after filtered, it the solvent from the filtrate was removed under reduced pressure; the crude product was recrystallized and purified by the toluene system, so that a white solid compound 194 (4.35 g, yield was 78.5%) was obtained. Mass spectrum: m/z=490.2 [M+H]$^+$.

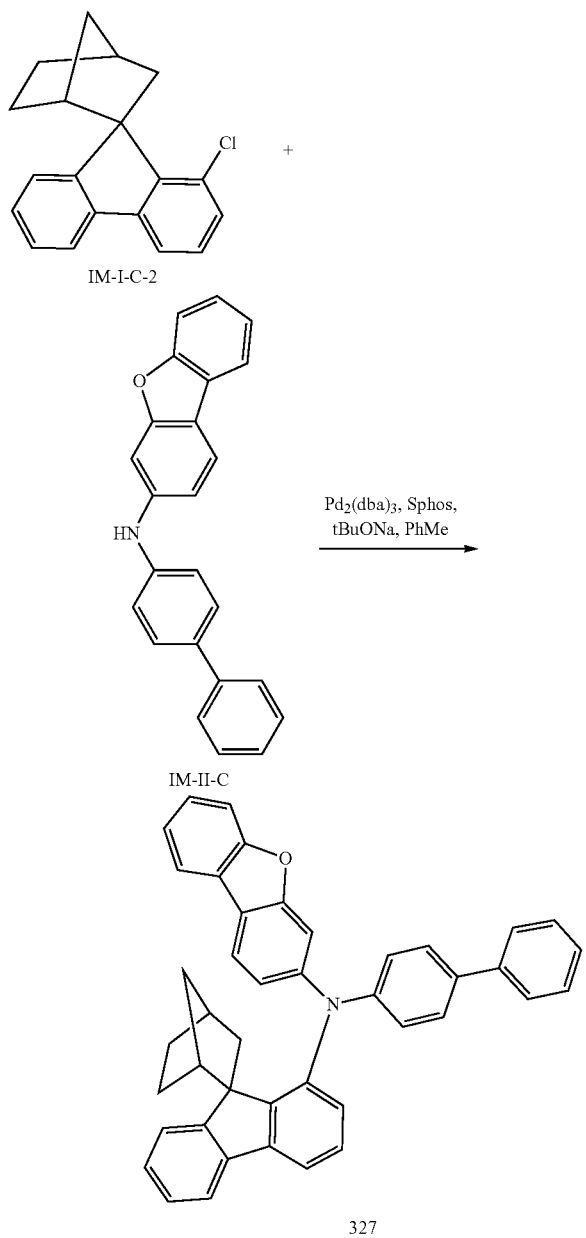

The intermediate IM-I-C-2 (3.05 g, 10.9 mmol), the intermediate IM-II-C (3.64 g, 10.9 mmol), tris (dibenzylidenacetone) dipalladium (0.20 g, 0.22 mmol), 2-dicyclohexylphosphino-2', 6'-dimethoxybiphenyl (0.18 g, 0.44 mmol) and sodium tert-butoxide (1.57 g, 16.4 mmol) were added into toluene (30 mL), the reaction solution was heated to 108° C. under the protection of nitrogen and stirred for 5 h. Then the reaction solution was cooled to room temperature, after the reaction solution was washed with water, magnesium sulfate was added, the reaction solution was dried and filtered, the filtrate was passed through a short silica gel column, the solvent was removed under reduced pressure; the crude product was recrystallized and purified by the dichloromethane/ethyl acetate system, so that a white solid compound 327 (4.73 g, yield was 75.1%) was obtained. Mass spectrum: m/z=580.3 [M+H]$^+$.

Nuclear magnetic data of some compounds are shown in Table 6 below

TABLE 6

| Nuclear Magnetic Data of Some Compounds | |
|---|---|
| Compound 1 | $^1$HNMR: (400 MHZ, $CD_2Cl_2$) 7.69 (d, 2 H), 7.66 (d, 2 H), 7.68-7.63 (m, 2 H), 7.55 (m, 4 H), 7.47-7.45 (m, 3 H), 7.39-7.18 (m, 8 H), 7.15-7.06 (d, 2 H), 2.44 (s, 1 H), 2.04-1.34 (m, 15 H). |
| Compound 5 | $^1$HNMR: (400 MHZ, $CD_2Cl_2$) 7.69 (d, 2 H), 7.68-7.63 (m, 4 H), 7.55 (m, 5 H), 7.50-7.45 (m, 8 H), 7.39-7.20 (m, 5 H), 6.98 (d, 1 H) 2.44 (s, 1 H), 2.04-1.34 (m, 9 H). |
| Compound 6 | $^1$HNMR: (400 MHZ, $CD_2Cl_2$): 7.93 (d, 1 H), 7.80-7.75 (m, 2 H), 7.69 (d, 2 H), 7.68-7.63 (m, 3 H), 7.55 (m, 4 H), 7.50-7.45 (m, 3 H), 7.39-7.20 (m, 7 H), 6.98 (d, 1 H), 2.44 (s, 1 H), 2.04-1.34 (m, 9 H). |
| Compound 8 | $^1$HNMR: (400 MHZ, $CD_2Cl_2$): 7.72 (d, 1 H), 7.68-7.63 (m, 6 H), 7.55 (m, 7 H), 7.50-7.45 (m, 6 H), 7.39-7.20 (m, 9 H), 2.44 (s, 1 H), 2.04-1.34 (m, 9 H). |
| Compound 343 | $^1$HNMR: (400 MHZ, $CD_2Cl_2$): 7.69 (d, 2 H), 7.66-7.63 (m, 2 H), 7.55 (d, 1 H), 7.47-7.45 (m, 5 H), 7.39-7.18 (m, 12 H), 7.15-7.06 (m, 5 H), 6.98 (d, 1 H), 6.83 (d, 1 H), 2.44 (s, 1 H), 2.04-1.34 (m, 9 H). |

Fabrication and Evaluation Embodiments of Organic Electroluminescent Devices

Fabrication of Blue Organic Electroluminescent Devices

Example 1

The anode was prepared through the following process: an ITO substrate (manufactured by Corning) with an ITO thickness of 1200 Å was cut into the dimension of 40 mm (length)×40 mm (width)×0.7 mm (thickness), then making it into an experimental substrate with cathode, anode and insulating layer patterns by the photolithography process. The experimental substrate was treated with ultraviolet ozone and $O_2$:$N_2$ plasma to increase the work function of the anode (experimental substrate) and remove scum.

m-MTDATA (4,4',4''-tris (N-3-methylphenyl-N-phenylamino) triphenylamine) was vacuum evaporated on the experimental substrate (anode) to form a hole injection layer (HIL) with a thickness of 100 Å, and the compound 1 was vacuum deposited on the hole injection layer to form a first hole transport layer (HTL1) with a thickness of 1120 Å.

TCTA (4,4',4''-tris (carbazole-9-yl) triphenylamine) was evaporated on the first hole transport layer to form a second hole transport layer (HTL2) with a thickness of 100 Å.

An organic light-emitting layer (EML) with a thickness of 220 Å was formed with α,β-ADN as the host material doped with BD-1 as the guest material at the film thickness ratio of 30:3.

DBimiBphen and LiQ (8-hydroquinoline-lithium) were mixed at the weight ratio of 1:1 and evaporated to form an electron transport layer (ETL) with a thickness of 300 Å, Yb (ytterbium) was evaporated on the electron transport layer to form an electron injection layer (EIL) with a thickness of 15 Å, then magnesium (Mg) and silver (Ag) were mixed at a deposition rate of 1:9 and vacuum vacuum-evaporated on the electron injection layer to form a cathode with a thickness of 115 Å.

In addition, as CP-1 was deposited with a thickness of 700 Å on the cathode, a capping layer (CPL) was formed, so that the manufacturing of the organic electroluminescent device was completed.

Wherein the structural formulas of m-MTDATA, TCTA, α,β-ADN, BD-1, DBimiBphen, LiQ and CP-1 are as follows:
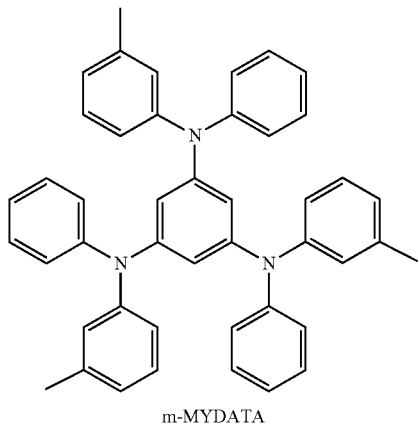
m-MYDATA
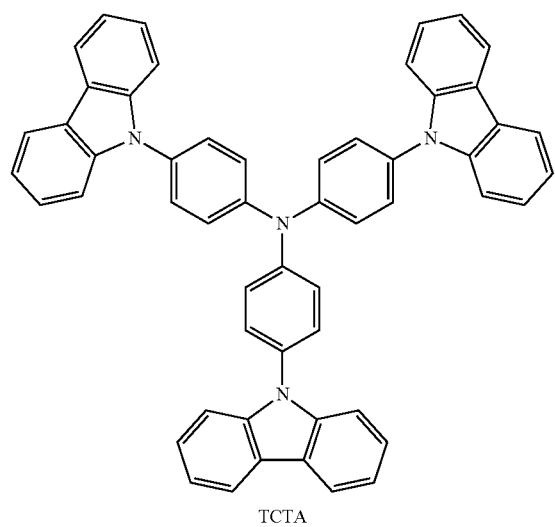
TCTA
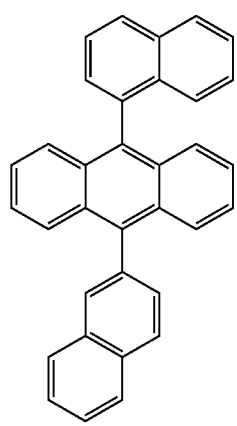
α,β-ADN
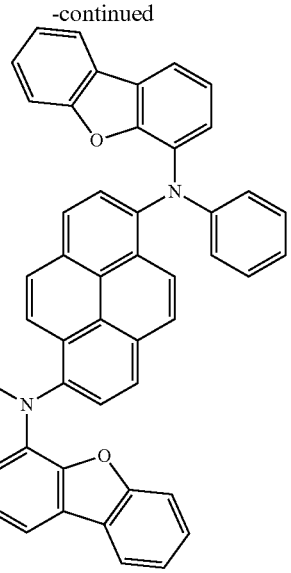
BD-1
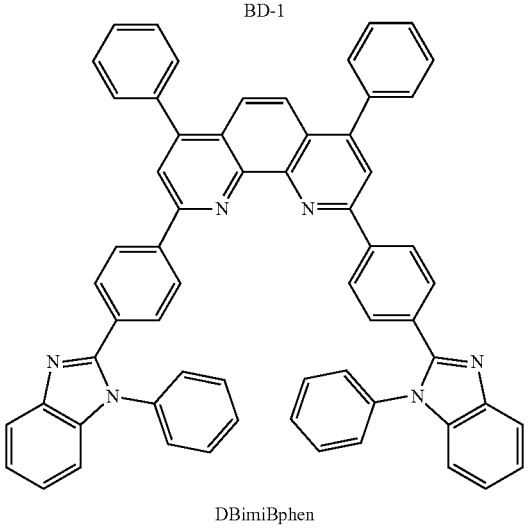
DBimiBphen
LiQ
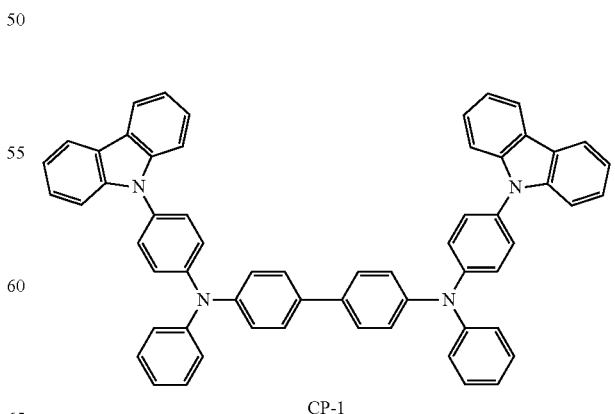
CP-1

Examples 2~15

Except that the compounds shown in Table 7 were used respectively when the first hole transport layer (HTL1) was formed, the organic electroluminescent device was manufactured by the same method as in Example 1. The device performance is shown in Table 7.

Comparative Example 1~Comparative Example 3

In Comparative Example 1~Comparative Example 3, the organic electroluminescent device was manufactured by the same method as in Example 1, except that NPB (N,N'-diphenyl-N,N'-(1-naphthyl)-1,1'-biphenyl-4,4'-diamine), compound A and compound B were used as the first hole transport layer instead of the compound 1.

Wherein the structures of the NPB, compound A and compound B are:

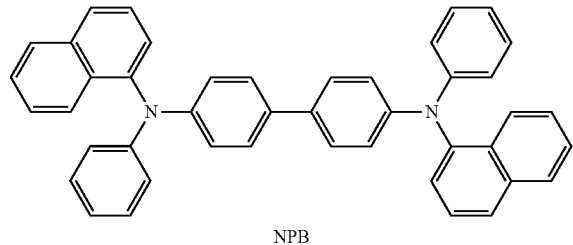
NPB

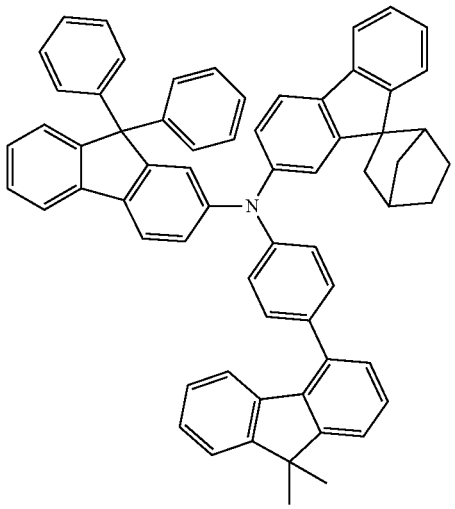
compound A

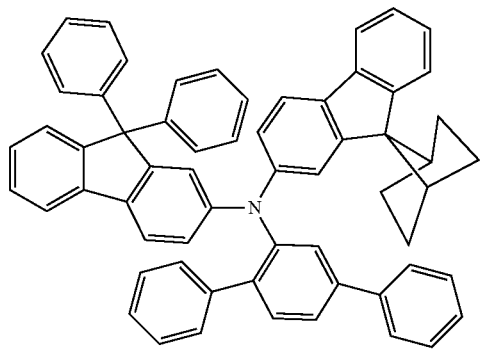
compound B

That is, the NPB was used to manufacture the organic electroluminescent device in Comparative Example 1, the compound A was used to manufacture the organic electroluminescent device in Comparative Example 2, and the compound B was used to manufacture the organic electroluminescent device in Comparative Example 3. The device performance is shown in Table 1. Wherein IVL (current-voltage-luminance) data compares the test results obtained at 10 mA/cm², and the T95 lifetime is the test result obtained at a current density of 20 mA/cm².

TABLE 7

Device Performance of Examples 1~15 and Comparative Examples 1~3

| Example | Compound | Operating voltage Volt (V) | Luminous efficiency (Cd/A) | External quantum efficiency EQE (%) | T95 lifetime (h) | Chromaticity coordinates CIEy |
|---|---|---|---|---|---|---|
| Example 1 | Compound 1 | 3.85 | 6.3 | 13.2 | 146 | 0.050 |
| Example 2 | Compound 2 | 3.83 | 6.2 | 13.3 | 145 | 0.049 |
| Example 3 | Compound 3 | 3.84 | 6.3 | 13.4 | 143 | 0.050 |
| Example 4 | Compound 4 | 3.84 | 6.3 | 13.3 | 142 | 0.050 |
| Example 5 | Compound 5 | 3.86 | 6.4 | 13.4 | 145 | 0.050 |
| Example 6 | Compound 17 | 3.82 | 6.2 | 13.2 | 146 | 0.049 |
| Example 7 | Compound 22 | 3.85 | 6.4 | 13.5 | 146 | 0.050 |
| Example 8 | Compound 26 | 3.82 | 6.3 | 13.4 | 143 | 0.049 |
| Example 9 | Compound 30 | 3.83 | 6.2 | 13.3 | 144 | 0.049 |
| Example 10 | Compound 31 | 3.82 | 6.3 | 13.4 | 146 | 0.050 |
| Example 11 | Compound 339 | 3.81 | 6.4 | 13.5 | 144 | 0.050 |
| Example 12 | Compound 340 | 3.83 | 6.2 | 13.2 | 146 | 0.049 |
| Example 13 | Compound 341 | 3.84 | 6.2 | 13.2 | 145 | 0.049 |

TABLE 7-continued

Device Performance of Examples 1~15 and Comparative Examples 1~3

| Example | Compound | Operating voltage Volt (V) | Luminous efficiency (Cd/A) | External quantum efficiency EQE (%) | T95 lifetime (h) | Chromaticity coordinates CIEy |
|---|---|---|---|---|---|---|
| Example 14 | Compound 342 | 3.82 | 6.3 | 13.2 | 144 | 0.049 |
| Example 15 | Compound 194 | 3.81 | 6.3 | 13.1 | 146 | 0.050 |
| Comparative Example 1 | NPB | 4.39 | 4.9 | 10.3 | 108 | 0.049 |
| Comparative Example 2 | Compound A | 5.04 | 5.5 | 11.7 | 100 | 0.049 |
| Comparative Example 3 | Compound B | 4.47 | 5.1 | 10.9 | 119 | 0.049 |

The results in Table 7 show that the first hole transport layer (HTL1) of Examples 1~15 uses compounds 1~5, compound 17, compound 22, compound 26, compound 30, compound 31, compound 339, compound 340, compound 341, compound 342 and compound 194 of the present application respectively; compared with Comparative Example 1, Comparative Example 2 and Comparative Example 3 using the well-known NPB, compound A and compound B, the operating voltage of Examples 1~15 is reduced by at least 0.53V, and the luminous efficiency (Cd/A) is improved by at least 12.7%. Therefore, the resulting organic electroluminescent device can achieve a low driving voltage and high luminous efficiency. Moreover, compared with Comparative Examples 1~3, the external quantum efficiency of the blue organic electroluminescent devices in Examples 1~15 is improved by at least 11.9%, and the T95 lifetime is improved by at least 17.6%, so that the performance of the organic electroluminescent devices can be significantly improved.

Fabrication of Red Organic Electroluminescent Devices

Example 16

The anode was prepared through the following process: an ITO substrate (manufactured by Corning) with an ITO thickness of 1500 Å was cut into the dimension of 40 mm (length)×40 mm (width)×0.7 mm (thickness), the ITO substrate was prepared into a top-emitting (TOP glass) experimental substrate having a cathode overlapping zone, a positive plate and insulation layer patterns by a photoetching procedure, and surface treatment was performed by ultraviolet ozone and $O_2:N_2$ plasma to increase the work function of the anode (experimental substrate) and clean the experimental substrate.

m-MTDATA was vacuum deposited on the experimental substrate (anode) to form a hole injection layer (HIL) with a thickness of 100 Å, and the NPB was deposited on the hole injection layer to form a first hole transport layer (HTL1) with a thickness of 1120 Å.

The compound 6 was vacuum-evaporated on the first hole transport layer to form a second hole transport layer (HTL2) with a thickness of 850 Å.

4,4'-N,N'-dicarbazole-biphenyl (hereinafter referred to as "CBP") was evaporated on the second hole transport layer as the host and doped with $Ir(piq)_2(acac)$, and the host and dopant formed an organic light-emitting layer (EML) with a thickness of 350 Å at a film thickness ratio of 35:5.

DBimiBphen and LiQ were mixed at the weight ratio of 1:1 and deposited to form an electron transport layer (ETL) with a thickness of 300 Å, Yb was deposited on the electron transport layer to form an electron injection layer (EIL) with a thickness of 15 Å, then magnesium (Mg) and silver (Ag) were mixed at a deposition rate of 1:9 and vacuum deposited on the electron injection layer to form a cathode with a thickness of 115 Å.

In addition, as CP-1 was deposited with a thickness of 700 Å on the cathode, a capping layer (CPL) was formed, so that the manufacturing of the organic electroluminescent device was completed.

Examples 17~45

Except that the compounds shown in Table 8 were used respectively when the second hole transport layer (HTL2) was formed, the red organic electroluminescent device was manufactured by the same method as in Example 16. The device performance is shown in Table 8.

Comparative Example 4~Comparative Example 5

In Comparative Examples 4~5, the organic electroluminescent device was manufactured by the same method as in Example 11, except that the compound A and compound B were used as the second hole transport layer instead of the compound 6.

That is, the compound A was used to manufacture the organic electroluminescent device in Comparative Example 4, and the compound B was used to manufacture the organic electroluminescent device in Comparative Example 5. The device performance is shown in Table 2.

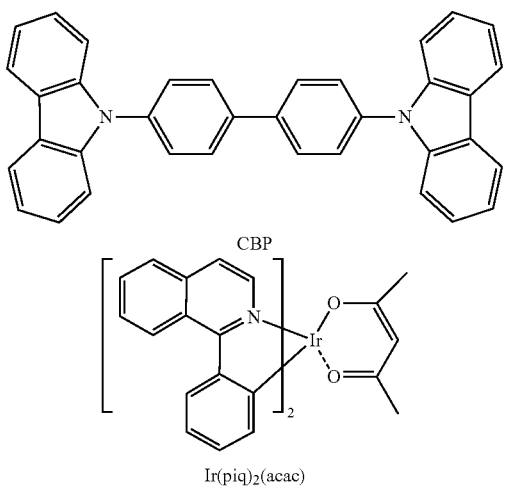

CBP $Ir(piq)_2(acac)$

For the organic electroluminescent device prepared above, the IVL performance of the device was analyzed under the condition of 10 mA/cm². The results are shown in Table 2. The T95 lifetime test was carried out at the current density of 30 mA/cm².

TABLE 8

Device Performance of Examples 16~45 and Comparative Examples 4~5

| Example | Compound | Operating voltage Volt (V) | Luminous efficiency (Cd/A) | External quantum efficiency EQE (%) | T95 lifetime (h) | Chromaticity coordinates CIEx |
|---|---|---|---|---|---|---|
| Example 16 | Compound 6 | 3.65 | 33.4 | 26.4 | 223 | 0.683 |
| Example 17 | Compound 7 | 3.69 | 34.5 | 26.4 | 229 | 0.685 |
| Example 18 | Compound 8 | 3.66 | 34.3 | 26.3 | 222 | 0.684 |
| Example 19 | Compound 9 | 3.66 | 34.7 | 26.5 | 220 | 0.685 |
| Example 20 | Compound 10 | 3.68 | 34.5 | 26.4 | 227 | 0.685 |
| Example 21 | Compound 11 | 3.65 | 33.9 | 26.2 | 223 | 0.683 |
| Example 22 | Compound 12 | 3.65 | 33.9 | 26.3 | 220 | 0.684 |
| Example 23 | Compound 13 | 3.66 | 35.0 | 26.4 | 228 | 0.685 |
| Example 24 | Compound 14 | 3.65 | 33.0 | 26.2 | 229 | 0.683 |
| Example 25 | Compound 15 | 3.65 | 33.3 | 26.3 | 229 | 0.683 |
| Example 26 | Compound 29 | 3.67 | 33.3 | 26.4 | 229 | 0.685 |
| Example 27 | Compound 143 | 3.66 | 34.3 | 26.2 | 221 | 0.683 |
| Example 28 | Compound 145 | 3.66 | 33.3 | 26.4 | 223 | 0.684 |
| Example 29 | Compound 146 | 3.66 | 34.6 | 26.2 | 229 | 0.683 |
| Example 30 | Compound 147 | 3.65 | 33.4 | 26.3 | 223 | 0.683 |
| Example 31 | Compound 334 | 3.69 | 33.7 | 26.3 | 227 | 0.683 |
| Example 32 | Compound 148 | 3.69 | 34.7 | 26.4 | 220 | 0.684 |
| Example 33 | Compound 335 | 3.67 | 34.4 | 26.3 | 227 | 0.683 |
| Example 34 | Compound 336 | 3.68 | 34.5 | 26.4 | 229 | 0.684 |
| Example 35 | Compound 337 | 3.69 | 33.2 | 26.0 | 227 | 0.683 |
| Example 36 | Compound 154 | 3.65 | 33.2 | 26.0 | 228 | 0.683 |
| Example 37 | Compound 155 | 3.68 | 34.5 | 26.3 | 229 | 0.684 |
| Example 38 | Compound 338 | 3.65 | 33.4 | 25.9 | 229 | 0.684 |
| Example 39 | Compound 317 | 3.66 | 33.1 | 26.1 | 223 | 0.683 |
| Example 40 | Compound 327 | 3.67 | 33.2 | 26.0 | 227 | 0.683 |
| Example 41 | Compound 343 | 3.65 | 35.9 | 26.6 | 234 | 0.683 |
| Example 42 | Compound 41 | 3.68 | 34.5 | 26.3 | 229 | 0.684 |
| Example 43 | Compound 344 | 3.65 | 33.4 | 25.9 | 229 | 0.684 |
| Example 44 | Compound 345 | 3.69 | 34.1 | 26.2 | 223 | 0.683 |
| Example 45 | Compound 346 | 3.66 | 33.5 | 26.3 | 222 | 0.684 |
| Comparative Example 4 | Compound A | 4.70 | 29.1 | 21.4 | 176 | 0.683 |
| Comparative Example 5 | Compound B | 4.14 | 27.7 | 18.9 | 194 | 0.683 |

The results in Table 8 show that when the compound as the second hole transport layer (HTL2) in the Examples 16~45 is compared with Comparative Example 4 and Comparative Example 5 using the well-known compound A and compound B, the operating voltage in Examples 16~45 is reduced by at least 0.45 V, meanwhile the luminous efficiency (Cd/A) is improved by at least 13.7%.

Moreover, compared with Comparative Examples 4 and 5, the external quantum efficiency of the red organic electroluminescent devices in Examples 16~45 is increased by at least 21.5%, and the T95 lifetime is increased by at least 13.4%, so that the performance of the organic electroluminescent devices can be significantly improved.

According to the experimental results recorded in Table 1 and Table 2, it is confirmed that the device performance of the compound in the present application is significantly improved compared with the compound A and compound B in the comparative Examples.

The reason is that a diphenylfluorene group with great steric hindrance was introduced into the compound A and compound B, which increased the spacing of molecules and reduced the overlap of wave functions, resulting in low hole mobility of materials.

According to the experimental results recorded in Table 7 and Table 8, it is confirmed that the organic electroluminescent devices prepared from the compound in the Examples of the present application have excellent performance of low operating voltage, high luminous efficiency and long lifetime compared with the compound in the comparative Examples. The reason is that the compounds in the present application can effectively reduce the hole injection barrier, and the hole mobility of the compounds used in the first hole transport layer (HTL1) and the second hole transport layer (HTL2) can reach above $4\times10^{-5}$ $cm^2V^{-1}s^{-1}$ at the electric field intensity of $400(V/cm)^{1/2}$, so the prepared organic electroluminescent devices have high current efficiency and low working voltage.

Moreover, the molecular weight of the organic substances used in the Examples of the present application is between 600 and 900, the organic substances have a good durability and heat resistance, so the lifetime of the devices are greatly improved.

It should be understood that the present application does not limit the present application to the detailed structure and arrangement of components provided herein. The present application can have other embodiments, and can be implemented and executed in many ways. The foregoing deformed and modified forms shall fall within the scope of the present application. It should be understood that the present application disclosed and defined herein extends to all alternative combinations of two or more individual features mentioned or evident in the text and/or drawings. All these different combinations constitute a plurality of alternative aspects of the present application. The embodiments stated herein illustrate the best modes known to be used to realize the present application, and will enable those skilled in the art to make use of the present application.

The invention claimed is:

1. A nitrogen-containing compound, wherein the structure of the nitrogen-containing compound is represented by formula I-A:

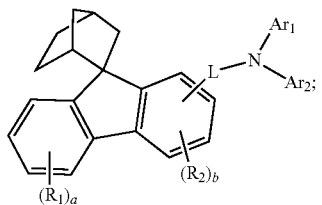

Formula I-A wherein L is selected from a single bond, a substituted or unsubstituted arylene with 6-30 carbon atoms, or a substituted or unsubstituted heteroarylene with 1-30 carbon atoms;

Ar₁ and Ar₂ are the same or different, and are independently selected from a a substituted or unsubstituted group V, and the unsubstituted group V is selected from the group consisting of the following groups:

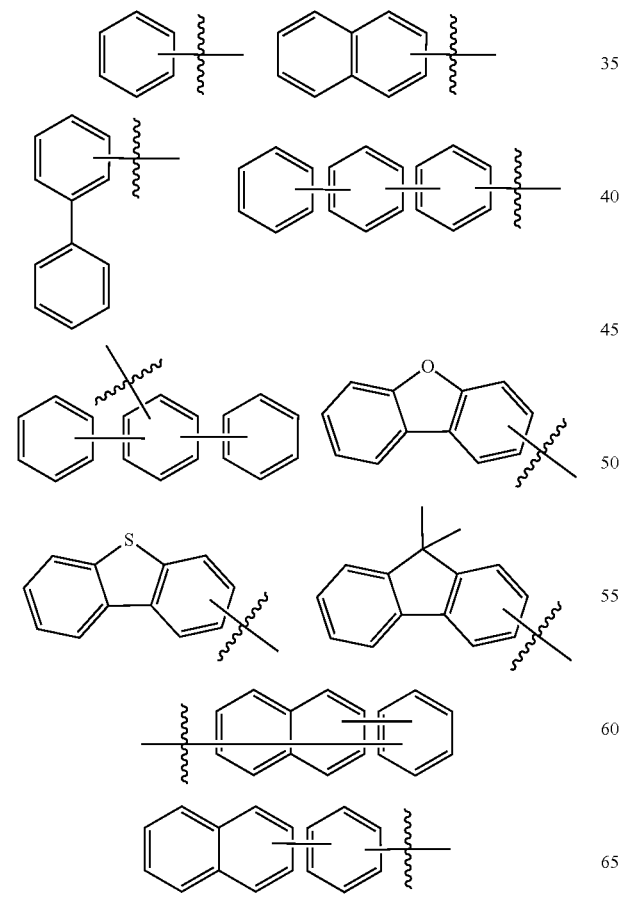

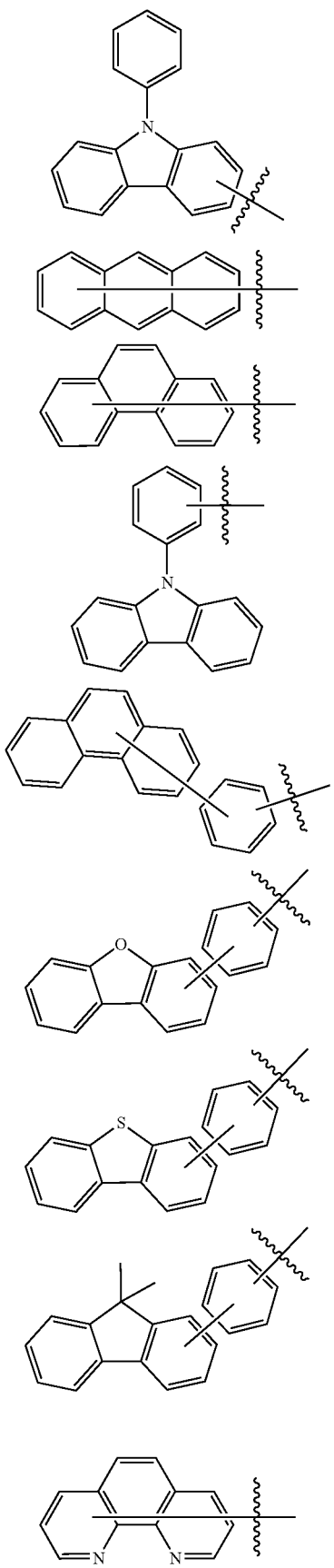

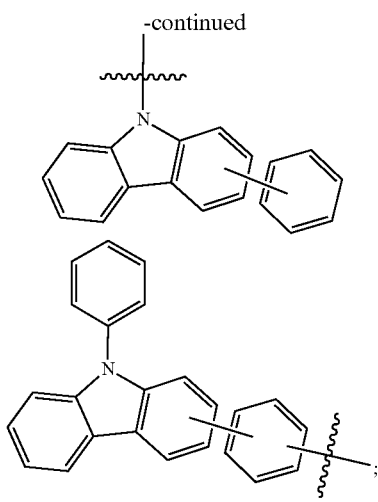

wherein ✳ represents a chemical bond; there is one or more substituents on the substituted V, and the substituents are independently selected from: deuterium, cyano, halogen, methyl, ethyl, n-propyl, isopropyl, tertiary butyl, phenyl, naphthyl, biphenyl or phenanthryl; when the number of substituents of V is greater than 1, the substituents are the same or different;

$R_1$ and $R_2$ are independently selected from deuterium, halogen, cyano, heteroaryl with 3~20 carbon atoms, aryl with 6~20 carbon atoms, trialkylsilyl with 3~12 carbon atoms, arylsilyl with 8~12 carbon atoms, alkyl with 1~10 carbon atoms, haloalkyl with 1~10 carbon atoms, alkenyl with 2~6 carbon atoms, alkynyl with 2~6 carbon atoms, cycloalkyl with 3~20 carbon atoms, heterocyclic alkyl with 2~10 carbon atoms, cycloalkenyl with 5~10 carbon atoms, heterocyclic alkenyl with 4~10 carbon atoms, alkoxyl with 1~10 carbon atoms, alkylthio with 1~10 carbon atoms, aryloxy with 6~18 carbon atoms, arylthio with 6~18 carbon atoms or triarylsilyl with 18~24 carbon atoms;

a is selected from 0, 1, 2, 3 or 4; when a is greater than 1, any two $R_1$ are the same or different;

b is selected from 0, 1, 2 or 3; when b is greater than 1, any two $R_2$ are the same or different;

the substituents of L are independently selected from deuterium, a halogen, cyano, heteroaryl with 3~20 carbon atoms, aryl with 6~20 carbon atoms which can be substituted with 0, 1, 2, 3, 4 or 5 substituents independently selected from deuterium, fluorine, chlorine, cyano, methyl and tertiary butyl, alkyl with 1~10 carbon atoms, haloalkyl with 1~10 carbon atoms, alkenyl with 2~6 carbon atoms, alkynyl with 2~6 carbon atoms, cycloalkyl with 3~10 carbon atoms, heterocyclic alkyl with 2~10 carbon atoms, cycloalkenyl with 5~10 carbon atoms, heterocyclic alkenyl with 4~10 carbon atoms, alkoxyl with 1~10 carbon atoms, alkylthio with 1~10 carbon atoms, aryloxy with 6~18 carbon atoms, arylthio with 6~18 carbon atoms or phosphinoxy with 6~18 carbon atoms.

2. The nitrogen-containing compound according to claim 1, wherein the structure of the nitrogen-containing compound is selected from the structures represented by formula I:

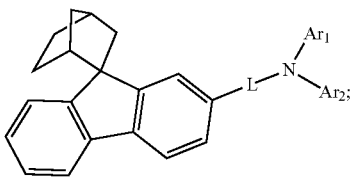

Formula I wherein L is selected from a single bond, a substituted or unsubstituted arylene with 6-30 carbon atoms, or a substituted or unsubstituted heteroarylene with 1-30 carbon atoms;

the substituents of L are the same or different, and are independently selected from deuterium, cyano, nitryl, a halogen, hydroxyl, alkyl with 1-20 carbon atoms, cycloalkyl with 3-20 carbon atoms, alkenyl with 2-20 carbon atoms, alkynyl with 2-24 carbon atoms, heterocyclic alkyl with 2-20 carbon atoms, alkoxy with 1-33 carbon atoms, alkylthio with 1-33 carbon atoms or arylsilyl with 6-33 carbon atoms.

3. The nitrogen-containing compound according to claim 1, wherein L is selected from a single bond, a substituted or unsubstituted phenylene, a substituted or unsubstituted naphthylene, a substituted or unsubstituted biphenylene, a substituted or unsubstituted triphenylidene, or a substituted or unsubstituted dimethyl fluorenylidene.

4. The nitrogen-containing compound according to claim 1, wherein L is selected from a single bond, a substituted or unsubstituted anthrylene, a substituted or unsubstituted phenanthrylene, a substituted or unsubstituted dibenzofuranylidene, a substituted or unsubstituted dibenzothienylidene, a substituted or unsubstituted N-phenylcarbazolylidene.

5. The nitrogen-containing compound according to claim 4, the substituents of L are selected from deuterium, fluorine, cyano, methyl, phenyl, naphthyl or biphenyl.

6. The nitrogen-containing compound according to claim 1, wherein L is selected from a single bond, or a substituted or unsubstituted group W, and the unsubstituted W is selected from the group consisting of the following groups:

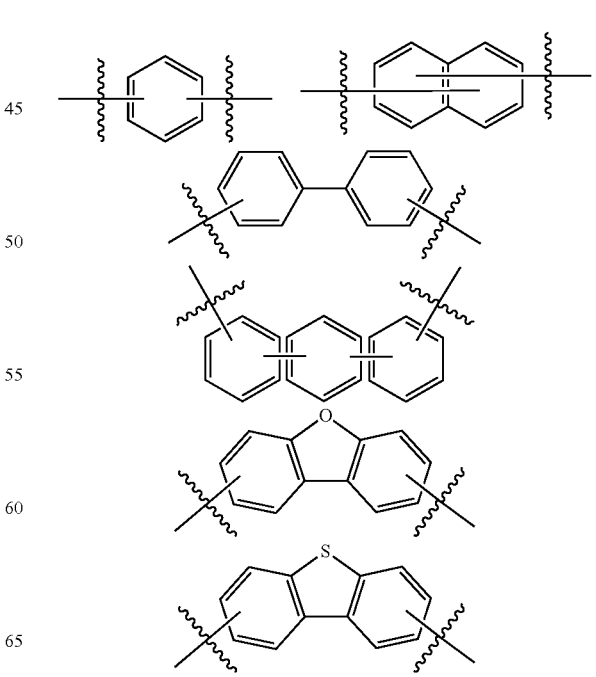

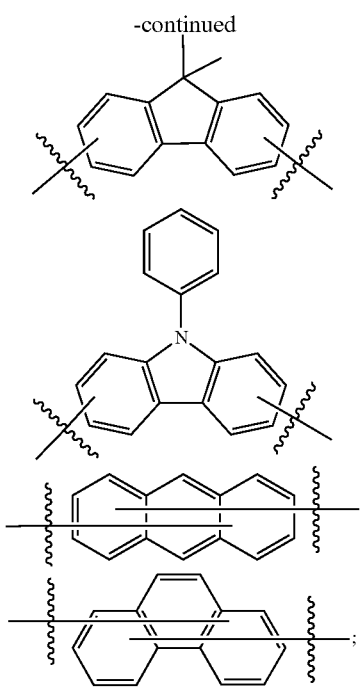

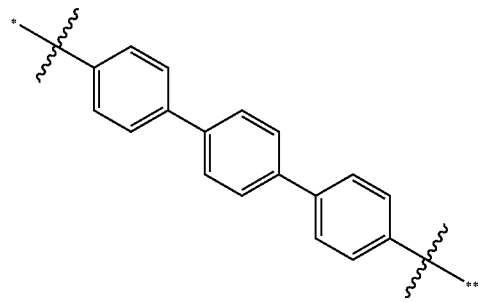

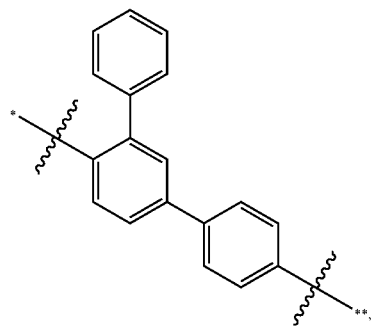

wherein ⁎ is a linking point of the above groups connected to

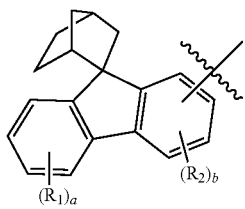

in formula I-A or

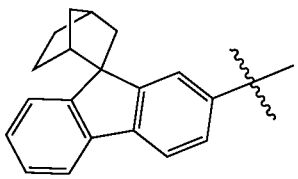 [SMILES: *c1ccc2c(c1)C1(CC3CCC1C3)c1ccccc1-2]

in formula I;

⁎⁎ is a linking point of the above groups connected to

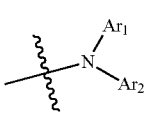

group in formula I-A.

wherein ⧸ represents a chemical bond; there is one or more substituents on the group W, and the substituents are independently selected from: deuterium, cyano, halogen, methyl, ethyl, n-propyl, isopropyl, tertiary butyl, phenyl, naphthyl, phenanthryl or biphenyl; when the number of substituents of W is greater than 1, the substituents are the same or different.

7. The nitrogen-containing compound according to claim 1, wherein L is selected from a single bond, or selected from the group consisting of the following groups:

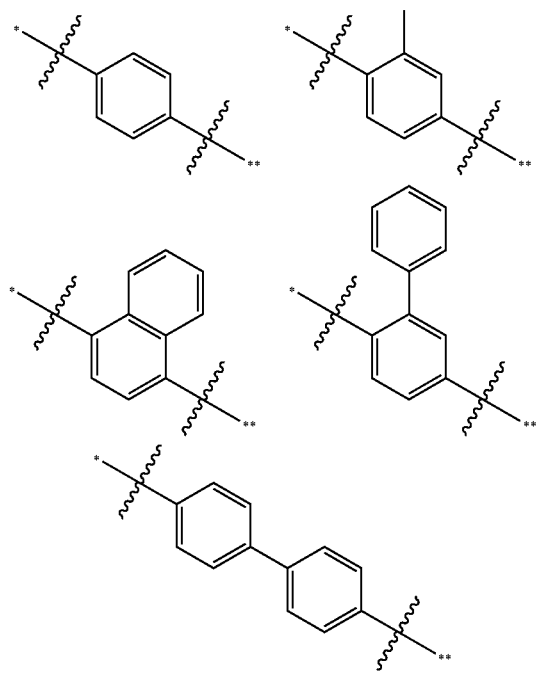

8. The nitrogen-containing compound according to claim 1, wherein L is selected from a single bond, or selected from the group consisting of the following groups:

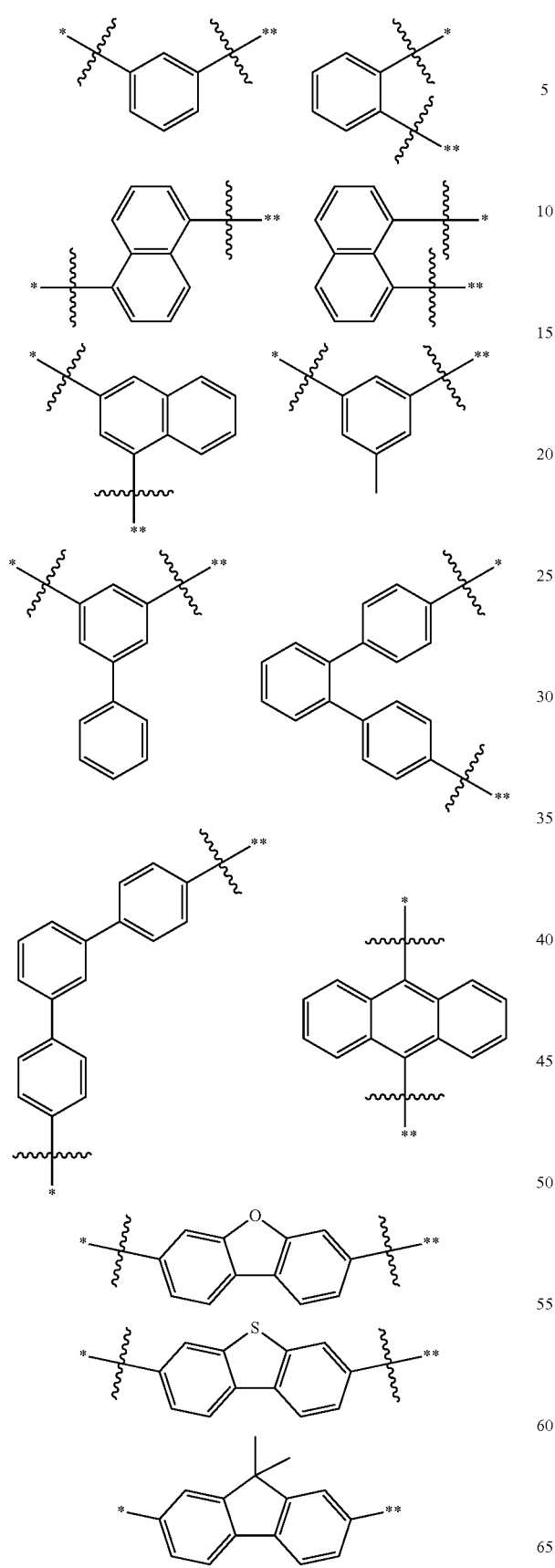
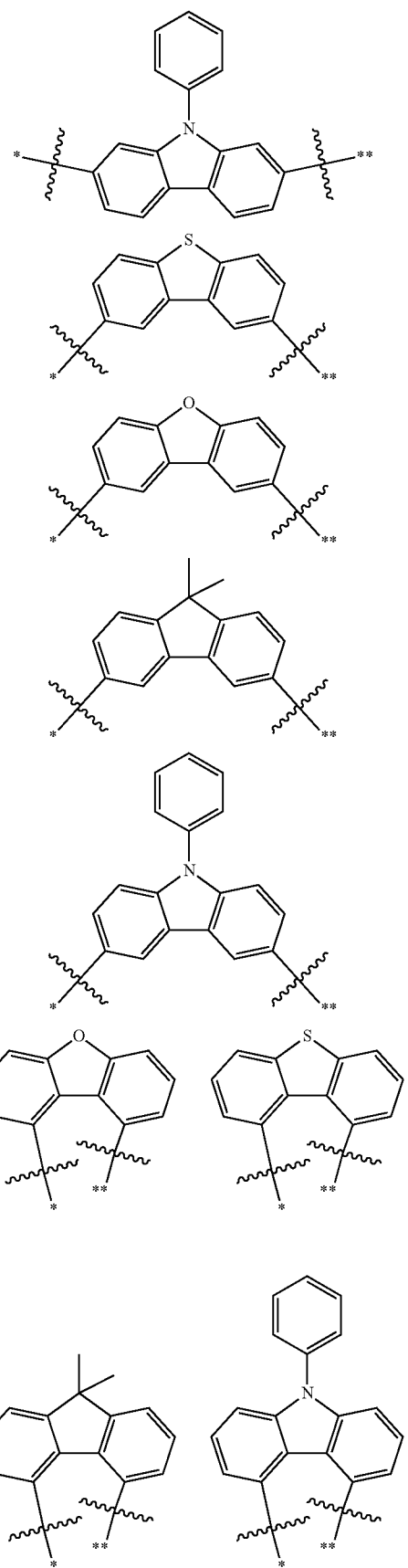
-continued

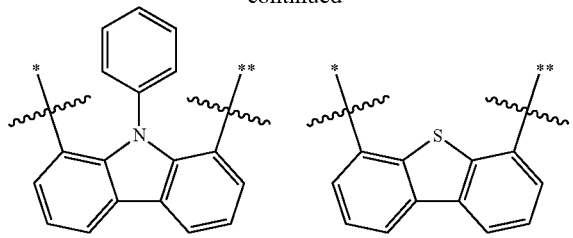

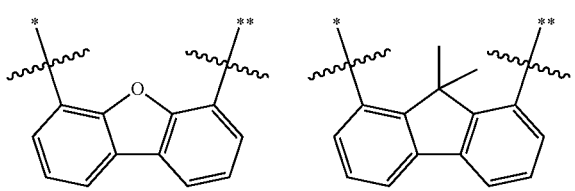

wherein * is a linking point of the above groups connected to

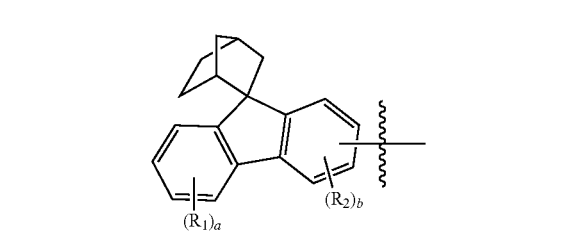

in formula I-A or

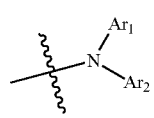

in formula I;

** is a linking point of the above groups connected to

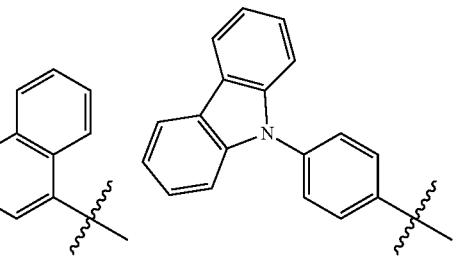

in formula I-A, formula I, formula II, formula III and formula IV.

9. The nitrogen-containing compound according to claim 1, wherein $Ar_1$ and $Ar_2$ are the same or different, and are independently selected from the group consisting of the following groups:

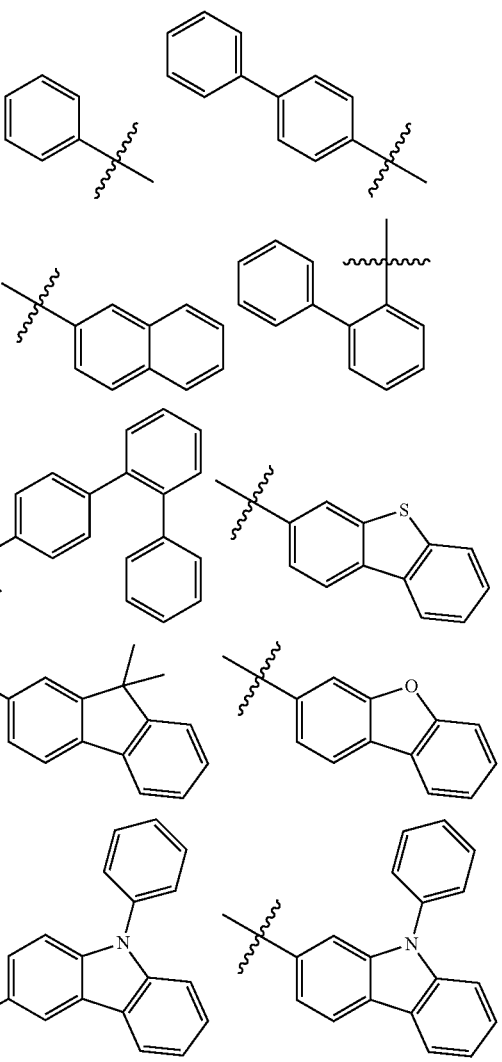

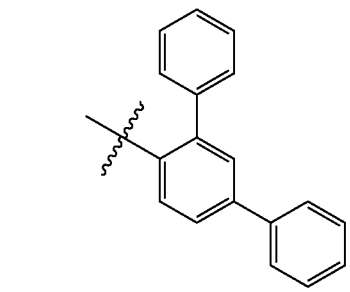

211
-continued
212
-continued
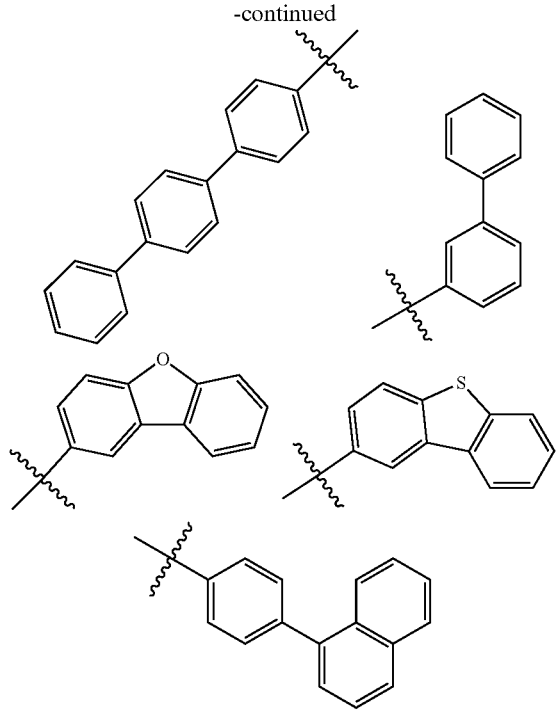
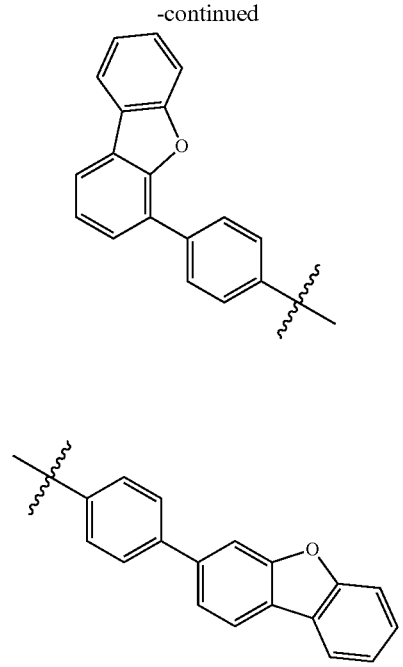
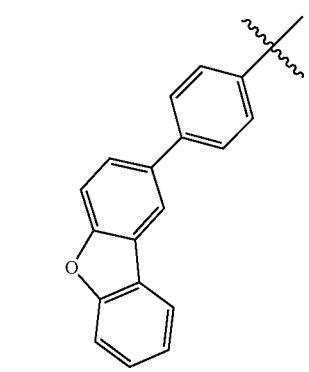
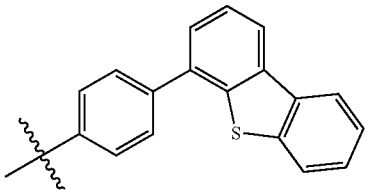
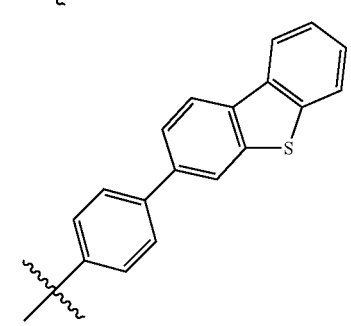

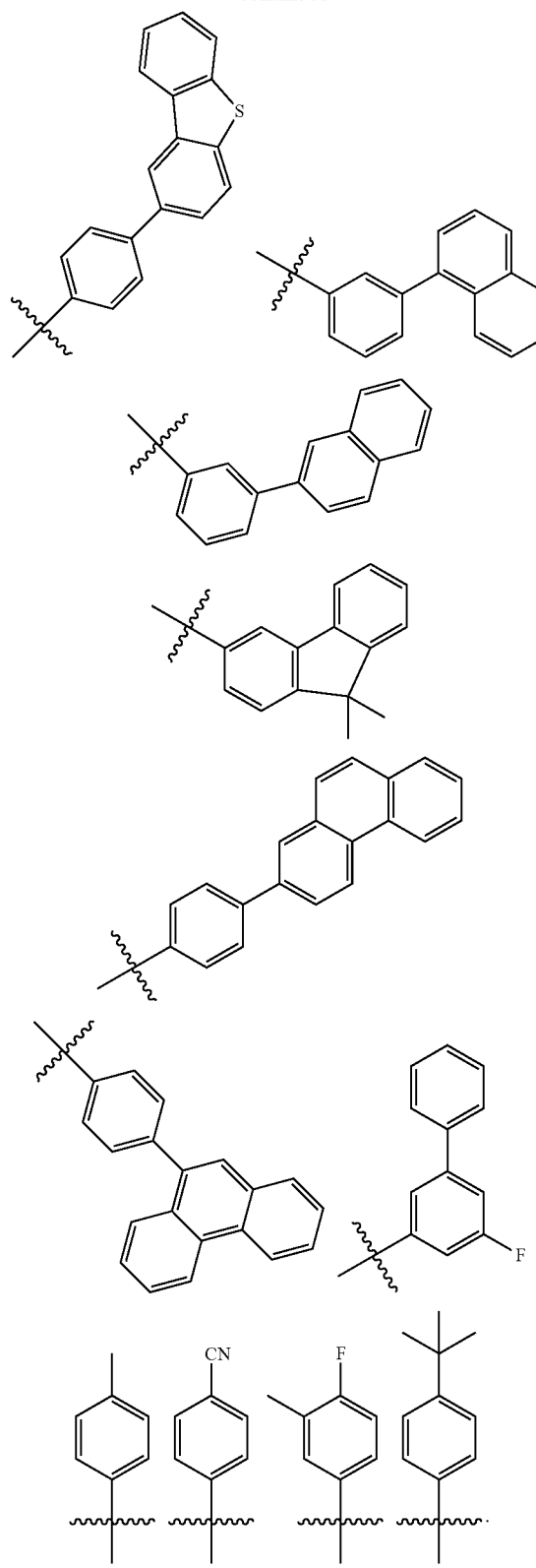
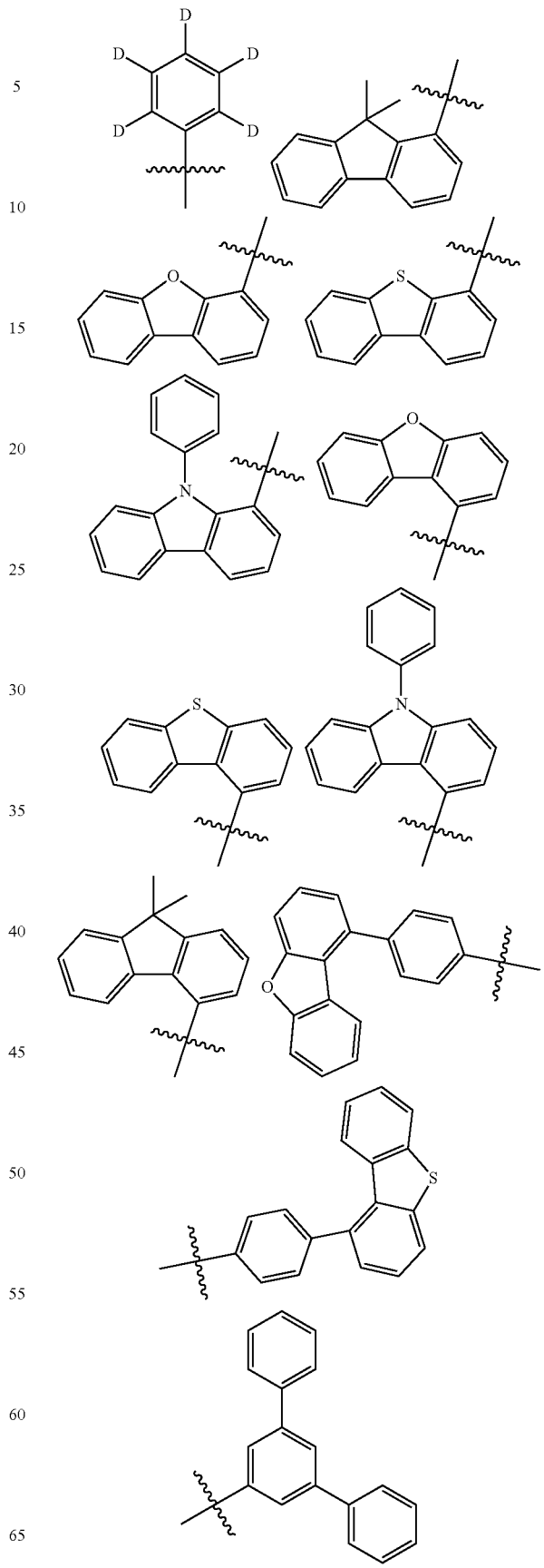
10. The nitrogen-containing compound according to claim 1, wherein $Ar_1$ and $Ar_2$ are the same or different, and are independently selected from the group consisting of the following groups:

215
-continued
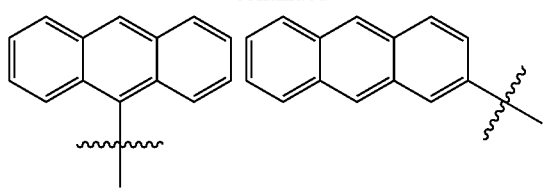
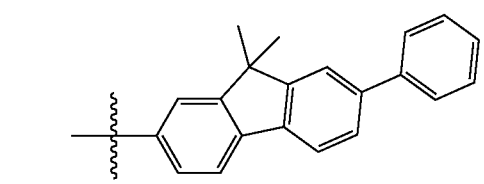
216
-continued
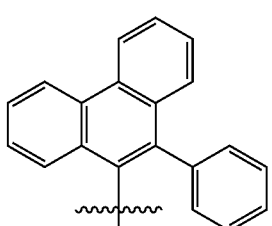 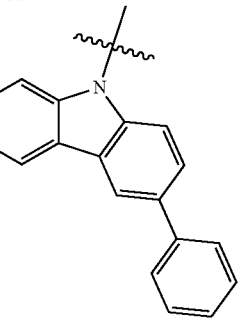
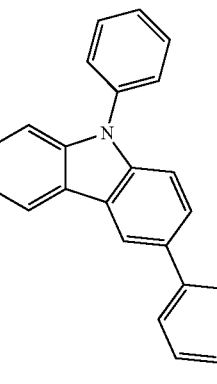 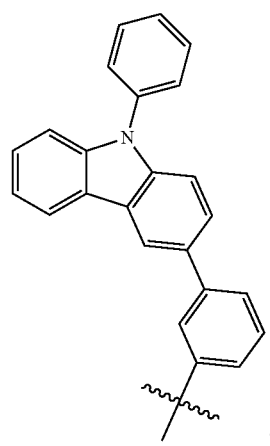
11. The nitrogen-containing compound according to claim 1, wherein the nitrogen-containing compound is selected from the group consisting of the following compounds:
1
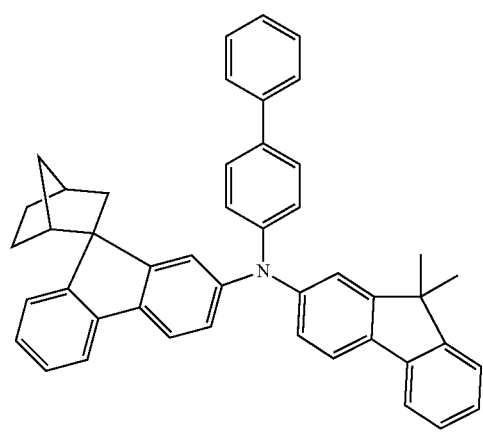
2
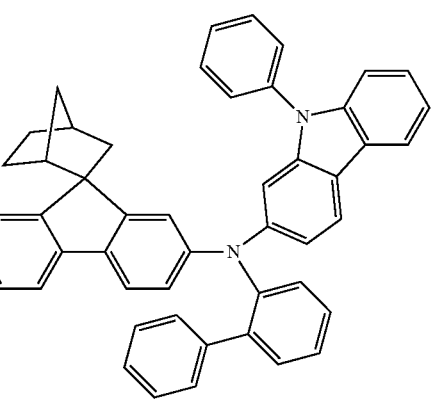

-continued
3
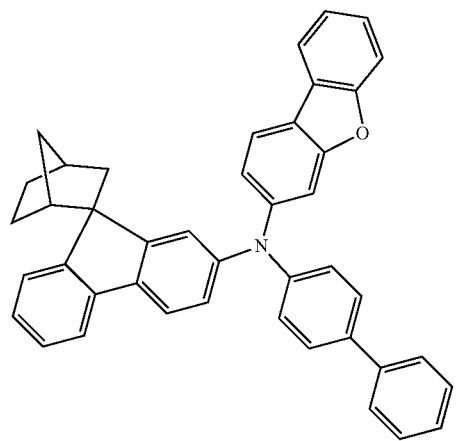
4
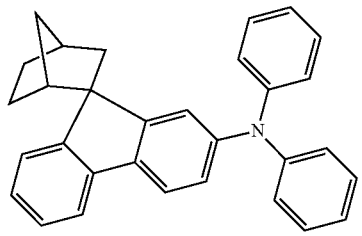
5
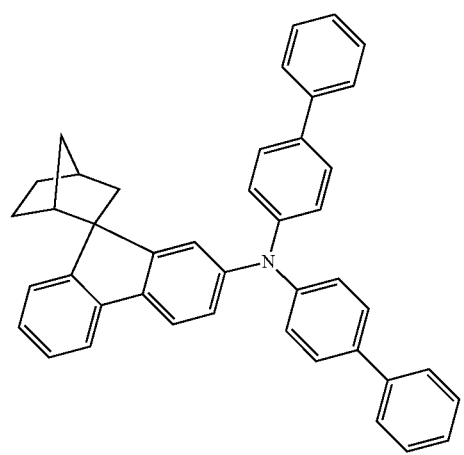
6
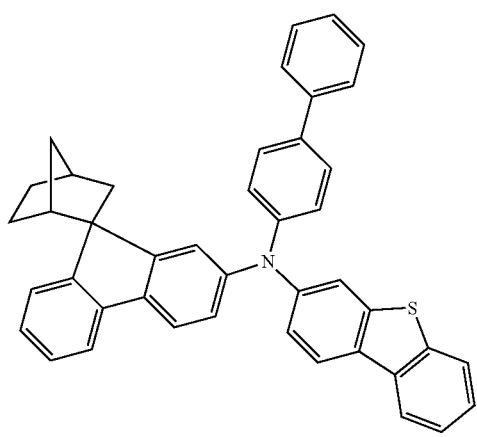
7
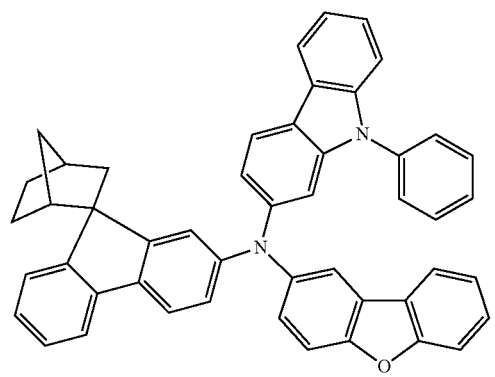
8
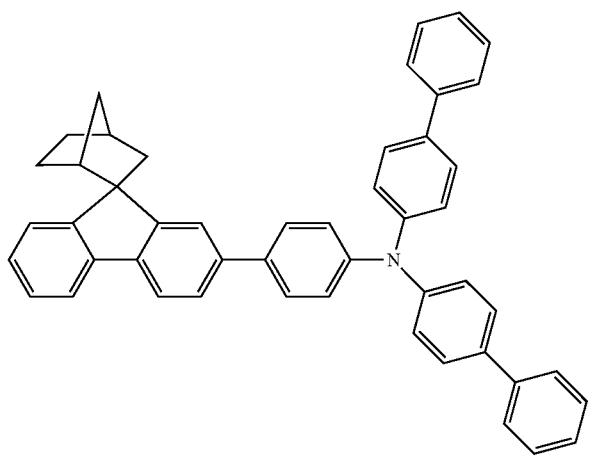

-continued
9
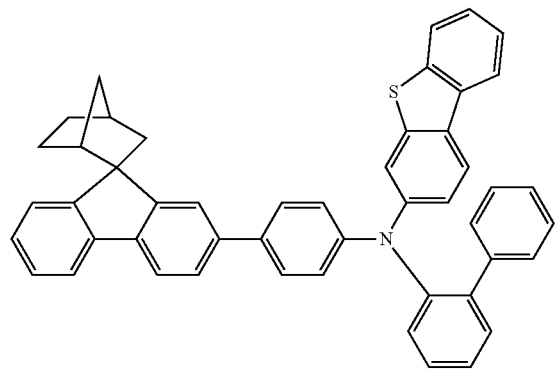
10
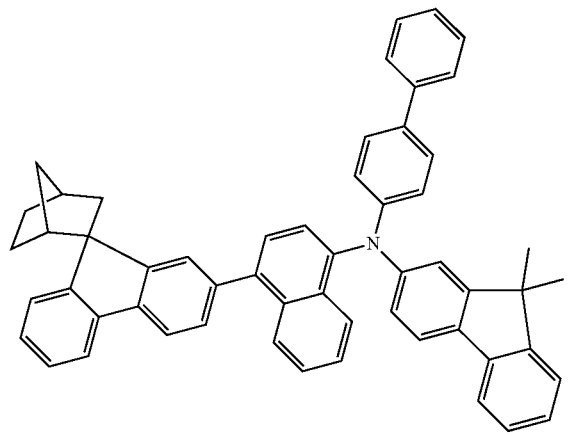
11
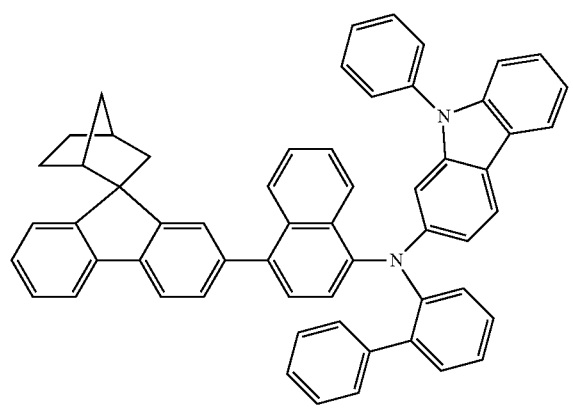
12
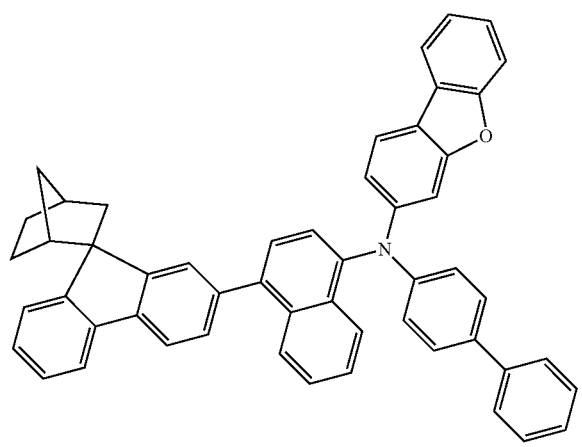
13
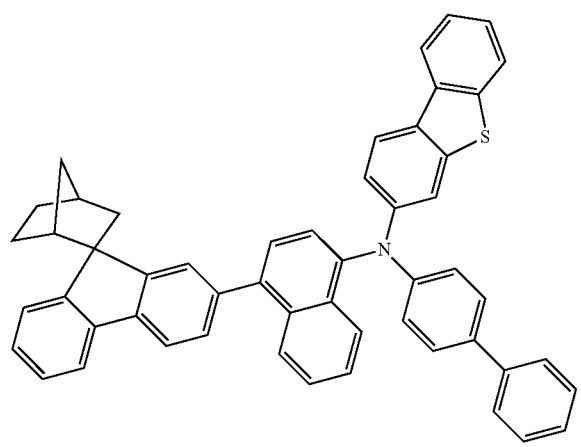
14
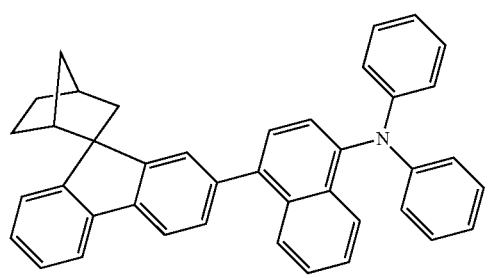

-continued
16
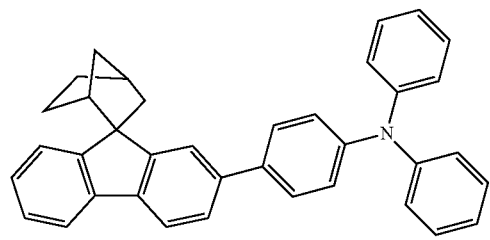
17
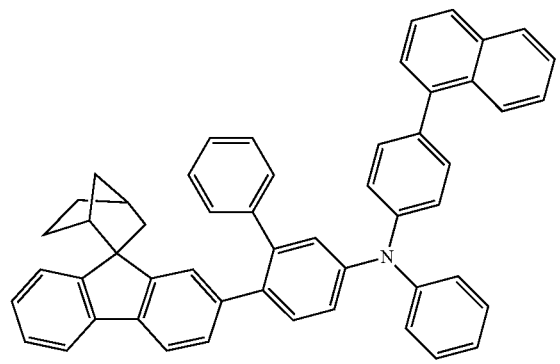
18
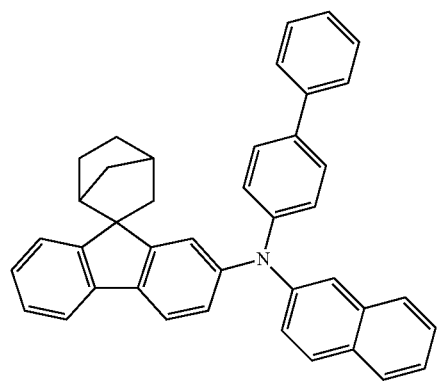
19
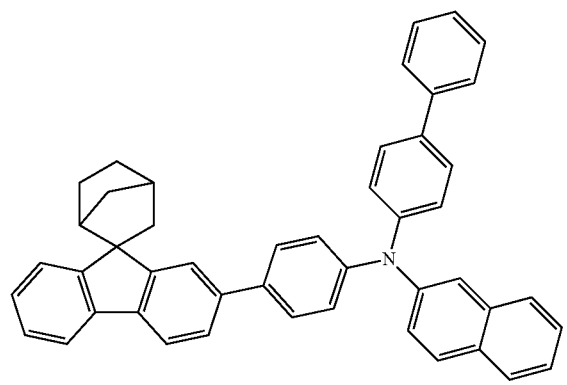
20
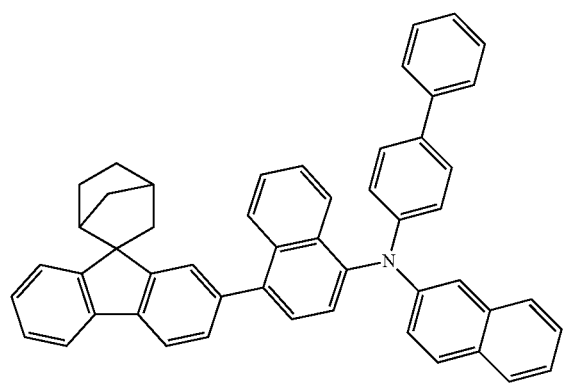
21
22
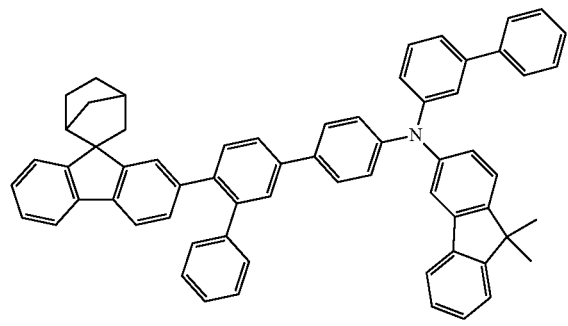
23
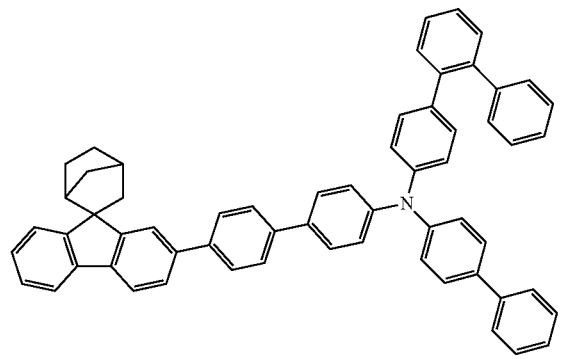

-continued
24
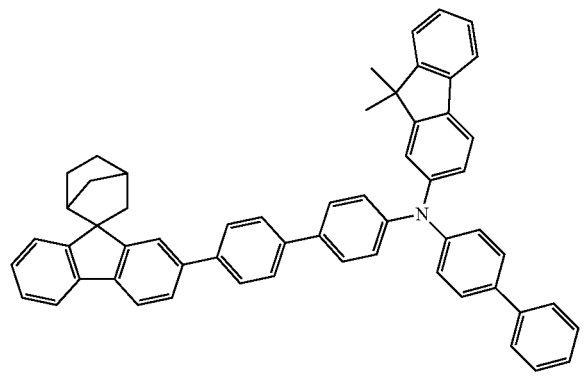
25
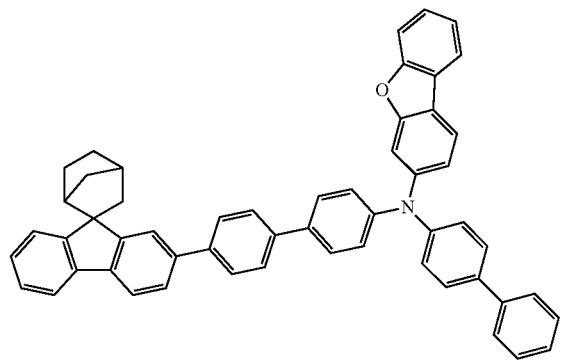
26
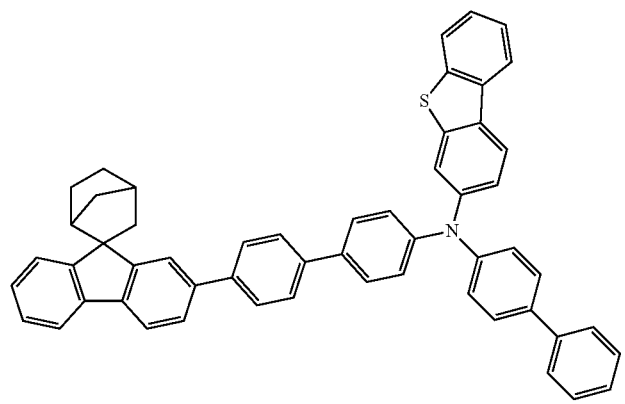
27
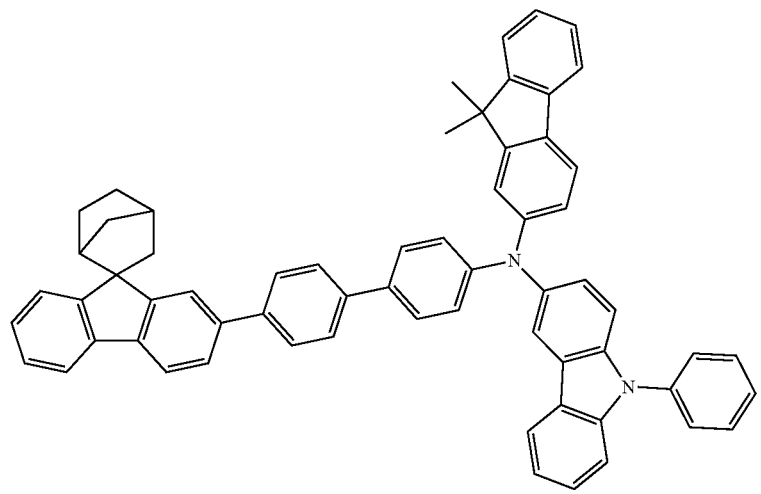
28
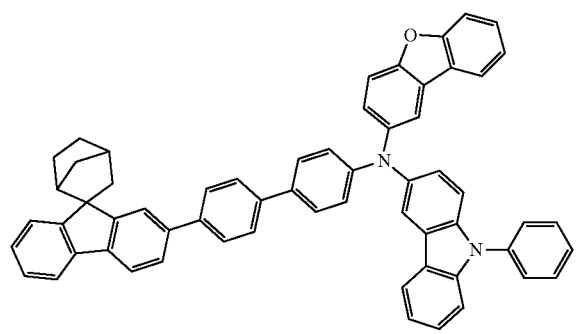
29
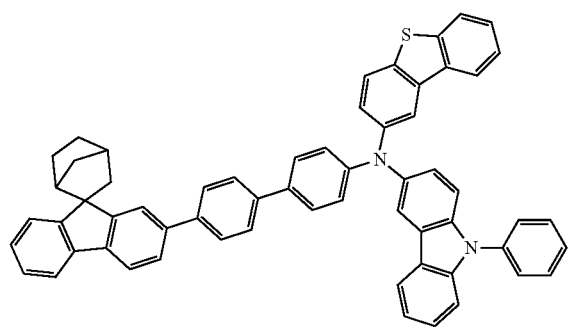

30
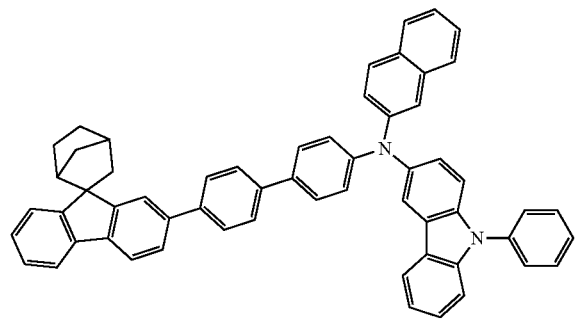
31
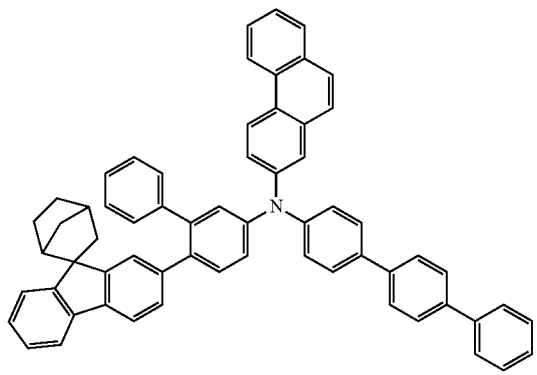
32
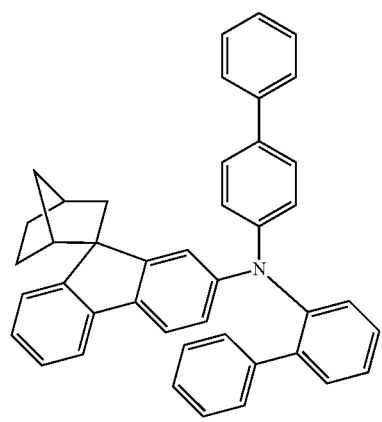
33
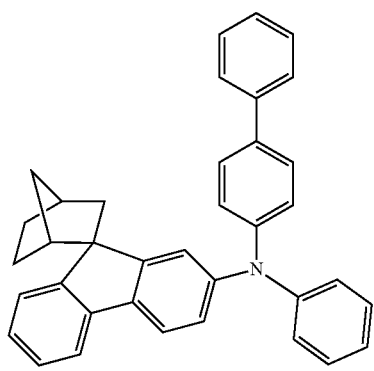
34
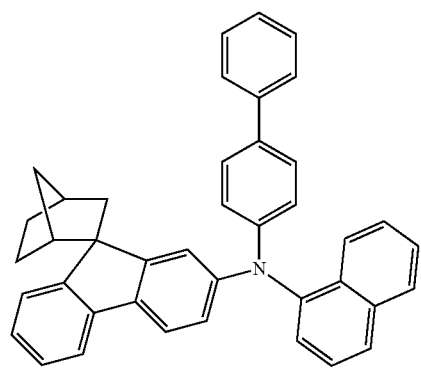
35
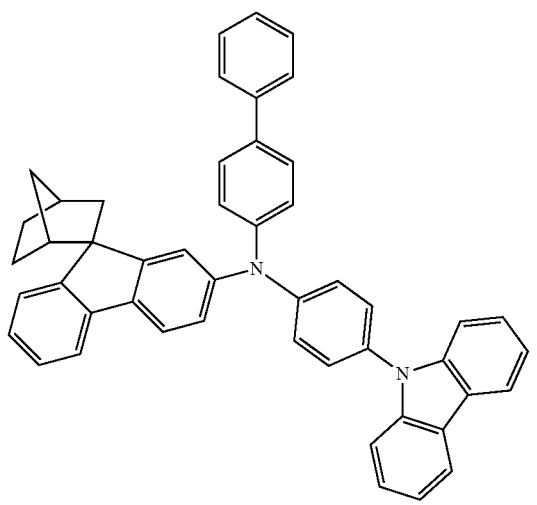

36
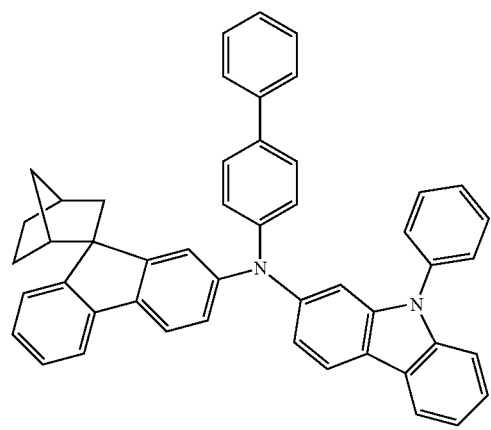
37
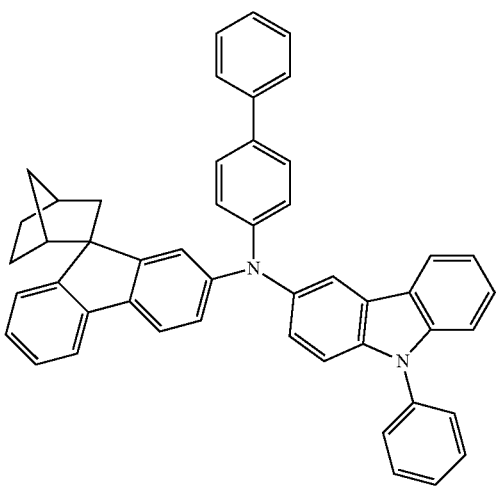
38
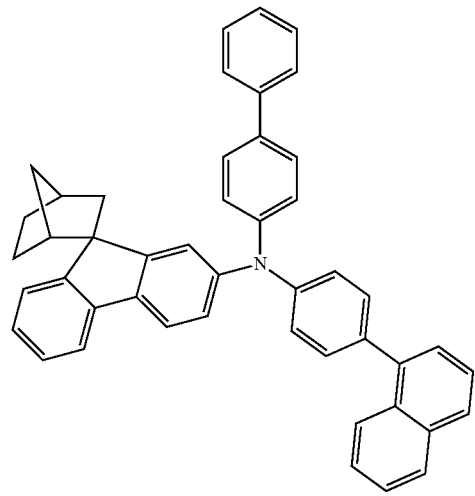
39
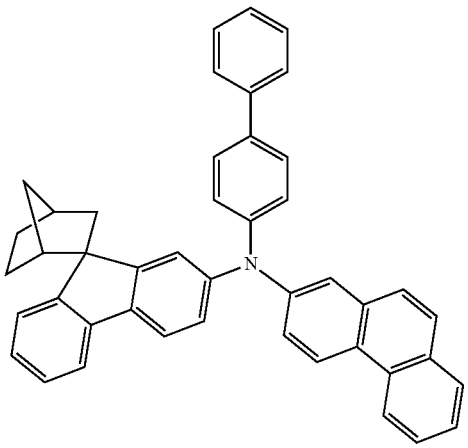
40
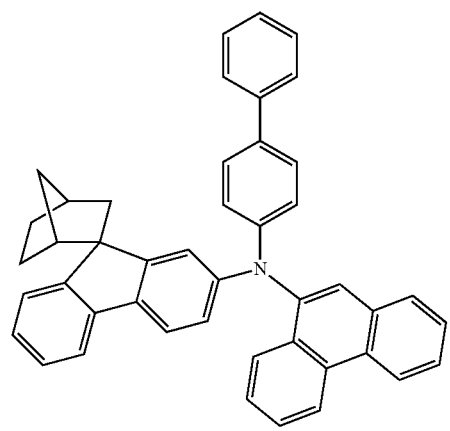
41
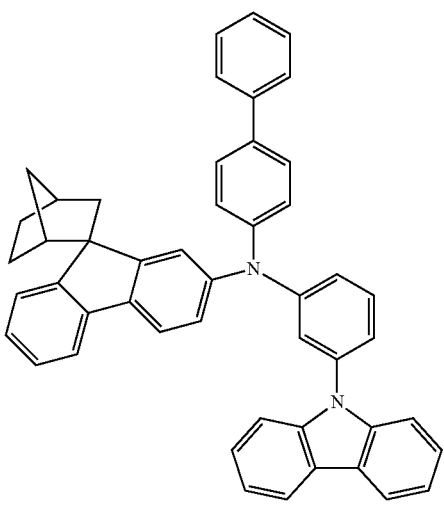

42
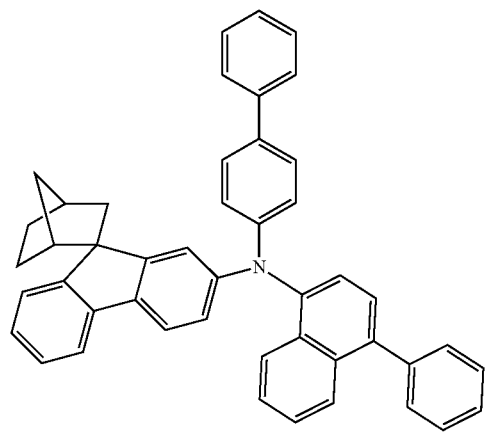
43
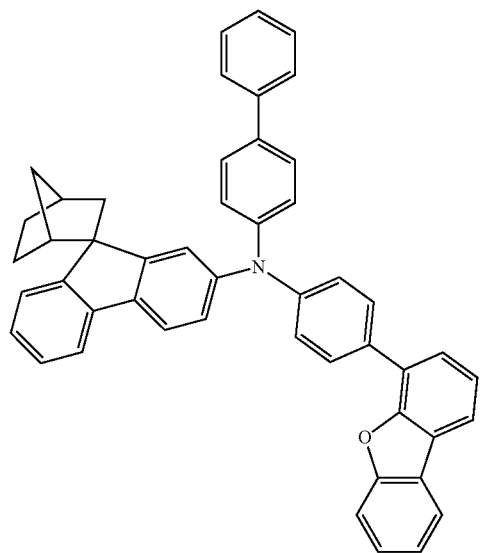
44
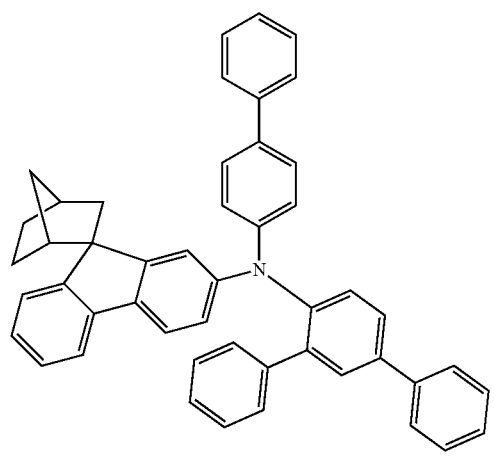
45
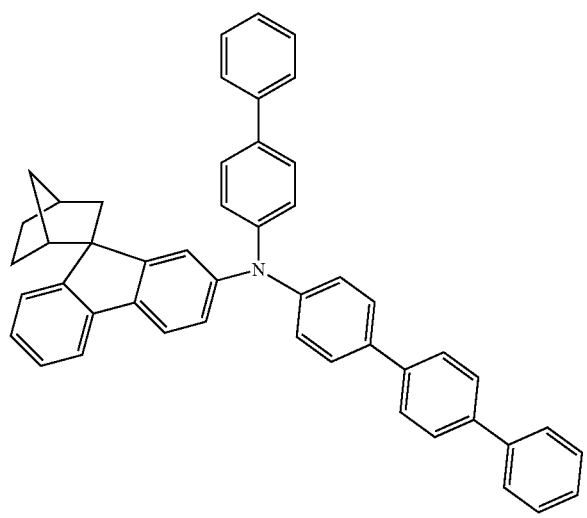
46
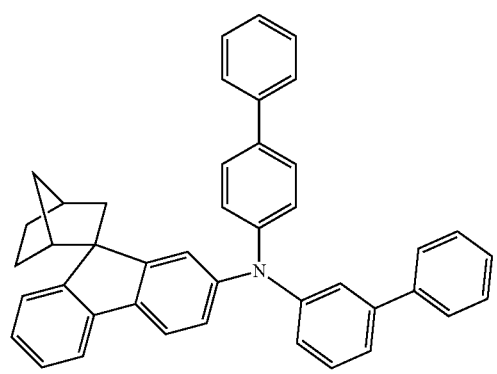
47
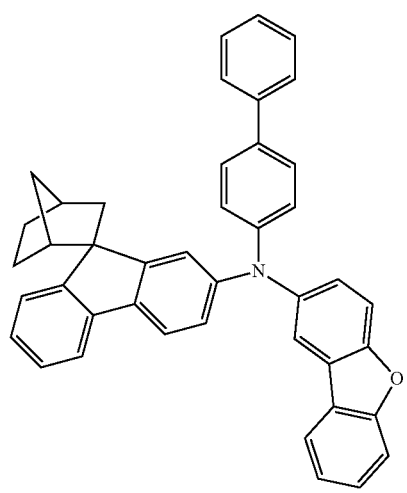

-continued
48
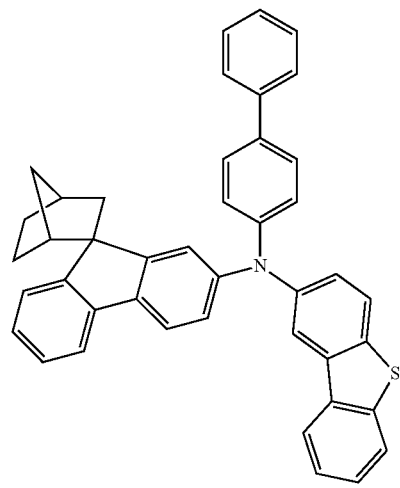
49
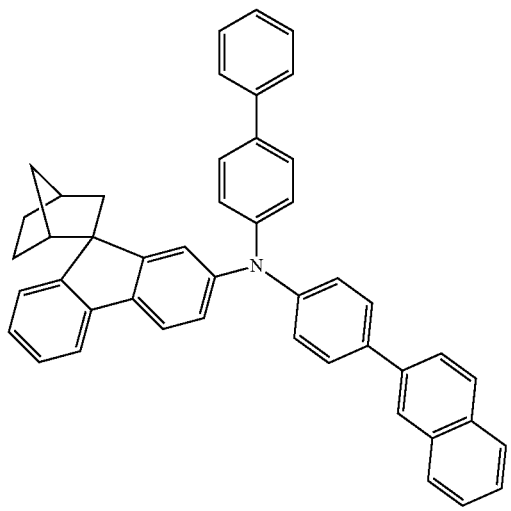
50
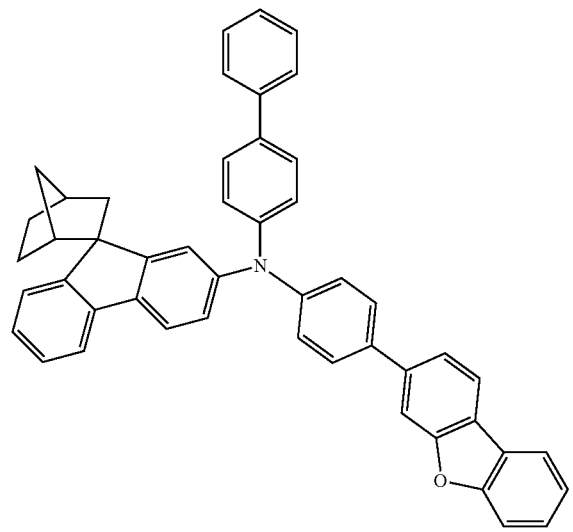
51
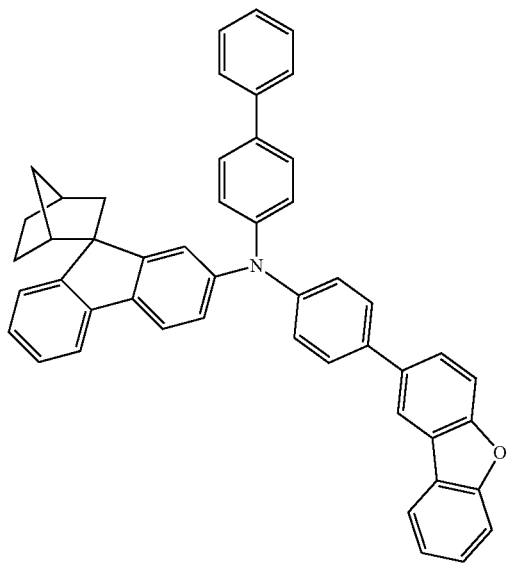
52
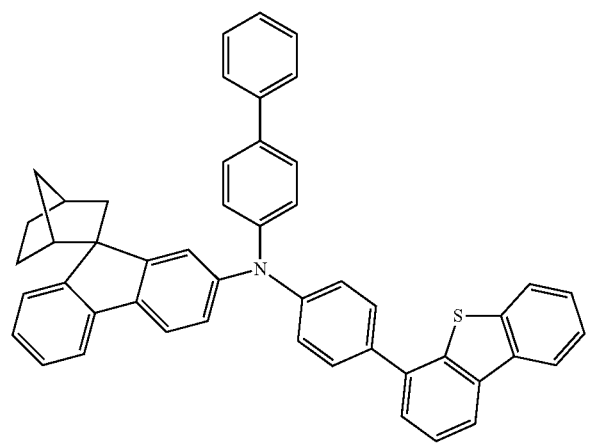
53
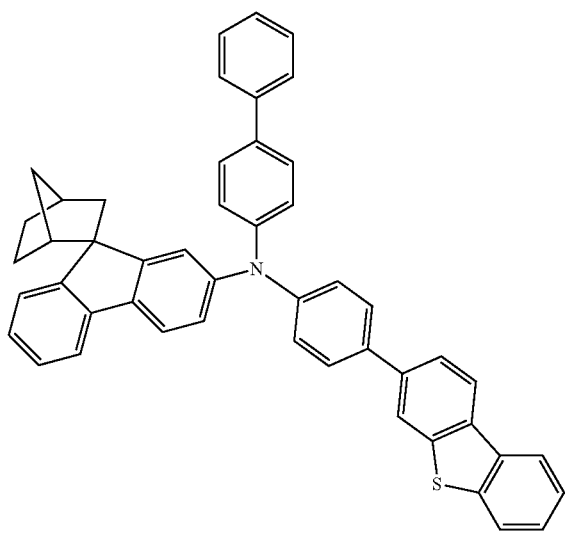

-continued
54
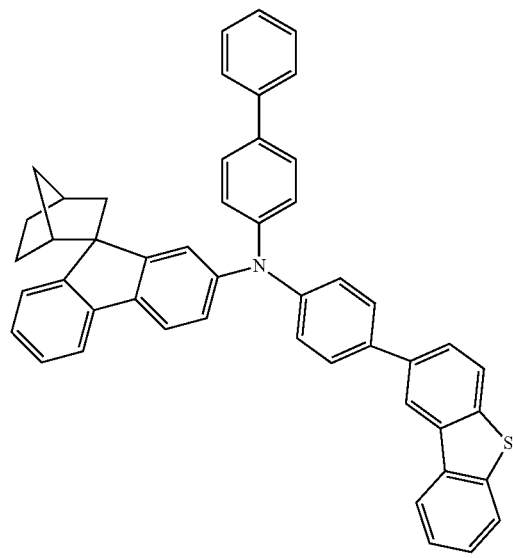
15
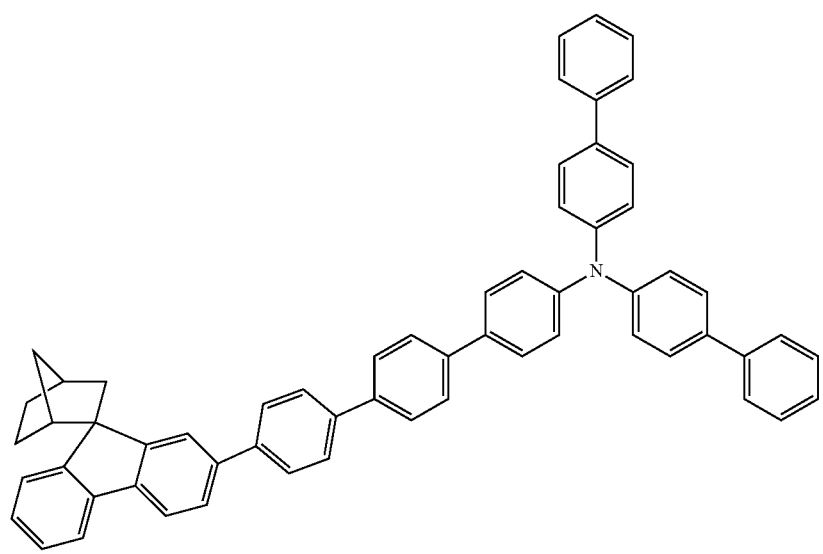
55 56
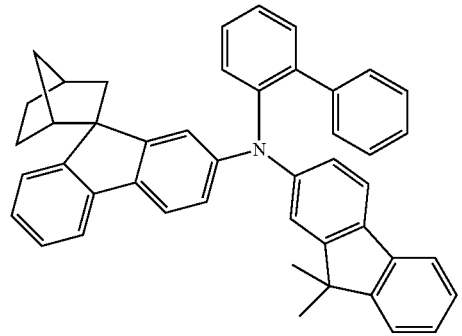

-continued
57
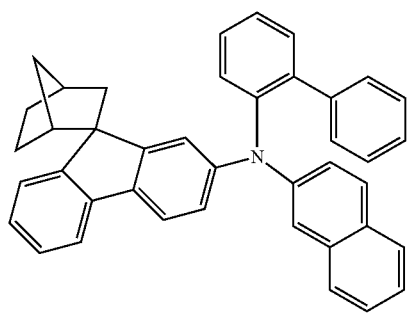
58
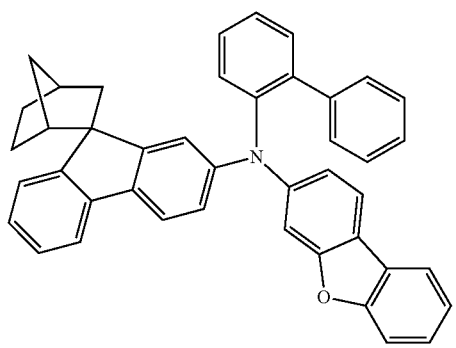
59
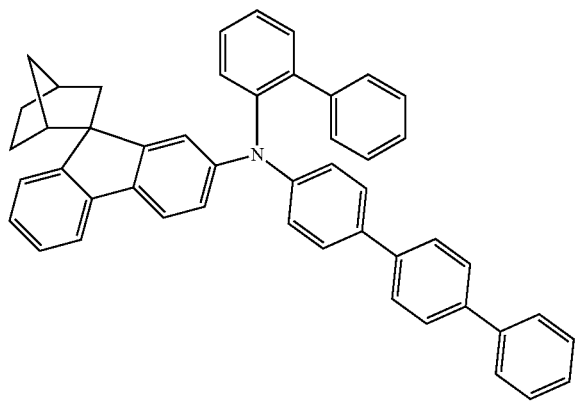
60
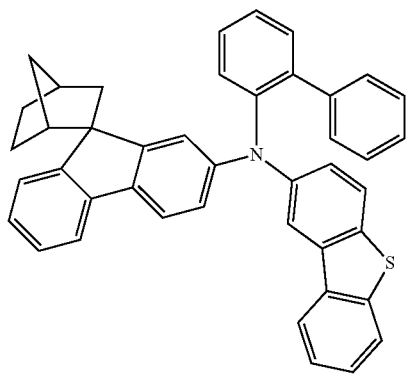
61
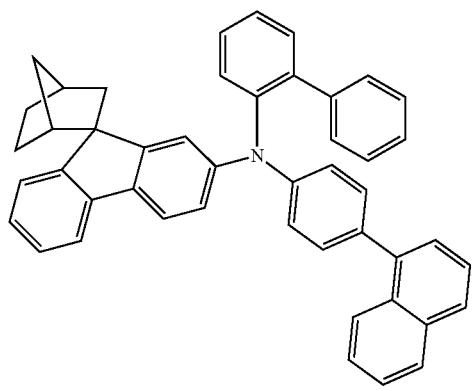
62
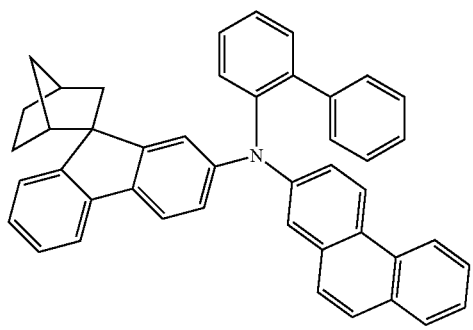
63
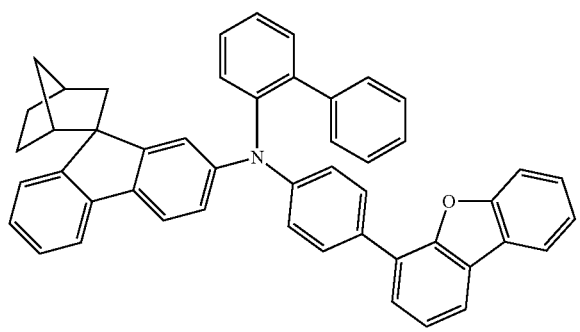
64
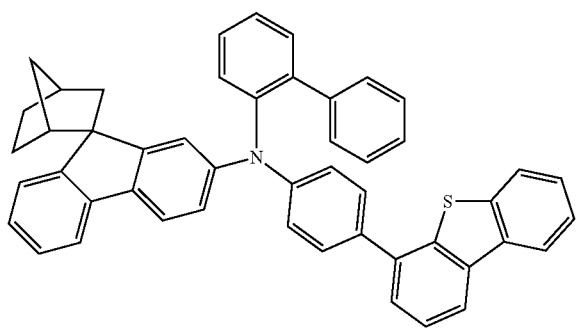

65
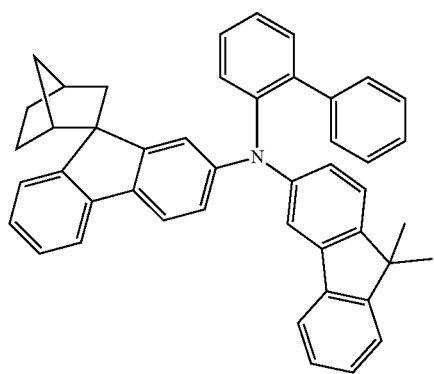
66
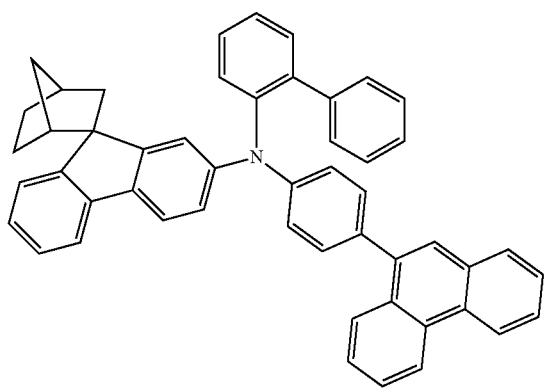
67
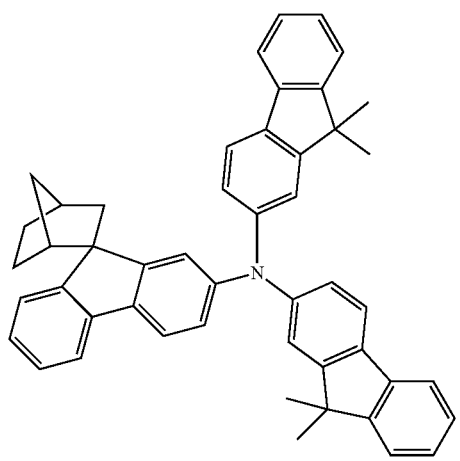
68
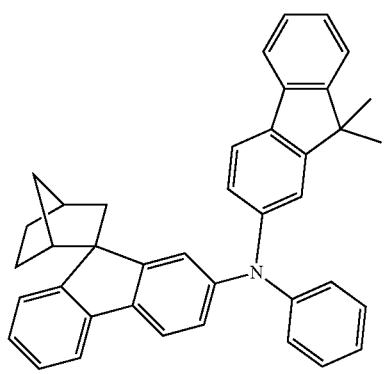
69
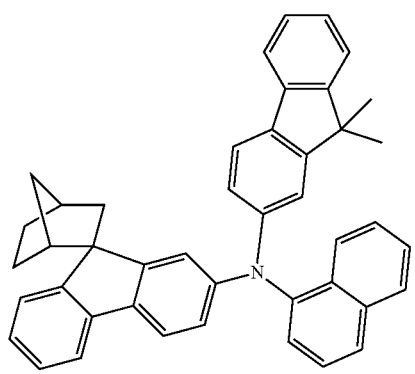
70
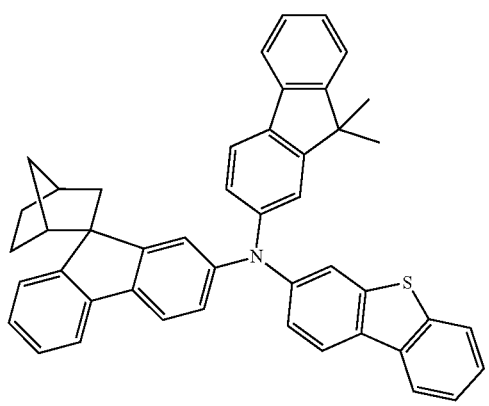

-continued
71
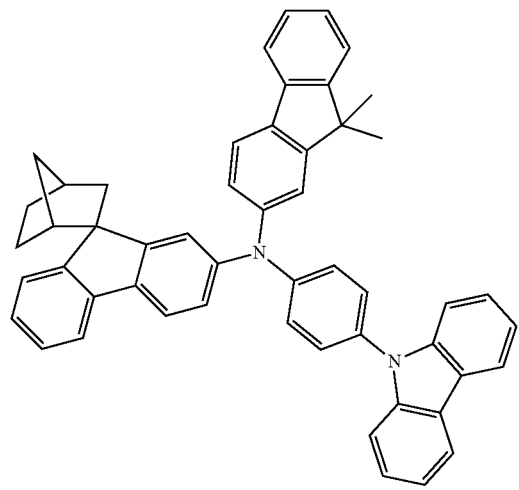
72
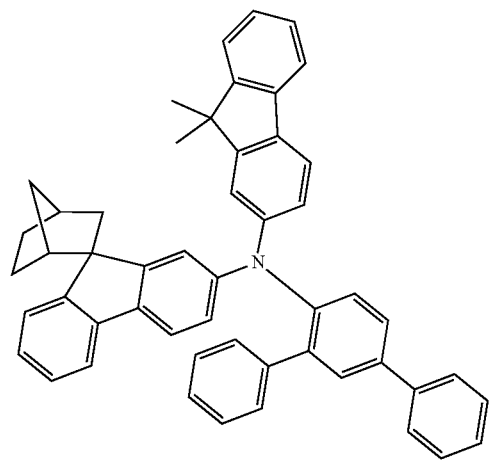
73
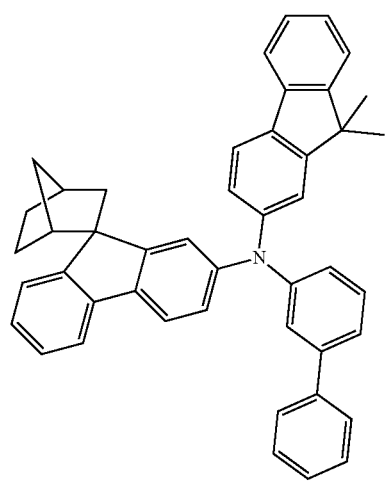
74
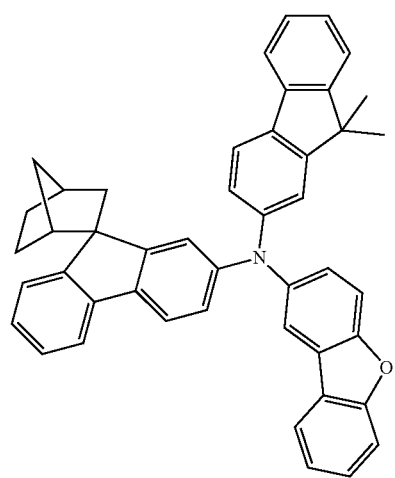
75
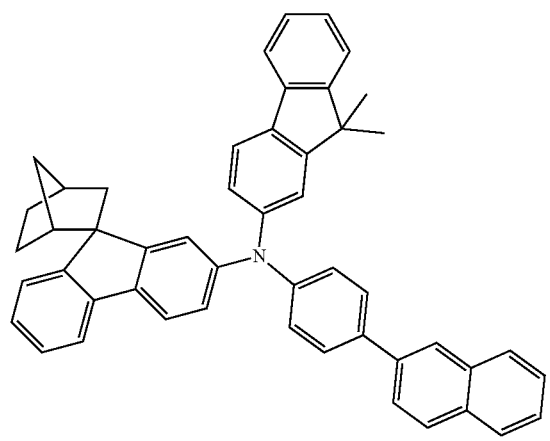
76
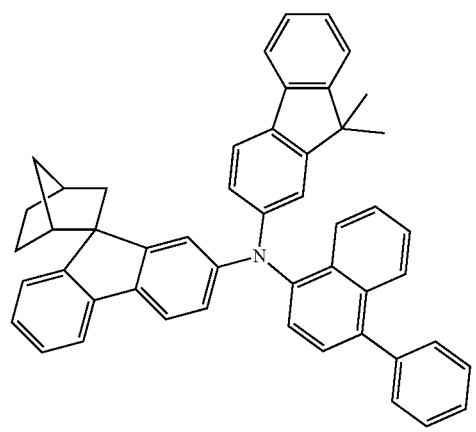

77
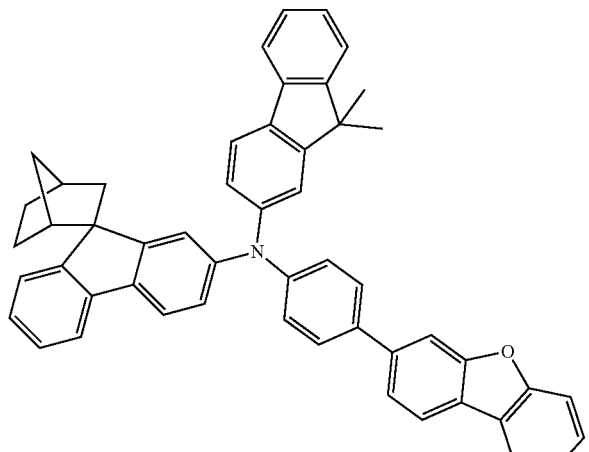
78
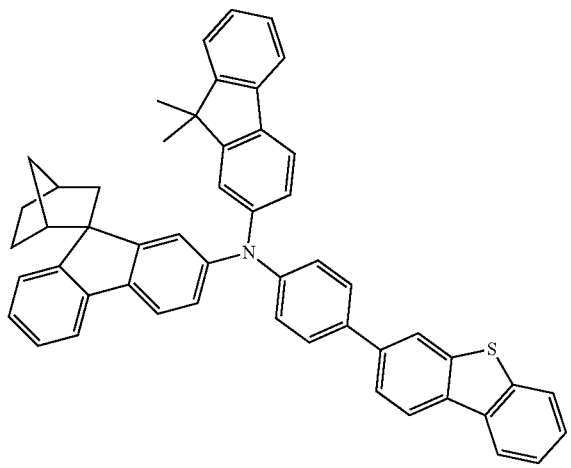
79
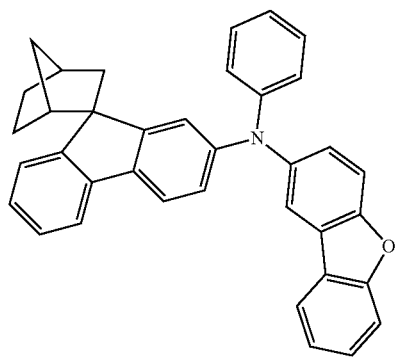
80
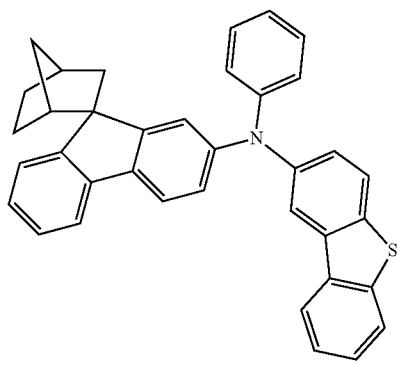
81
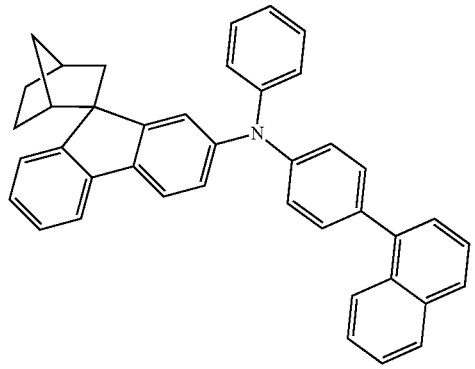
82
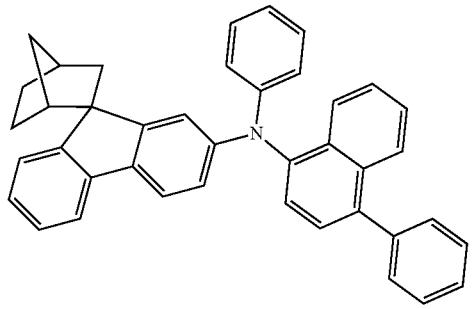
83
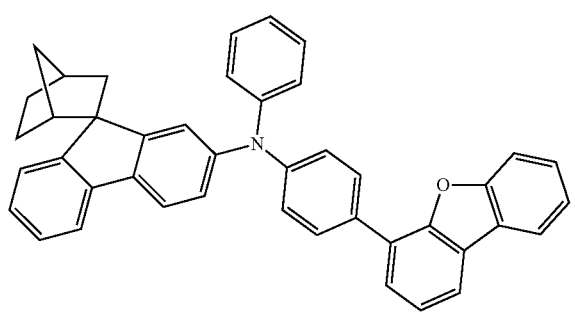
84
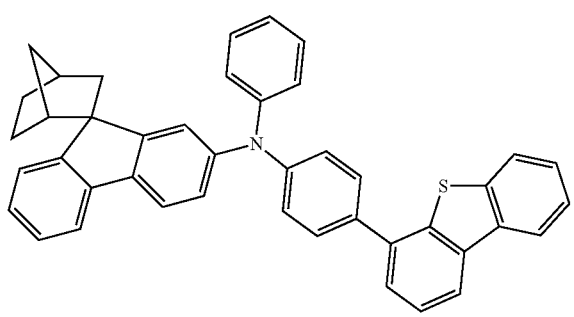

85
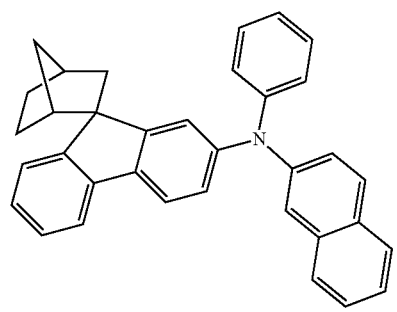
86
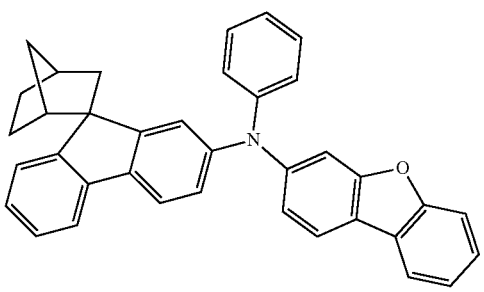
87
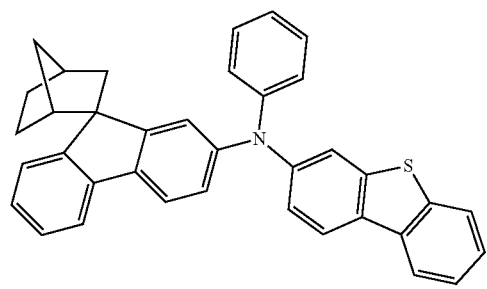
88
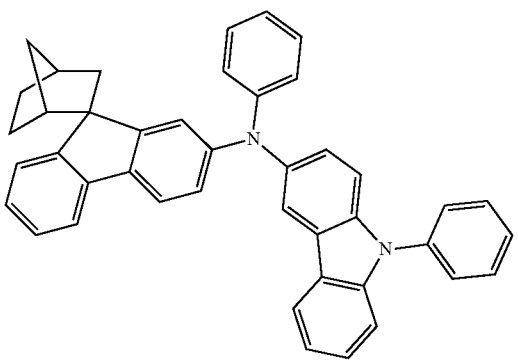
89
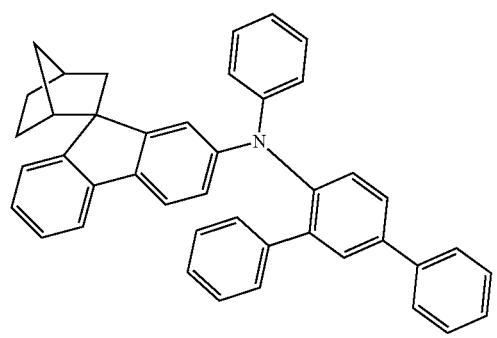
90
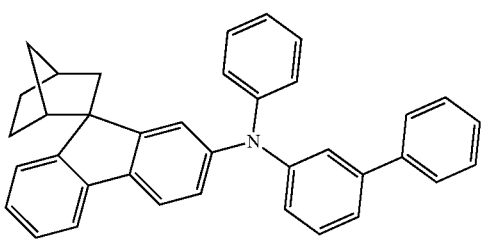
91
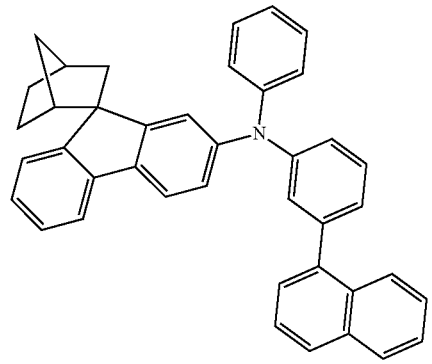
92
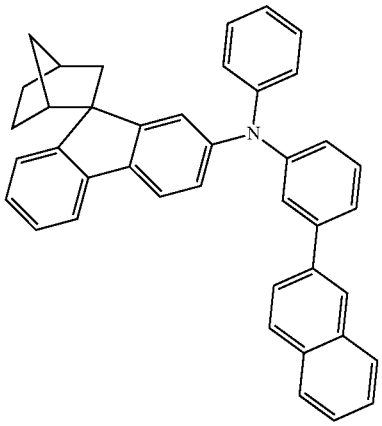

-continued
93
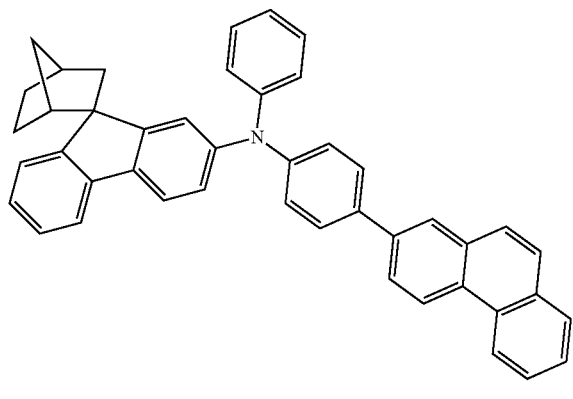
94
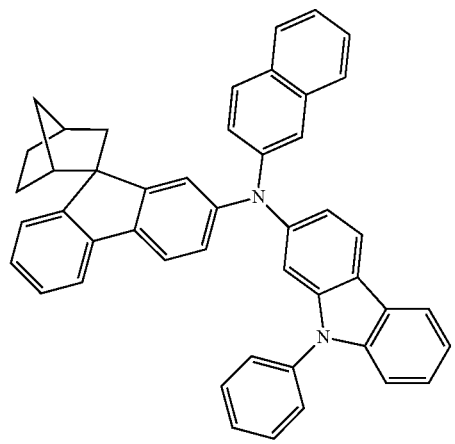
95
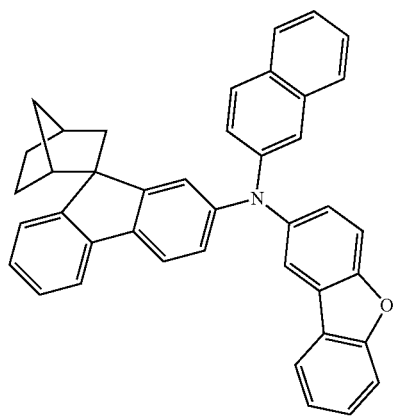
96
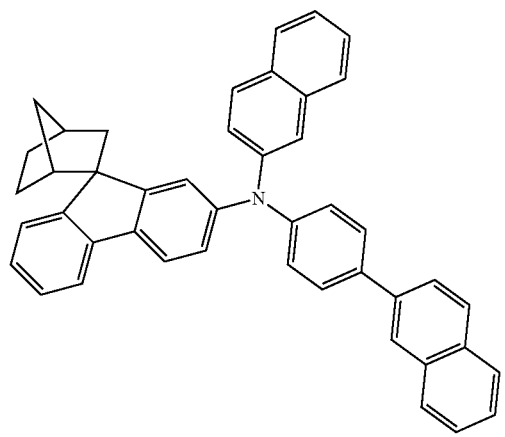
97
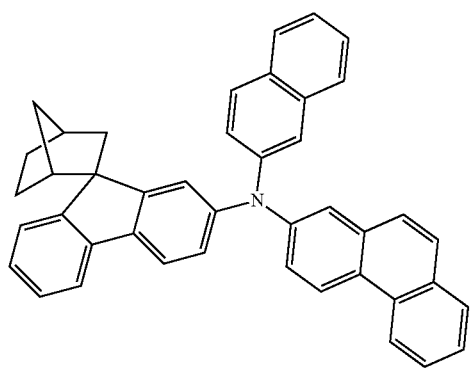
98
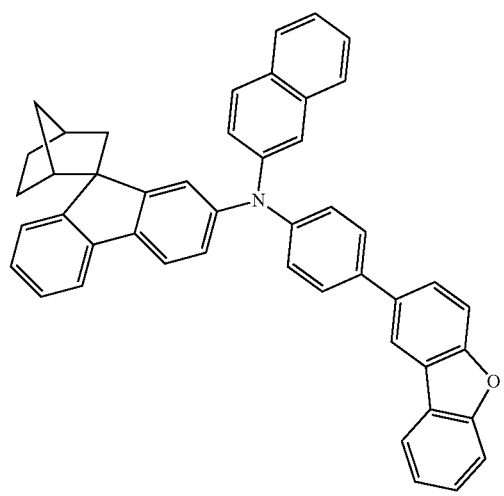

-continued
99
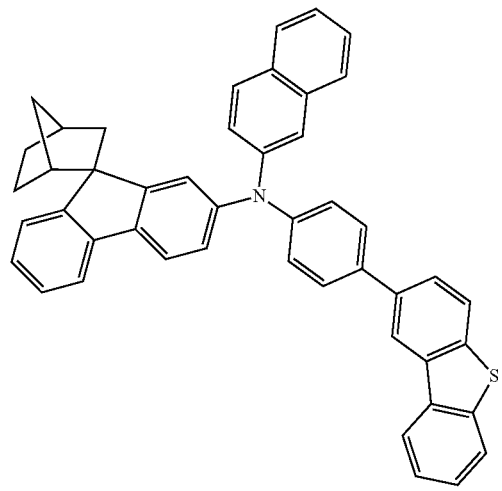
100
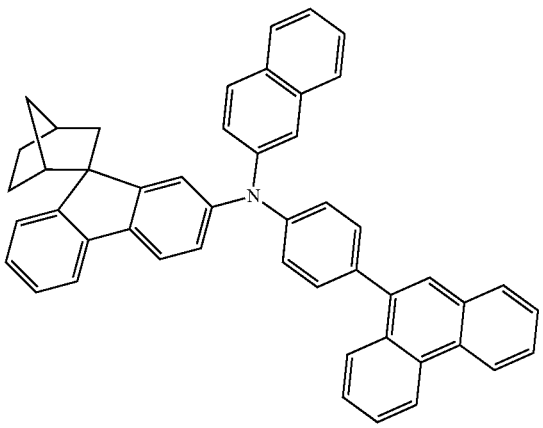
101
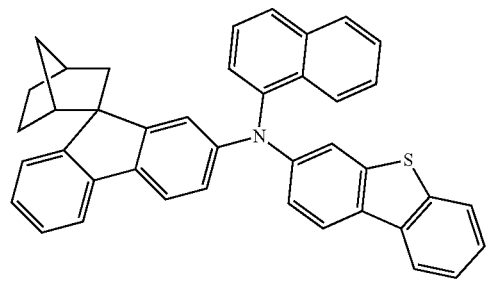
102
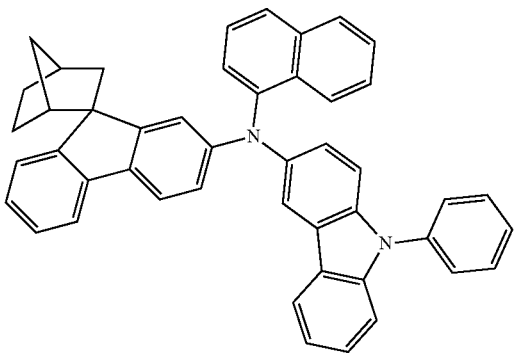
103
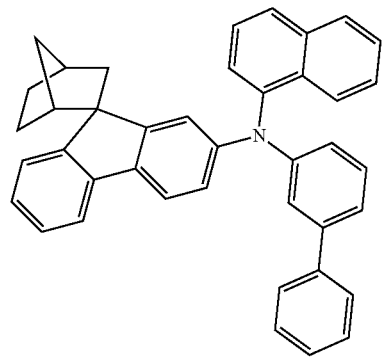
104
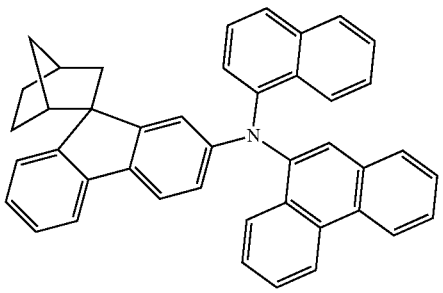
105
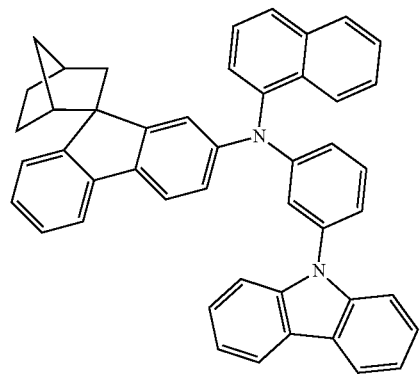
106
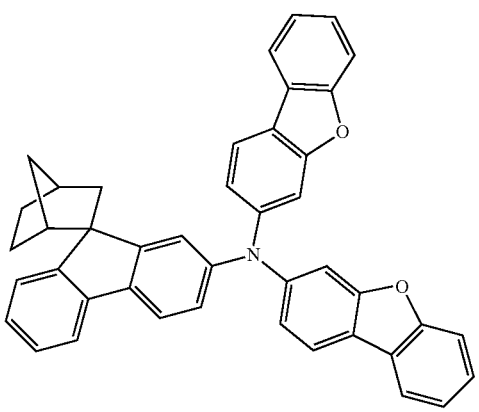

-continued
107
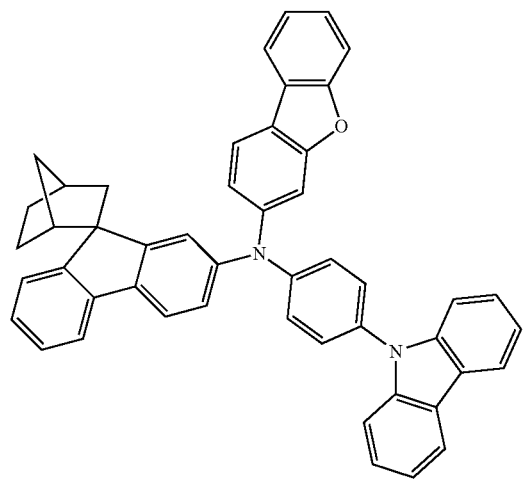
108
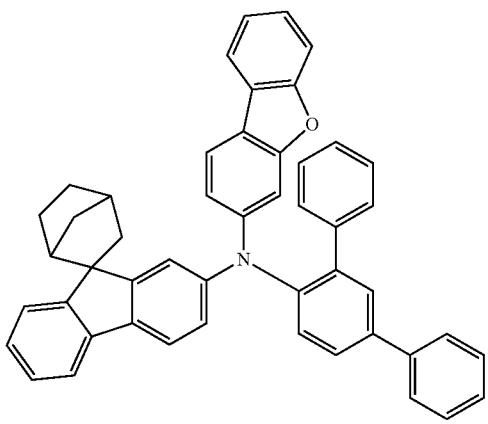
109
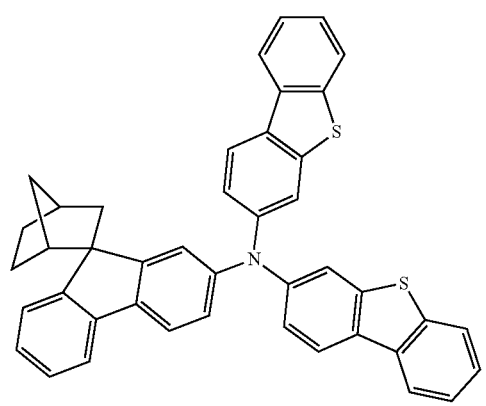
110
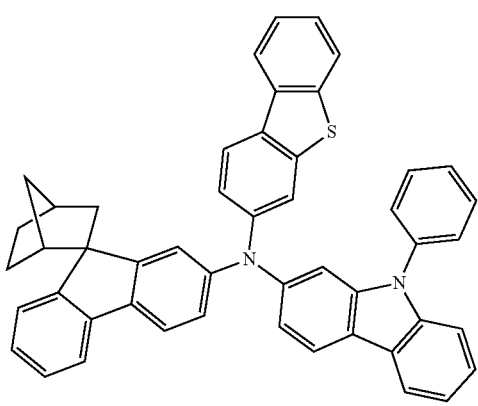
111
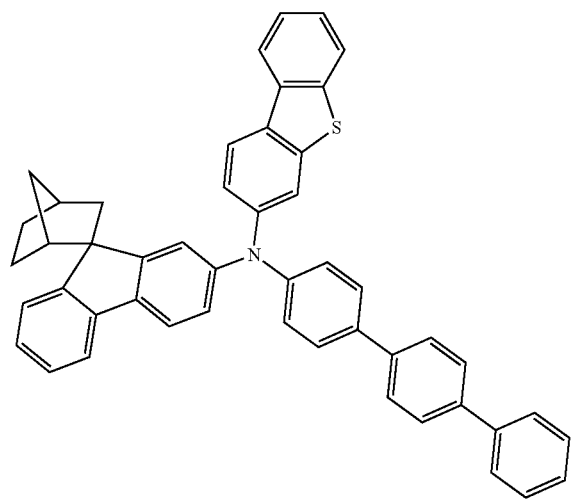
112
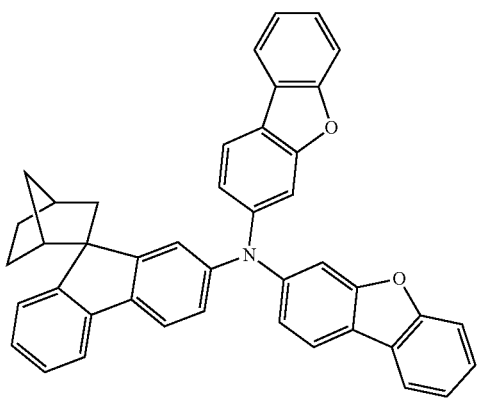

-continued
113
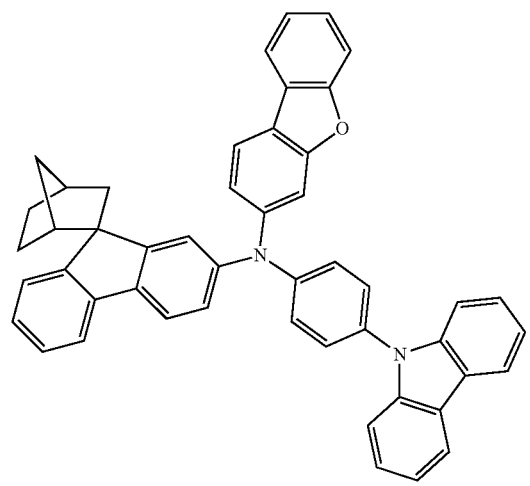
114
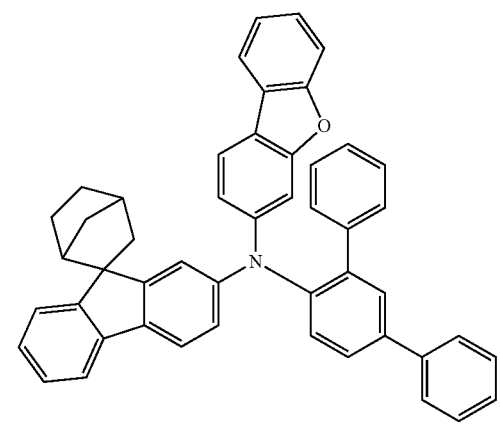
115
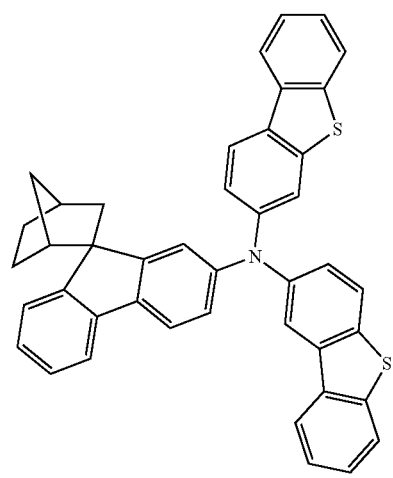
116
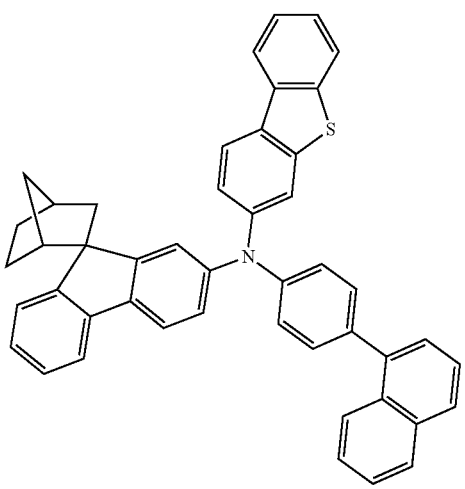
117
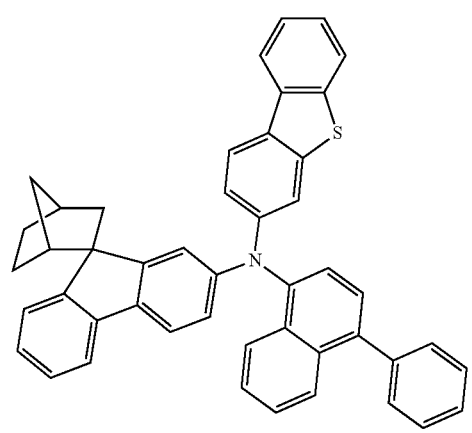
118
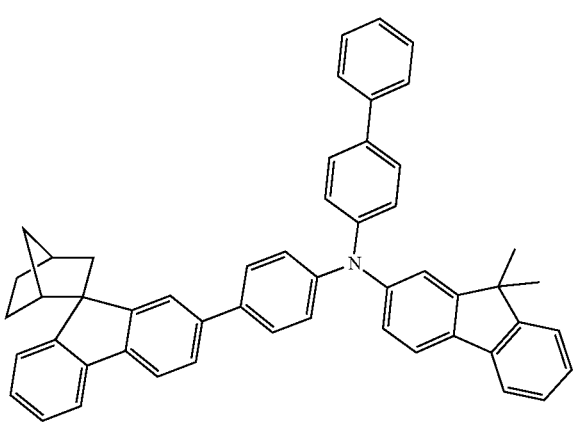

-continued
119
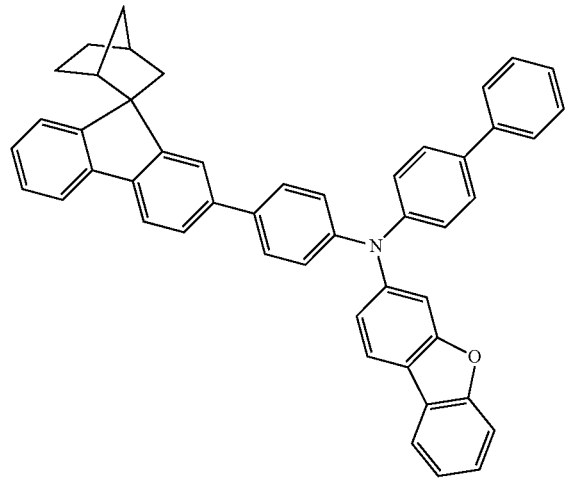
121
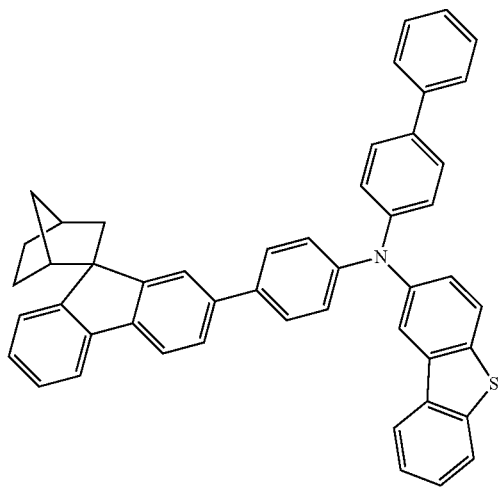
122
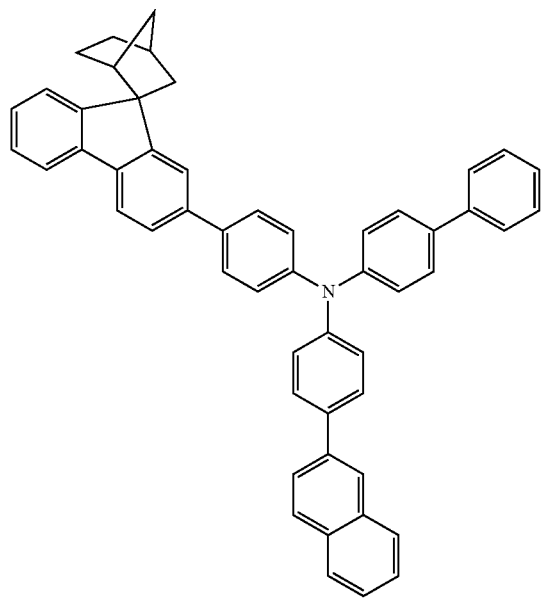
123
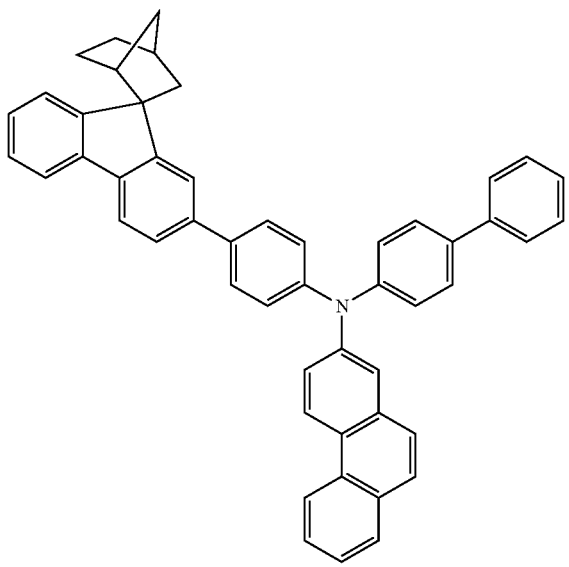
120
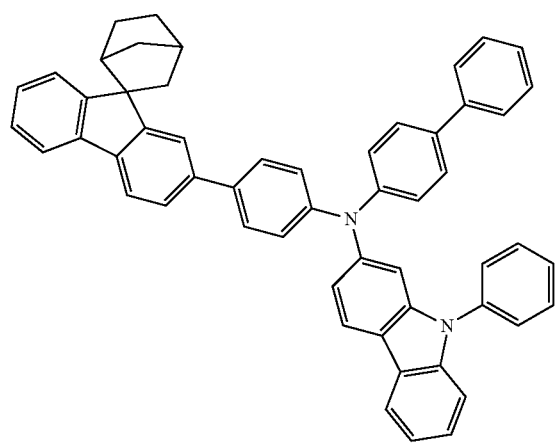
124
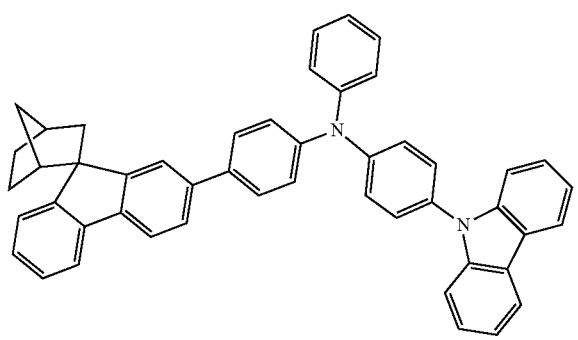

-continued
125
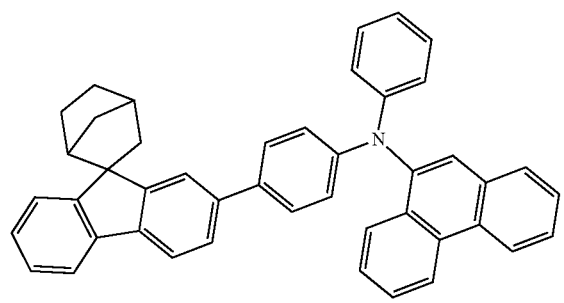
126
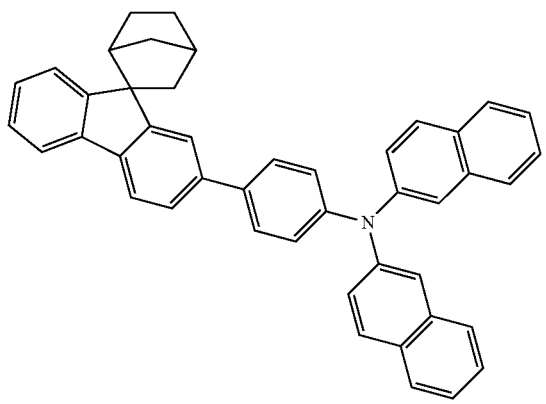
127
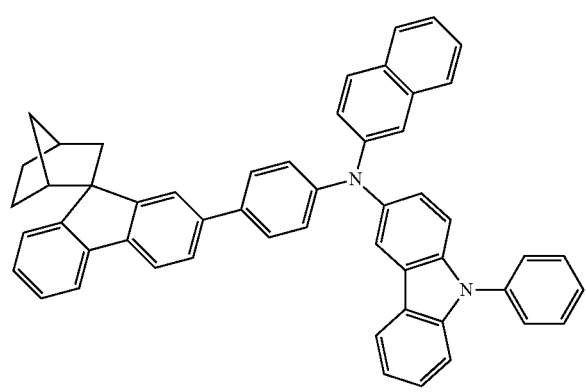
128
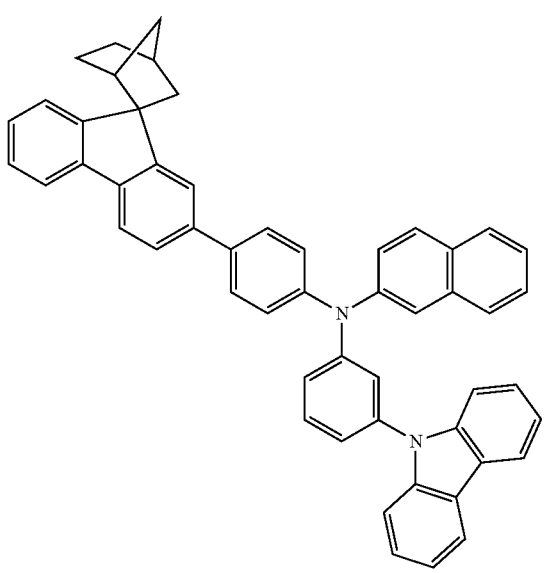
129
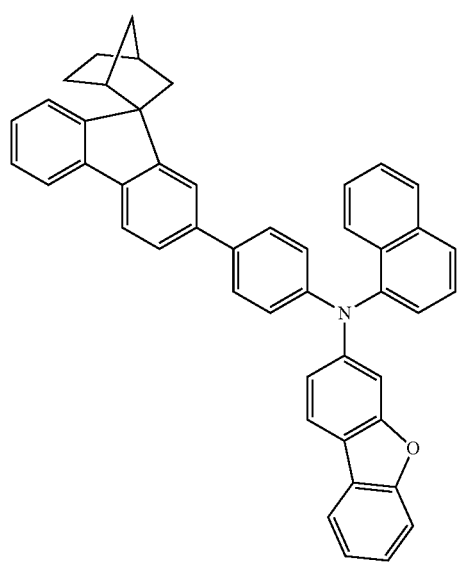
130
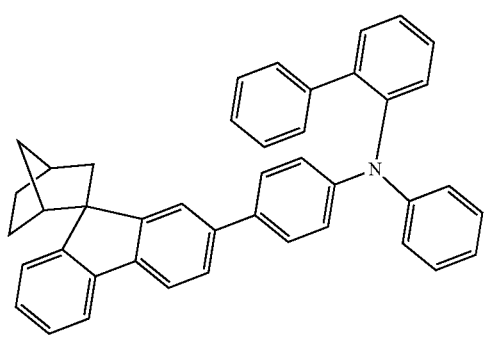

-continued
131
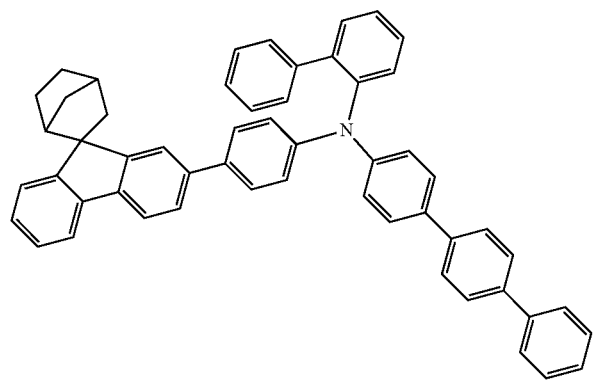
132
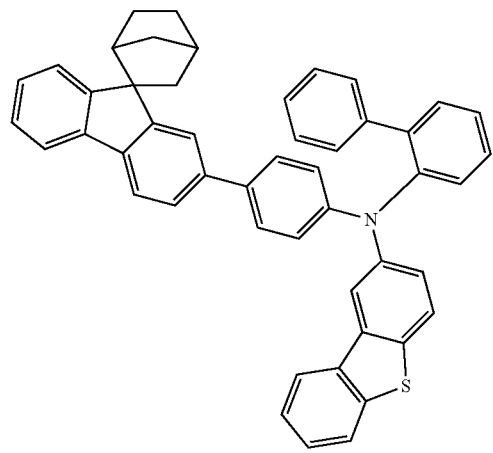
-continued
133
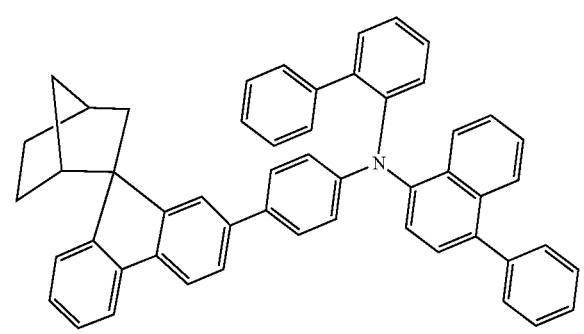
135
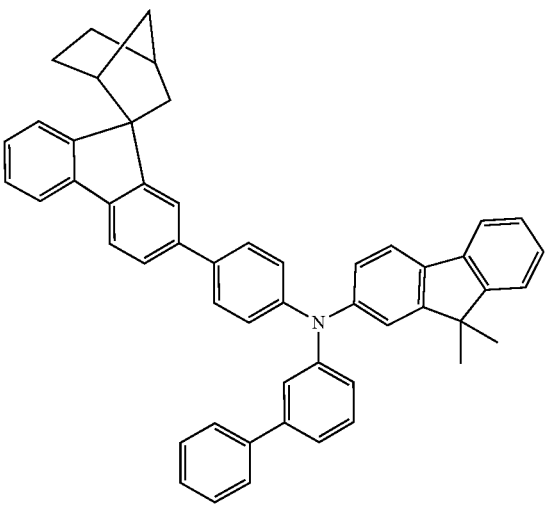
134
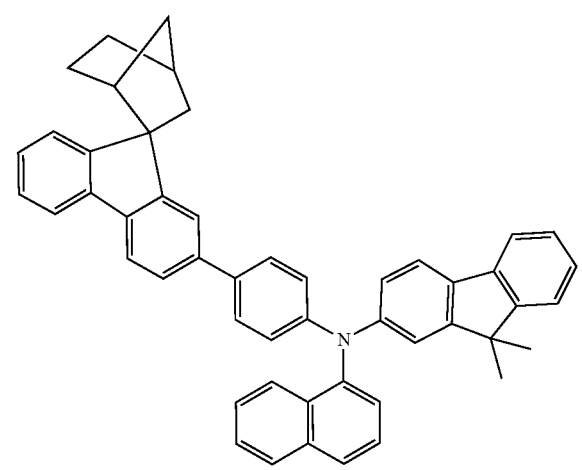
136
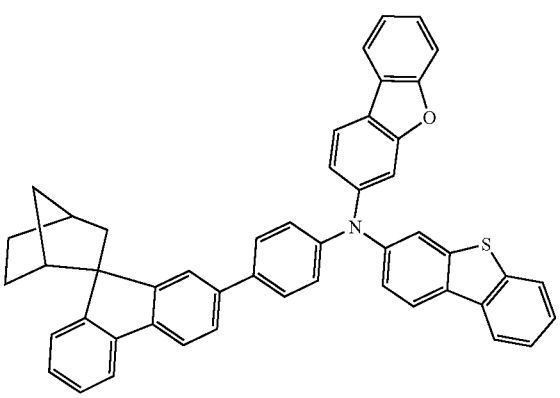

259
-continued
137
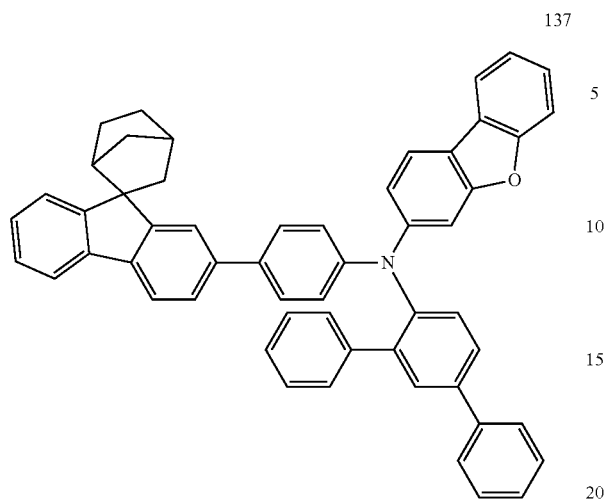
138
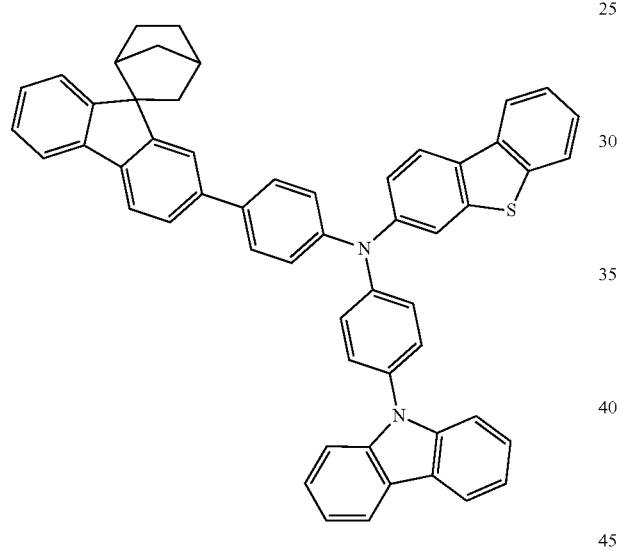
139
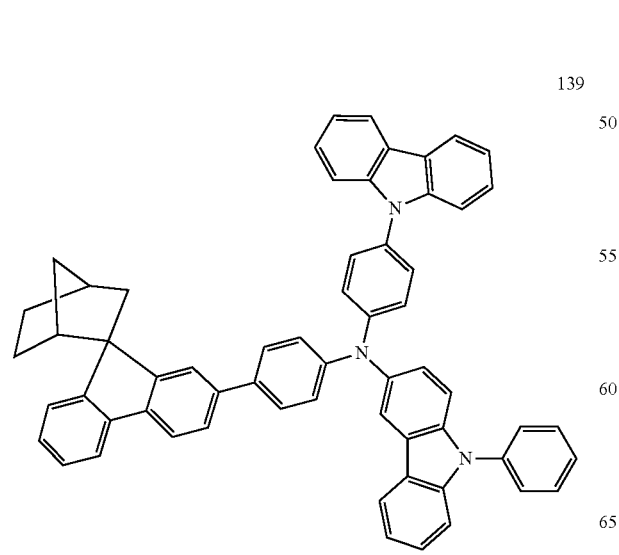
260
-continued
140
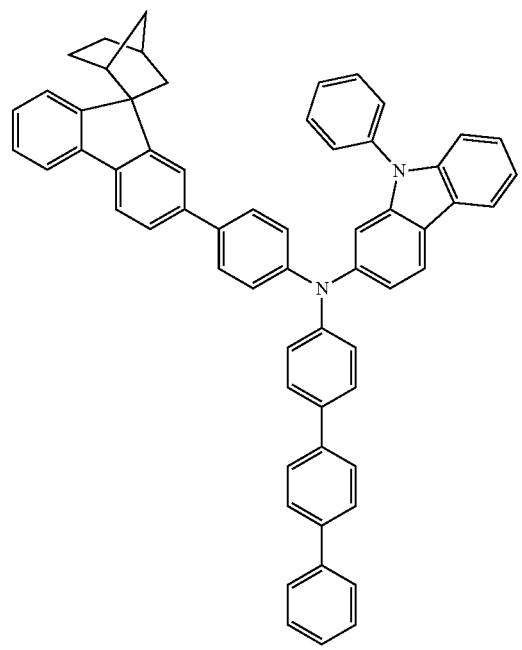
141
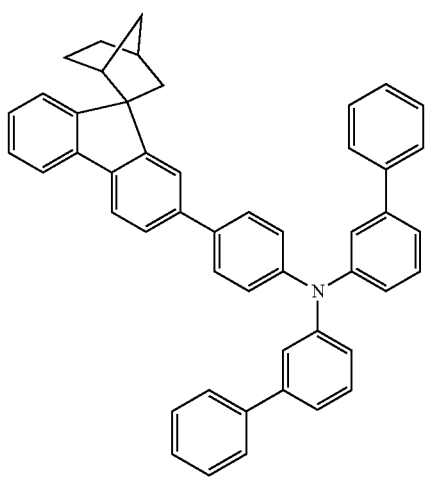
142
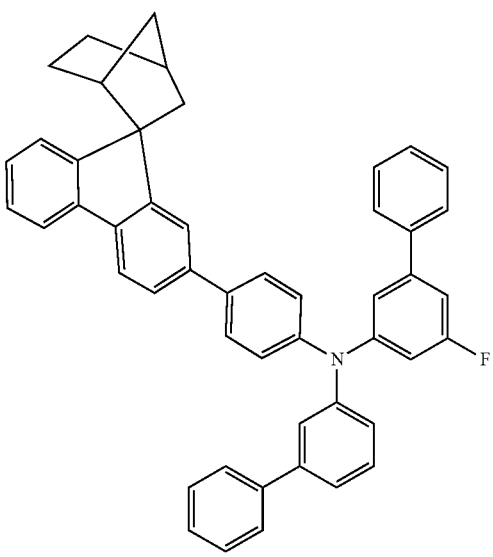

143 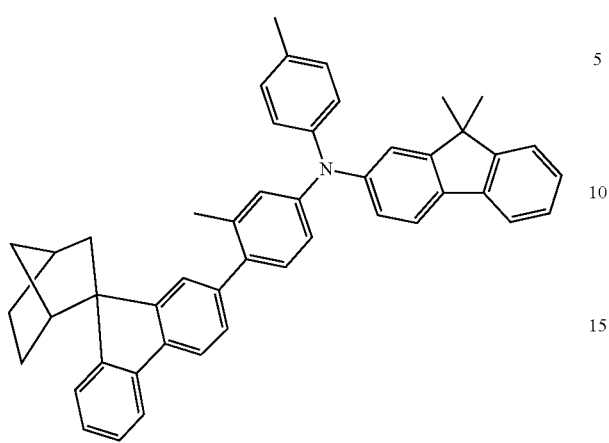
144 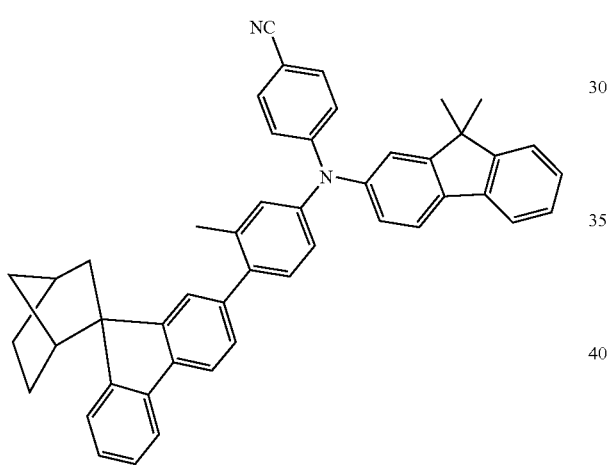
145 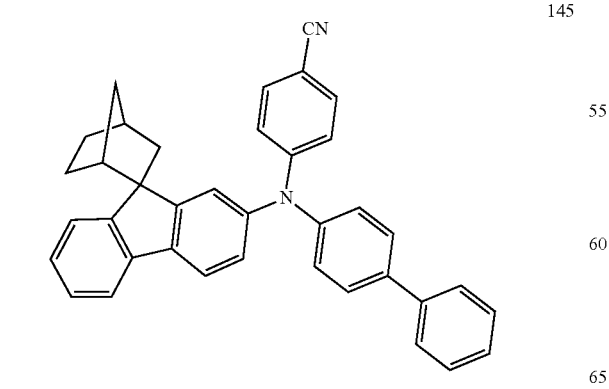
146 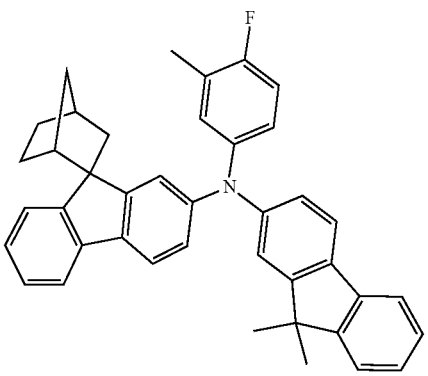
147 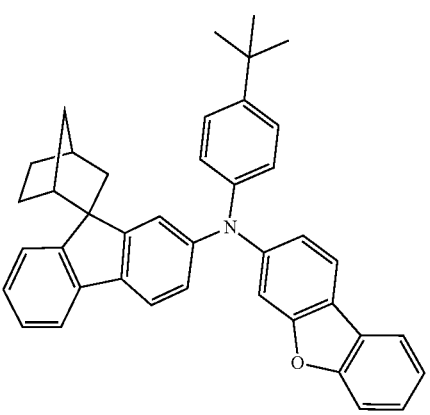
148 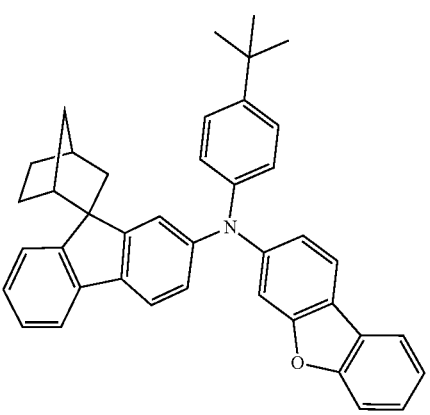
149 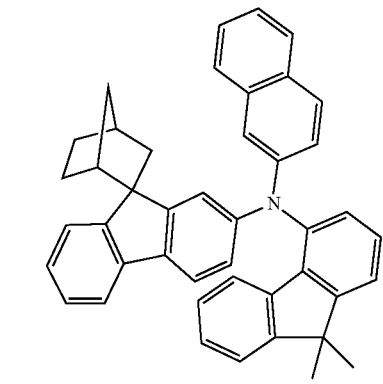

263
-continued
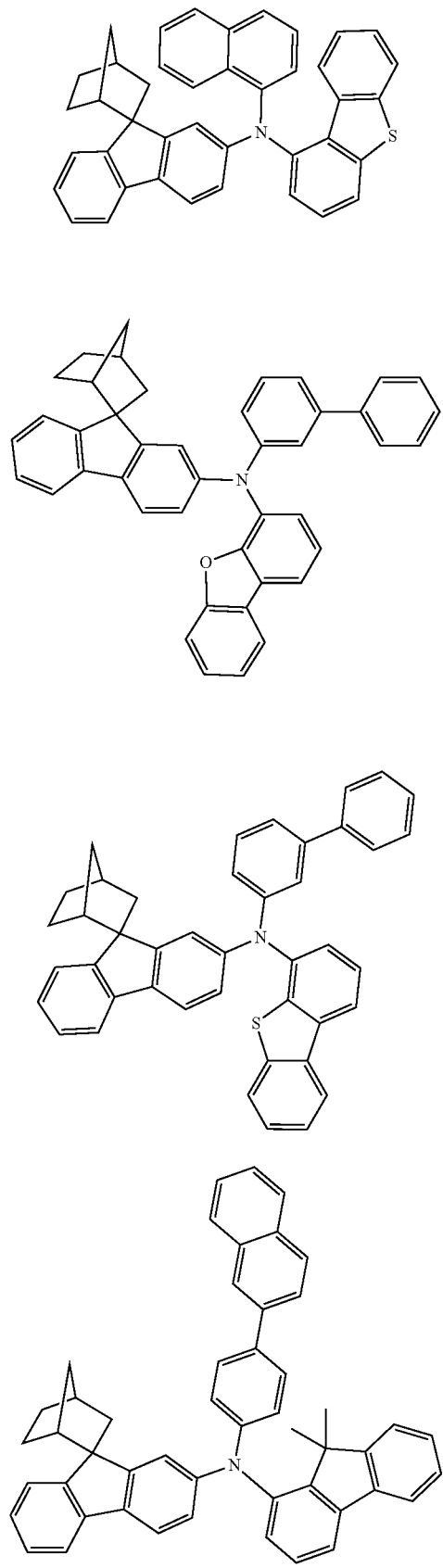
150
151
152
153
264
-continued
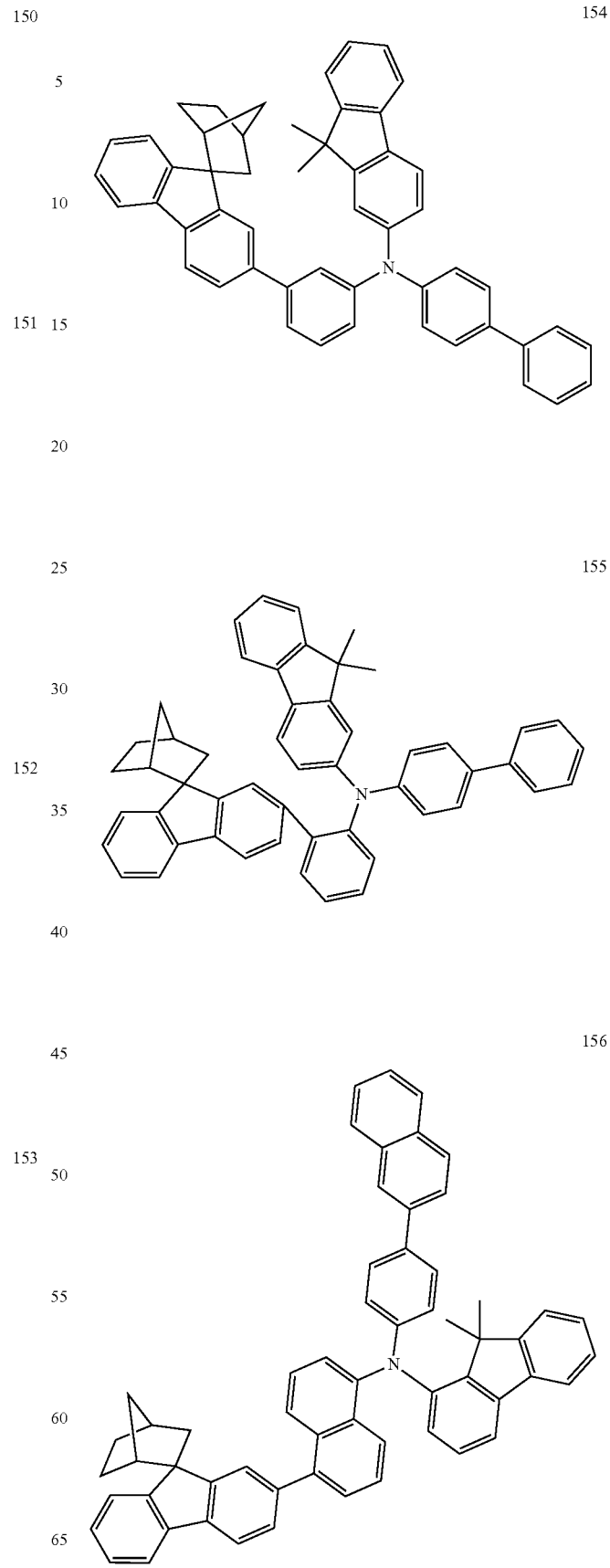
154
155
156

265
-continued
157
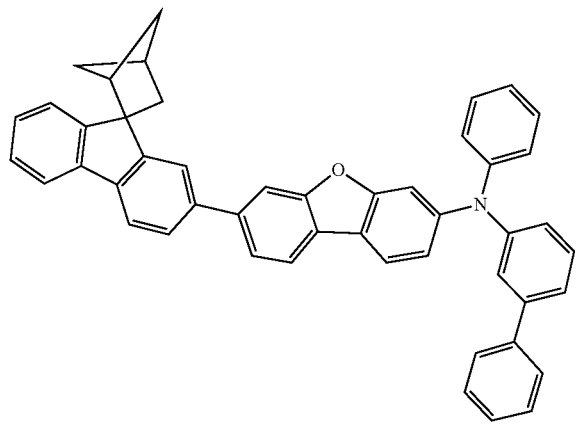
158
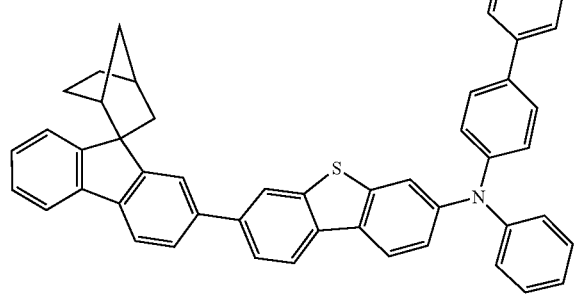
159
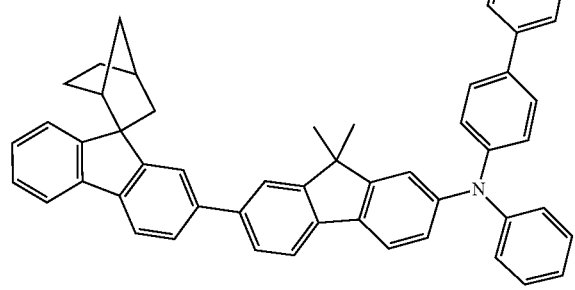
160
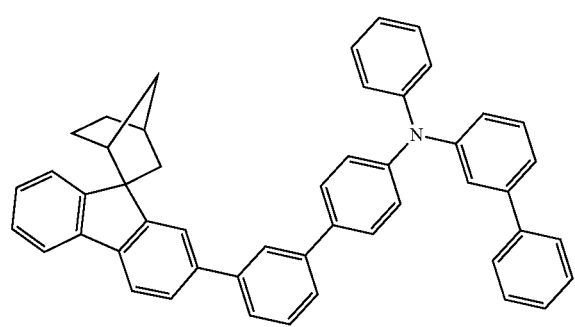
266
-continued
161
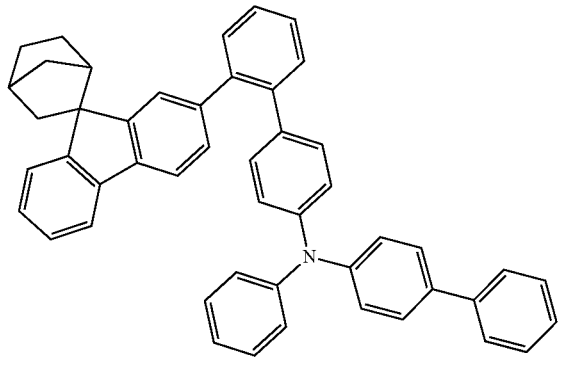
162
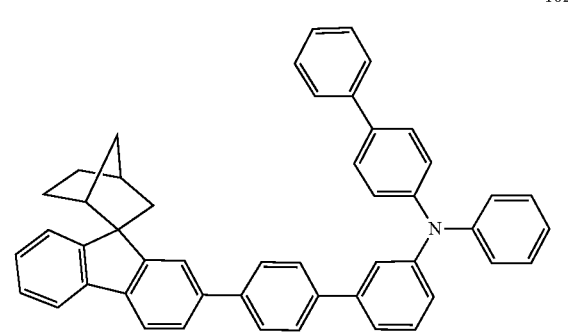
164
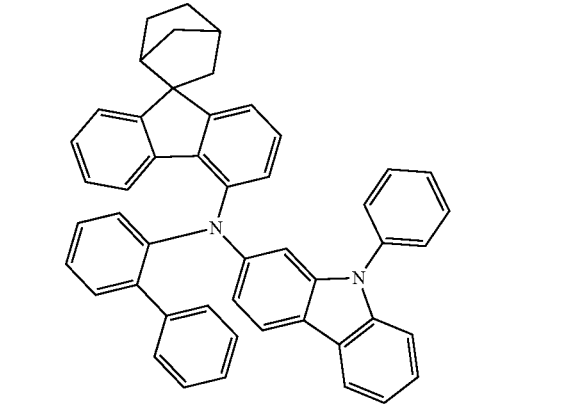
165
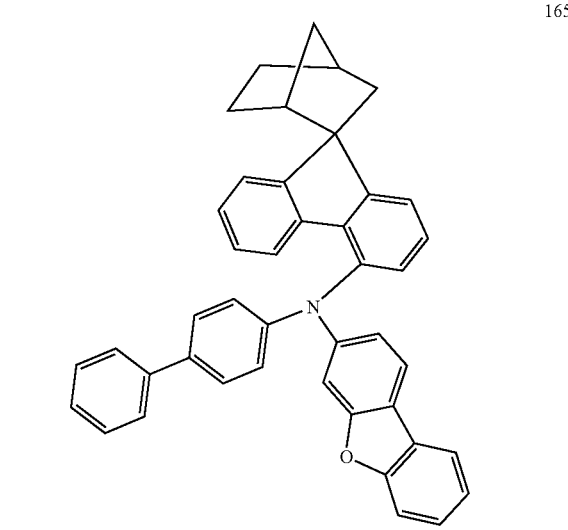

US 12,289,988 B2
267
-continued
166
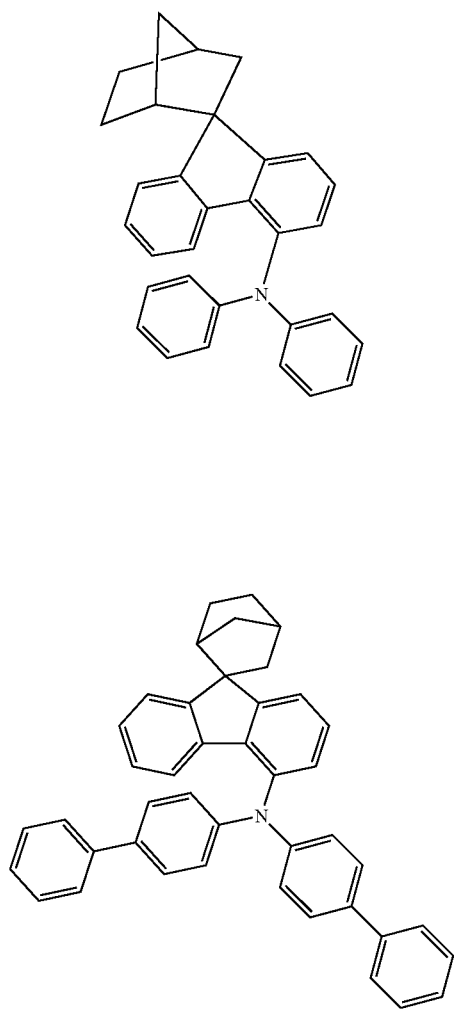
167
168
268
-continued
169
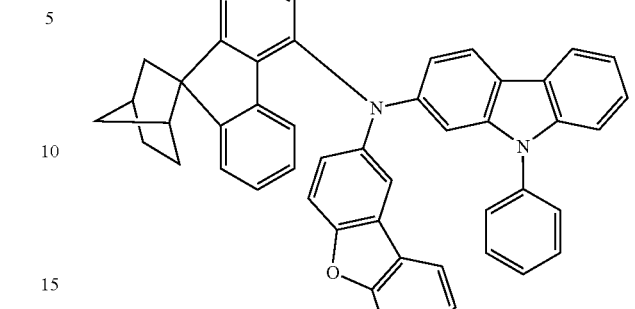
170
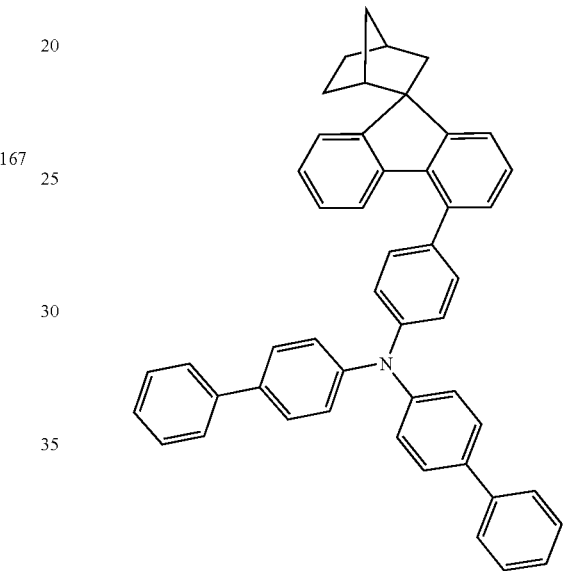
171
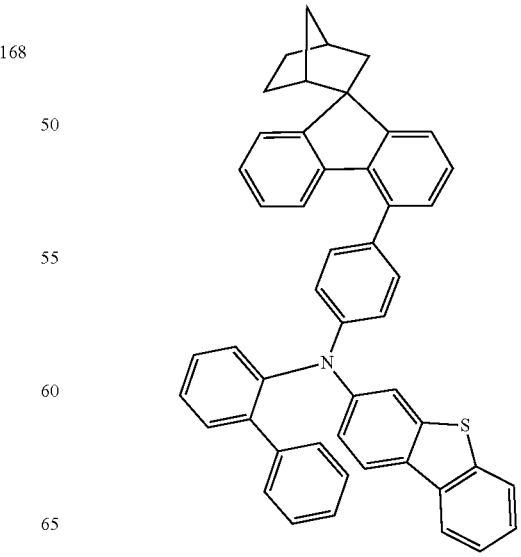
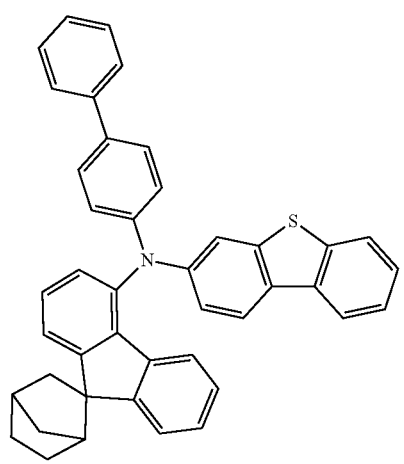

269
-continued
172
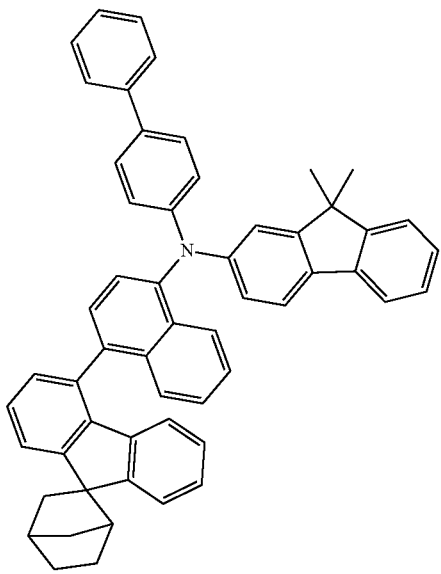
173
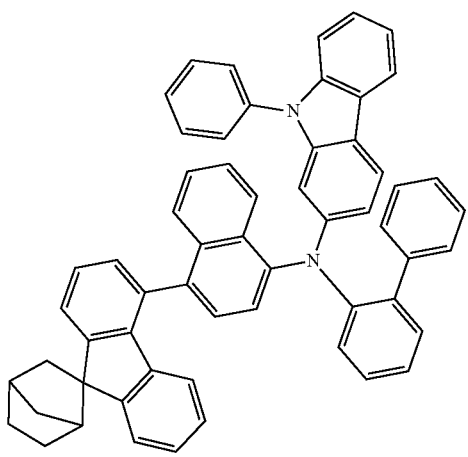
174
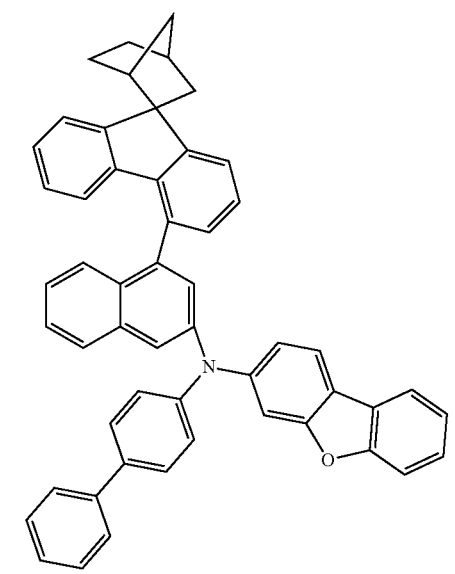
270
-continued
175
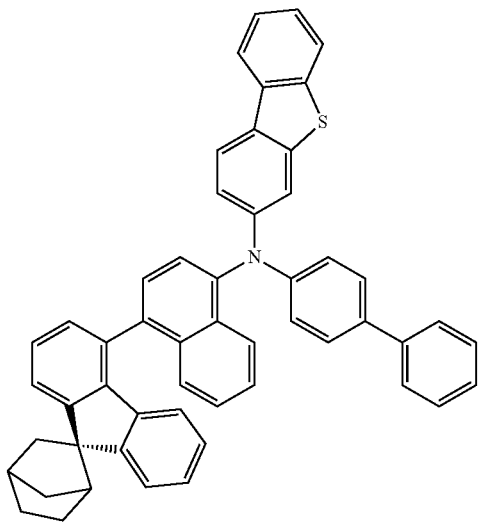
176
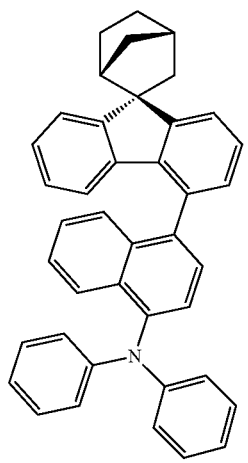
177
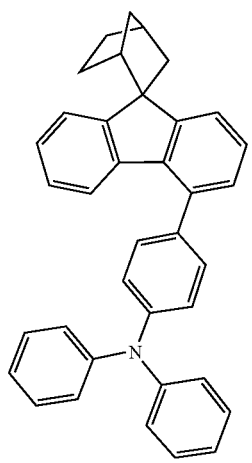

271 272
-continued
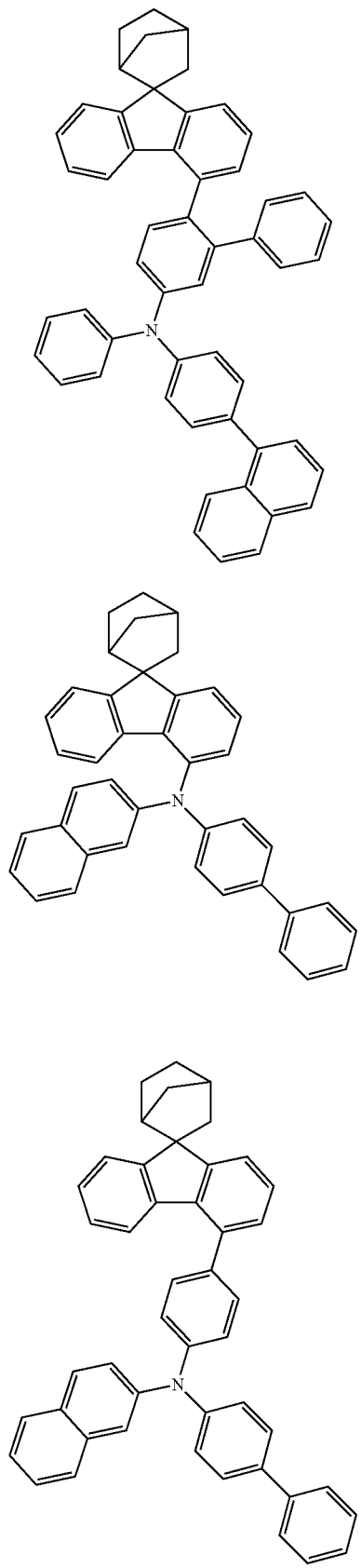
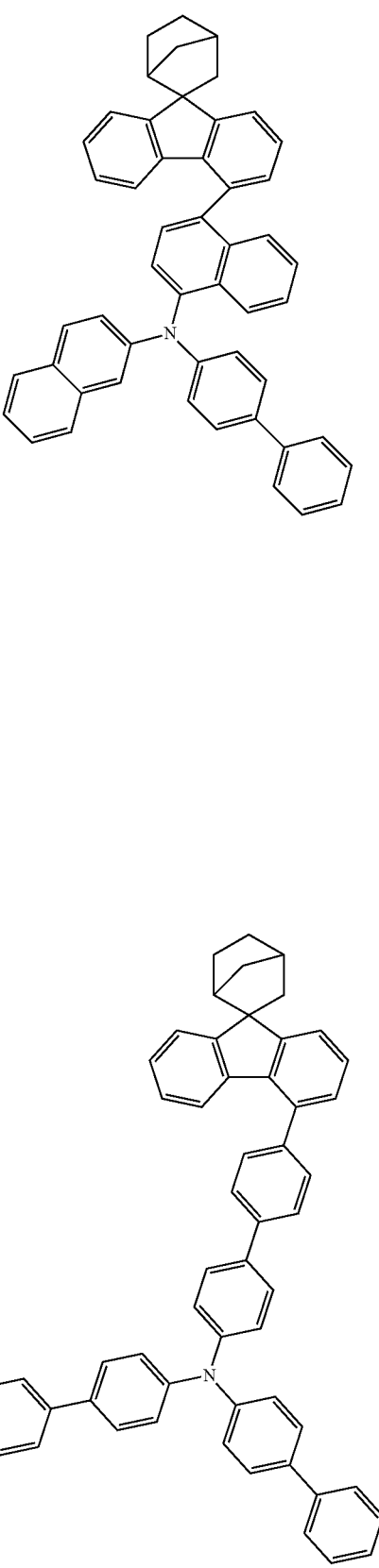

183
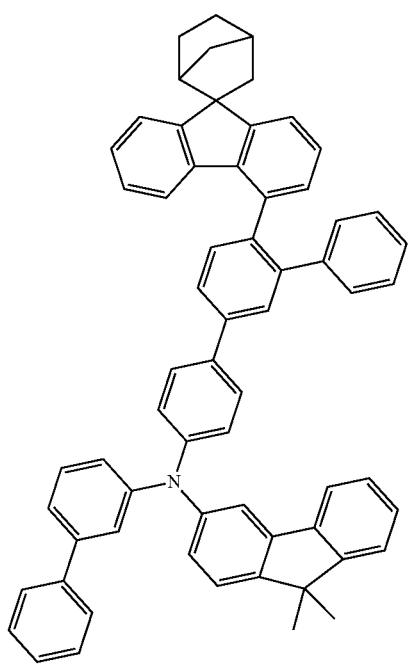
184
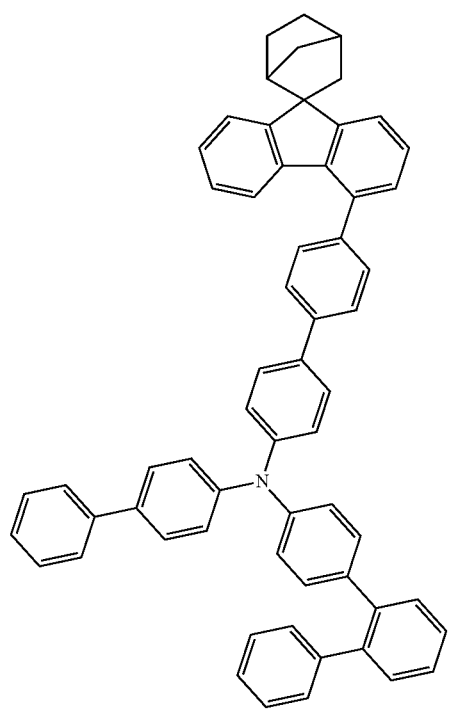
185
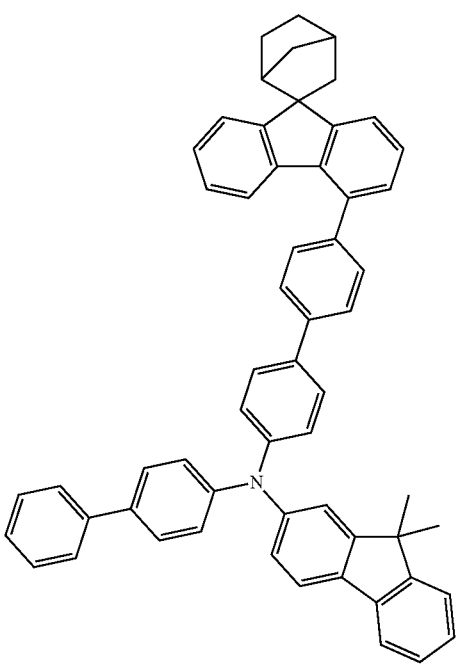
186
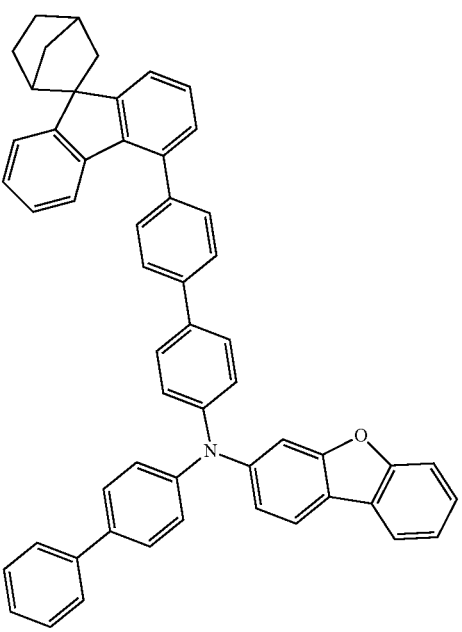

187
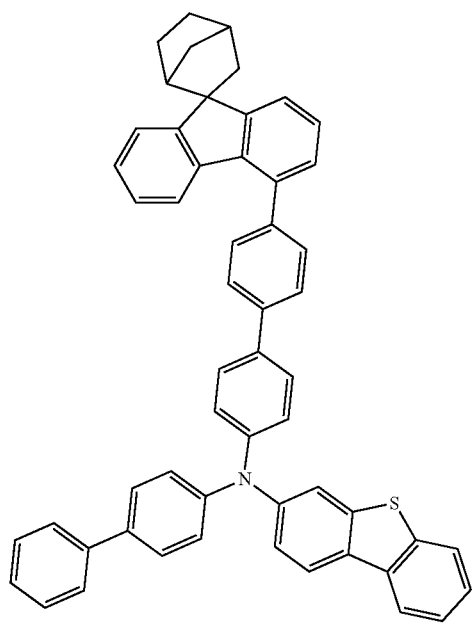
188
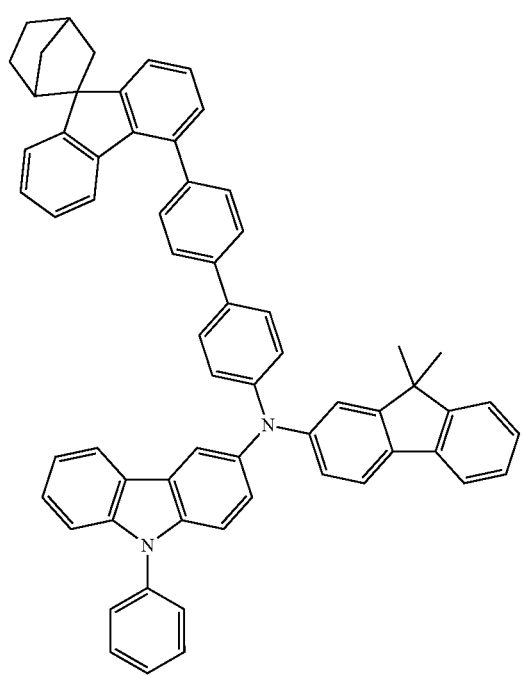
189
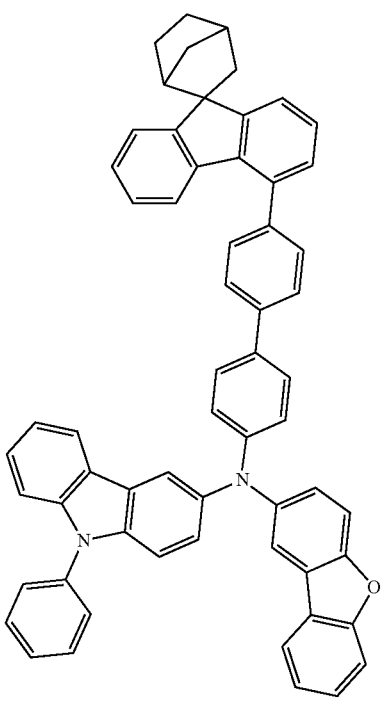
190
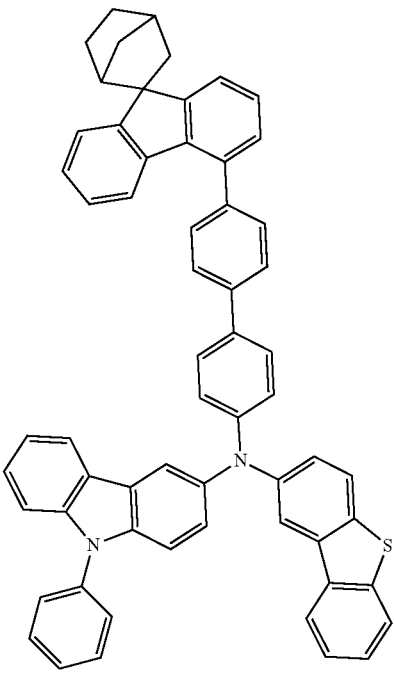

191
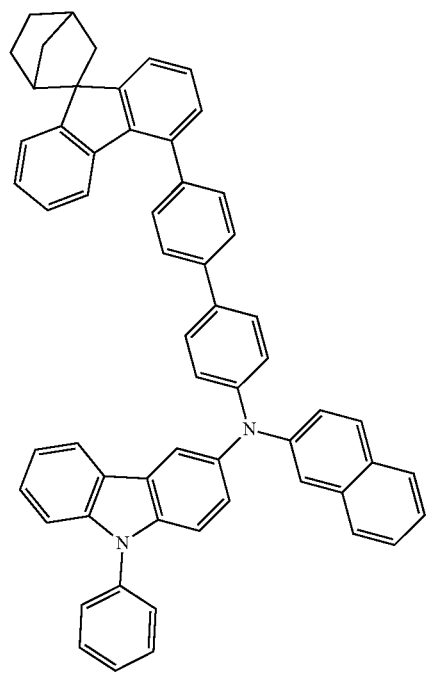
192
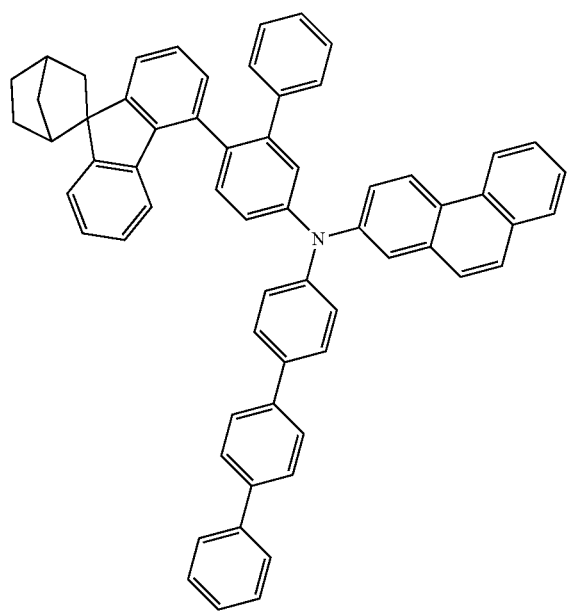
193
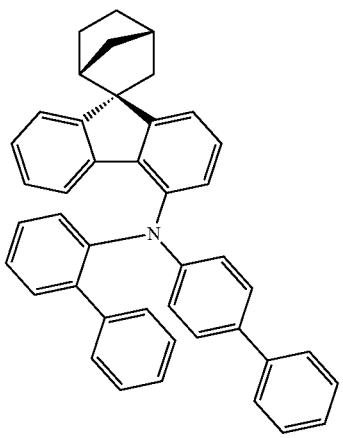
194
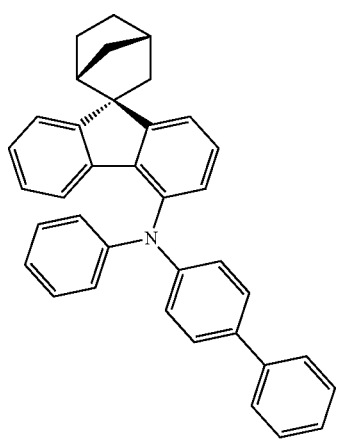
195
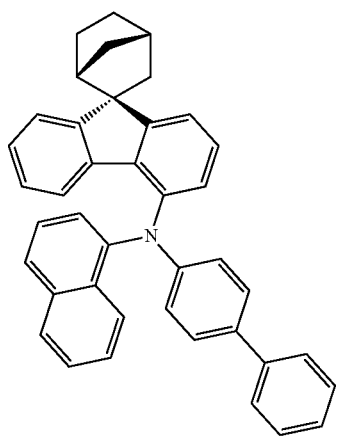

196
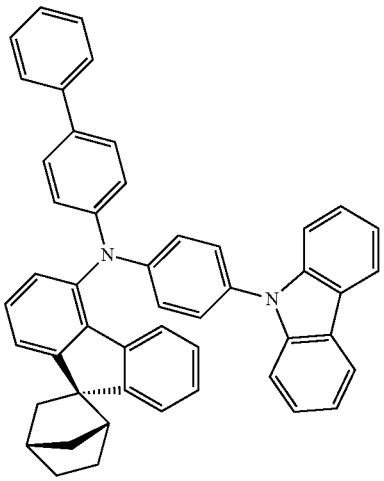
197
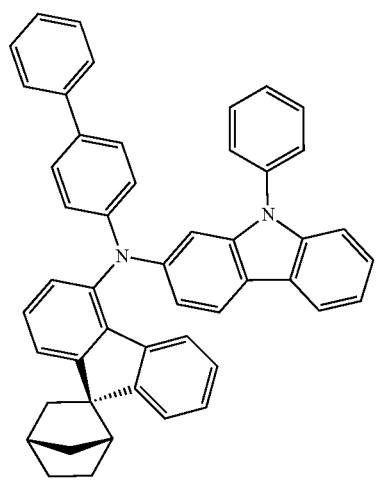
198
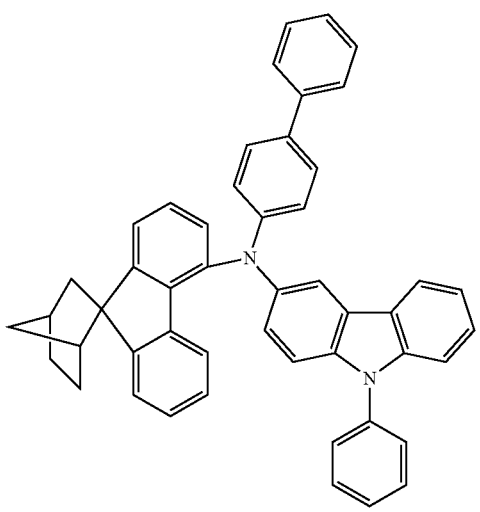
199
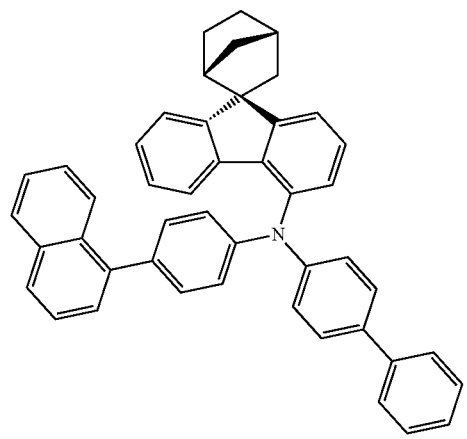
200
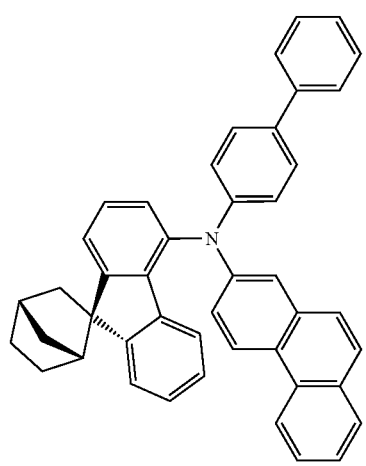
201
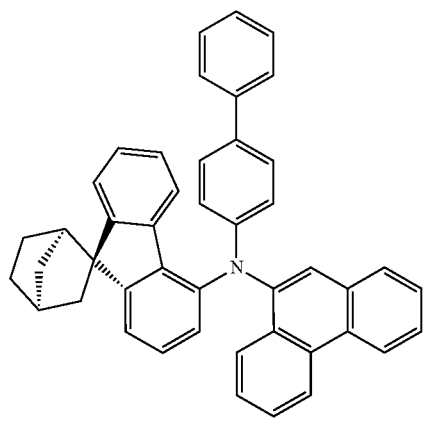

281
-continued
282
-continued
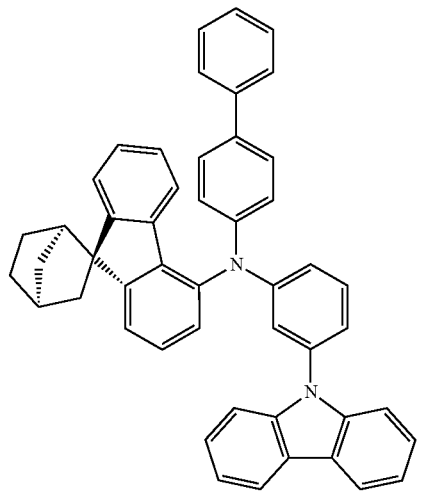
202
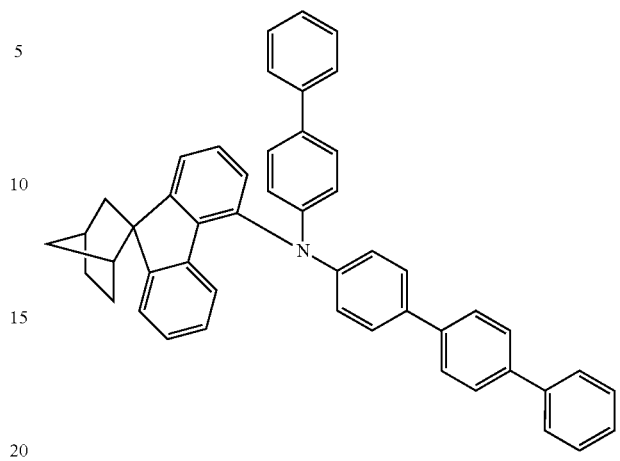
206
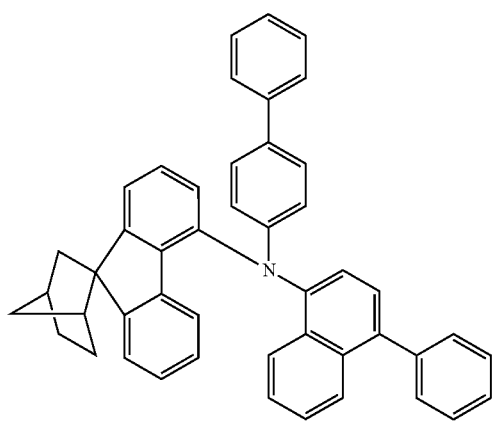
203
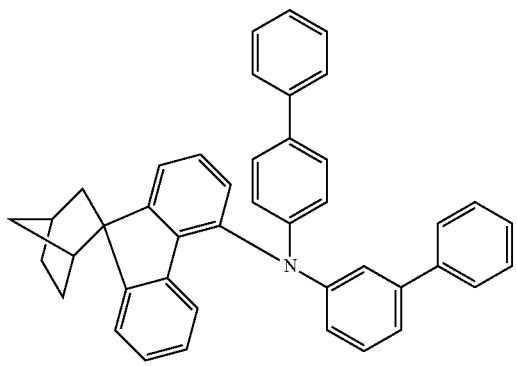
207
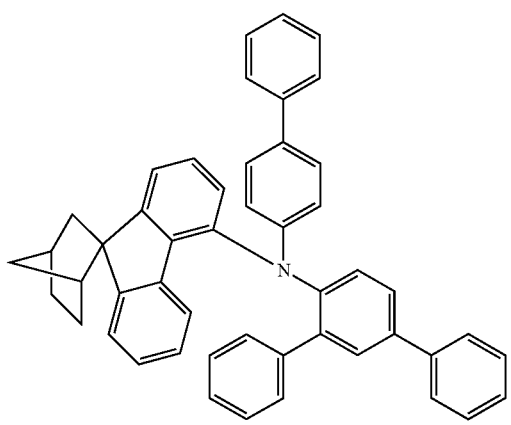
205
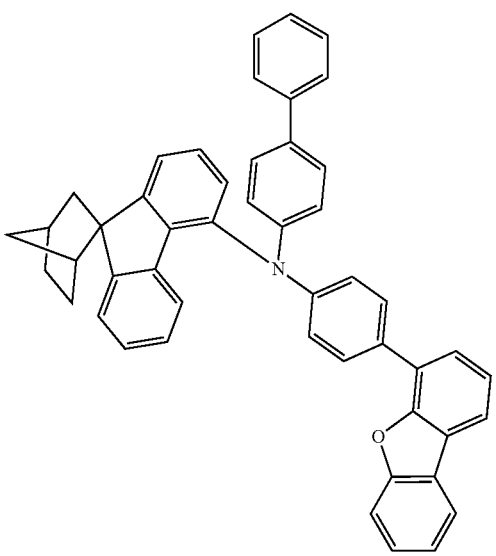
204

208
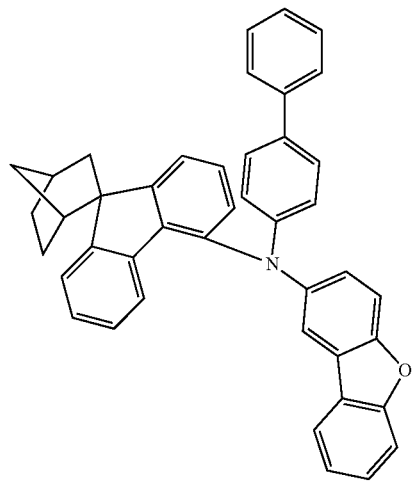
209
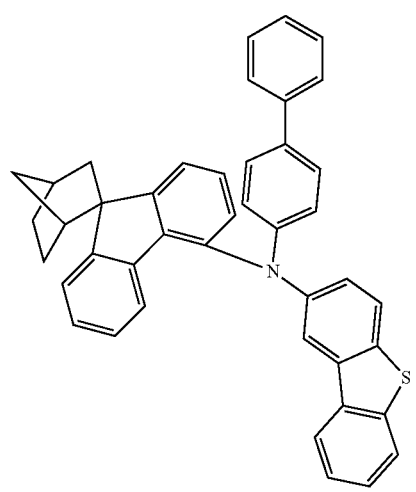
210
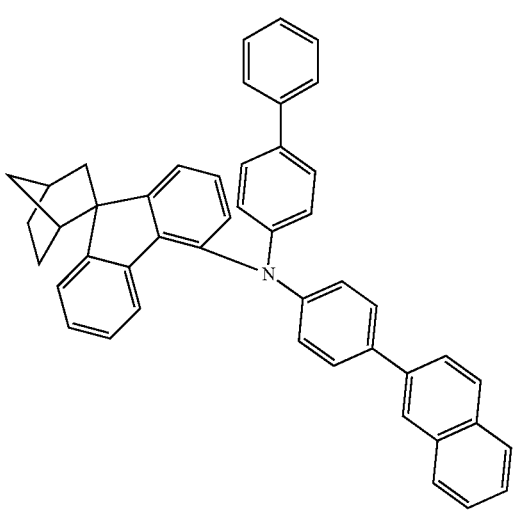
211
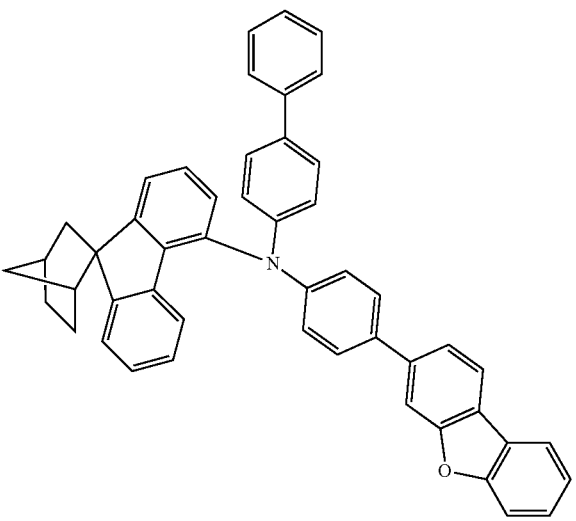
212
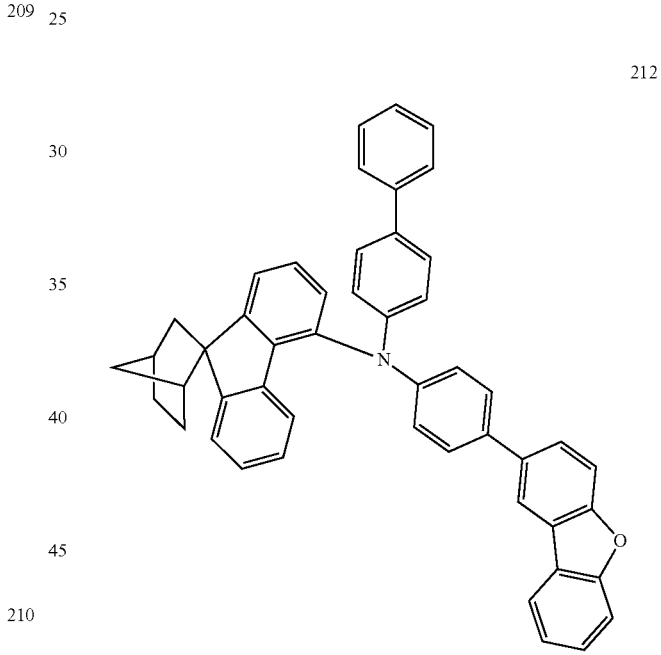
213
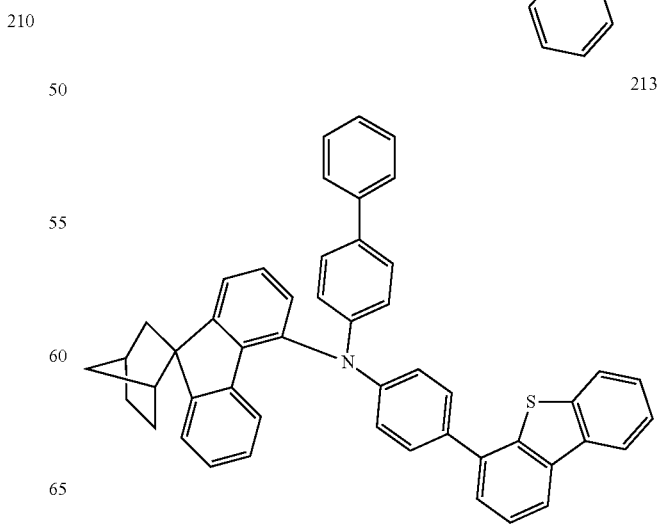

285 286
-continued -continued
214
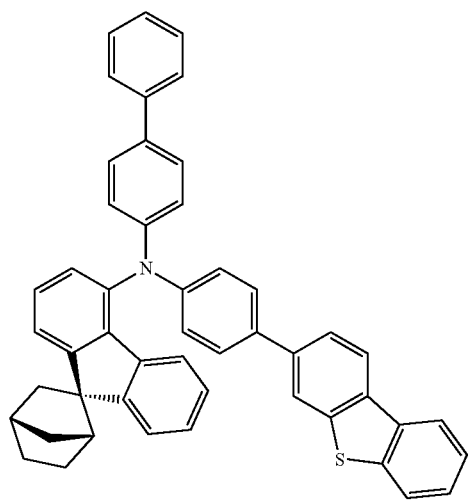
215
217
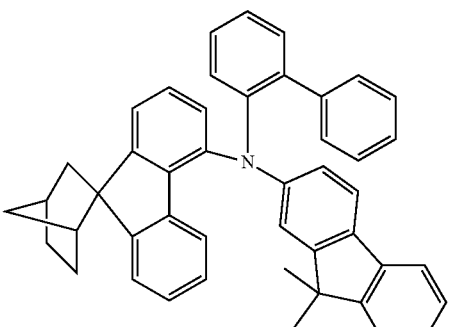
218
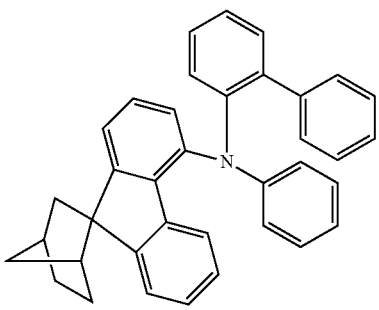
219
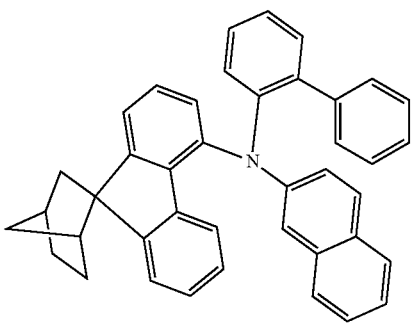
216
220
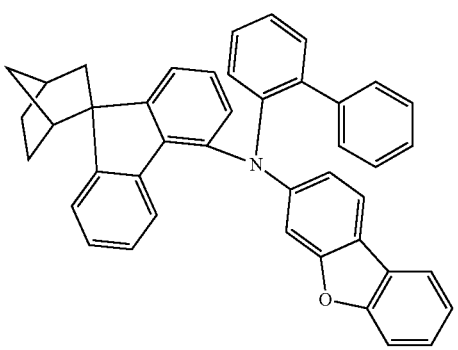

287
-continued
221
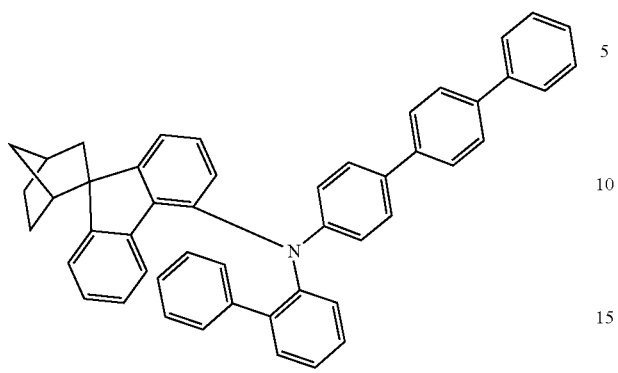
222
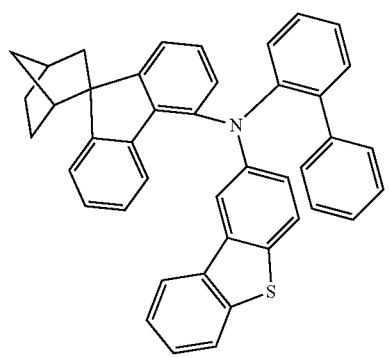
223
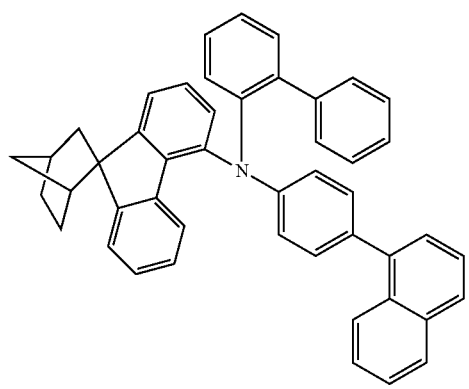
224
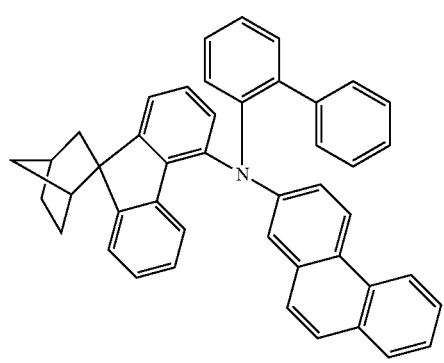
288
-continued
225
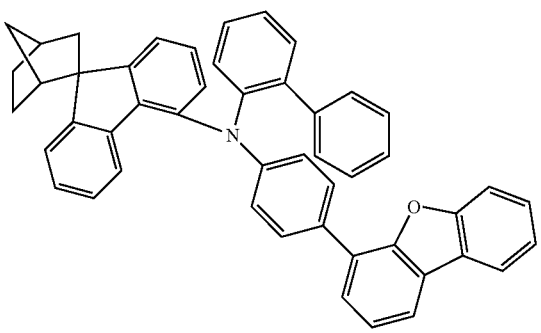
226
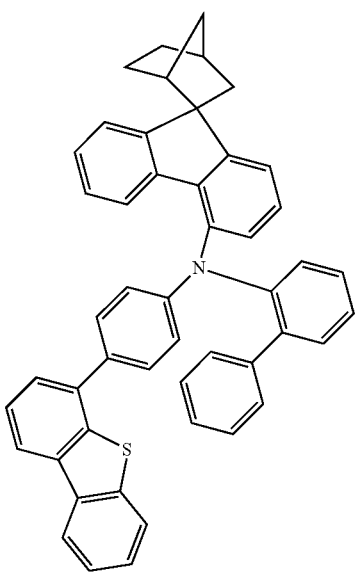
227
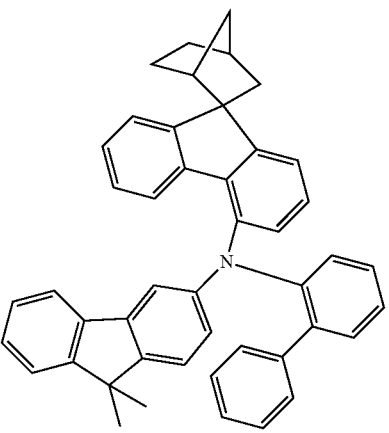

228
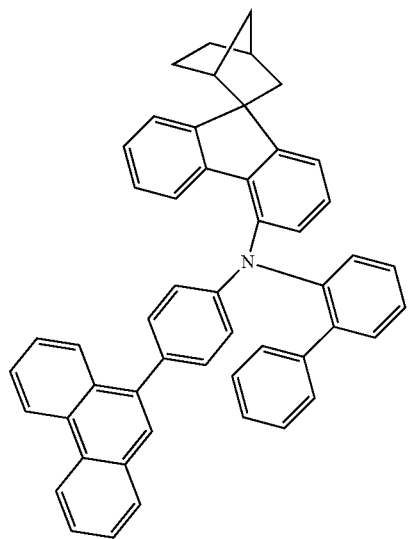
229
231
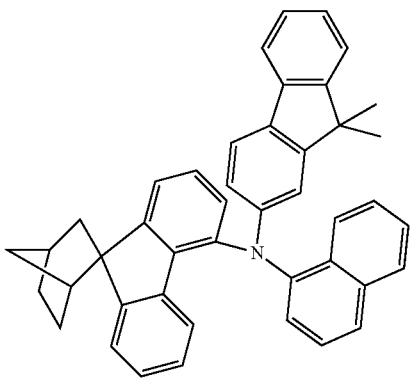
232
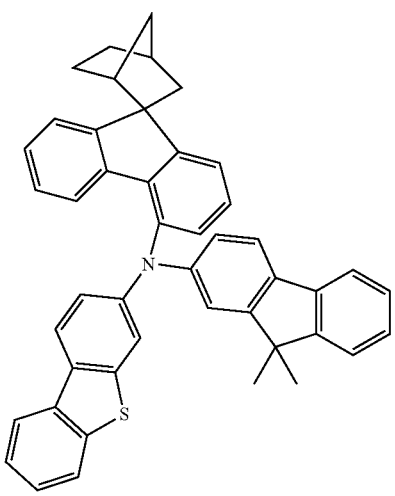
230
233
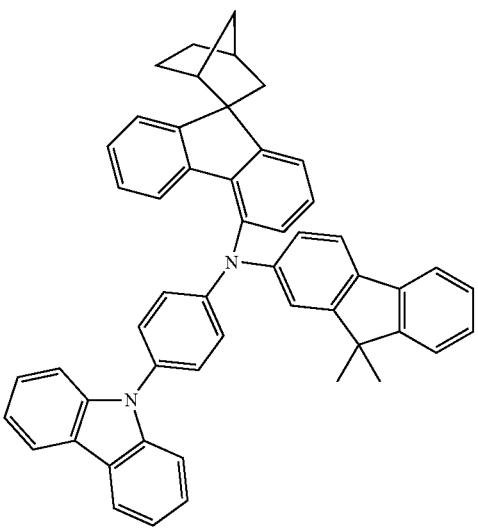

234
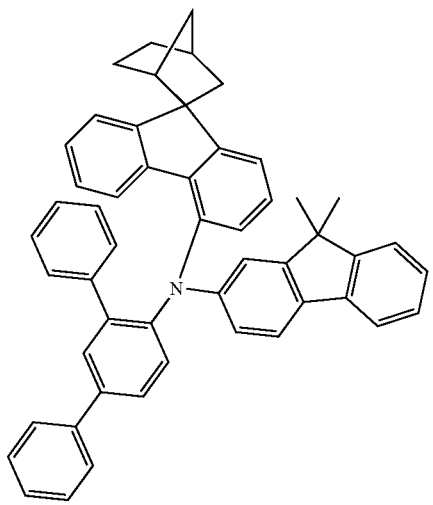
235
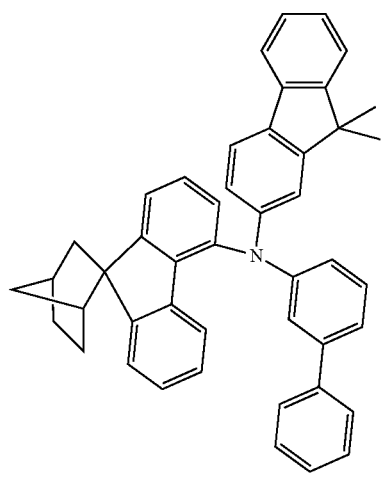
236
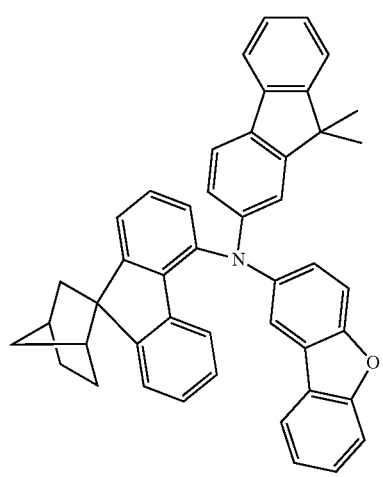
237
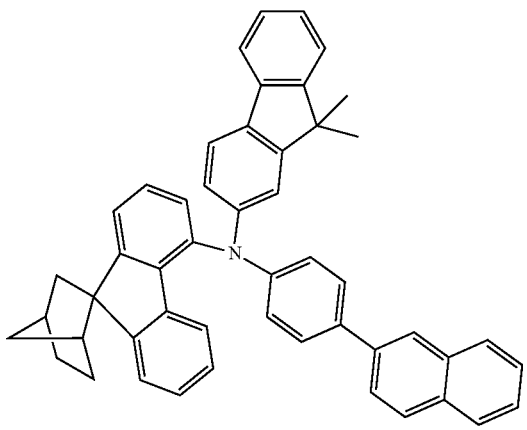
238
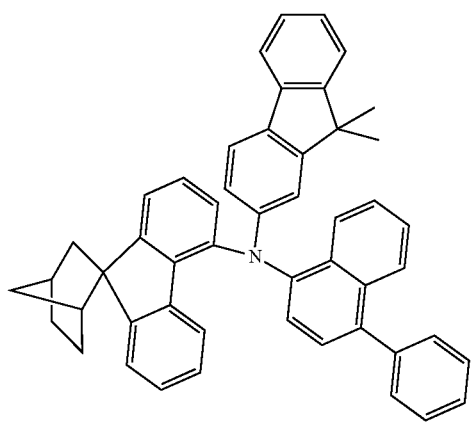
239
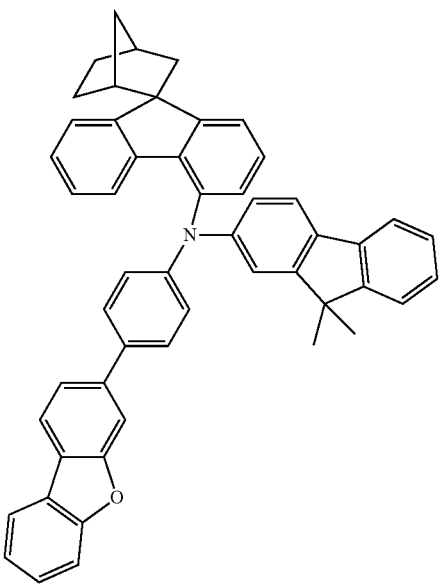

| 240 | 243 |
|---|---|
| 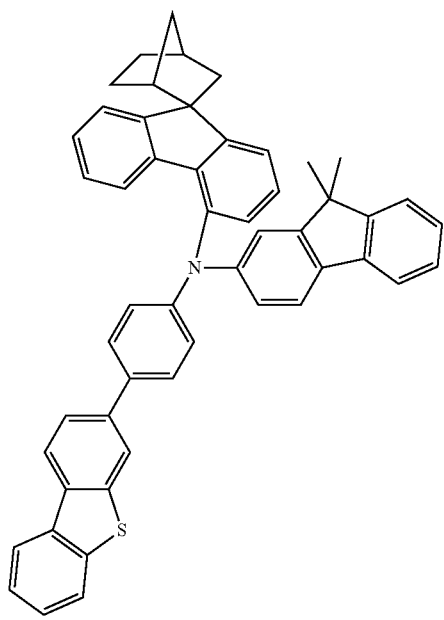 | 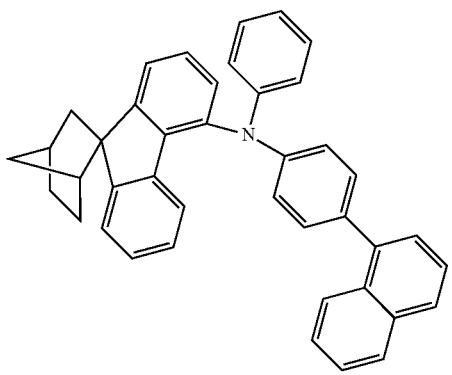 |
| 241 | 244 |
| 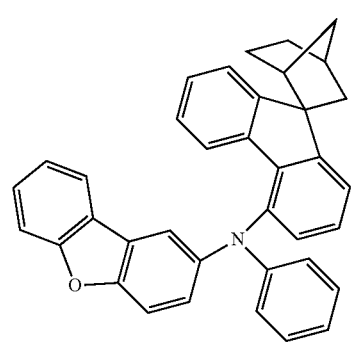 | 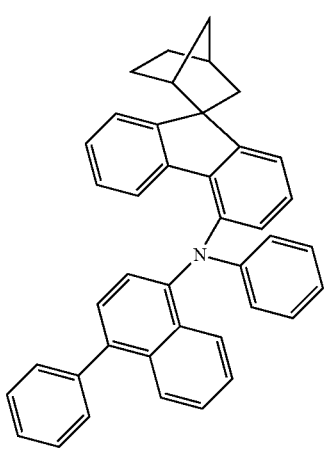 |
| 242 | 245 |
| 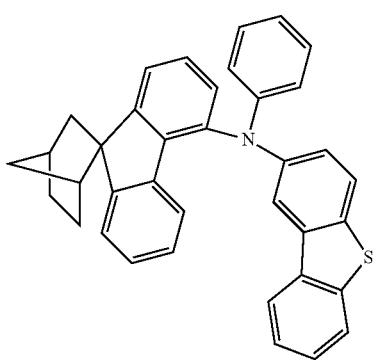 | 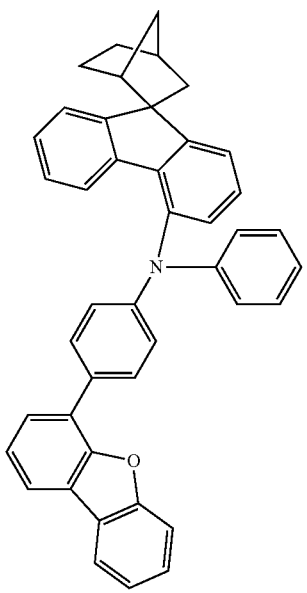 |

-continued
246
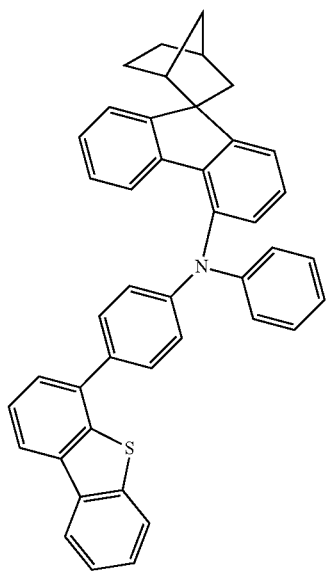
247
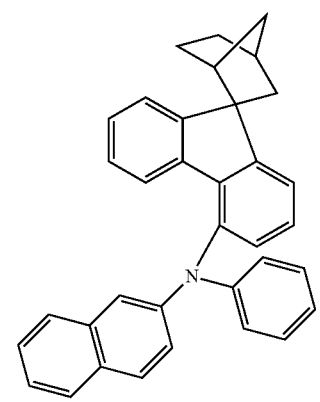
248
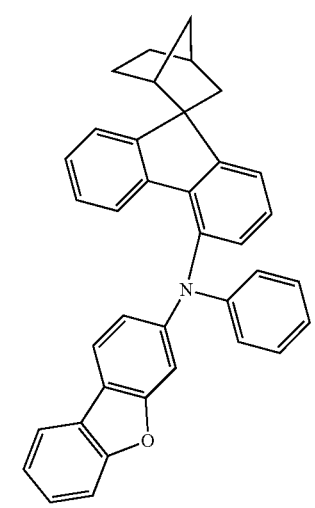
-continued
249
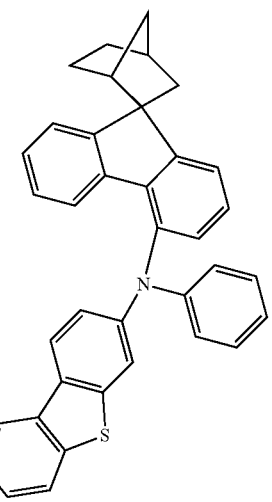
250
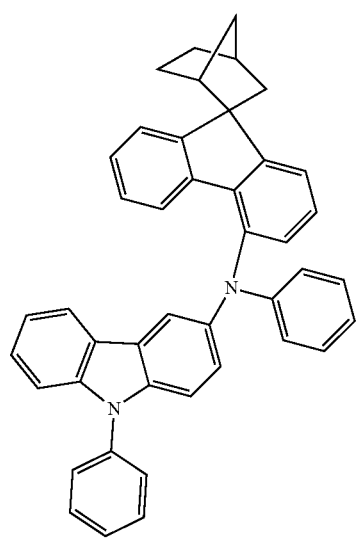
251
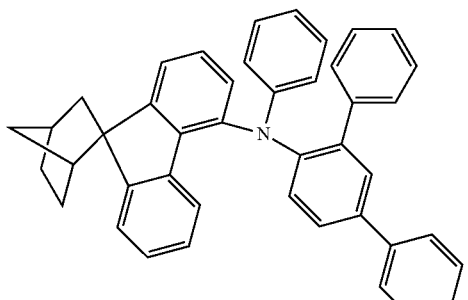
252
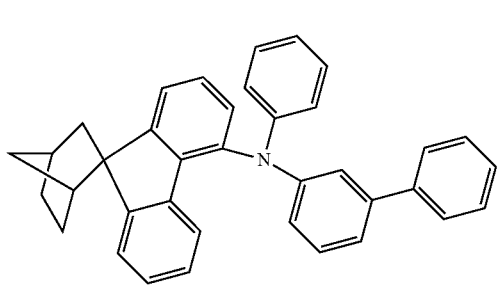

253
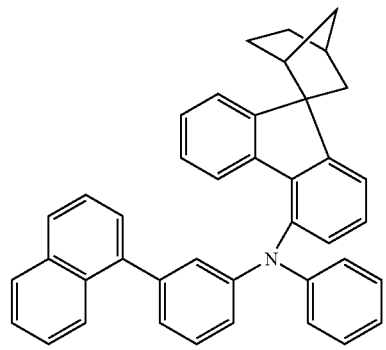
254
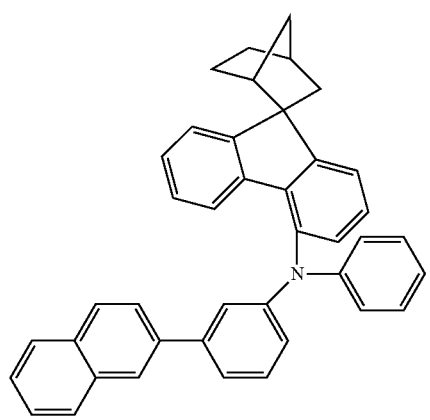
255
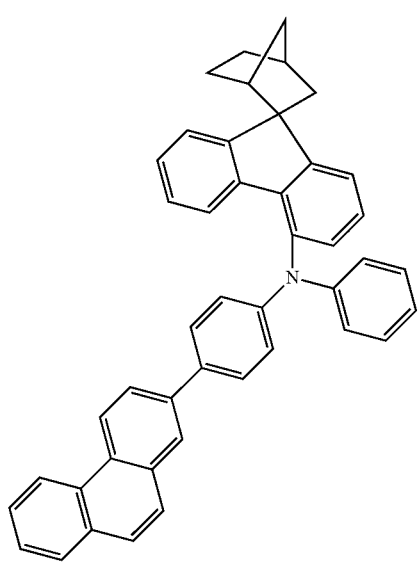
256
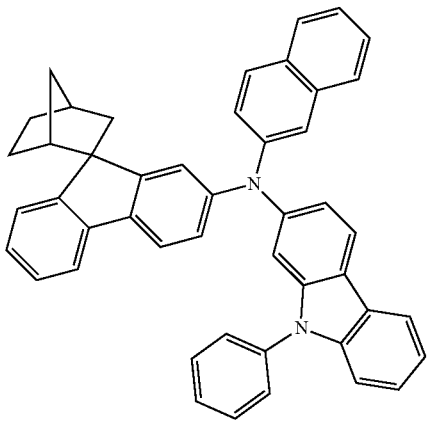
257
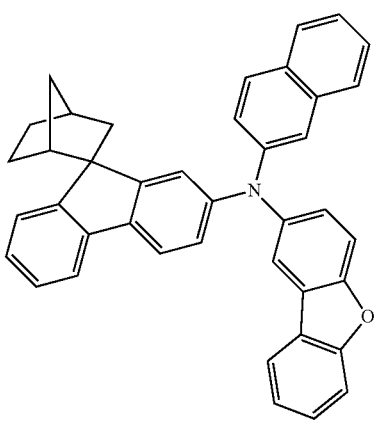
258
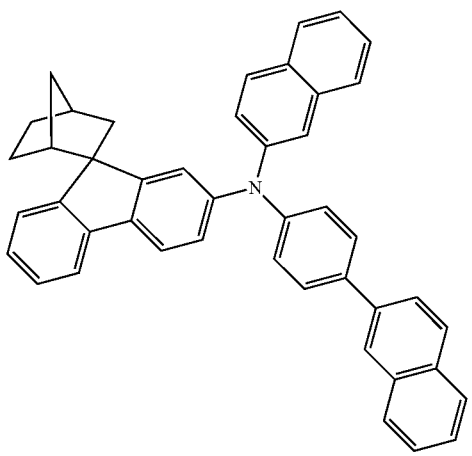

259 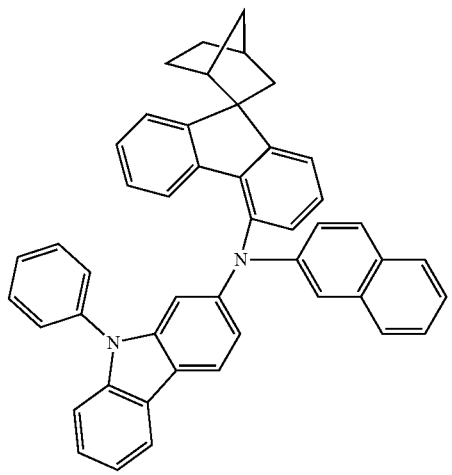
260 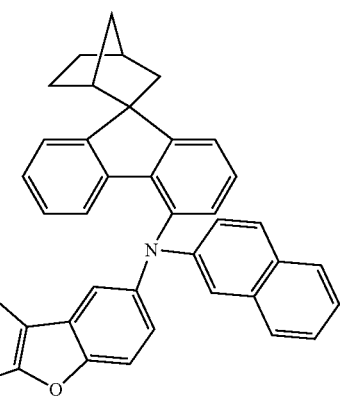
261 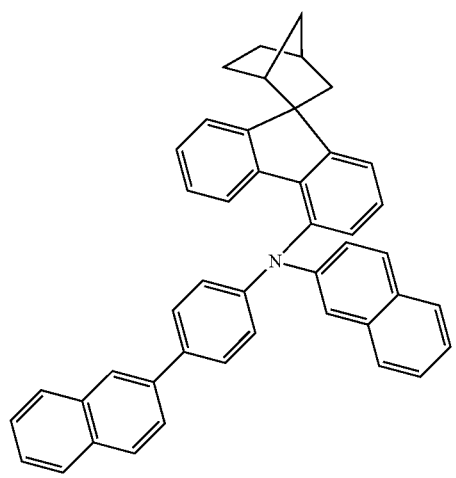
262 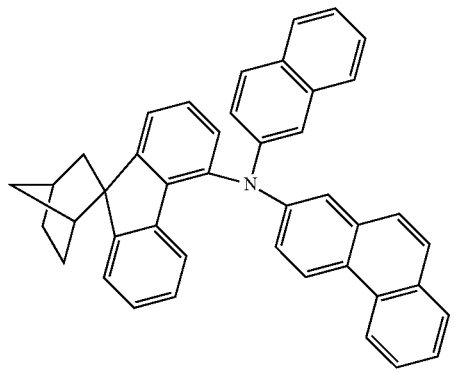
263 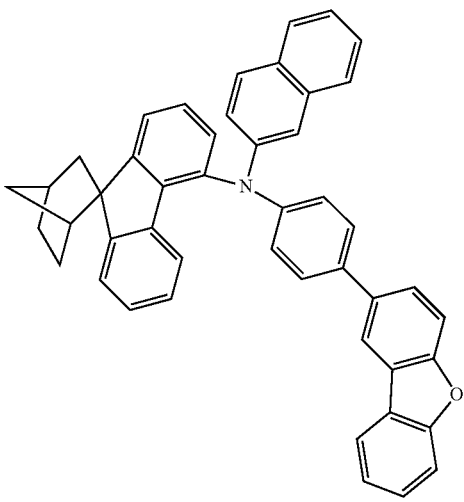
264 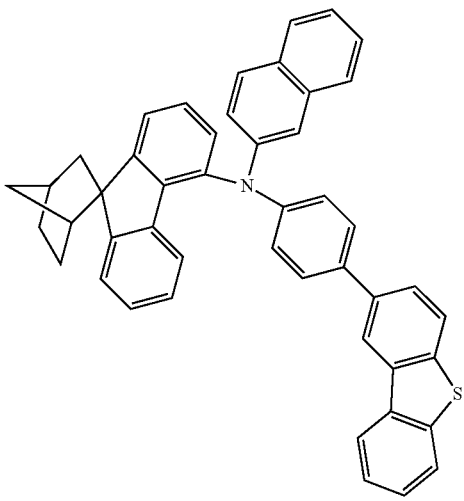

301
-continued
265
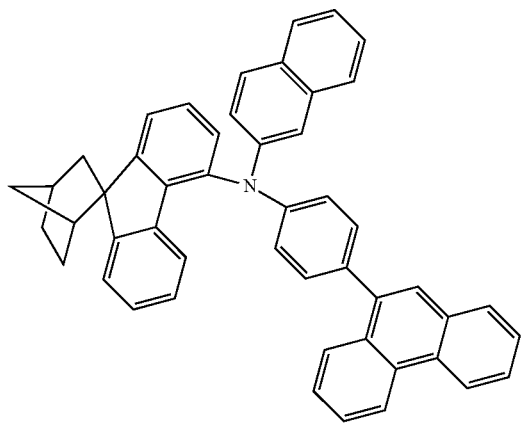
266
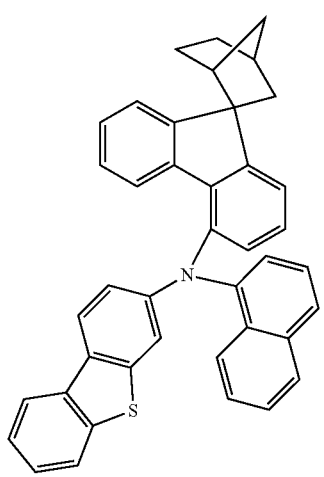
267
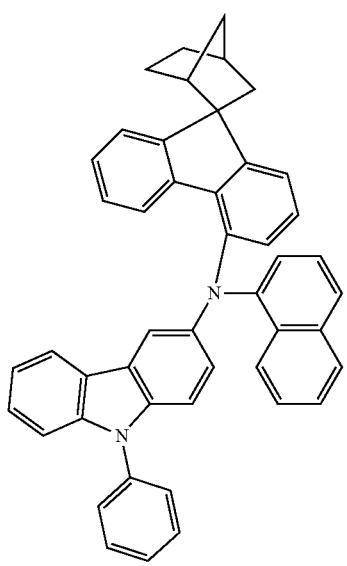
302
-continued
268
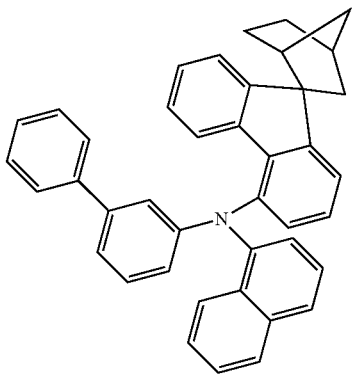
269
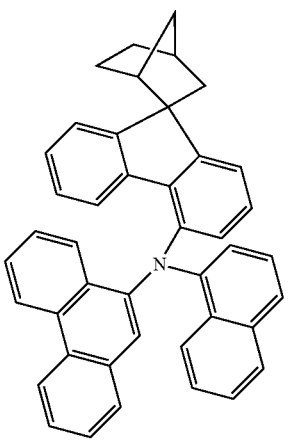
270
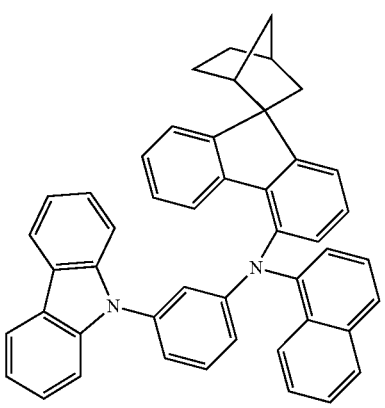

303
-continued
271
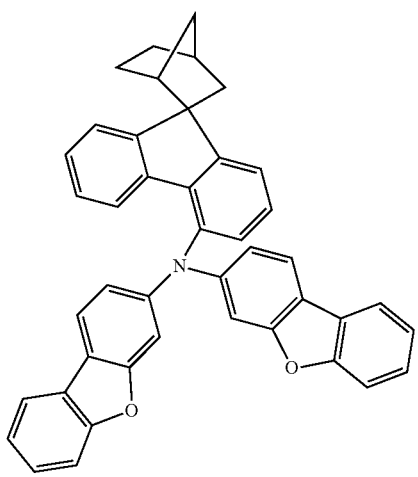
272
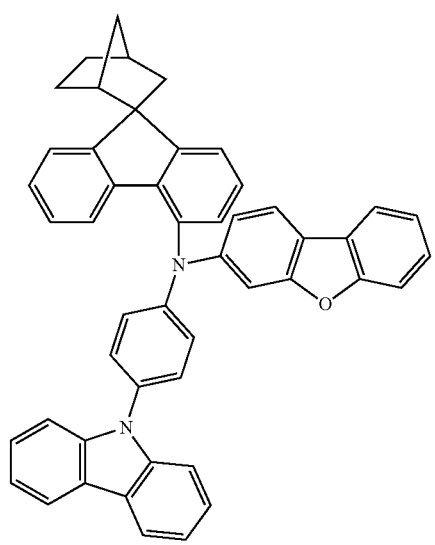
273
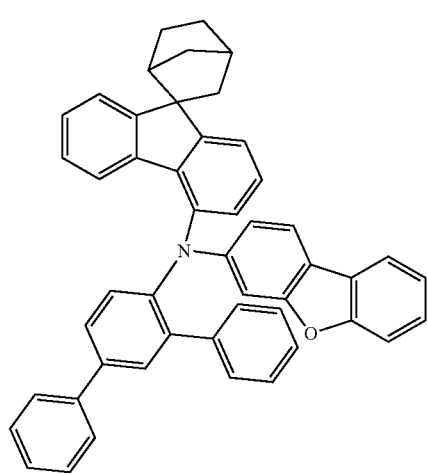
304
-continued
274
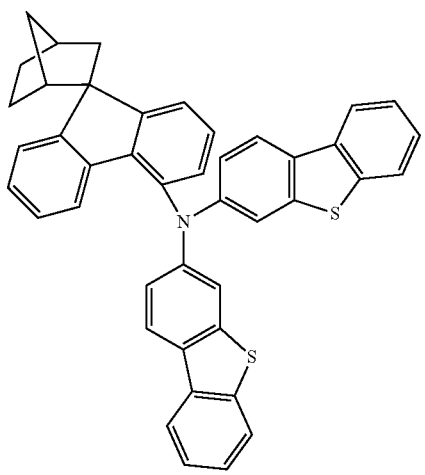
275
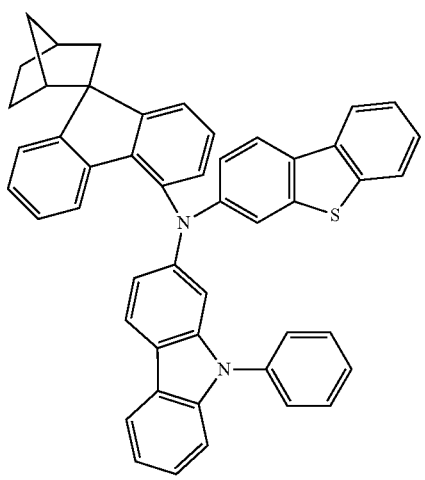
277
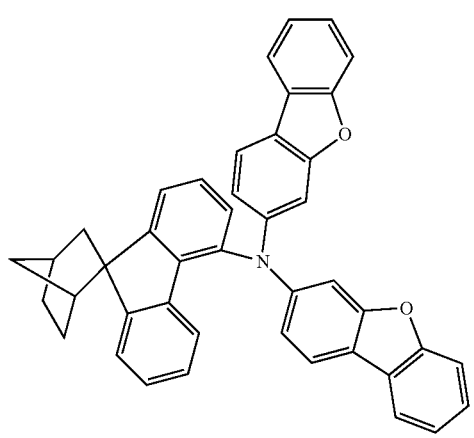

278
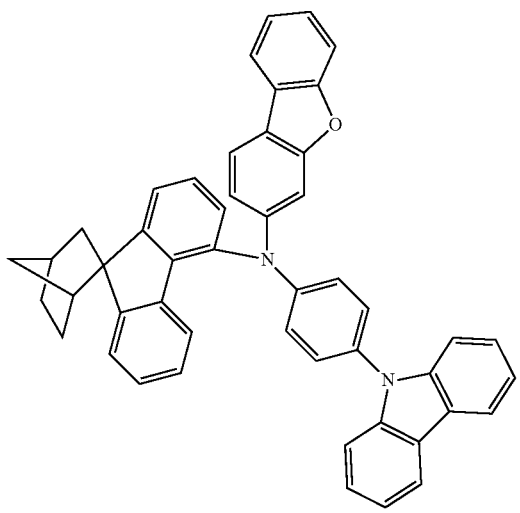
279
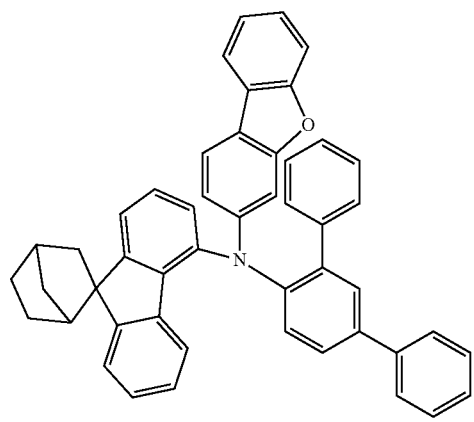
276
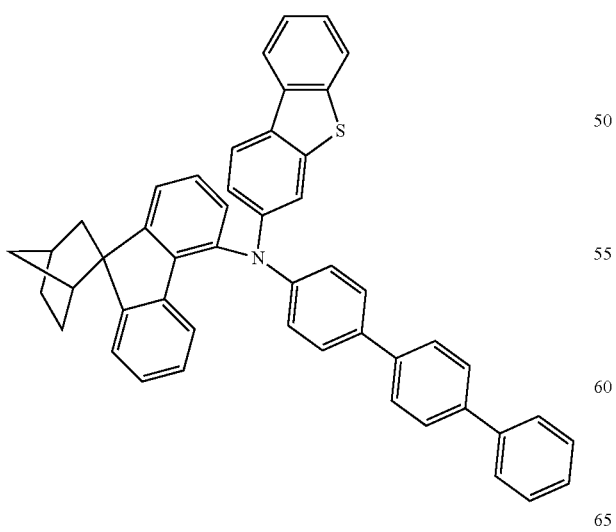
280
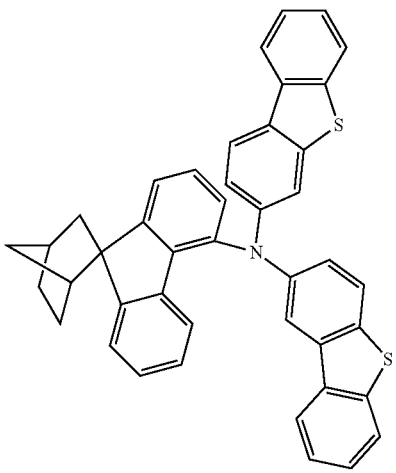
281
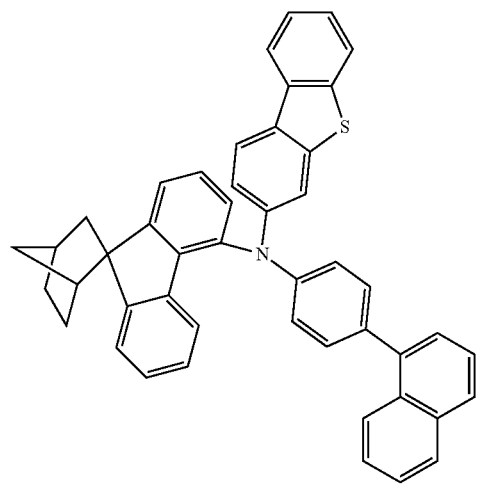
282
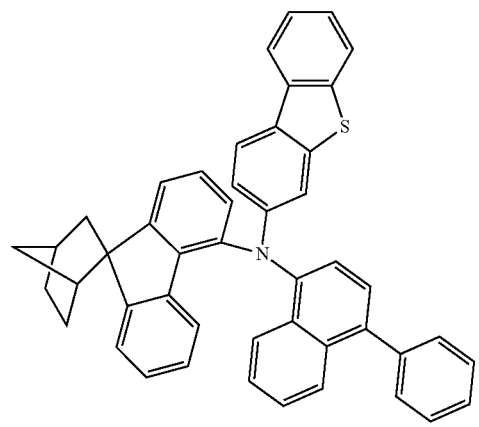

283
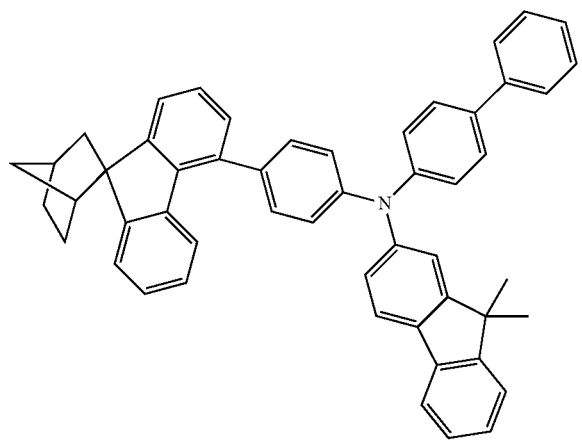
284
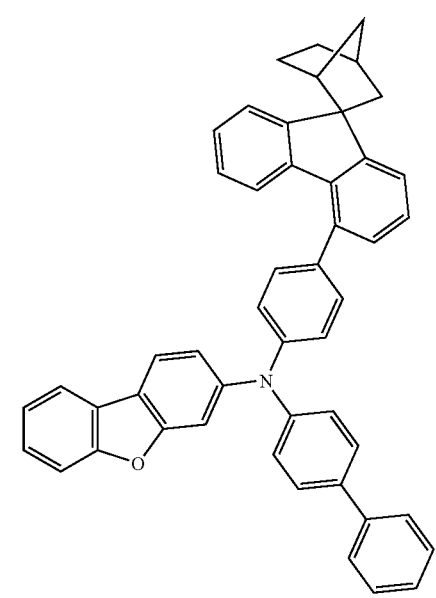
285
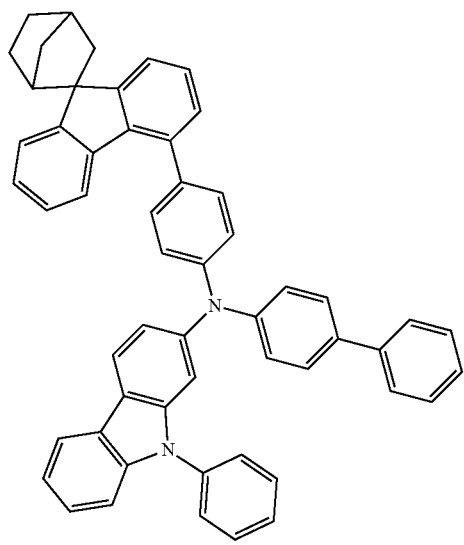
286
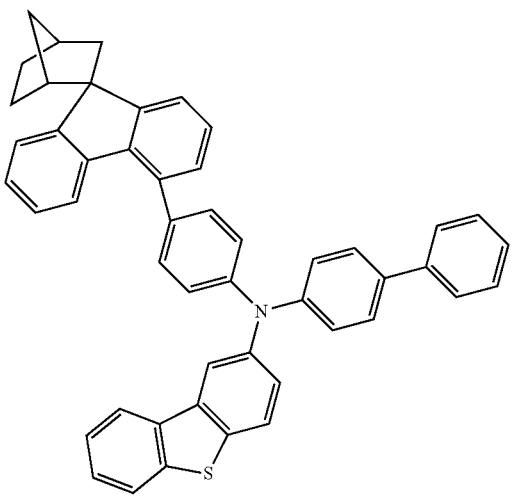
287
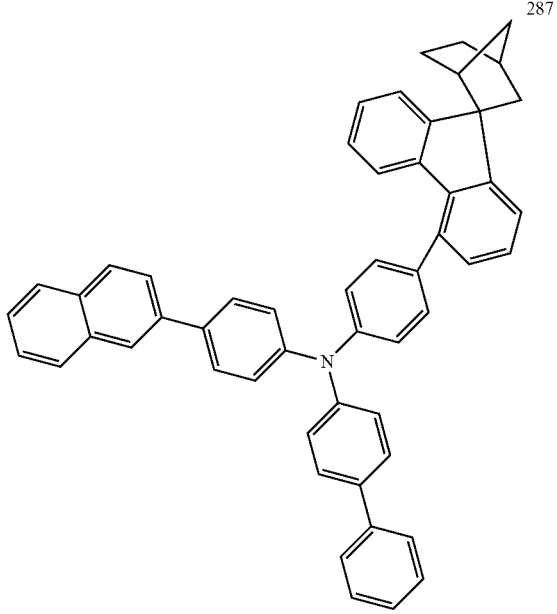

309 -continued | 310 -continued
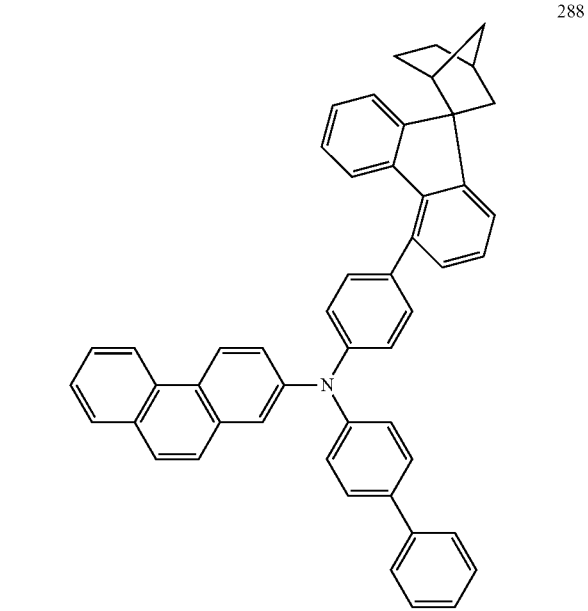
288
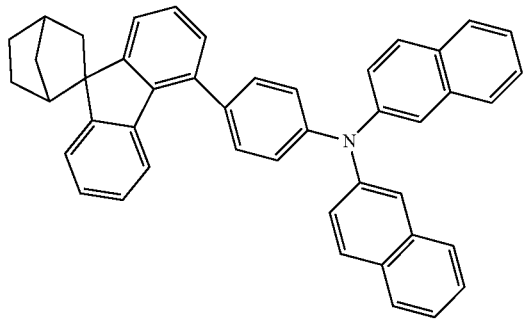
291
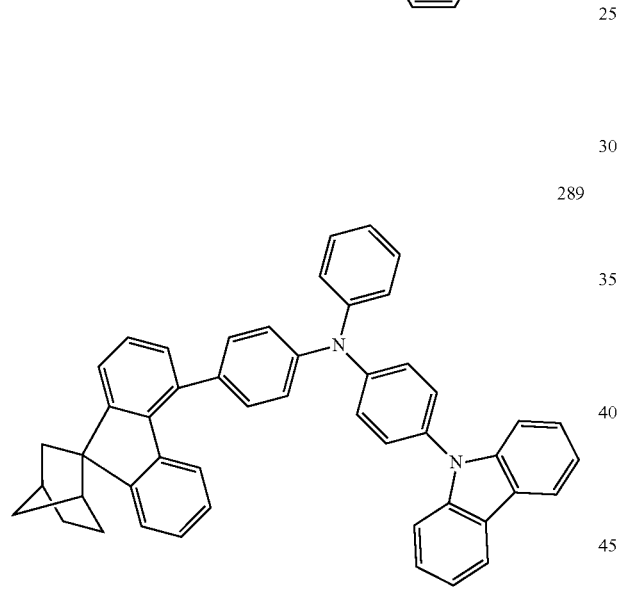
289
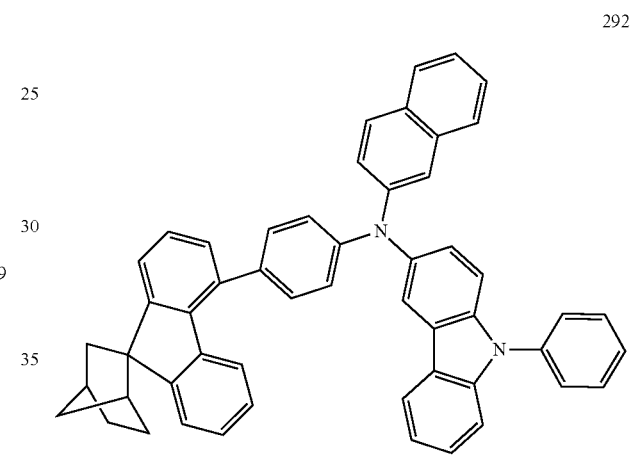
292
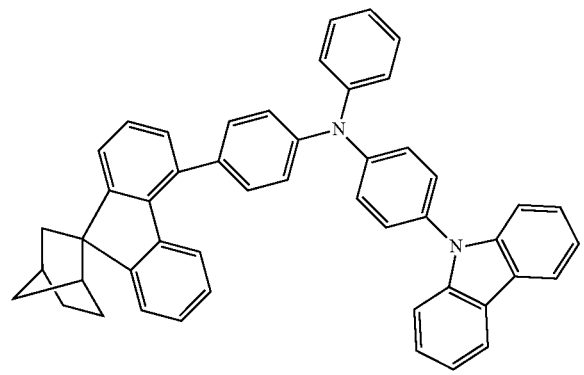
290
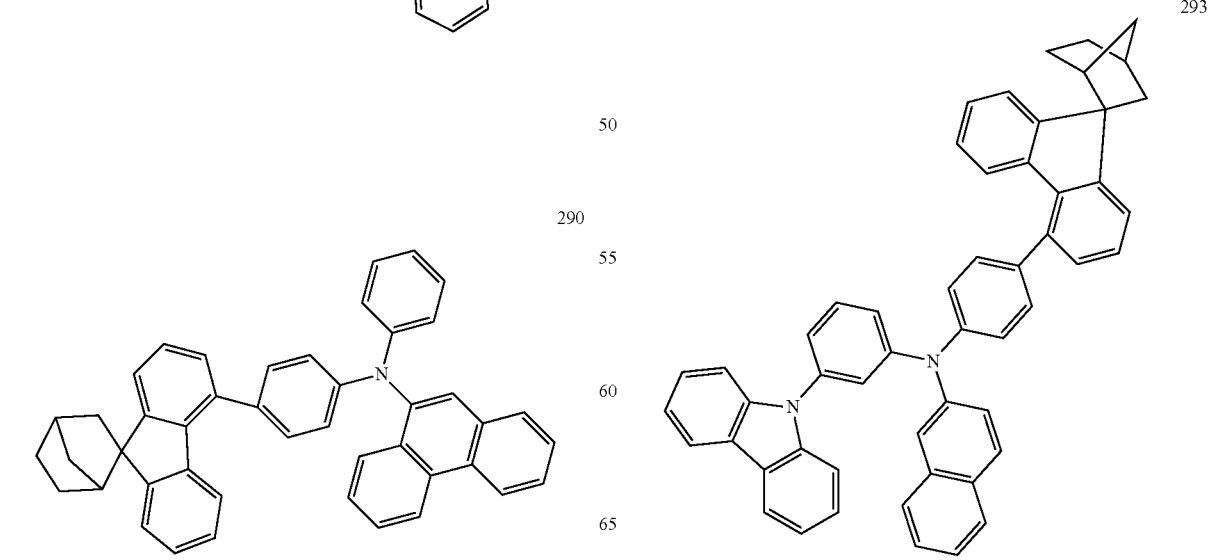
293

311
-continued
294
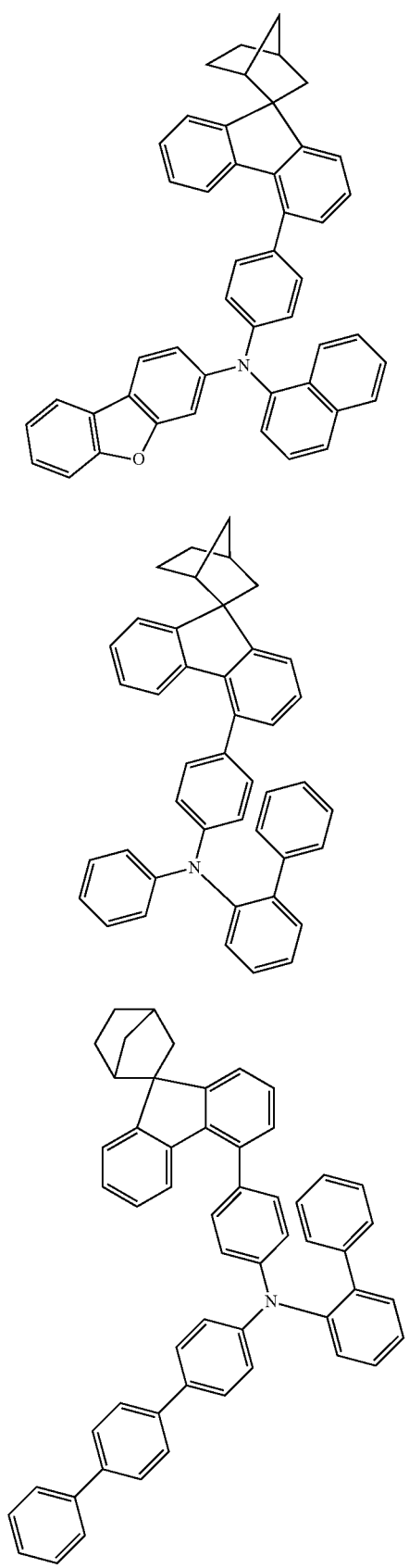
295
296
312
-continued
297
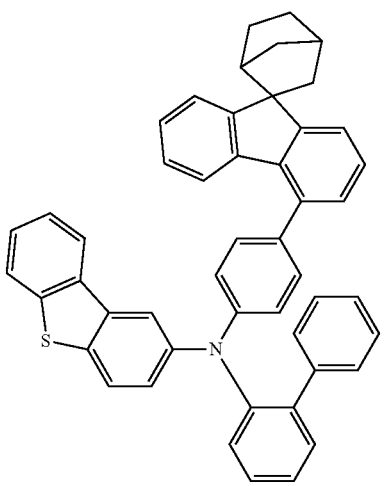
298
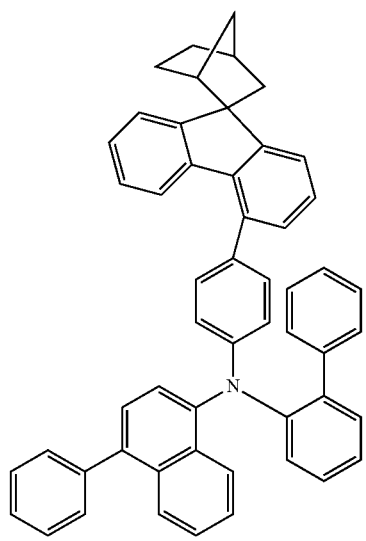
299
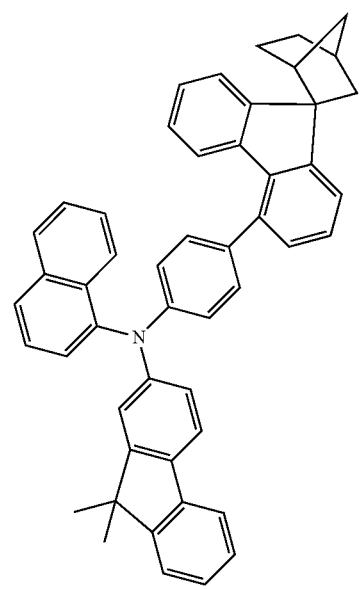

313
-continued
314
-continued
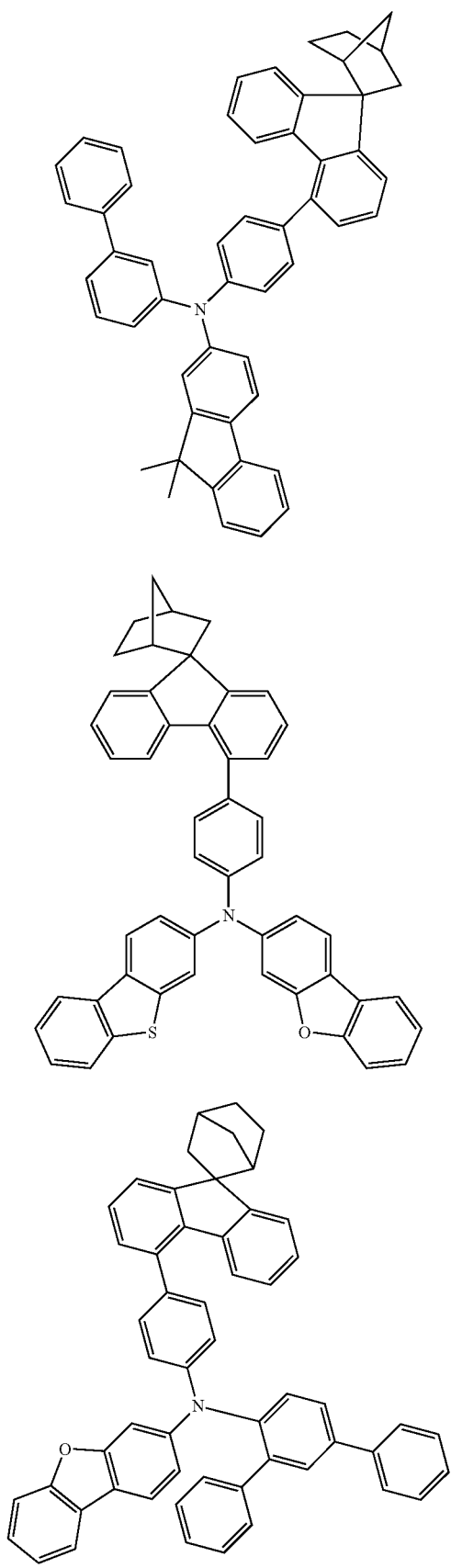
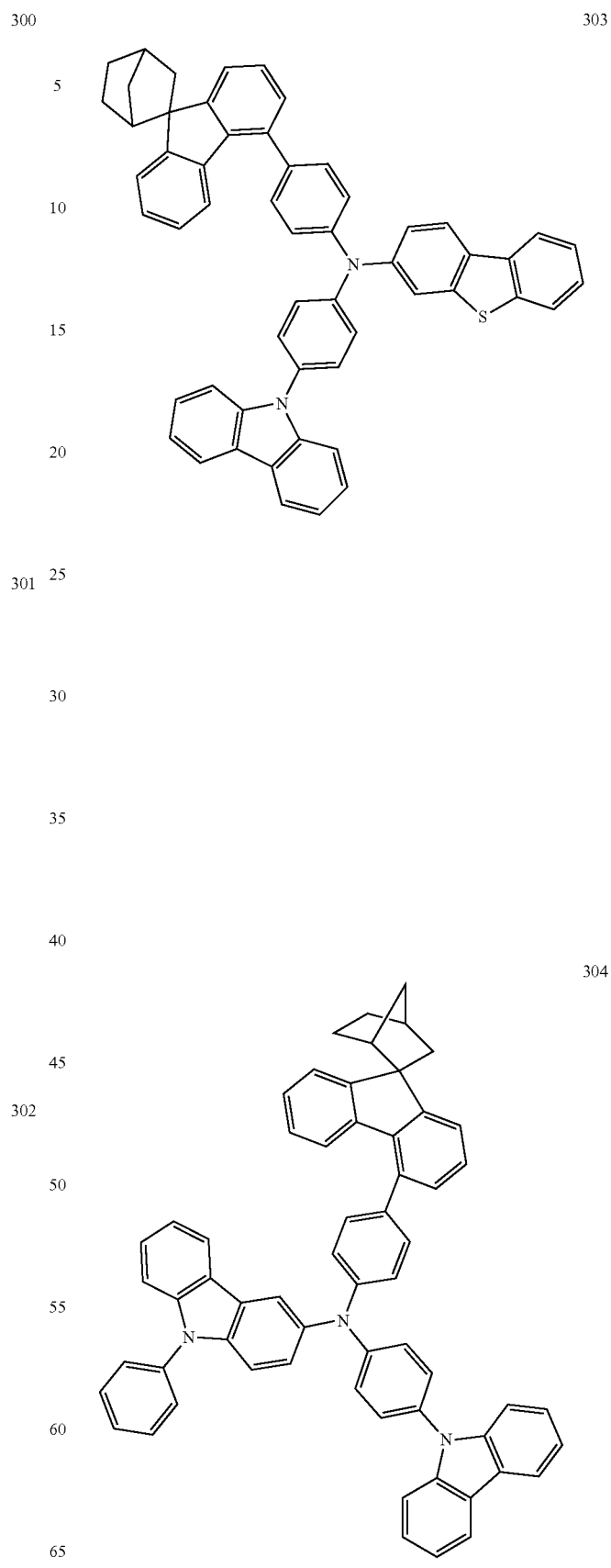

315
-continued
305
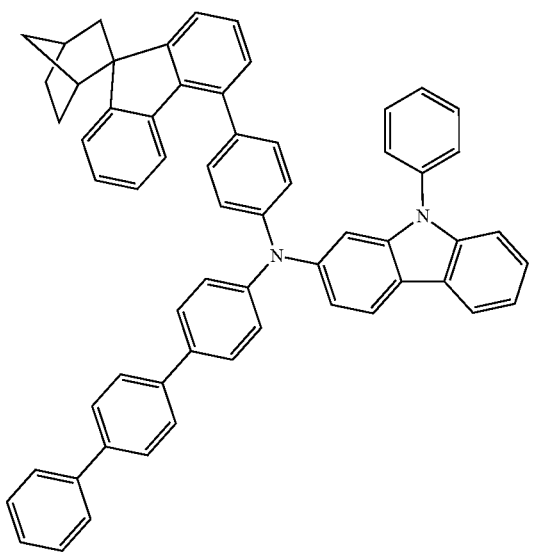
306
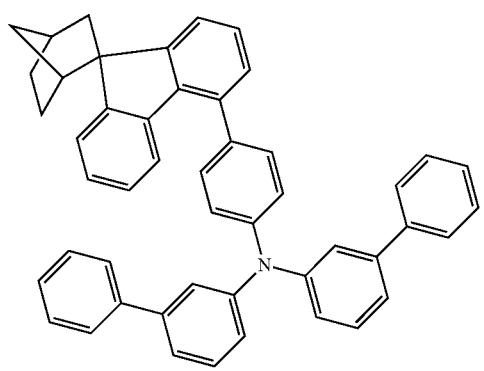
307
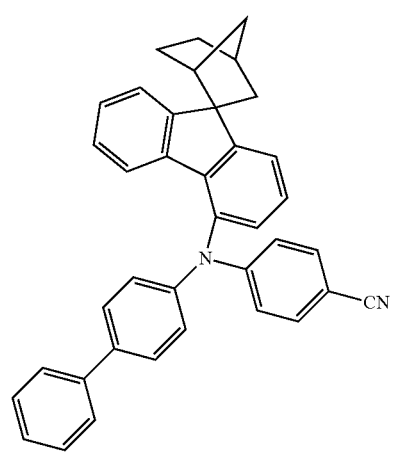
316
-continued
308
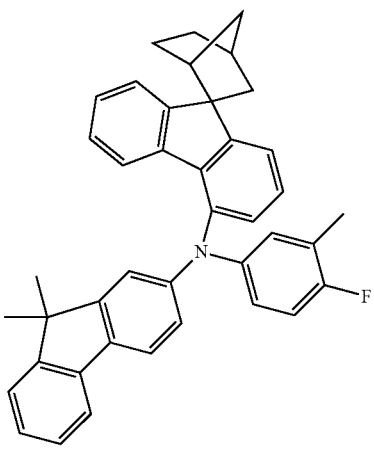
309
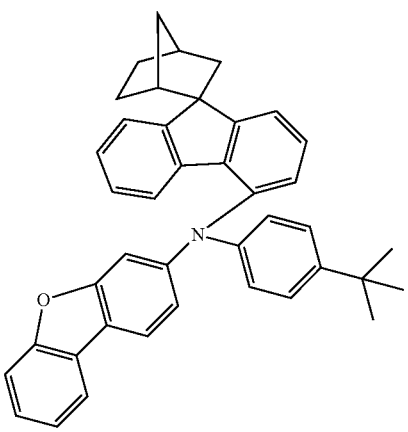
310
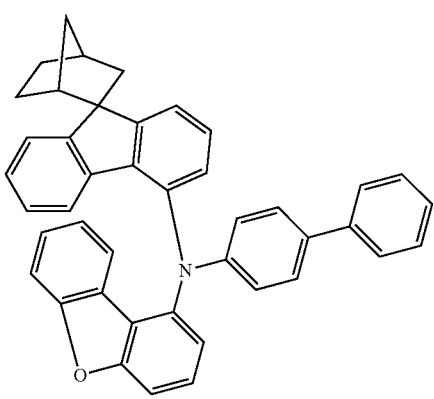

-continued
311
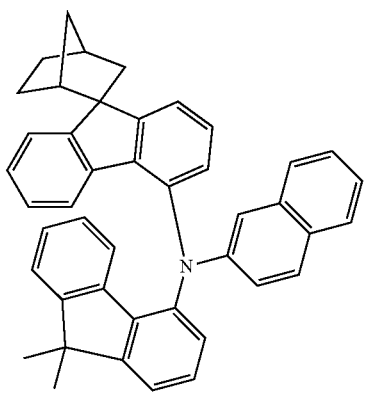
312
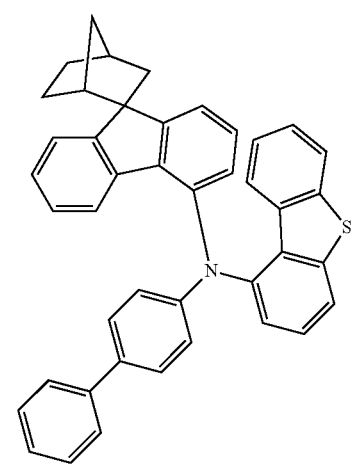
313
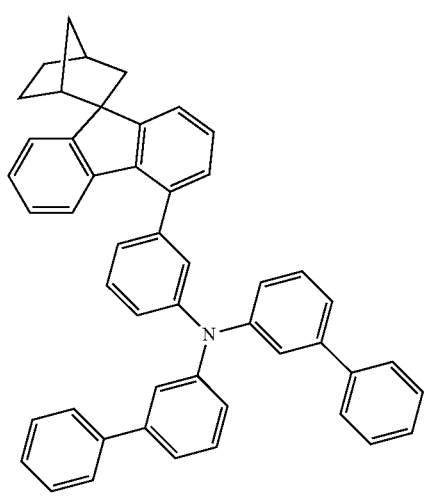
-continued
314
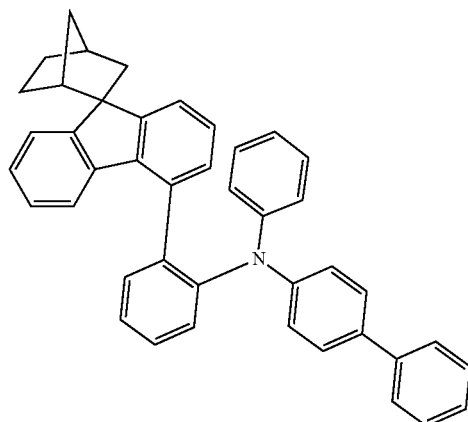
315
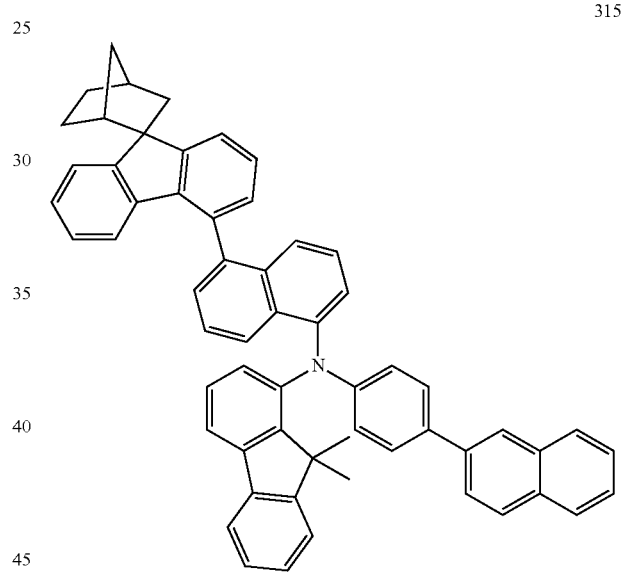
316
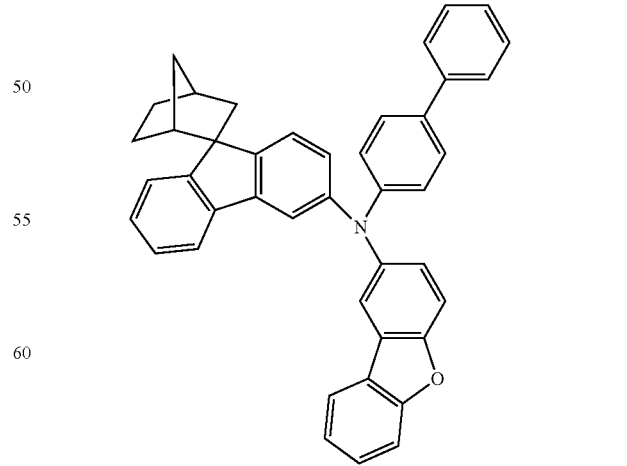

317
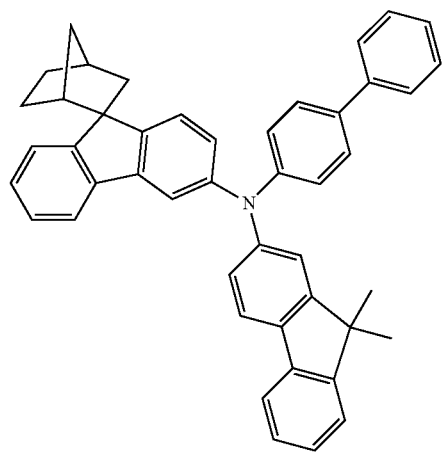
320
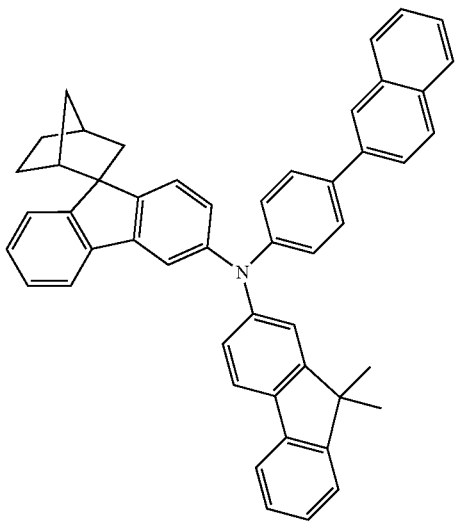
318
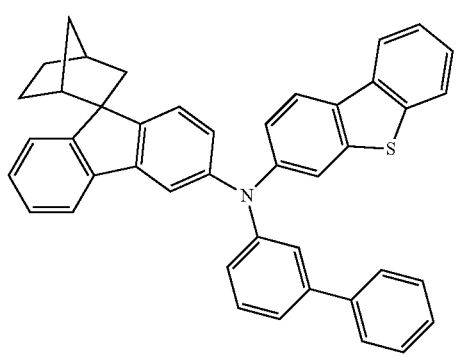
321
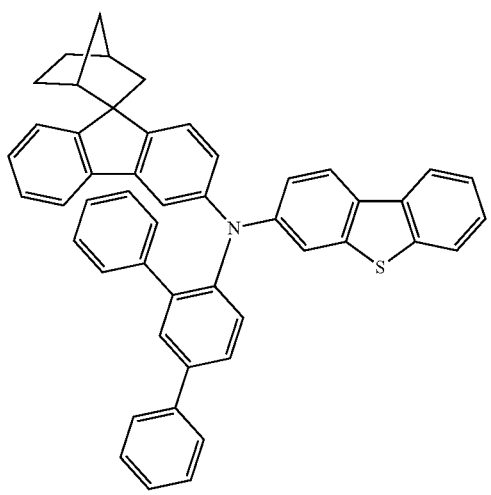
319
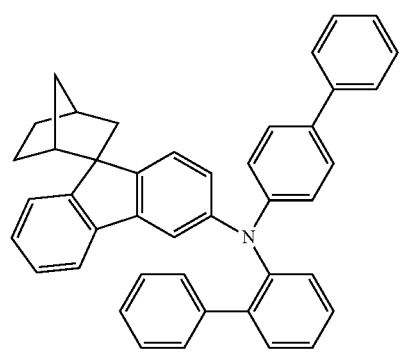
322
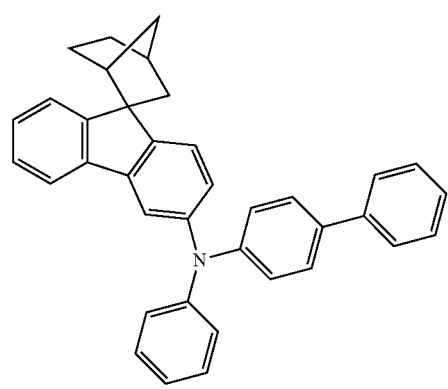

321
-continued
323
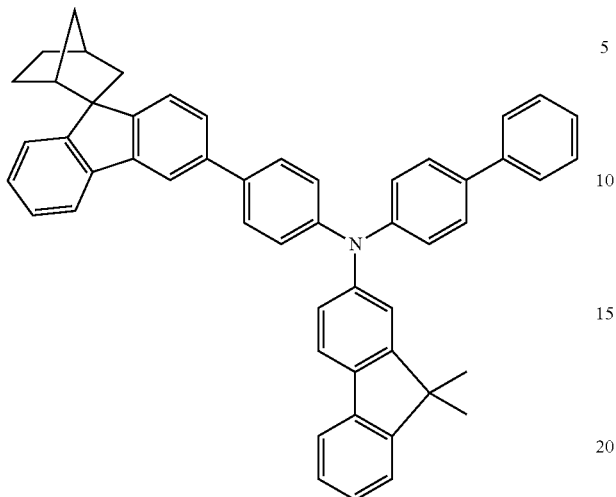
324
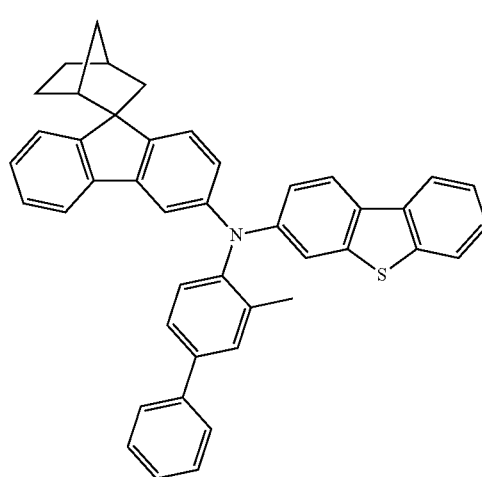
325
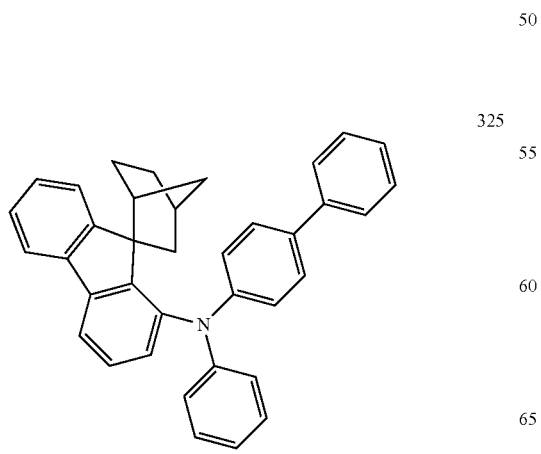
322
-continued
326
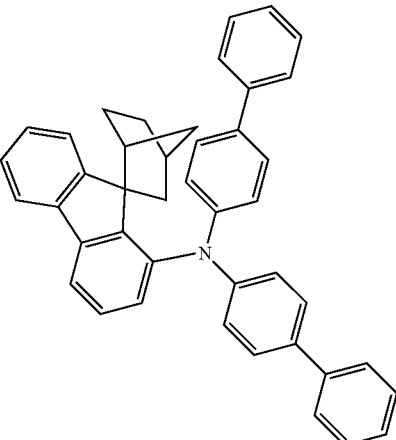
327
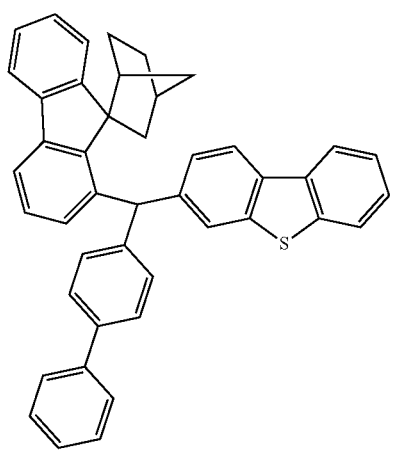
328
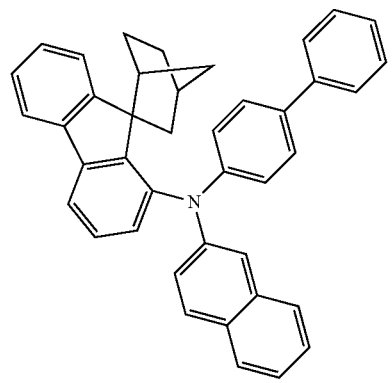

329
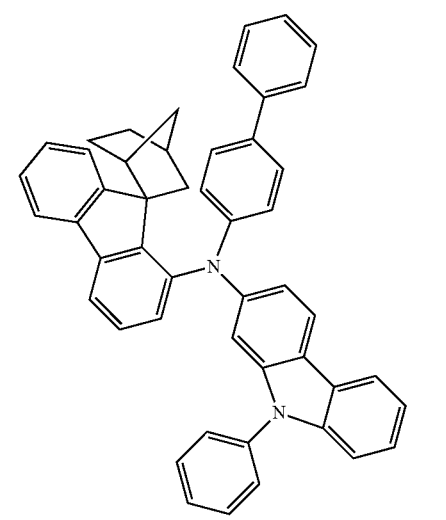
330
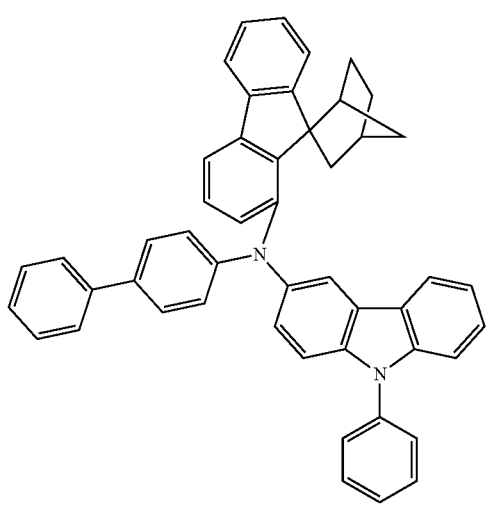
331
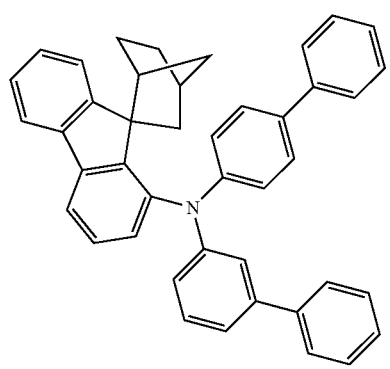
332
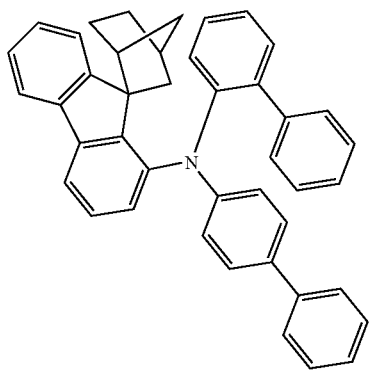
333
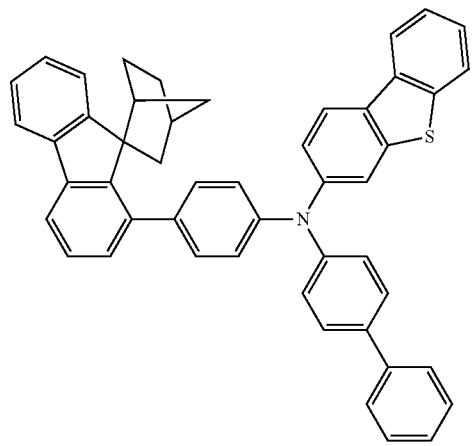
334
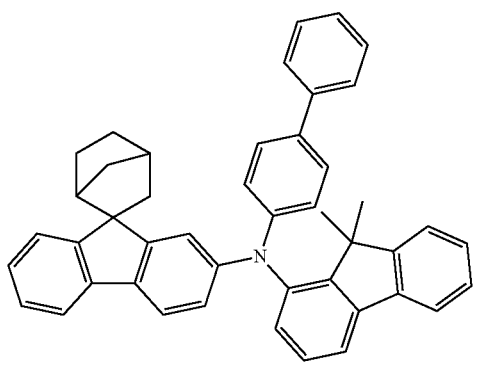
335
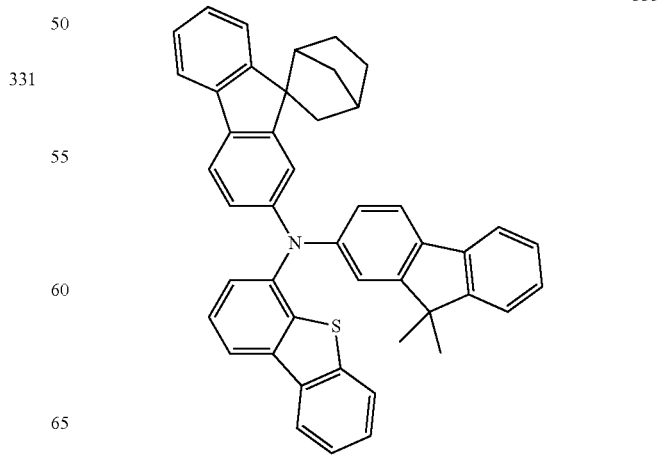

325
-continued
326
-continued
| 336 | 339 |
|---|---|
| 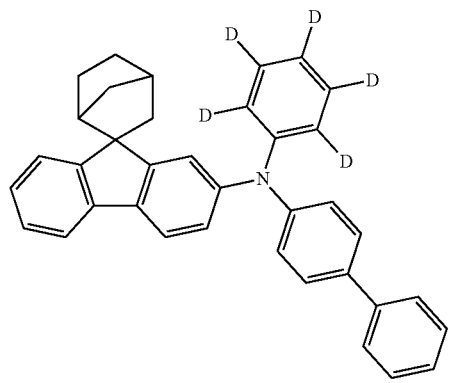 | 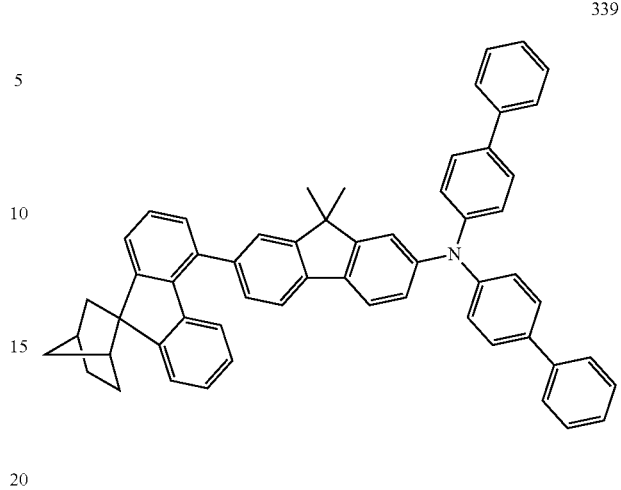 |
| 337 | 340 |
|---|---|
| 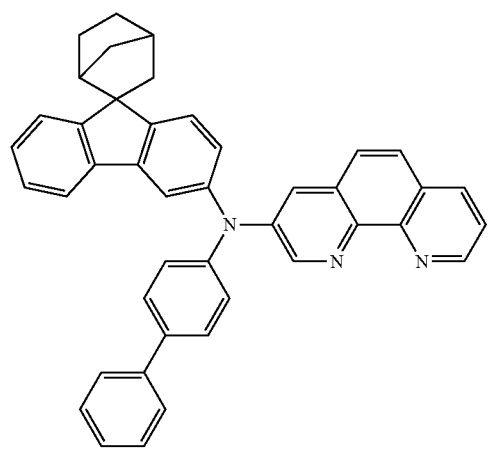 | 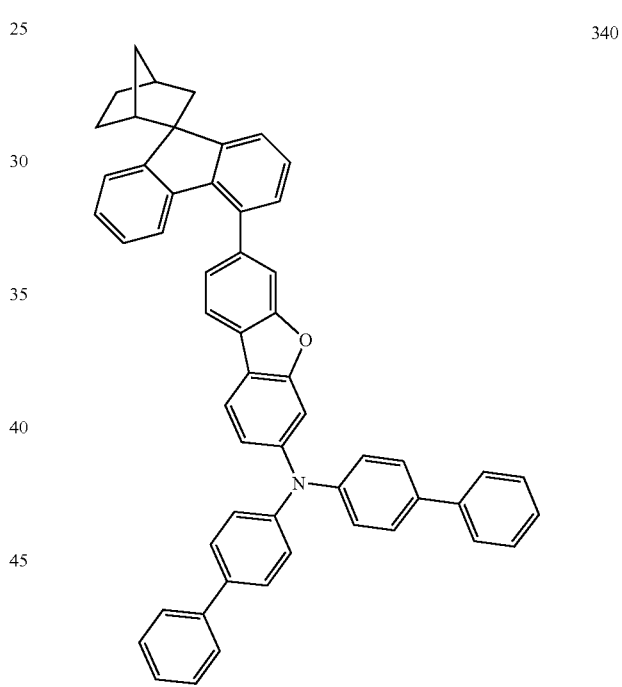 |
| 338 | 341 |
|---|---|
| 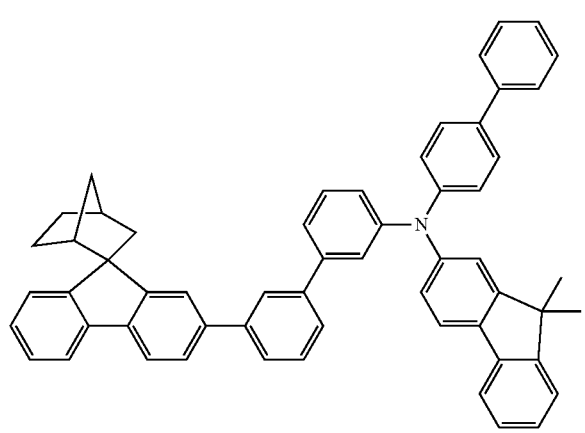 | 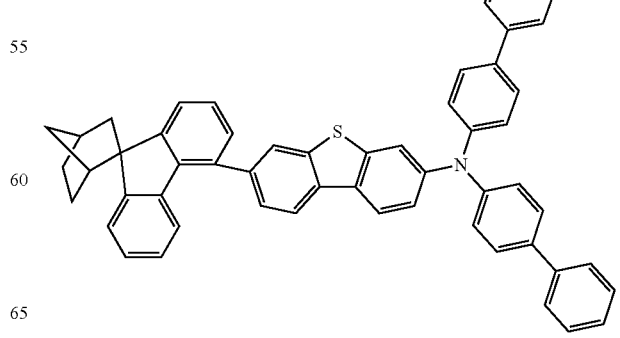 |

327
328
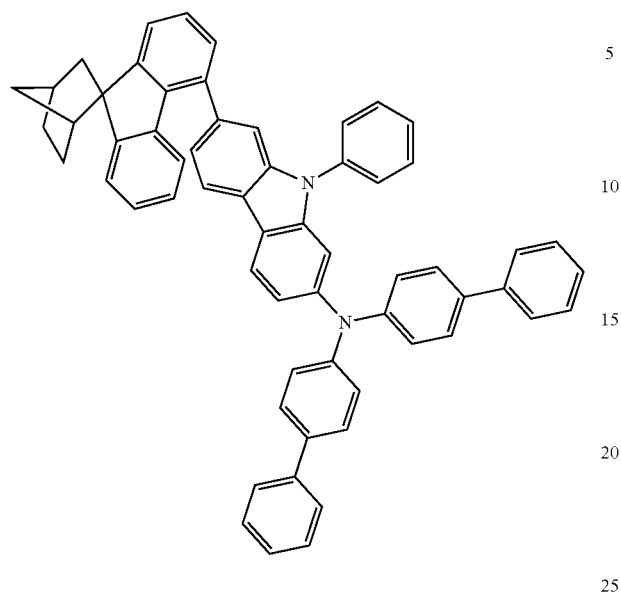
342
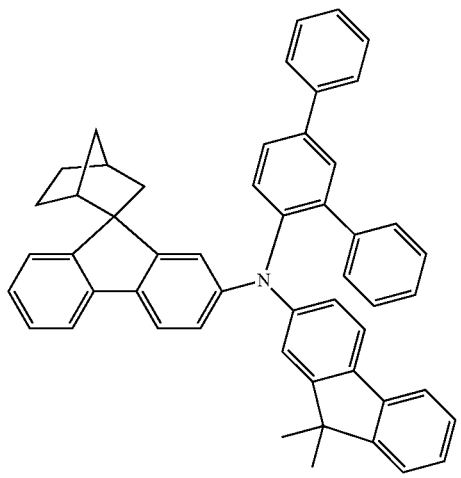
345
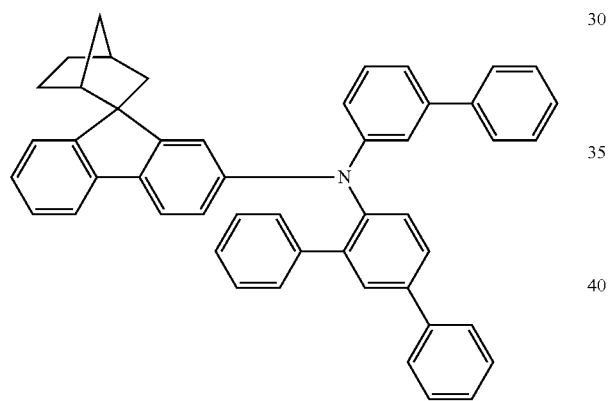
343
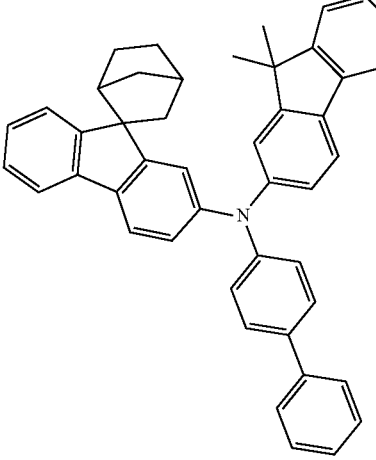
347
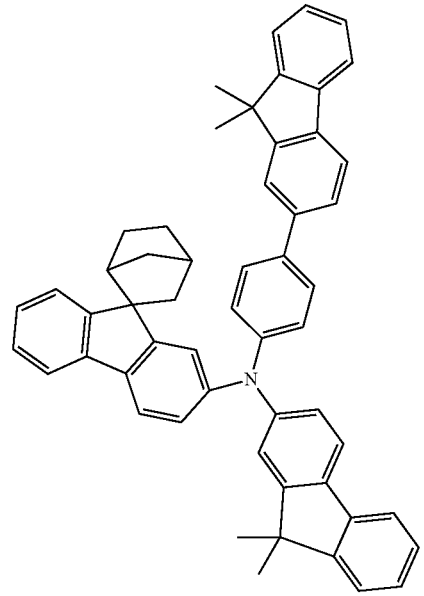
348
344

351
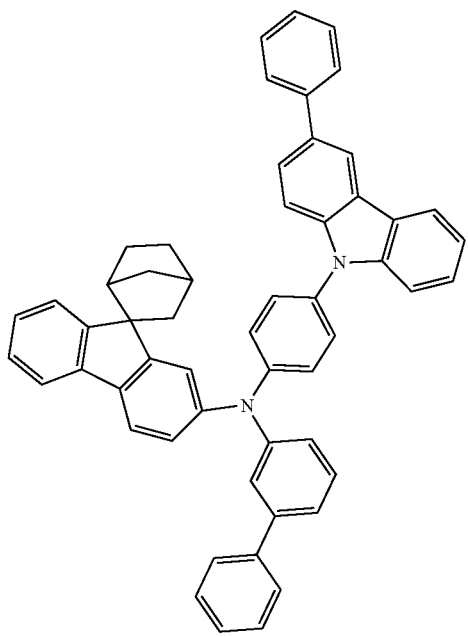
346
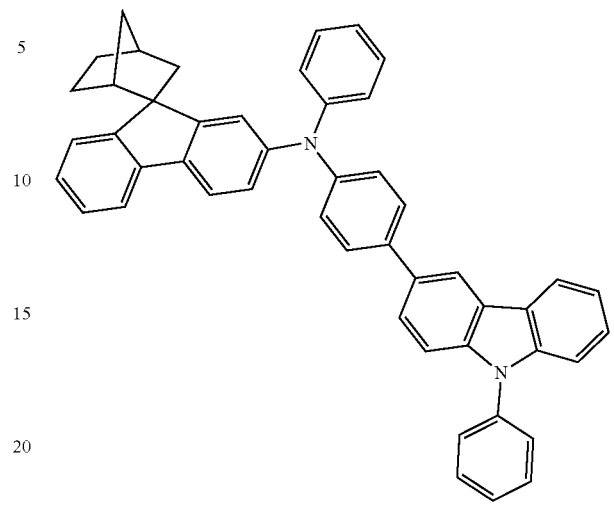
352
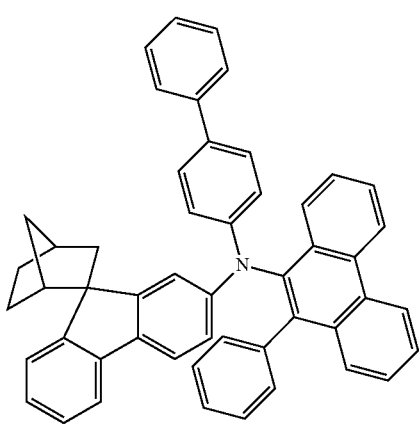
349
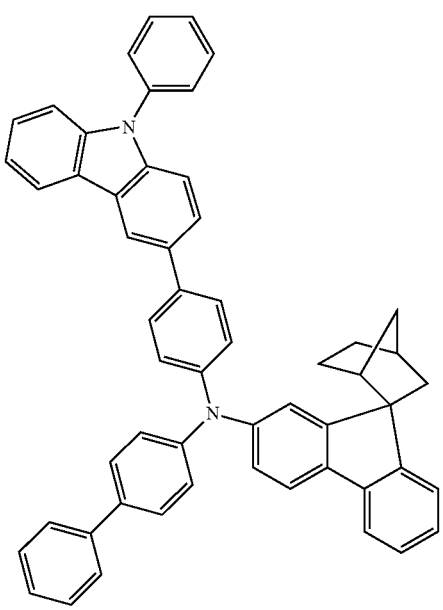

331
-continued

332
-continued

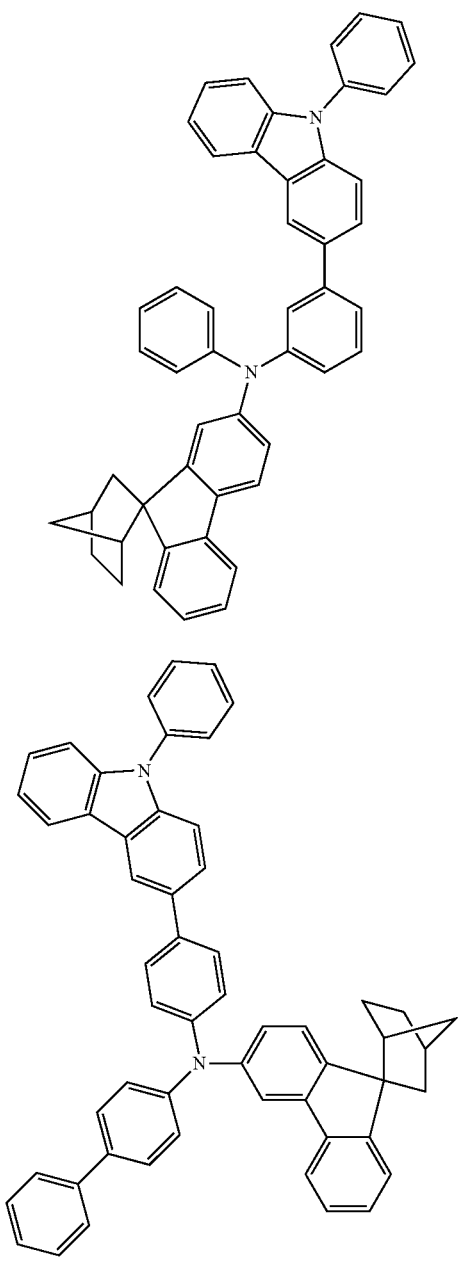

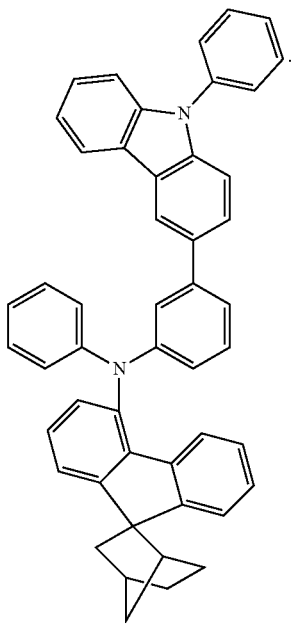

12. An electronic element, wherein the electronic element contains an anode and a cathode oppositely disposed, and a functional layer disposed between the anode and the cathode;
    the functional layer contains a hole transport layer, the hole transport contains the nitrogen-containing compound according to claim 1.

13. The electronic element according to claim 12, wherein the electronic element is an organic electroluminescent device or a solar cell.

14. The electronic element according to claim 13, wherein the electronic element is an organic electroluminescent device,
    the hole transport layer contains a first hole transport layer and a second hole transport layer;
    the first hole transport layer is adjacent to the second hole transport layer and closer to the anode relative to the second hole transport layer;
    the first hole transport layer and/or the second hole transport layer contain(s) the nitrogen-containing compound.

15. An electronic device, wherein the electronic device contains the electronic element according to claim 12.

\* \* \* \* \*

UNITED STATES PATENT AND TRADEMARK OFFICE
CERTIFICATE OF CORRECTION

PATENT NO. : 12,289,988 B2  Page 1 of 7
APPLICATION NO. : 17/620353
DATED : April 29, 2025
INVENTOR(S) : Tiantian Ma, Qiqi Nie and Jiamei Cao It is certified that error appears in the above-identified patent and that said Letters Patent is hereby corrected as shown below:

In the Specification

Column 56, Compound 94

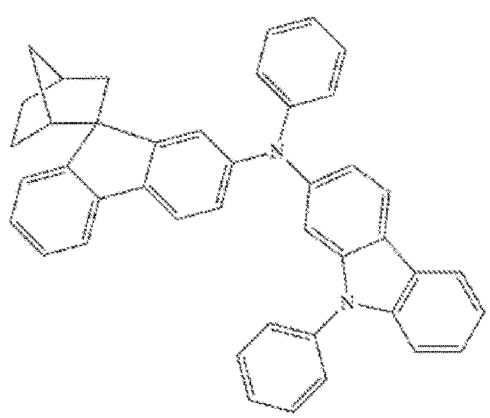

Should be

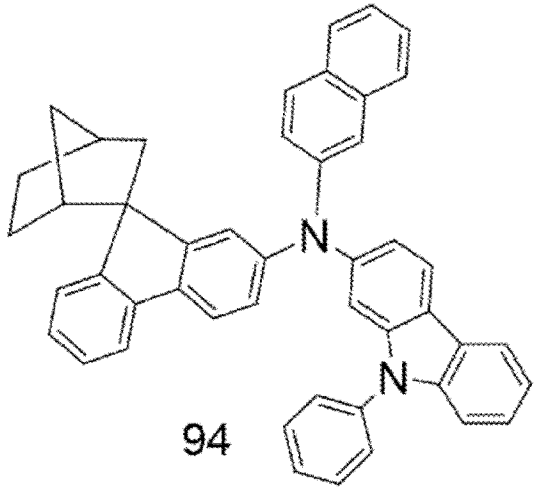

Signed and Sealed this
Twenty-second Day of July, 2025

Coke Morgan Stewart
*Acting Director of the United States Patent and Trademark Office*

CERTIFICATE OF CORRECTION (continued)
U.S. Pat. No. 12,289,988 B2

Column 69, Compound 137

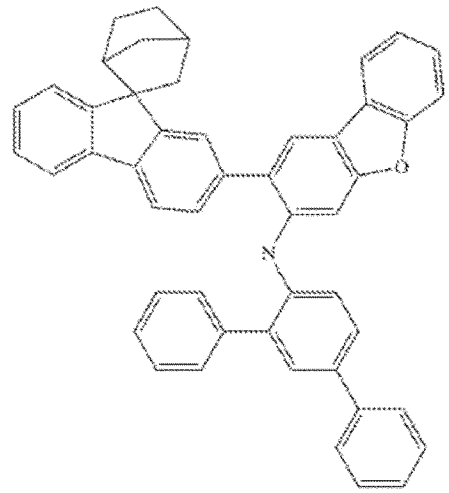

Should be

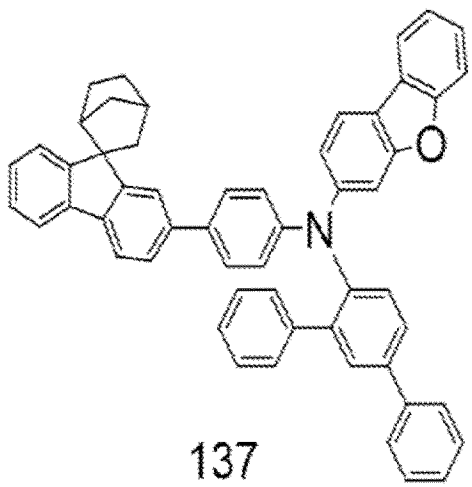

CERTIFICATE OF CORRECTION (continued)
U.S. Pat. No. 12,289,988 B2

Page 3 of 7

Column 75, Compound 156

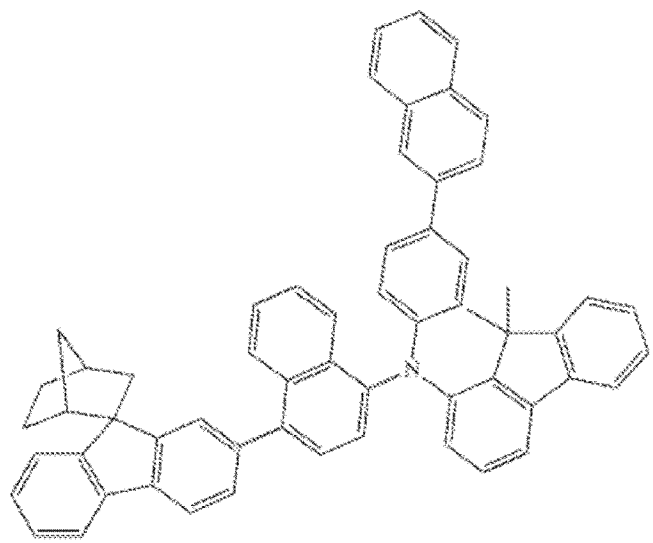

Should be

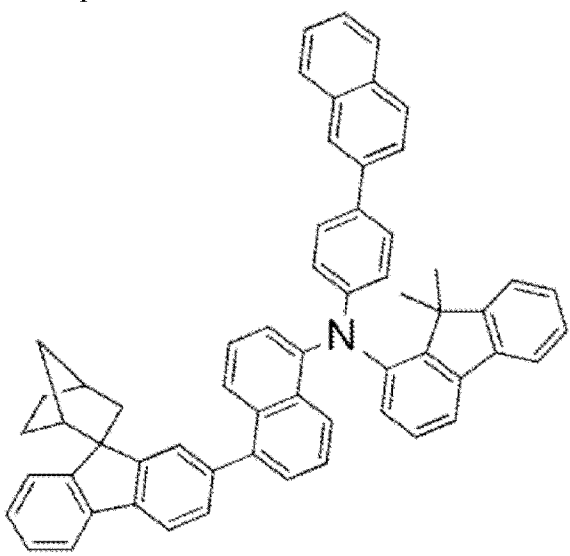

156

CERTIFICATE OF CORRECTION (continued)
U.S. Pat. No. 12,289,988 B2

Column 80, Compound 173

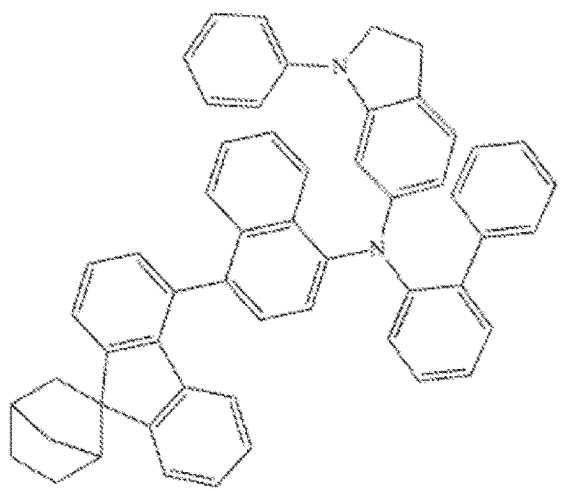

Should be

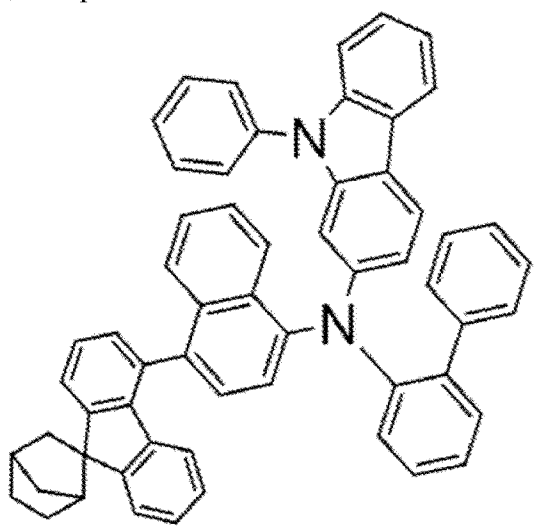

CERTIFICATE OF CORRECTION (continued)
U.S. Pat. No. 12,289,988 B2

Column 80, Compound 174

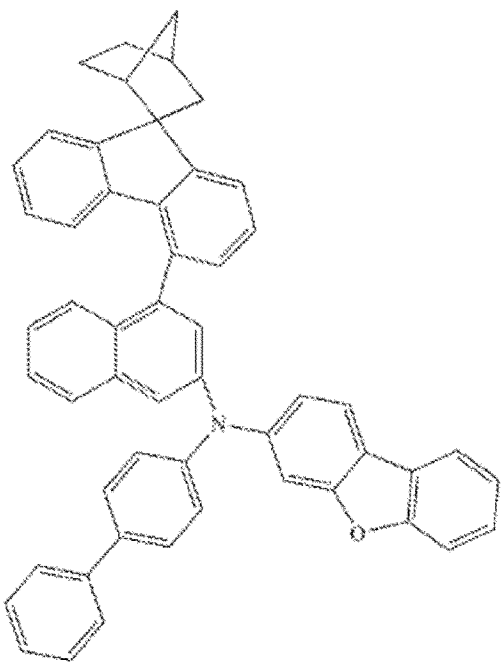

Should be

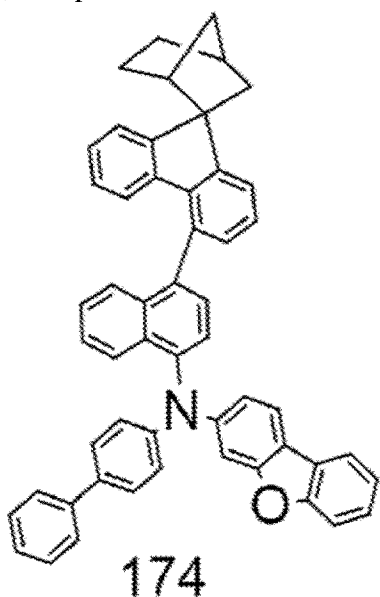

174

CERTIFICATE OF CORRECTION (continued)
U.S. Pat. No. 12,289,988 B2

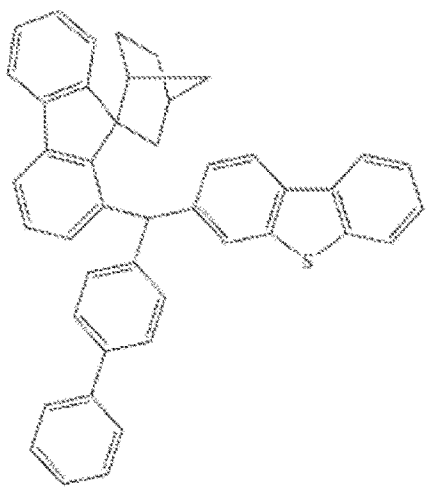

Column 132, Compound 327

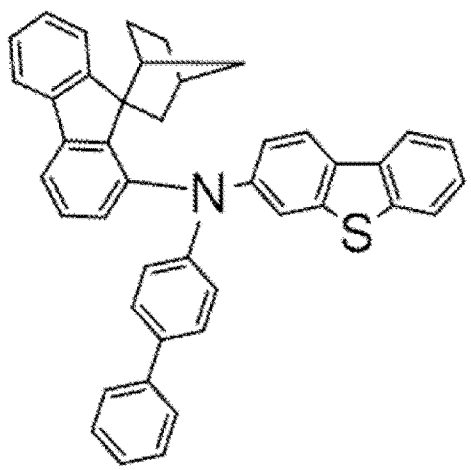

Should be  327

CERTIFICATE OF CORRECTION (continued)
U.S. Pat. No. 12,289,988 B2

Page 7 of 7

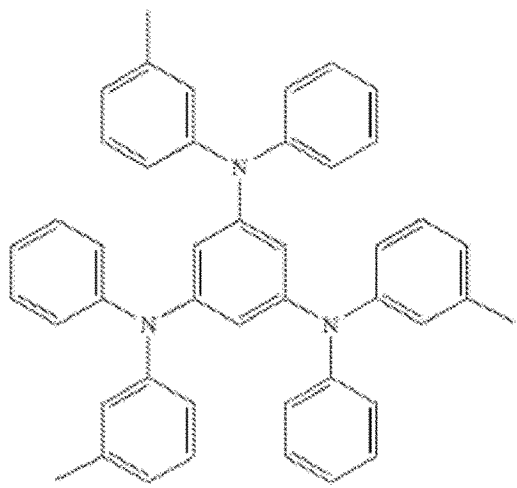

Column 193, m-MYDATA

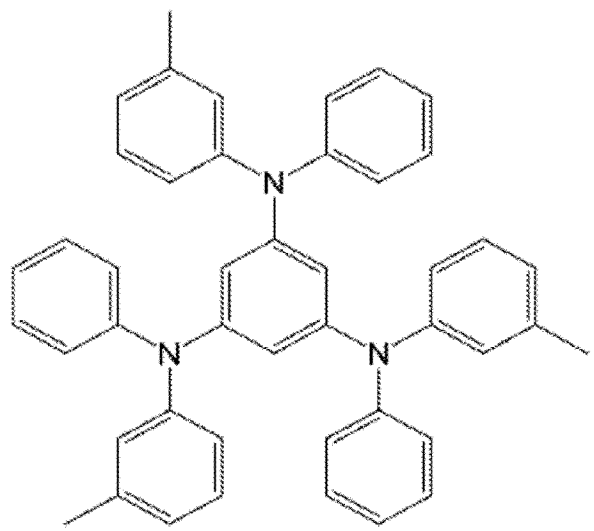

Should be m-MTDATA